United States Patent
Damude et al.

(10) Patent No.: US 8,338,152 B2
(45) Date of Patent: Dec. 25, 2012

(54) DELTA-8 DESATURASES AND THEIR USE IN MAKING POLYUNSATURATED FATTY ACIDS

(75) Inventors: Howard Glenn Damude, Hockessin, DE (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/449,395

(22) Filed: Apr. 18, 2012

(65) Prior Publication Data

US 2012/0196347 A1  Aug. 2, 2012

Related U.S. Application Data

(62) Division of application No. 12/099,799, filed on Apr. 9, 2008, now Pat. No. 8,188,338.

(60) Provisional application No. 60/910,831, filed on Apr. 10, 2007.

(51) Int. Cl.
*C12N 9/02* (2006.01)

(52) U.S. Cl. .......................................... 435/189

(58) Field of Classification Search ........................ None
See application file for complete search history.

(56) References Cited

U.S. PATENT DOCUMENTS

| | | | |
|---|---|---|---|
| 6,825,017 B1 | 11/2004 | Browse et al. |
| 7,256,033 B2 | 8/2007 | Damude et al. |
| 7,550,286 B2 | 6/2009 | Damude et al. |
| 7,550,651 B2 | 6/2009 | Damude |
| 7,588,931 B2 | 9/2009 | Damude et al. |
| 7,807,849 B2 | 10/2010 | Singh et al. |
| 7,863,502 B2 | 1/2011 | Damude et al. |
| 7,932,077 B2 | 4/2011 | Damude et al. |
| 7,943,823 B2 | 5/2011 | Damude et al. |
| 2010/0099900 A1 | 4/2010 | Damude et al. |

FOREIGN PATENT DOCUMENTS

| | | |
|---|---|---|
| WO | WO 0034439 | 6/2000 |
| WO | WO 02077213 | 10/2002 |
| WO | WO 2004057001 | 7/2004 |
| WO | WO 2004071467 | 8/2004 |
| WO | WO 2004101753 | 11/2004 |
| WO | WO 2004101757 | 11/2004 |
| WO | WO 2005103253 | 11/2005 |
| WO | WO 2006012325 | 2/2006 |
| WO | WO 2006012326 | 2/2006 |
| WO | WO 2006052870 | 5/2006 |
| WO | WO 2006052871 | 5/2006 |
| WO | WO 2006055322 | 5/2006 |

OTHER PUBLICATIONS

Dnyaneshwar Warude et al., "Polyunsaturated Fatty Acids: Biotechnology, Critical Reviews in Biotechnology", 2006, pp. 83-93, vol. 26.
Fourgoux-Nicol et al. Plant Mol Biol 40: 857-872, 1999.
National Center for Biotechnology Information, General Identifier No. 17226123, Qi et al., "Identification of a cDNA encoding a novel C18-delta (9) polyunsaturated fatty acid-specific elongating activity from the docosahexaenoic acid (DHA)-producing microalga, isochrysis galbana", Accession No. AAL37626, 2006.
National Center for Biotechnology Information, General Identifier No. 5639724, Wallis et al., "The delta 8-desaturase of euglena gracilis: an alternate pathway for synthesis of 20-carbon polyunsaturated fatty acids", Accession No. AAD45877, 1999.
National Center for Biotechnology Information, General Identifier No. 5639723, Wallis et al., "The delta 8-desaturase of *Euglena gracilis*: an alternate pathway for synthesis of 20-carbon polyunsaturated fatty acids", Accession No. AF139720, 1999.
Sayanova et al., "The alternative pathway C20 delta 8-desaturase from the non-photosynthetic organism acanthamoeba castellanii is an atypical cytochrome b5-fusion desaturase", FEBS Letter, vol. 580, pp. 1946-1952, 2006.
Wallis et al., "The delta-8 desaturase of *Euglena gracilis*: an alternate pathway for synthesis of 20-carbon polyunsaturated fatty acids", Arch. Biochem. & Biophys., vol. 365, pp. 307-316, 1999.
U.S. Appl. No. 12/099,799, Notice of Allowance, mailed Feb. 22, 2012.
U.S. Appl. No. 12/099,799, Final Rejection, mailed Sep. 8, 2011.
U.S. Appl. No. 12/099,799, Non-Final Rejection , mailed Mar. 15, 2011.
U.S. Appl. No. 12/099,799, Non-Final Rejection, mailed Nov. 18, 2010.
U.S. Appl. No. 12/099,799, Restriction Requirement, mailed Aug. 20, 2010.

*Primary Examiner* — David J Steadman

(57) ABSTRACT

Isolated nucleic acid fragments and recombinant constructs comprising such fragments encoding delta-8 desaturases along with a method of making long-chain polyunsaturated fatty acids (PUFAs) and using these delta-8 desaturases in plants.

6 Claims, 18 Drawing Sheets

FIG. 4

| Event | Fatty Acid | Fatty acid composition (wt. %) | | | | | | | | | | | | | | C20 % delta-8 desat | Ave. C20 % delta-8 desat | Ratio (EDA/ERA) % desat |
|---|---|---|---|---|---|---|---|---|---|---|---|---|---|---|---|---|---|---|
| | | 16:0 | 16:1 | 18:0 | 18:1 | LA | ALA | 20:1 | EDA | DGLA | ERA | ETA | 24:0 | 24:1 | | | |
| pY175-1 | EDA | 13.1 | 10.0 | 1.2 | 20.4 | 50.8 | 0.1 | 0.2 | 1.5 | 1.6 | 0.0 | 0.0 | 0.2 | 1.0 | 51.4 | 52.2 | 1.2 |
| Y175-2 | EDA | 13.5 | 9.8 | 1.2 | 21.0 | 50.7 | 0.1 | 0.1 | 1.3 | 1.5 | 0.0 | 0.0 | 0.3 | 0.5 | 52.6 | | |
| Y175-2 | EDA | 13.5 | 9.7 | 1.2 | 21.1 | 50.8 | 0.1 | 0.2 | 1.3 | 1.4 | 0.0 | 0.0 | 0.2 | 0.4 | 52.6 | | |
| Y176-1 | EDA | 13.6 | 9.5 | 1.1 | 18.3 | 52.6 | 0.1 | 0.1 | 1.8 | 1.8 | 0.0 | 0.0 | 0.2 | 0.9 | 50.7 | 52.2 | 1.2 |
| Y176-2 | EDA | 13.3 | 10.6 | 1.1 | 20.7 | 50.8 | 0.1 | 0.1 | 1.1 | 1.3 | 0.0 | 0.0 | 0.2 | 0.6 | 53.0 | | |
| Y176-3 | EDA | 13.2 | 10.6 | 1.1 | 21.1 | 50.5 | 0.1 | 0.1 | 1.1 | 1.3 | 0.0 | 0.0 | 0.2 | 0.7 | 53.0 | | |
| Y177-1 | EDA | 13.3 | 10.3 | 1.1 | 19.2 | 52.3 | 0.1 | 0.1 | 1.4 | 1.6 | 0.0 | 0.0 | 0.1 | 0.3 | 52.6 | 52.3 | 1.1 |
| Y177-2 | EDA | 13.3 | 10.1 | 1.2 | 21.5 | 50.4 | 0.1 | 0.1 | 1.2 | 1.3 | 0.0 | 0.0 | 0.2 | 0.6 | 52.7 | | |
| Y177-3 | EDA | 13.3 | 10.2 | 1.1 | 22.6 | 49.7 | 0.1 | 0.1 | 1.2 | 1.2 | 0.0 | 0.0 | 0.2 | 0.2 | 51.5 | | |
| Y178-1 | EDA | 13.5 | 9.6 | 1.2 | 21.8 | 50.5 | 0.1 | 0.2 | 1.4 | 1.3 | 0.0 | 0.0 | 0.1 | 0.3 | 47.5 | 49.2 | 1.1 |
| Y178-2 | EDA | 13.7 | 9.2 | 1.2 | 19.5 | 51.9 | 0.1 | 0.2 | 1.9 | 1.8 | 0.0 | 0.0 | 0.1 | 0.3 | 48.4 | | |
| Y178-3 | EDA | 13.6 | 9.8 | 1.2 | 22.2 | 49.8 | 0.1 | 0.2 | 1.3 | 1.4 | 0.0 | 0.0 | 0.1 | 0.3 | 51.5 | | |
| Y175-1 | ERA | 12.2 | 8.8 | 1.3 | 21.9 | 40.8 | 7.2 | 0.1 | 0.1 | 0.1 | 3.8 | 3.1 | 0.1 | 0.5 | 44.3 | 44.3 | |
| Y175-2 | ERA | 12.1 | 9.2 | 1.3 | 21.4 | 40.9 | 7.2 | 0.1 | 0.1 | 0.1 | 3.9 | 3.1 | 0.1 | 0.4 | 44.1 | | |
| Y175-3 | ERA | 12.1 | 9.1 | 1.2 | 21.2 | 41.1 | 7.3 | 0.1 | 0.1 | 0.1 | 3.9 | 3.2 | 0.1 | 0.3 | 44.5 | | |
| Y176-1 | ERA | 12.1 | 8.8 | 1.2 | 20.1 | 41.1 | 8.1 | 0.1 | 0.1 | 0.1 | 4.3 | 3.3 | 0.1 | 0.5 | 43.6 | 44.7 | |
| Y176-2 | ERA | 12.3 | 9.6 | 1.3 | 23.0 | 40.5 | 6.3 | 0.1 | 0.1 | 0.1 | 3.3 | 2.7 | 0.2 | 0.3 | 45.2 | | |
| Y176-3 | ERA | 12.0 | 9.6 | 1.3 | 21.0 | 41.3 | 7.4 | 0.1 | 0.1 | 0.1 | 3.7 | 3.0 | 0.0 | 0.4 | 45.3 | | |
| Y177-1 | ERA | 12.1 | 9.5 | 1.2 | 22.4 | 40.4 | 7.1 | 0.1 | 0.1 | 0.1 | 3.5 | 3.0 | 0.1 | 0.3 | 45.7 | 45.5 | |
| Y177-2 | ERA | 12.0 | 9.9 | 1.2 | 21.3 | 40.3 | 7.6 | 0.1 | 0.1 | 0.1 | 3.6 | 3.0 | 0.1 | 0.6 | 45.1 | | |
| Y177-3 | ERA | 12.0 | 9.8 | 1.2 | 20.1 | 40.6 | 7.7 | 0.1 | 0.1 | 0.1 | 3.8 | 3.2 | 0.1 | 1.0 | 45.9 | | |
| Y178-1 | ERA | 11.7 | 9.8 | 1.0 | 19.5 | 42.6 | 8.3 | 0.1 | 0.1 | 0.1 | 3.7 | 2.7 | 0.1 | 0.4 | 42.3 | 44.1 | |
| Y178-2 | ERA | 12.0 | 9.8 | 1.2 | 20.8 | 40.9 | 7.8 | 0.1 | 0.1 | 0.1 | 3.7 | 3.0 | 0.1 | 0.3 | 44.6 | | |
| Y178-3 | ERA | 12.2 | 10.2 | 1.2 | 24.4 | 40.4 | 5.6 | 0.1 | 0.1 | 0.1 | 2.8 | 2.3 | 0.2 | 0.4 | 45.5 | | |

FIG. 7A

```
     M..KR.ALPLT.DG.TYDVSAW.N.HPGGA.IIENY.GRDATD.FMVMHS Consensus #1
              10        20        30        40        50
  1  M-VKRPALPLTVDGVTYDVSAWLNHHPGGADIIENYRGRDATDVFMVMHS EaD8Des1 (SEQ ID NO21).pro
  1  M-VKRPALPLTVDGVTYDVSAWLNHHPGGADIIENYRGRDATDVFMVMHS EaD8Des2 (SEQ ID NO22).pro
  1  M-VKRPALPLTVDGVTYDVSAWLNHHPGGADIIENYRGRDATDVFMVMHS EaD8Des3 (SEQ ID NO23).pro
  1  M-VKRPALPLTVDGVTYDVSAWLNHHPGGADIIENYRGRDATDVFMVMHS EaD8Des4 (SEQ ID NO24).pro
  1  MKSKRQALPLTIDGTTYDVSAWVNFHPGGAEIIENYQGRDATDAFMVMHS corrected EgD8 (SEQ ID NO25).pro ..A..KL.RMP...PSS.L...PP......E.QEDFRKLR.ELIA.GMFDA Consensus #1
              60        70        80        90        100
 50  ENAVSKLRRMPIMEPSSPLTPTPPKPNSDEPQEDFRKLRDELIAAGMFDA EaD8Des1 (SEQ ID NO21).pro
 50  ENAVSKLRRMPIMEPSSPLTPTPPKPNSDEPQEDFRKLRDELIAAGMFDA EaD8Des2 (SEQ ID NO22).pro
 50  ENAVSKLRRMPIMEPSSPLTPTPPKPNSDEPQEDFRKLRDELIAAGMFDA EaD8Des3 (SEQ ID NO23).pro
 50  ENAVSKLRRMPIMEPSSPLTPTPPKPNSDEPQEDFRKLRDELIAAGMFDA EaD8Des4 (SEQ ID NO24).pro
 51  QEAFDKLKRMPKINPSSEL---PPQAAVNEAQEDFRKLREELIATGMFDA corrected EgD8 (SEQ ID NO25).pro SP.WY.YK...TLGLGVL...LM.Q...Y..GA..LG.H.QQMGWLSHDI Consensus #1
             110       120       130       140       150
100  SPMWYAYKTLTTLGLGVLAVLLMTQWHWYLVGAIVLGIHFQQMGWLSHDI EaD8Des1 (SEQ ID NO21).pro
100  SPMWYAYKTLSTLGLGVLAVLLMTQWHWYLVGAIVLGIHFQQMGWLSHDI EaD8Des2 (SEQ ID NO22).pro
100  SPMWYAYKTLSTLGLGVLAVLLMTQWHWYLVGAIVLGIHFQQMGWLSHDI EaD8Des3 (SEQ ID NO23).pro
100  SPMWYAYKTLSTLGLGVLAVLLMTQWHWYLVGAIVLGIHFQQMGWLSHDI EaD8Des4 (SEQ ID NO24).pro
 98  SPLWYSYKISTTLGLGVLGYFLMVQYQMYFIGAVLLGMHYQQMGWLSHDI corrected EgD8 (SEQ ID NO25).pro
```

FIG. 7B

```
    CHHQ.FK.R..NN..GL.FGN.LQGFSVTWWKDRHNAHHSATNVQGHDPD Consensus #1
                 160       170       180       190       200
150 CHHQLFKDRSINNAIGLLFGNVLQGFSVTWWKDRHNAHHSATNVQGHDPD EaD8Des1 (SEQ ID NO21).pro
150 CHHQLFKDRSINNAIGLLFGNVLQGFSVTWWKDRHNAHHSATNVQGHDPD EaD8Des2 (SEQ ID NO22).pro
150 CHHQLFKDRSINNAIGLLFGNVLQGFSVTWWKDRHNAHHSATNVQGHDPD EaD8Des3 (SEQ ID NO23).pro
150 CHHQLFKDRSINNAIGLLFGNVLQGFSVTWWKDRHNAHHSATNVQGHDPD EaD8Des4 (SEQ ID NO24).pro
148 CHHQTFKNRNWNNLVGLVFGNGLQGFSVTWWKDRHNAHHSATNVQGHDPD corrected EgD8 (SEQ ID NO25).pro IDNLPLLAWS..DV.RA.P.SR..I..QQYYF..IC.LLRFIWCFQS..T Consensus #1
                 210       220       230       240       250
200 IDNLPLLAWSKEDVERAGPFSRRMIKYQQYYFFFICALLRFIWCFQSIHT EaD8Des1 (SEQ ID NO21).pro
200 IDNLPLLAWSKEDVERAGPFSRRIIKYQQYYFFFICALLRFIWCFQSIHT EaD8Des2 (SEQ ID NO22).pro
200 IDNLPLLAWSKEDVERAGPFSRRMIKYQQYYFFFICALLRFIWCFQSIHT EaD8Des3 (SEQ ID NO23).pro
200 IDNLPLLAWSKEDVERAGPFSRRMIKYQQYYFFFICALLRFIWCFQSIHT EaD8Des4 (SEQ ID NO24).pro
198 IDNLPLLAWSEDDVTRASPISRKLIQFQQYYFLVICILLRFIWCFQSVLT corrected EgD8 (SEQ ID NO25).pro ...LKDR.NQ.YR.QY.KE..GLALHW.LK.LF..F.MPS.LT.L.VFFV Consensus #1
                 260       270       280       290       300
250 AKGLKDRSNQYYRRQYEKESVGLALHWGLKALFYYFYMPSFLTGLMVFFV EaD8Des1 (SEQ ID NO21).pro
250 ATGLKDRSNQYYRRQYEKESVGLALHWGLKALFYYFYMPSFLTGLMVFFV EaD8Des2 (SEQ ID NO22).pro
250 ATGLKDRSNQYYRRQYEKESVGLALHWGLKALFYYFYMPSFLTGLMVFFV EaD8Des3 (SEQ ID NO23).pro
250 AKGLKDRSNQYYRRQYEKESVGLALHWGLKALFYYFYMPSFLTGLMVFFV EaD8Des4 (SEQ ID NO24).pro
248 VRSLKDRDNQFYRSQYKKEAIGLALHWTLKTLFHLFFMPSILTSLLVFFV corrected EgD8 (SEQ ID NO25).pro
```

FIG. 7C

```
    SEL.GGFGIAIVVFMNHYPLEKI.DSVWDGHGF..GQIHETMN..RG..T  Consensus #1
            310       320       330       340       350
300 SELLGGFGIAIVVFMNHYPLEKIQDSVWDGHGFCAGQIHETMNVQRGLVT  EaD8Des1 (SEQ ID NO21).pro
300 SELLGGFGIAIVVFMNHYPLEKIQDSVWDGHGFCAGQIHETMNVQRGLVT  EaD8Des2 (SEQ ID NO22).pro
300 SELLGGFGIAIVVFMNHYPLEKIQDSVWDGHGFCAGQIHETMNVQRGLVT  EaD8Des3 (SEQ ID NO23).pro
300 SELLGGFGIAIVVFMNHYPLEKIQDSVWDGHGFCAGQIHETMNVQRGLVT  EaD8Des4 (SEQ ID NO24).pro
298 SELVGGFGIAIVVFMNHYPLEKIGDSVWDGHGFSVGQIHETMNIRRGIIT  corrected EgD8 (SEQ ID NO25).pro DWFFGGLNYQIEHHLWPTLPRHNLTA.S..VEQLC.KHNLPYR.P...EG  Consensus #1
            360       370       380       390       400
350 DWFFGGLNYQIEHHLWPTLPRHNLTAASIKVEQLCKKHNLPYRSPPMLEG  EaD8Des1 (SEQ ID NO21).pro
350 DWFFGGLNYQIEHHLWPTLPRHNLTAASIKVEQLCKKHNLPYRSPPMLEG  EaD8Des2 (SEQ ID NO22).pro
350 DWFFGGLNYQIEHHLWPTLPRHNLTAASIKVEQLCKKHNLPYRSPPMLEG  EaD8Des3 (SEQ ID NO23).pro
350 DWFFGGLNYQIEHHLWPTLPRHNLTAASIKVEQLCKKHNLPYRSPPMLEG  EaD8Des4 (SEQ ID NO24).pro
348 DWFFGGLNYQIEHHLWPTLPRHNLTAVSYQVEQLCQKHNLPYRNPLPHEG  corrected EgD8 (SEQ ID NO25).pro ..IL.YL..FARM..K..A..KA.                            Consensus #1
            410       420
400 VGILISYLGTFARMVAK--ADKA                             EaD8Des1 (SEQ ID NO21).pro
400 VGILISYLGTFARMVAK--ADKA                             EaD8Des2 (SEQ ID NO22).pro
400 VGILISYLGTFARMVAK--ADKA                             EaD8Des3 (SEQ ID NO23).pro
400 VGILISYLGTFARMVAK--ADKA                             EaD8Des4 (SEQ ID NO24).pro
398 LVILLRYLAVFARMAEKQPAGKAL                            corrected EgD8 (SEQ ID NO25).pro
```

EaD8Des3 (SEQ ID NO:19) and EaD8S (SEQ ID NO:48)

| Event | Fatty acid composition (wt.%) | | | | | | | | | C18 % delta-9 elong | C20 % delta-8 desat |
|---|---|---|---|---|---|---|---|---|---|---|---|
| | 16:0 | 18:0 | 18:1 | LA | ALA | EDA | DGLA | ERA | ETA | | |
| 2136-1-3-1 | 17.7 | 4.2 | 12.0 | 30.3 | 12.0 | 8.8 | 10.2 | 1.0 | 3.1 | 35.3 | 57.8 |
| 2136-1-3-2 | 17.7 | 3.6 | 11.3 | 25.9 | 9.3 | 10.7 | 15.4 | 1.3 | 4.4 | 47.4 | 62.2 |
| 2136-1-3-3 | 17.8 | 3.8 | 9.1 | 25.2 | 9.3 | 10.3 | 17.4 | 1.3 | 5.0 | 49.6 | 65.9 |
| 2136-1-3-4 | 18.9 | 4.5 | 8.2 | 32.3 | 20.8 | 3.4 | 7.5 | 0.7 | 2.1 | 20.6 | 70.2 |
| 2136-1-3-5 | 17.9 | 4.0 | 14.4 | 27.1 | 10.5 | 8.4 | 12.5 | 0.9 | 3.8 | 40.5 | 63.6 |
| Avg. | 18.0 | 4.0 | 11.0 | 28.2 | 12.3 | 8.3 | 12.6 | 1.0 | 3.7 | 38.7 | 64.0 |
| 2136-2-8-1 | 17.0 | 3.8 | 12.1 | 25.7 | 9.7 | 11.6 | 13.9 | 1.3 | 4.5 | 46.9 | 58.8 |
| 2136-2-8-2 | 17.1 | 4.0 | 9.7 | 22.6 | 7.5 | 11.4 | 22.3 | 1.0 | 4.4 | 56.5 | 68.3 |
| 2136-2-8-3 | 18.3 | 3.6 | 9.0 | 25.9 | 10.9 | 10.6 | 14.8 | 1.5 | 4.7 | 46.2 | 61.7 |
| 2136-2-8-4 | 18.5 | 3.6 | 9.3 | 25.1 | 11.6 | 9.7 | 15.2 | 1.5 | 4.9 | 46.0 | 64.2 |
| 2136-2-8-5 | 18.8 | 3.9 | 11.0 | 24.6 | 12.4 | 8.4 | 13.8 | 1.3 | 4.8 | 43.3 | 65.8 |
| Avg. | 17.9 | 3.8 | 10.2 | 24.8 | 10.4 | 10.3 | 16.0 | 1.3 | 4.7 | 47.8 | 63.8 |
| 2136-2-15-1 | 18.7 | 3.0 | 14.7 | 28.9 | 9.8 | 8.9 | 12.9 | 0.8 | 4.2 | 41.1 | 63.7 |
| 2136-2-15-2 | 16.5 | 3.1 | 12.0 | 30.2 | 12.3 | 8.0 | 12.5 | 1.0 | 4.1 | 37.6 | 65.0 |
| 2136-2-15-3 | 16.7 | 3.3 | 13.4 | 29.2 | 8.4 | 9.8 | 14.0 | 0.9 | 4.0 | 43.3 | 62.8 |
| 2136-2-15-4 | 17.8 | 3.4 | 13.3 | 27.6 | 12.5 | 7.5 | 11.8 | 1.1 | 4.5 | 38.3 | 65.5 |
| 2136-2-15-5 | 16.6 | 3.3 | 15.3 | 28.3 | 8.8 | 9.2 | 13.6 | 0.6 | 3.7 | 42.4 | 63.4 |
| Avg. | 16.9 | 3.2 | 13.7 | 28.9 | 10.3 | 8.7 | 13.0 | 0.9 | 4.1 | 40.5 | 64.1 |
| 2136-3-8-1 | 18.1 | 2.9 | 8.5 | 29.4 | 12.7 | 8.2 | 13.3 | 1.5 | 5.0 | 39.9 | 65.5 |
| 2136-3-8-2 | 20.1 | 3.1 | 6.6 | 39.3 | 28.2 | 0.7 | 0.8 | 0.3 | 0.4 | 2.9 | 52.3 |
| 2136-3-8-3 | 19.8 | 3.3 | 7.1 | 27.9 | 15.3 | 7.2 | 12.0 | 1.7 | 4.9 | 37.4 | 65.4 |
| 2136-3-8-4 | 19.2 | 3.6 | 9.1 | 25.9 | 13.1 | 7.9 | 13.9 | 1.8 | 5.8 | 42.1 | 65.8 |
| 2136-3-8-5 | 16.6 | 3.2 | 9.2 | 29.8 | 11.8 | 9.3 | 13.6 | 1.6 | 4.6 | 41.1 | 62.6 |
| Avg. | 18.7 | 3.2 | 8.1 | 30.5 | 16.2 | 6.6 | 10.5 | 1.4 | 4.1 | 32.7 | 62.4 |
| 2136-4-2-1 | 18.8 | 5.0 | 12.8 | 26.1 | 11.9 | 8.6 | 11.2 | 1.3 | 4.0 | 39.7 | 60.6 |
| 2136-4-2-2 | 16.8 | 3.8 | 9.4 | 25.9 | 9.8 | 11.2 | 15.7 | 1.8 | 5.3 | 48.9 | 61.8 |
| 2136-4-2-3 | 17.0 | 3.8 | 8.8 | 26.6 | 10.5 | 10.5 | 15.5 | 1.7 | 5.3 | 46.9 | 63.1 |
| 2136-4-2-4 | 16.8 | 3.9 | 9.0 | 26.3 | 11.2 | 11.1 | 15.1 | 1.8 | 5.3 | 47.0 | 61.3 |
| 2136-4-2-5 | 17.0 | 2.9 | 6.0 | 44.1 | 29.4 | 0.2 | 0.0 | 0.0 | 0.0 | 0.3 | 0.0 |
| Avg. | 17.2 | 3.7 | 9.1 | 29.8 | 14.5 | 8.3 | 11.5 | 1.3 | 4.0 | 36.6 | 49.3 |

FIG. 13

| Event | Fatty acid composition (wt.%) | | | | | | | | | C18 % delta-9 elong | C20 % delta-8 desat |
|---|---|---|---|---|---|---|---|---|---|---|---|
| | 16:0 | 18:0 | 18:1 | LA | ALA | EDA | DGLA | ERA | ETA | | |
| 2130-1-29-1 | 17.5 | 3.4 | 10.8 | 23.7 | 5.6 | 17.4 | 15.0 | 2.2 | 3.8 | 56.7 | 49.0 |
| 2130-1-29-2 | 16.9 | 3.9 | 11.5 | 24.1 | 6.6 | 15.3 | 14.9 | 3.0 | 4.2 | 54.3 | 52.5 |
| 2130-1-29-3 | 17.4 | 3.7 | 11.1 | 22.3 | 6.1 | 17.0 | 14.5 | 2.8 | 4.5 | 57.6 | 49.2 |
| 2130-1-29-4 | 17.8 | 3.8 | 10.5 | 21.8 | 5.7 | 17.1 | 16.0 | 2.4 | 4.4 | 59.1 | 51.1 |
| 2130-1-29-5 | 17.2 | 4.3 | 9.8 | 23.1 | 6.6 | 15.9 | 14.5 | 2.9 | 5.0 | 56.3 | 50.9 |
| Avg. | 17.4 | 3.8 | 10.7 | 23.0 | 6.1 | 16.5 | 15.0 | 2.4 | 4.4 | 56.8 | 50.5 |
| 2130-1-43-1 | 17.5 | 2.9 | 6.9 | 45.5 | 26.3 | 0.4 | 0.0 | 0.1 | 0.0 | 0.6 | 0.0 |
| 2130-1-43-2 | 18.0 | 3.4 | 7.5 | 24.3 | 7.2 | 11.8 | 20.2 | 1.5 | 5.5 | 55.3 | 65.8 |
| 2130-1-43-3 | 20.7 | 5.5 | 12.3 | 23.8 | 5.6 | 11.2 | 16.1 | 1.2 | 3.8 | 51.7 | 60.4 |
| 2130-1-43-4 | 18.3 | 4.0 | 8.7 | 23.6 | 7.8 | 12.1 | 17.2 | 1.9 | 5.5 | 63.9 | 61.8 |
| 2130-1-43-5 | 23.9 | 7.6 | 16.1 | 17.7 | 4.5 | 10.6 | 13.9 | 1.3 | 3.9 | 57.2 | 59.9 |
| Avg. | 19.7 | 4.7 | 10.3 | 27.0 | 10.3 | 9.2 | 13.3 | 1.2 | 3.8 | 43.7 | 49.6 |
| 2130-1-51-1 | 17.4 | 4.6 | 9.8 | 24.1 | 7.2 | 13.8 | 16.7 | 2.1 | 4.3 | 63.5 | 55.6 |
| 2130-1-51-2 | 18.7 | 3.9 | 9.4 | 20.7 | 6.0 | 14.1 | 18.3 | 2.8 | 5.8 | 60.4 | 58.8 |
| 2130-1-51-3 | 18.4 | 3.8 | 9.3 | 20.4 | 6.6 | 13.4 | 19.0 | 2.3 | 5.9 | 60.0 | 61.3 |
| 2130-1-51-4 | 17.9 | 4.1 | 9.6 | 20.4 | 5.2 | 15.2 | 19.1 | 2.3 | 5.2 | 62.0 | 58.2 |
| 2130-1-51-5 | 21.6 | 6.4 | 12.6 | 20.1 | 7.6 | 11.4 | 12.4 | 2.4 | 4.1 | 52.3 | 54.5 |
| Avg. | 18.8 | 4.6 | 10.2 | 21.1 | 6.5 | 13.6 | 16.9 | 2.3 | 5.0 | 57.6 | 57.7 |
| 2130-1-54-1 | 16.4 | 4.2 | 13.5 | 28.5 | 6.9 | 11.0 | 14.6 | 1.0 | 3.7 | 46.1 | 60.6 |
| 2130-1-54-2 | 18.1 | 4.1 | 10.8 | 26.2 | 6.9 | 12.3 | 15.9 | 1.3 | 3.9 | 50.3 | 59.4 |
| 2130-1-54-3 | 17.5 | 4.1 | 11.9 | 27.2 | 7.3 | 10.2 | 18.6 | 0.8 | 3.7 | 47.6 | 64.9 |
| 2130-1-54-4 | 16.7 | 4.2 | 10.9 | 28.3 | 7.3 | 14.9 | 12.3 | 1.6 | 3.2 | 47.3 | 48.4 |
| 2130-1-54-5 | 17.1 | 4.3 | 12.0 | 27.0 | 7.3 | 10.6 | 15.6 | 1.1 | 4.3 | 47.9 | 62.9 |
| Avg. | 17.2 | 4.2 | 11.8 | 27.5 | 7.1 | 11.8 | 15.0 | 1.2 | 3.8 | 47.9 | 59.2 |
| 2130-1-61-1 | 21.4 | 5.2 | 7.3 | 19.5 | 6.1 | 13.7 | 15.6 | 3.2 | 7.0 | 60.7 | 57.2 |
| 2130-1-61-2 | 17.2 | 3.5 | 5.4 | 20.3 | 7.8 | 14.4 | 18.0 | 4.1 | 8.7 | 61.6 | 58.9 |
| 2130-1-61-3 | 17.3 | 4.4 | 8.9 | 25.0 | 9.4 | 13.1 | 14.1 | 3.1 | 5.7 | 51.1 | 55.0 |
| 2130-1-61-4 | 21.0 | 7.1 | 11.2 | 18.1 | 6.6 | 11.0 | 15.7 | 2.7 | 6.0 | 58.9 | 61.2 |
| 2130-1-61-5 | 20.1 | 4.3 | 6.7 | 19.9 | 5.9 | 14.7 | 17.3 | 3.3 | 6.7 | 61.9 | 57.2 |
| Avg. | 18.4 | 4.9 | 7.5 | 20.6 | 7.2 | 13.4 | 16.1 | 3.3 | 6.8 | 58.8 | 57.9 |

Fatty acid composition (wt. %)

| Event | 16:0 | 18:0 | 18:1 | LA | ALA | 20:0 | 20:1 (11) | EDA | DGLA | ERA | ETA | C20 % delta-8 desat |
|---|---|---|---|---|---|---|---|---|---|---|---|---|
| ff1192-1 | 9.1 | 3.2 | 24.8 | 38.7 | 1.3 | 0.8 | 3.6 | 10.5 | 6.8 | 0.8 | 0.4 | 38.8 |
| ff1192-2 | 9.5 | 3.4 | 20.0 | 30.0 | 0.8 | 0.9 | 3.6 | 18.2 | 11.7 | 1.3 | 0.6 | 38.7 |
| ff1192-3 | 8.1 | 2.7 | 27.7 | 54.7 | 1.3 | 0.7 | 0.7 | 3.0 | 0.9 | 0.2 | 0.0 | 22.5 |
| ff1192-4 | 7.5 | 2.7 | 25.7 | 41.1 | 0.7 | 0.7 | 2.6 | 13.0 | 5.1 | 0.8 | 0.2 | 27.9 |
| ff1192-5 | 10.5 | 3.0 | 25.3 | 56.1 | 3.5 | 0.9 | 0.4 | 0.2 | 0.1 | 0.0 | 0.0 | 39.1 |
| ff1192-6 | 8.0 | 3.0 | 23.2 | 39.9 | 0.6 | 0.7 | 2.3 | 14.9 | 6.1 | 0.8 | 0.2 | 28.7 |
| ff1192-7 | 8.5 | 3.3 | 26.2 | 36.1 | 0.9 | 0.8 | 4.4 | 11.8 | 6.8 | 0.8 | 0.3 | 36.2 |
| ff1192-8 | 10.4 | 3.8 | 20.1 | 34.9 | 1.4 | 1.1 | 2.2 | 16.3 | 8.3 | 1.2 | 0.4 | 33.3 |
| ff1192-9 | 9.2 | 3.4 | 23.0 | 27.6 | 0.7 | 0.9 | 5.0 | 16.6 | 12.0 | 1.1 | 0.6 | 41.5 |
| ff1192-10 | 9.9 | 3.4 | 20.5 | 25.7 | 0.6 | 1.0 | 3.8 | 17.5 | 15.4 | 1.3 | 0.8 | 46.3 |
| ff1192-11 | 8.5 | 2.9 | 18.7 | 39.6 | 1.8 | 0.8 | 1.7 | 23.5 | 0.8 | 1.6 | 0.1 | 3.5 |
| ff1192-12 | 7.7 | 2.9 | 23.1 | 33.6 | 0.4 | 0.7 | 4.3 | 18.0 | 7.7 | 1.0 | 0.3 | 29.8 |
| ff1192-13 | 10.0 | 4.0 | 22.6 | 32.6 | 1.5 | 1.2 | 3.7 | 13.8 | 8.9 | 1.1 | 0.6 | 38.7 |
| ff1192-14 | 8.9 | 3.2 | 22.4 | 37.0 | 0.9 | 0.9 | 3.1 | 14.8 | 7.6 | 1.1 | 0.4 | 33.3 |
| ff1192-15 | 8.7 | 3.1 | 26.3 | 44.2 | 1.2 | 0.8 | 3.3 | 7.1 | 4.6 | 0.5 | 0.2 | 38.9 |
| ff1192-16 | 10.7 | 2.8 | 24.8 | 56.8 | 3.2 | 0.9 | 0.4 | 0.3 | 0.2 | 0.0 | 0.0 | 34.7 |
| ff1192-17 | 8.5 | 2.9 | 21.8 | 39.9 | 3.1 | 0.8 | 3.4 | 12.7 | 5.5 | 1.0 | 0.3 | 29.7 |
| ff1192-18 | 8.3 | 3.1 | 23.3 | 38.4 | 0.7 | 0.7 | 3.3 | 14.4 | 6.6 | 0.8 | 0.3 | 31.2 |
| ff1192-19 | 9.6 | 3.2 | 23.7 | 38.9 | 1.2 | 1.1 | 2.4 | 9.5 | 9.1 | 0.8 | 0.6 | 48.2 |
| ff1192-20 | 7.9 | 2.7 | 24.3 | 43.5 | 0.8 | 0.8 | 2.4 | 11.8 | 5.0 | 0.7 | 0.2 | 29.4 |
| ff1192-21 | 8.5 | 3.0 | 23.7 | 38.0 | 0.7 | 0.8 | 3.7 | 13.7 | 6.7 | 0.9 | 0.3 | 32.2 |

DELTA-8 DESATURASES AND THEIR USE IN MAKING POLYUNSATURATED FATTY ACIDS

This application claims the benefit of U.S. Provisional Patent Application No. 60/910,831, filed Apr. 10, 2007, the entire content of which is hereby incorporated by reference.

FIELD OF THE INVENTION

This invention is in the field of biotechnology. More specifically, this invention pertains to polynucleotide sequences encoding delta-8 desaturases and the use of these desaturases in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further elongation and desaturation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs produces cardiovascular protective effects (Dyerberg et al., Amer. J. Clin. Nutr. 28:958-966 (1975); Dyerberg et al., Lancet. 2(8081):117-119 (1978); Shimokawa, H., World Rev. Nutr. Diet 88:100-108 (2001); von Schacky et al., World Rev. Nutr. Diet 88:90-99 (2001)). Numerous other studies document wide-ranging health benefits conferred by administration of omega-3 and/or omega-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production via numerous divergent efforts. Although the natural PUFA-producing abilities of the host organisms are sometimes essential to a given methodology, genetic engineering has also proven that the natural abilities of some hosts (even those natively limited to LA and ALA fatty acid production) can be substantially altered to result in high-level production of various long-chain omega-3/omega-6 PUFAs. Whether this effect is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) all require expression of either the delta-9 elongase/delta-8 desaturase pathway (which operates in some organisms, such as euglenoid species and which is characterized by the production of eicosadienoic acid (EDA; 20:2 ω-6) and/or eicosatrienoic acid (ETrA; 20:3 ω-3)) or the delta-6 desaturase/delta-6 elongase pathway (which is predominantly found in algae, mosses, fungi, nematodes and humans and which is characterized by the production of γ-linoleic acid (GLA; 18:3 ω-6) and/or stearidonic acid (STA; 18:4 ω-3)) (FIG. 6). A delta-6 elongase is also known as a $C_{18/20}$ elongase.

The delta-8 desaturase enzymes identified thus far have the ability to convert both EDA to dihomo-γ-linolenic acid (DGLA; 20:3) and ETrA to eicosatetraenoic acid (ETA; 20:4) (wherein ARA are EPA are subsequently synthesized from DGLA and ETA, respectively, following reaction with a delta-5 desaturase, while DHA synthesis requires subsequent expression of an additional $C_{20/22}$ elongase and a delta-4 desaturase).

Based on the role delta-8 desaturase enzymes play in the synthesis of e.g., ARA, EPA and DHA, there has been effort to identify and characterize these enzymes. Initial efforts on the isolation and characterization of delta-8 desaturases from *Euglena gracilis*; and, several sequence variations within the *Euglena gracilis* delta-8 desaturase have been reported (see, e.g., Wallis et al., Arch. Biochem. and Biophys. 365(2):307-316 (1999); PCT Publication No. WO 2000/34439; U.S. Pat. No. 6,825,017; PCT Publication No. WO 2004/057001). Also, Applicants' Assignee's co-pending applications having U.S. application Ser. Nos. 11/166,003 and 11/166,993 filed Jun. 24, 2005, respectively (PCT Publication Nos. WO 2006/012325 and WO 2006/012326; both published Feb. 2, 2006)) discloses amino acid and nucleic acid sequences for a *Euglena gracilis* delta-8 desaturase.

More recently, PCT Publication No. WO 2005/103253 (published Apr. 22, 2005) discloses amino acid and nucleic acid sequences for a delta-8 desaturase enzyme from Pavlova salina (see also U.S. Publication No. 2005/0273885). Sayanova et al. (FEBS Lett. 580:1946-1952 (2006)) describes the isolation and characterization of a cDNA from the free living soil amoeba *Acanthamoeba castellanii* that, when expressed in *Arabidopsis*, encodes a $C_{20}$ delta-8 desaturase. Also, Applicants' Assignee's co-pending application having U.S. patent application Ser. No. 11/737,772 (filed Apr. 20, 2007; discloses amino acid and nucleic acid sequences for a delta-8 desaturase enzyme from *Pavlova lutheri* (CCMP459). U.S. patent application Ser. No. 11/876,115 (filed Oct. 22, 2007; discloses amino acid and nucleic acid sequences for a delta-8 desaturase enzyme from *Tetruetreptia pomquetensis* CCMP1491, *Eutreptiella* sp. CCMP389 and *Eutreptiella cf_gymnastica* CCMP1594.

Based on the utility of expressing delta-8 desaturases in conjunction with delta-9 elongases, there has also been considerable effort to identify and characterize delta-9 elongases from various sources. A delta-9 elongase from *Isochrysis galbana* has been publicly available (described in GenBank Accession No. AAL37626, as well as PCT Publication No. WO 02/077213). Applicants' Assignee's co-pending application having U.S. application Ser. No. 11/601,563 (filed Nov., 16, 2006, which published May 24, 2007; discloses a delta-9 elongase from *Eulgena gracilis*.

Applicants' Assignee has a number of patent applications concerning the production of PUFAs in oleaginous yeasts (i.e., *Yarrowia lipolytica*), including: PCT Publication Nos. WO 2004/101757 and WO 2004/101753 (both published Nov. 25, 2004); U.S. application Ser. No. 11/265,761 (filed Nov. 2, 2005); U.S. application Ser. No. 11/264,784 (filed Nov. 1, 2005); and U.S. application Ser. No. 11/264,737 (filed Nov. 1, 2005).

Relatedly, PCT Publication No. WO 2004/071467 (published Aug. 26, 2004; concerns the production of PUFAs in plants, while PCT Publication No. WO 2004/071178 (published Aug. 26, 2004) concerns annexin promoters and their use in expression of transgenes in plants; both are Applicants' Assignee's copending applications.

SUMMARY OF THE INVENTION

The present invention concerns an isolated polynucleotide comprising:
  (a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:21, SEQ ID NO:22, SEQ ID NO:23 or SEQ ID NO:24;

(b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:17, SEQ ID NO:18, SEQ ID NO:19 or SEQ ID NO:20;

(c) a nucleotide sequence encoding a polypeptide having delta-8 desaturase activity, wherein the nucleotide sequence hybridizes under stringent conditions to a nucleotide sequence as set forth in SEQ ID NO:17, SEQ ID NO:18, SEQ ID NO:19 or SEQ ID NO:20; or (d) a complement of the nucleotide sequence of (a), (b) or (c), wherein the complement and the nucleotide sequence consist of the same number of nucleotides and are 100% complementary.

In a second embodiment, the invention concerns a recombinant DNA construct comprising any of the isolated polynucleotides of the invention operably linked to at least one regulatory sequence.

In a third embodiment, the invention concerns a plant cell comprising in its genome the recombinant DNA construct of the invention.

In a fourth embodiment, the invention concerns a method for transforming a plant cell, comprising transforming a plant cell with a recombinant construct of the invention or an isolated polynucleotide of the invention and selecting those plant cells transformed with the recombinant construct or the isolated polynucleotide.

In a fifth embodiment, the invention concerns transgenic seed comprising in its genome the recombinant construct of the invention or a transgenic seed obtained from a plant made by a method of the invention. Also of interest is oil or by-products obtained from such transgenic seeds.

In a sixth embodiment, the invention concerns a method for making long-chain polyunsaturated fatty acids in a plant cell comprising:

(a) transforming a plant cell with the recombinant construct of the invention; and (b) selecting those transformed plant cells that make long-chain polyunsaturated fatty acids.

In a seventh embodiment, the invention concerns a method for producing at least one polyunsaturated fatty acid in an oilseed plant cell comprising:

(a) transforming an oilseed plant cell with a first recombinant DNA construct comprising an isolated polynucleotide encoding at least one delta-8 desaturase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase;

(b) regenerating an oilseed plant from the transformed cell of step (a); and (c) selecting those seeds obtained from the plants of step (b) having an altered level of polyunsaturated fatty acids when compared to the level in seeds obtained from a nontransformed oilseed plant.

In an eighth embodiment, the invention concerns an oilseed plant comprising in its genome the recombinant construct of the invention. Suitable oilseed plants include, but are not limited to, soybean, *Brassica* species, sunflower, maize, cotton, flax and safflower.

In a ninth embodiment, the invention concerns an oilseed plant comprising:

(a) a first recombinant DNA construct comprising an isolated polynucleotide encoding at least one delta-8 desaturase polypeptide, operably linked to at least one regulatory sequence; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and a $C_{20/22}$ elongase.

Also of interest are transgenic seeds obtained from such oilseed plants as well as oil or by-products obtained from these transgenic seeds. A preferred product is lecithin.

In a tenth embodiment, the invention concerns food or feed incorporating an oil or seed of the invention or food or feed comprising an ingredient derived from the processing of the seeds.

In an eleventh embodiment, the invention concerns a method for making long-chain polyunsaturated fatty acids in a plant cell having a reduced level of by-product fatty acids, said method comprising:

(a) transforming a plant host cell with at least one recombinant DNA construct comprising an isolated polynucleotide encoding at least two delta-8 desaturases operably linked to at least one regulatory sequence; and (b) selecting those transformed plant host cells obtained having a reduced level of by-product fatty acids, when compared to the level of such metabolic by-product fatty acids in a transformed host cell having at least one recombinant DNA construct comprising an isolated polynucleotide encoding one delta-8 desaturase operably linked to a regulatory sequence.

In a twelfth embodiment, the invention concerns progeny plants obtained from obtained from a plant made by the method of the invention or an oilseed plant of the invention.

BIOLOGICAL DEPOSITS

The following plasmid has been deposited with the American Type Culture Collection (ATCC), 10801 University Boulevard, Manassas, Va. 20110-2209, and bears the following designation, Accession Number and date of deposit (Table 1).

TABLE 1

| ATCC Deposit | | |
|---|---|---|
| Plasmid | Accession Number | Date of Deposit |
| pKR72 | PTA-6019 | May 28, 2004 |

BRIEF DESCRIPTION OF THE DRAWINGS AND SEQUENCE LISTINGS

The invention can be more fully understood from the following detailed description and the accompanying drawings and Sequence Listing, which form a part of this application.

FIG. 4 are the fatty acid profiles for *Yarrowia lipolytica* expressing pY175-pY178 (see Example 4).

FIGS. 7A, 7B and 7C show a Clustal V alignment of the delta-8 desaturase sequences for EaD8Des1 (SEQ ID NO:21), EaD8Des2 (SEQ ID NO:22), EaD8Des3 (SEQ ID NO:23) and EaD8Des4 (SEQ ID NO:24), and the corrected Euglena gracilis delta-8 desaturase amino acid sequence (EgD8; SEQ ID NO:25; described as Eg5 in PCT Application No. WO 2006/012325).

Figure 8:
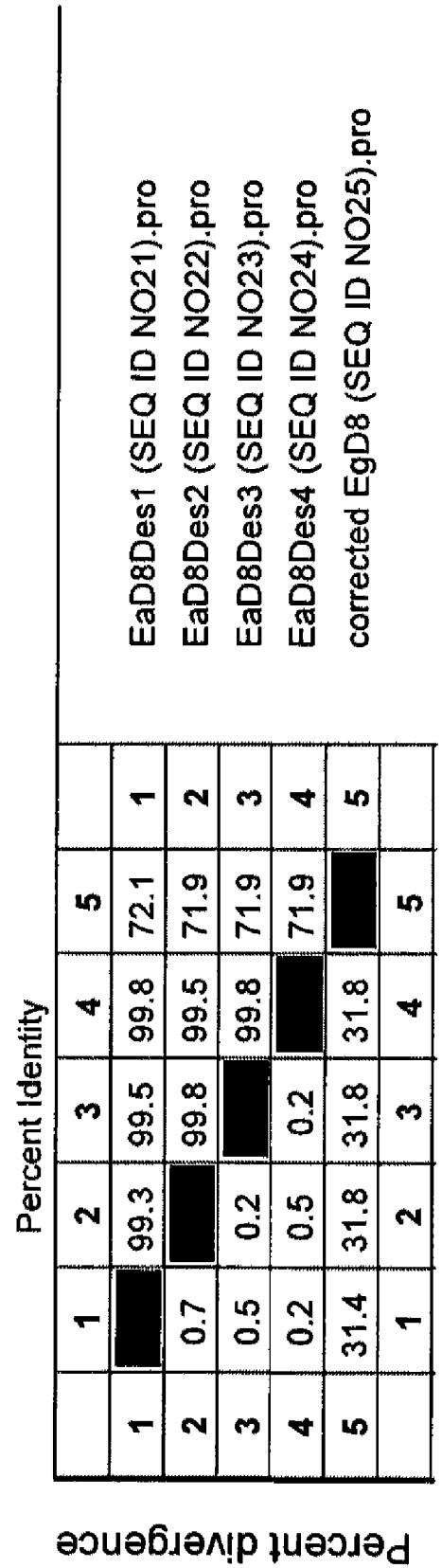

FIG. 8 is a chart setting forth a comparison of the percent identity (and percent divergence in the lower half triangle), among the five delta-8 desaturase sequences aligned in FIGS. 7A, 7B and 7C.

Figure 9A:
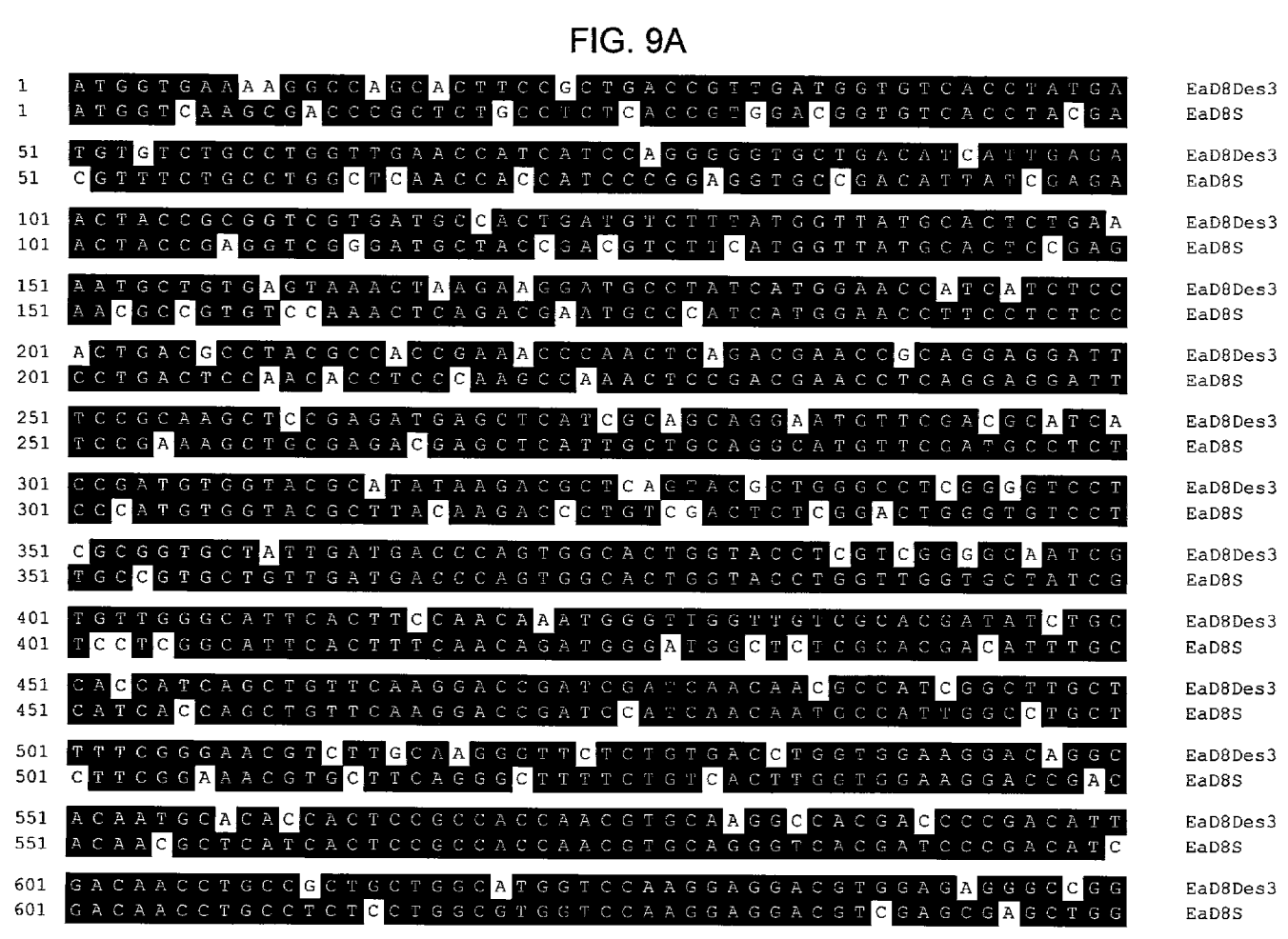
Figure 9B:
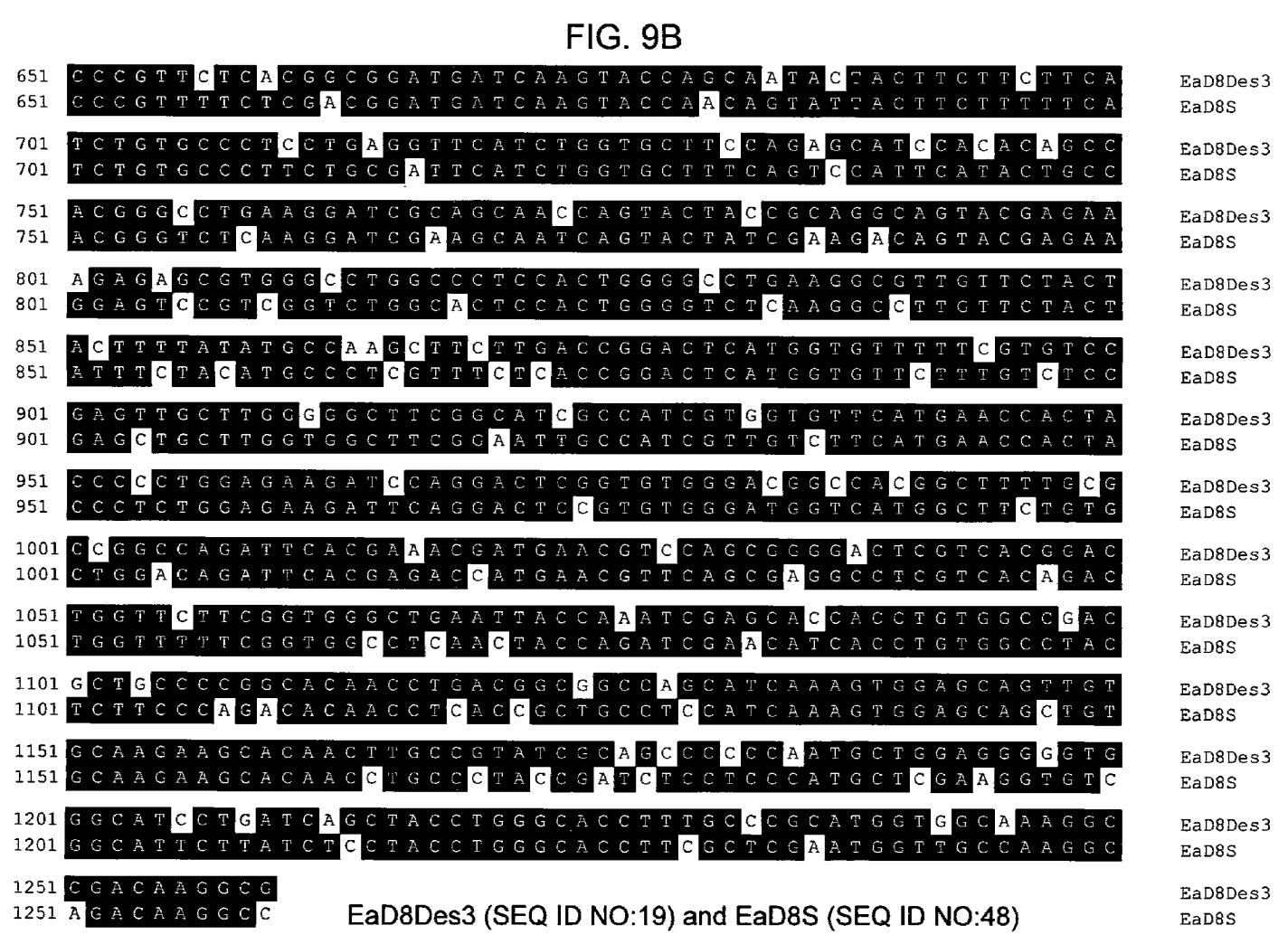

FIGS. 9A and 9B shows a comparison of the nucleotide sequences of EaD8Des3 (SEQ ID NO:19) and EaD8S (SEQ ID NO:48).

Figure 10:
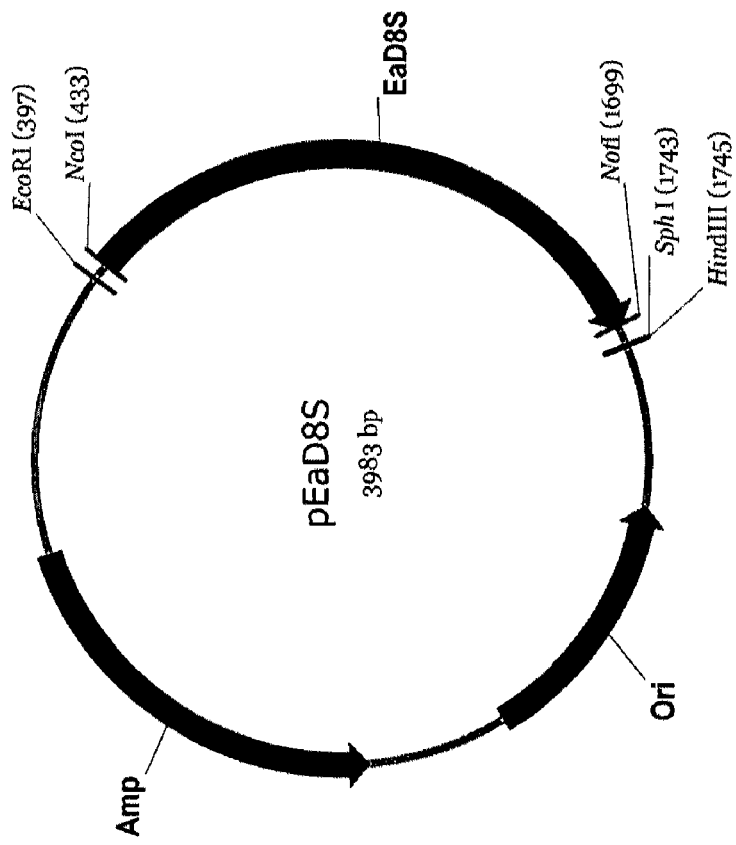

FIG. 10 is a map of plasmid pEaD8S (SEQ ID NO:49).

Figure 11:
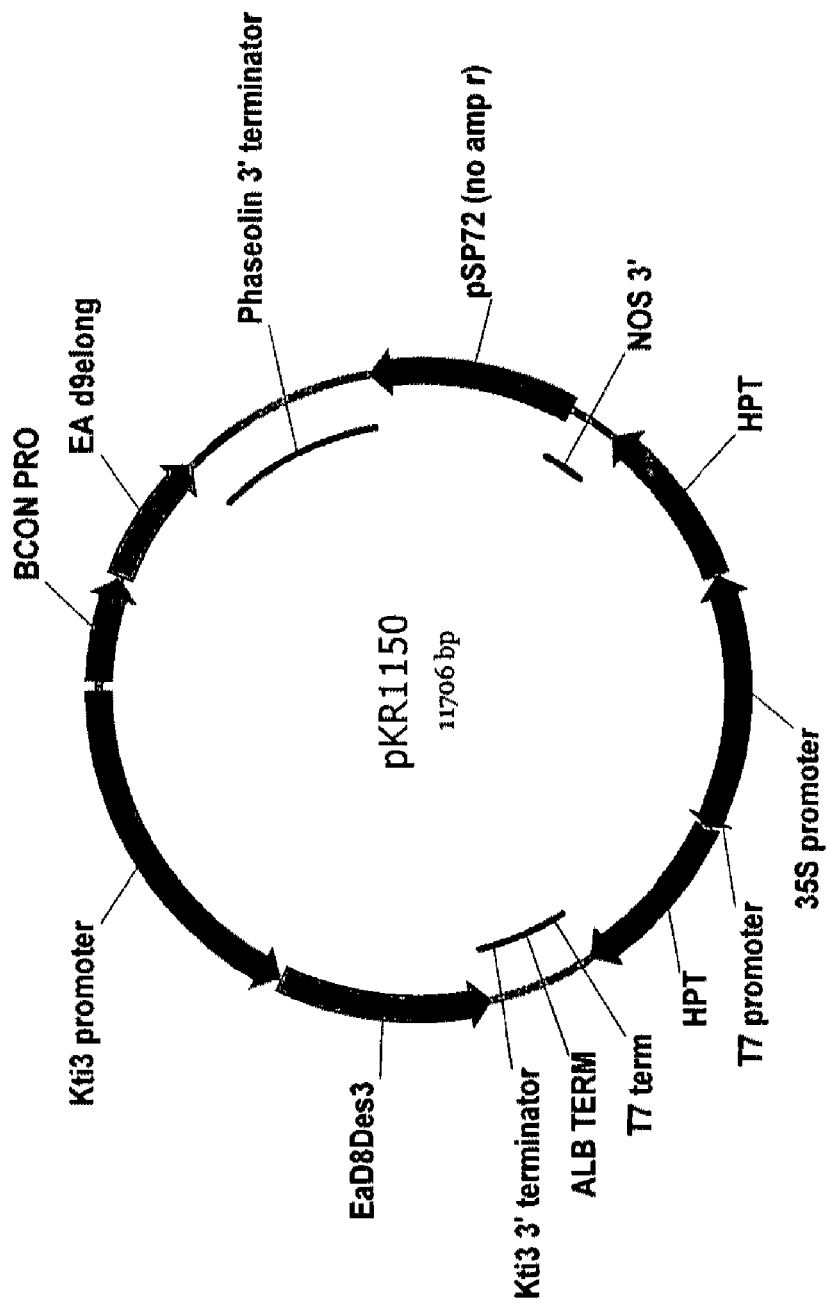

FIG. 11 is a map of plasmid pKR1150 (SEQ ID NO:60).

Figure 12:
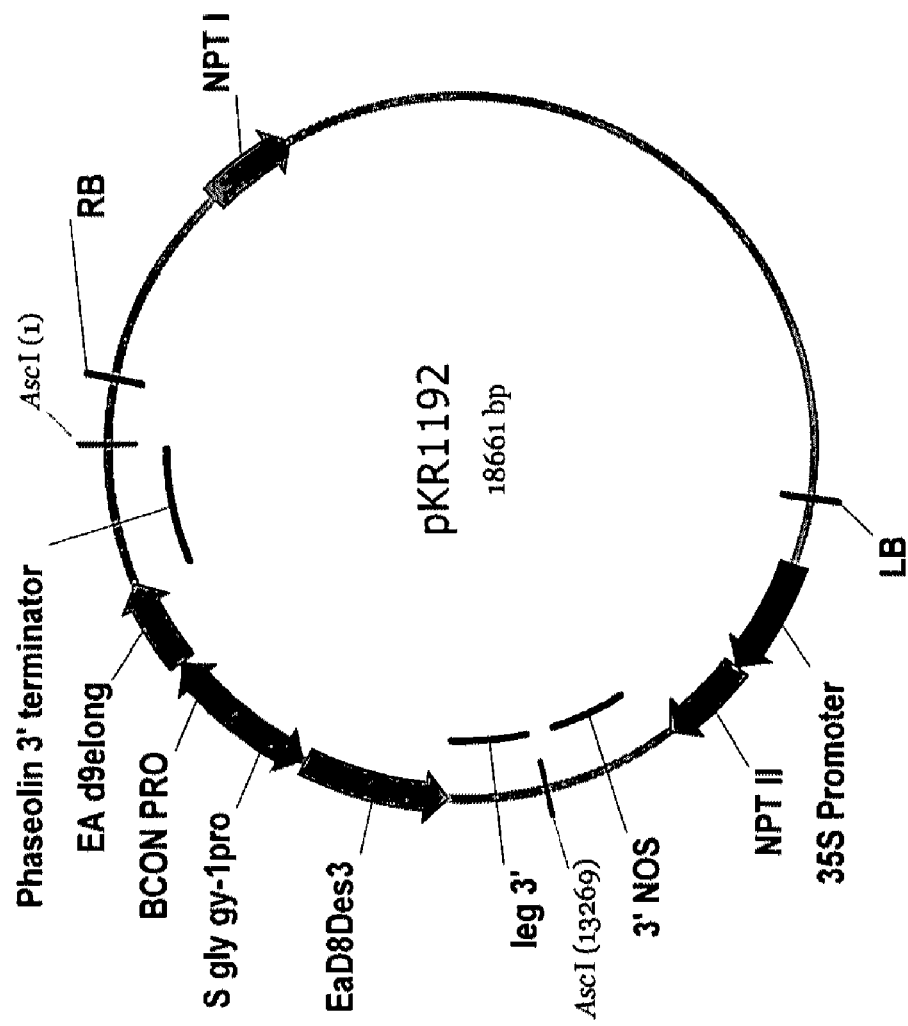

FIG. 12 is a map of plasmid pKR1192 (SEQ ID NO:66).

FIG. 13 shows the average fatty acid profiles (average of 5 soybean somatic embryos) for 5 events transformed with pKR1152 having the highest average DGLA. Fatty acids are identified as 16:0 (palmitate), 18:0 (stearic acid), 18:1 (oleic acid), LA, ALA, EDA, ERA, DGLA and ETA. Fatty acid compositions are expressed as a weight percent (wt. %) of total fatty acids. Elongation activity is expressed as % delta-9 elongation of C18 fatty acids (C18% delta-9 elong), calculated according to the following formula: ([product]/[substrate+product])*100. More specifically, the combined percent elongation for LA and ALA is determined as: ([DGLA+ETA+EDA+ERA]/[LA+ALA+DGLA+ETA+EDA+ERA])*100. The combined percent desaturation for EDA and ERA is shown as "C20% delta-8 desat", determined as: ([DGLA+ETA]/[DGLA+ETA+EDA+ERA])*100. This is also referred to as the overall % desaturation.

FIG. 14 shows the average fatty acid profiles (average of 5 soybean somatic embryos) for 5 events transformed with pKR1150 having the highest average DGLA. Fatty acids are identified as 16:0 (palmitate), 18:0 (stearic acid), 18:1 (oleic acid), LA, ALA, EDA, ERA, DGLA and ETA. Fatty acid compositions are expressed as a weight percent (wt. %) of total fatty acids. Elongation activity is expressed as % delta-9 elongation of C18 fatty acids (C18% delta-9 elong), calculated according to the following formula: ([product]/[substrate+product])*100. More specifically, the combined percent elongation for LA and ALA is determined as: ([DGLA+ETA+EDA+ERA]/[LA+ALA+DGLA+ETA+EDA+ERA])*100. Tthe combined percent desaturation for EDA and ERA is shown as "C20% delta-8 desat", determined as: ([DGLA+ETA]/[DGLA+ETA+EDA+ERA])*100. This is also referred to as the overall % desaturation.

FIG. 15 shows the lipid profiles of T2 bulk *Arabidopsis* seed for the 21 transformed events. Fatty acids are identified as 16:0 (palmitate), 18:0 (stearic acid), 18:1 (oleic acid), LA, ALA, 20:0 (eicosanoic acid), 20:1 (eicosenoic acid), EDA, DGLA, ERA and ETA; and, fatty acids are expressed as a weight percent (wt. %) of total fatty acids. The combined percent desaturation for EDA and ERA is shown as "C20% delta-8 desat", determined as: ([DGLA+ETA]/[DGLA+ETA+EDA+ERA])*100. This is also referred to as the overall % desaturation.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

SEQ ID NO:1 is the nucleotide sequence of the *Euglena anabaena* delta-8 desaturase partial sequence.

SEQ ID NO:2 is the amino acid sequence of the *Euglena gracilis* delta-8 desaturase CDS (Eg5).

SEQ ID NO:3 is the nucleotide sequence of the vector-specific primer pDonor222Eg5-1.

SEQ ID NO:4 is the nucleotide sequence of D8DEG3-1.

SEQ ID NO:5 is the nucleotide sequence of D8DEG3-2.

SEQ ID NO:6 is the nucleotide sequence of D8DEG3-3.

SEQ ID NO:7 is the nucleotide sequence of D8DEG3-4.

SEQ ID NO:8 is the nucleotide sequence of the T7 primer.

SEQ ID NO:9 is the nucleotide sequence of M13-28Rev.

SEQ ID NO:10 is the nucleotide sequence of pHD23-1.

SEQ ID NO:11 is the amino acid sequence of *Euglena gracilis* delta-8 desaturase (NCBI Accession No. AAD45877).

SEQ ID NO:12 is the nucleotide sequence of EaD8seq-1.

SEQ ID NO:13 is the nucleotide sequence of pLF118-1.

SEQ ID NO:14 is the nucleotide sequence of pLF118-2.

SEQ ID NO:15 is the nucleotide sequence of pLF118-3.

SEQ ID NO:16 is the nucleotide sequence of pLF118-4.

SEQ ID NO:17 is the coding sequence of the *Euglena anabaena* delta-8 desaturase (EaD8Des1 CDS).

SEQ ID NO:18 is the coding sequence of the *Euglena anabaena* delta-8 desaturase (EaD8Des2 CDS).

SEQ ID NO:19 is the coding sequence of the *Euglena anabaena* delta-8 desaturase (EaD8Des3 CDS).

SEQ ID NO:20 is the coding sequence of the *Euglena anabaena* delta-8 desaturase (EaD8Des4 CDS).

SEQ ID NO:21 is the amino acid sequence of the *Euglena anabaena* delta-8 desaturase (EaD8Des1).

SEQ ID NO:22 is the amino acid sequence of the *Euglena anabaena* delta-8 desaturase (EaD8Des2).

SEQ ID NO:23 is the amino acid sequence of the *Euglena anabaena* delta-8 desaturase (EaD8Des3).

SEQ ID NO:24 is the amino acid sequence of the *Euglena anabaena* delta-8 desaturase (EaD8Des4).

SEQ ID NO:25 is the amino acid sequence of the corrected *Euglena gracilis* delta-8 desaturase (EgD8).

SEQ ID NO:26 is the nucleotide sequence of oligonucleotide EaD8-5.

SEQ ID NO:27 is the nucleotide sequence of oligonucleotide EaD8-3.

SEQ ID NO:28 is the nucleotide sequence of pLF120-1.

SEQ ID NO:29 is the nucleotide sequence of pLF120-2.

SEQ ID NO:30 is the nucleotide sequence of pLF120-3.

SEQ ID NO:31 is the nucleotide sequence of pLF120-4.

SEQ ID NO:32 is the nucleotide sequence of pDMW263.

SEQ ID NO:33 is the nucleotide sequence of pDMW237.

SEQ ID NO:34 is the nucleotide sequence of pY115.

SEQ ID NO:35 is the nucleotide sequence of pY175.

SEQ ID NO:36 is the nucleotide sequence of pY176.

SEQ ID NO:37 is the nucleotide sequence of pY177.
SEQ ID NO:38 is the nucleotide sequence of pY178.
SEQ ID NO:39 is the coding sequence of the *Euglena gracilis* delta-9 elongase.
SEQ ID NO:40 is the nucleotide sequence of the *Euglena gracilis* elongase sense oligonucleotide oEugEL1-1.
SEQ ID NO:41 is the nucleotide sequence of the *Euglena gracilis* sense oligonucleotide oEugEL1-2.
SEQ ID NO:42 is the nucleotide sequence of pKR906.
SEQ ID NO:43 is the nucleotide sequence of pKR72.
SEQ ID NO:44 is the nucleotide sequence of pKR912.
SEQ ID NO:45 is the nucleotide sequence of pKR457.
SEQ ID NO:46 is the nucleotide sequence of pKR1138.
SEQ ID NO:47 is the nucleotide sequence of pKR1152.
SEQ ID NO:48 is the nucleotide sequence of the codon optimized EaD8S gene.
SEQ ID NO:49 is the nucleotide sequence of plasmid pEaD8S.
SEQ ID NO:50 is the nucleotide sequence of pLF121-1.
SEQ ID NO:51 is the nucleotide sequence of pLF121-2.
SEQ ID NO:52 is the coding sequence of the *Euglena anabaena* delta-9 elongase-1 (EaD9Elo1).
SEQ ID NO:53 is the coding sequence of the *Euglena anabaena* delta-9 elongase-2 (EaD9Elo2).
SEQ ID NO:54 is the amino acid sequence of the *Euglena anabaena* delta-9 elongase-1 (EaD9Elo1).
SEQ ID NO:55 is the amino acid sequence of the *Euglena anabaena* delta-9 elongase-2 (EaD9Elo2).
SEQ ID NO:56 is the nucleotide sequence of oligonucleotide oEAd9el1-1.
SEQ ID NO:57 is the nucleotide sequence of oligonucleotide oEAd9el1-2.
SEQ ID NO:58 is the nucleotide sequence of pKR1137.
SEQ ID NO:59 is the nucleotide sequence of pKR1140.
SEQ ID NO:60 is the nucleotide sequence of pKR1150.
SEQ ID NO:61 is the nucleotide sequence of pKR1173.
SEQ ID NO:62 is the nucleotide sequence of pKR393.
SEQ ID NO:63 is the nucleotide sequence of pKR407.
SEQ ID NO:64 is the nucleotide sequence of pKR1176.
SEQ ID NO:65 is the nucleotide sequence of pKR1178.
SEQ ID NO:66 is the nucleotide sequence of pKR1192.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

The present invention relates to delta-8 desaturase enzymes and nucleic acid for encoding the same isolated from *Euglena anabaena*. These are useful for, inter alia, for the manipulation of biochemical pathways for the production of healthful PUFAs. Thus, the subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with EPA can result not only in increased levels of EPA, but also downstream products of EPA such as eicosanoids (i.e., prostaglandins, leukotrienes, thromboxanes). Complex regulatory mechanisms can make it desirable to combine various PUFAs, or add different conjugates of PUFAs, in order to prevent, control or overcome such mechanisms to achieve the desired levels of specific PUFAs in an individual.

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein X is number of carbon (C) atoms in the particular fatty acid and Y is the number of double bonds. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified, 18:1, 18:2 and 18:3 refer to oleic, LA and ALA fatty acids, respectively. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the table summarizes the common names of omega-3 and omega-6 fatty acids and their precursors, the abbreviations that will be used throughout the remainder of the specification, and each compounds' chemical name.

TABLE 2

Nomenclature of Polyunsaturated Fatty Acids and Precursors

| Common Name | Abbreviation | Chemical Name | Shorthand Notation |
|---|---|---|---|
| myristic | — | tetradecanoic | 14:0 |
| palmitic | PA | hexadecanoic | 16:0 |
| palmitoleic | — | 9-hexadecenoic | 16:1 |
| stearic | — | octadecanoic | 18:0 |
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA | cis-8,11,14-eicosatrienoic | 20:3 ω-6 |
| sciadonic | SCI | cis-5,11,14-eicosatrienoic | 20:3b ω-6 |
| arachidonic | ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |
| eicosatrienoic | ETrA or ERA | cis-11,14,17-eicosatrienoic | 20:3 ω-3 |
| eicosatetraenoic | ETA | cis-8,11,14,17-eicosatetraenoic | 20:4 ω-3 |
| juniperonic | JUP | cis-5,11,14,17-eicosatrienoic | 20:4b ω-3 |
| eicosapentaenoic | EPA | cis-5,8,11,14,17-eicosapentaenoic | 20:5 ω-3 |
| docosapentaenoic | DPA | cis-7,10,13,16,19-docosapentaenoic | 22:5 ω-3 |
| docosahexaenoic | DHA | cis-4,7,10,13,16,19-docosahexaenoic | 22:6 ω-3 |

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzyme" refers to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

Figure 1:
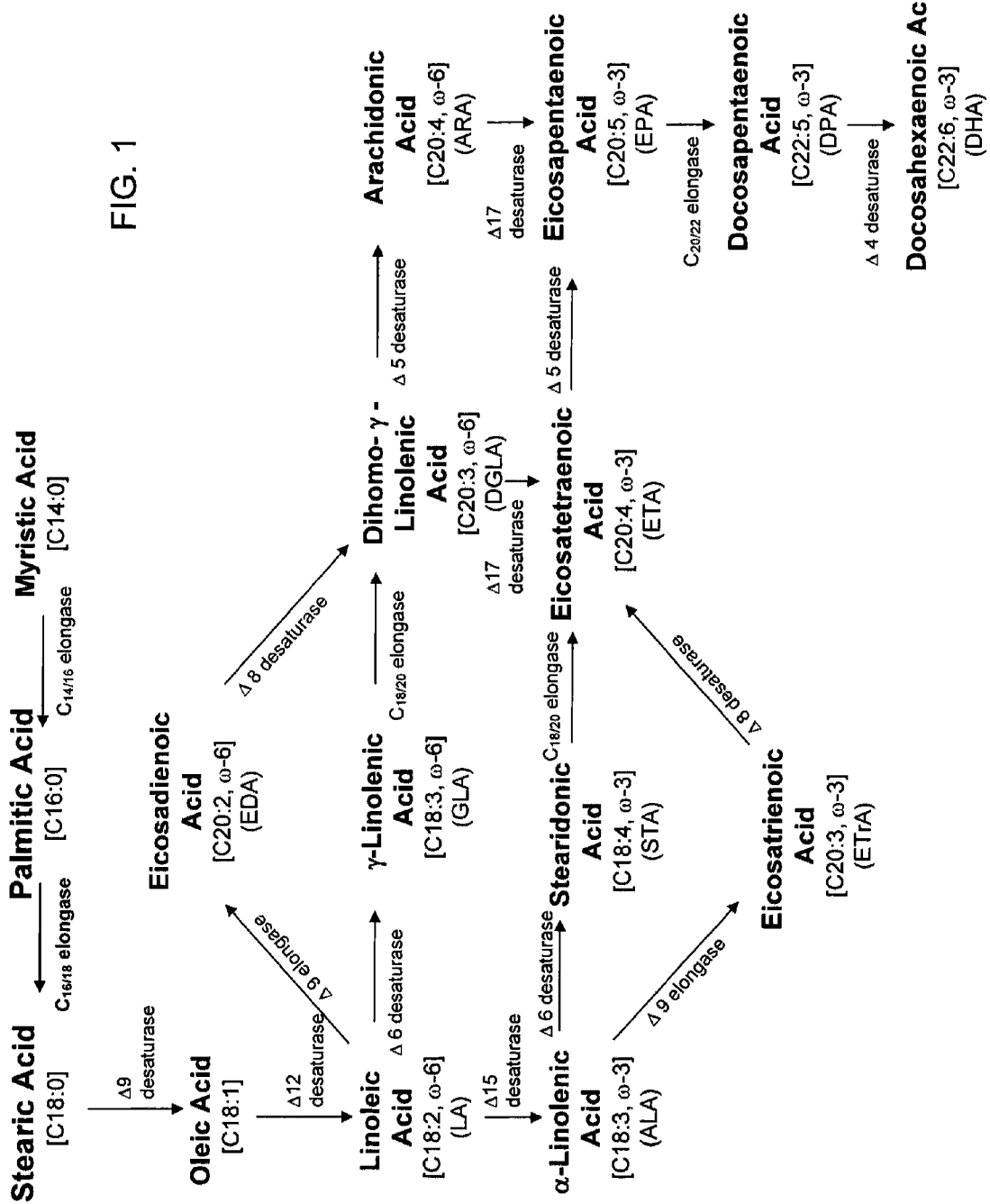
FIG. 1 is a representative omega-3 and omega-6 fatty acid pathway providing for the conversion of myristic acid through various intermediates to DHA.

The term "omega-3/omega-6 fatty acid biosynthetic pathway" refers to a set of genes which, when expressed under the appropriate conditions encode enzymes that catalyze the production of either or both omega-3 and omega-6 fatty acids. Typically the genes involved in the omega-3/omega-6 fatty acid biosynthetic pathway encode PUFA biosynthetic pathway enzymes. A representative pathway is illustrated in FIG. 1, providing for the conversion of myristic acid through various intermediates to DHA, which demonstrates how both omega-3 and omega-6 fatty acids may be produced from a common source. The pathway is naturally divided into two portions where one portion will generate omega-3 fatty acids and the other portion, omega-6 fatty acids.

The term "functional" as used herein in context with the omega-3/omega-6 fatty acid biosynthetic pathway means that some (or all of) the genes in the pathway express active enzymes, resulting in in vivo catalysis or substrate conversion. It should be understood that "omega-3/omega-6 fatty acid biosynthetic pathway" or "functional omega-3/omega-6 fatty acid biosynthetic pathway" does not imply that all the PUFA biosynthetic pathway enzyme genes are required, as a number of fatty acid products will only require the expression of a subset of the genes of this pathway.

The term "delta-9 elongase/delta-8 desaturase pathway" refers to a biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the delta-9 elongase/delta-8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the delta-9 elongase/delta-8 desaturase pathway, sciadonic acid (SCI) and juniperonic acid (JUP) also can be produced by the action of a delta-5 desaturase on either EDA or ETrA, respectively. They are considered to be "by-product fatty acids" since neither can be further converted to EPA by the action of other metabolic pathway enzymes.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example: (1) delta-5 desaturases that catalyze the conversion of DGLA to ARA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of ARA to EPA and/or DGLA to ETA; and (7) delta-9 desaturases that catalyze the conversion of palmitic acid to palmitoleic acid (16:1) and/or stearic acid to oleic acid (18:1). In the art, delta-15 and delta-17 desaturases are also occasionally referred to as "omega-3 desaturases", "w-3 desaturases", and/or "ω-3 desaturases", based on their ability to convert omega-6 fatty acids into their omega-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

For the purposes herein, the term "EaD8Des1" refers to a delta-8 desaturase enzyme (SEQ ID NO:21) isolated from *Euglena anabaena*, encoded by SEQ ID NO:17 herein. The term "EaD8Des2" refers to a delta-8 desaturase enzyme (SEQ ID NO:22) isolated from *Euglena anabaena*, encoded by SEQ ID NO:18 herein. Likewise, the term "EaD8Des3" refers to a delta-8 desaturase enzyme (SEQ ID NO:23) isolated from *Euglena anabaena*, encoded by SEQ ID NO:19 herein. The term "EaD8Des4" refers to a delta-8 desaturase enzyme (SEQ ID NO:24) isolated from *Euglena anabaena*, encoded by SEQ ID NO:20 herein.

Similarly, the term "EgD8" refers to a delta-8 desaturase enzyme (SEQ ID NO:2 is the nucleic acid coding sequence) isolated from *Euglena gracilis*. EgD8 is 100% identical and functionally equivalent to "Eg5", as described in PCT Publication Nos. WO 2006/012325 and WO 2006/012326 (SEQ ID NO:2 of U.S. Publication No. 20050287652-A1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA, LA to EDA, ALA to ETrA and EPA to DPA.

For the purposes herein, an enzyme catalyzing the first condensation reaction (i.e., conversion of malonyl-CoA and long-chain acyl-CvoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). Similarly, a "delta-9 elongase" may be able to catalyze the conversion of LA to EDA and/or ALA to ETrA. It is important to note that some elongases have broad specificity and thus a single enzyme may be capable of catalyzing several elongase reactions. Thus, for example, a delta-9 elongase may also act as a $C_{16/18}$ elongase, $C_{18/20}$ elongase and/or $C_{20/22}$ elongase and may have alternate, but not preferred, specificities for delta-5 and delta-6 fatty acids such as EPA and/or GLA, respectively.

For the purposes herein, the term "IgD9e" refers to a delta-9 elongase (NCBI Accession No. AAL37626 [GI 17226123], locus AAL37626, CDS AF390174; GenBank Accession No. AF390174) isolated from *Isochrysis galbana*. In contrast, the term "IgD9eS" refers to a synthetic (codon-optimized) delta-9 elongase derived from the DNA sequence of the *Isochrysis galbana* delta-9 elongase which can be used for expression in *Yarrowia lipolytica*.

Similarly for the purposes herein, the term "EgD9e" refers to a delta-9 elongase isolated from *Euglena gracilis*, encoded by SEQ ID NO:39 (see Example 5 herein).

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single-or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS.* 5:151-153 (1989); Higgins, D. G. et al. (1992) *Comput. Appl. Biosci.* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondrial, plastid) of the cell.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single-or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved.)

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre-or propeptides present in the primary translation product have been removed). "Precursor" protein refers to the primary product of translation of mRNA (i.e., with pre-and propeptides still present). Pre-and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., Plant J. 16:651-659 (1998); Gura, Nature 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050, published Oct. 21, 1999; PCT Publication No. WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083, published Aug. 20, 1998). Both of these co-suppressing phenomena have not been elucidated mechanistically, although genetic evidence has begun to unravel this complex situation (Elmayan et al., Plant Cell 10:1747-1757 (1998)).

The term "oleaginous" refers to those organisms that tend to store their energy source in the form of lipid (Weete, In: Fungal Lipid Biochemistry, 2nd Ed., Plenum, 1980). A class of plants identified as oleaginous are commonly referred to as "oilseed" plants. Examples of oilseed plants include, but are not limited to: soybean (Glycine and Soja sp.), flax (Linum sp.), rapeseed (Brassica sp.), maize, cotton, safflower (Carthamus sp.) and sunflower (Helianthus sp.).

Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, Appl. Environ. Microbiol. 57:419-25 (1991)). The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: Yarrowia, Candida, Rhodotorula, Rhodosporidium, Cryptococcus, Trichosporon and Lipomyces.

The term "Euglenophyceae" refers to a group of unicellular colorless or photosynthetic flagellates ("euglenoids") found living in freshwater, marine, soil, and parasitic environments. The class is characterized by solitary unicells, wherein most are free-swimming and have two flagella (one of which may be nonemergent) arising from an anterior invagination known as a reservoir. Photosynthetic euglenoids contain one to many grass-green chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: Euglena, Eutreptiella and Tetruetreptia.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: (1) the esterification of one molecule of acyl-CoA to glycerol-3-phosphate via an acyltransferase to produce lysophosphatidic acid; (2) the esterification of a second molecule of acyl-CoA via an acyltransferase to yield 1,2-diacylglycerol phosphate (commonly identified as phosphatidic acid); (3) removal of a phosphate by phosphatidic acid phosphatase to yield 1,2-diacylglycerol (DAG); and (4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to long chain omega-3/omega-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific long chain omega-3/omega-6 fatty acid.

Specifically, all pathways require the initial conversion of oleic acid to LA, the first of the omega-6 fatty acids, by a delta-12 desaturase. Then, using the "delta-9 elongase/delta-8 desaturase pathway", long chain omega-6 fatty acids are formed as follows: (1) LA is converted to EDA by a delta-9 elongase; (2) EDA is converted to DGLA by a delta-8 desaturase; and (3) DGLA is converted to ARA by a delta-5 desaturase. Alternatively, the "delta-9 elongase/delta-8 desaturase pathway" can be utilized for formation of long chain omega-3 fatty acids as follows: (1) LA is converted to ALA, the first of the omega-3 fatty acids, by a delta-15 desaturase; (2) ALA is converted to ETrA by a delta-9 elongase; (3) ETrA is converted to ETA by a delta-8 desaturase; (4) ETA is converted to EPA by a delta-5 desaturase; (5) EPA is converted to DPA by a $C_{20/22}$ elongase; and (6) DPA is converted to DHA by a delta-4 desaturase. Optionally, omega-6 fatty acids may be converted to omega-3 fatty acids; for example, ETA and EPA are produced from DGLA and ARA, respectively, by delta-17 desaturase activity.

Alternate pathways for the biosynthesis of omega-3/omega-6 fatty acids utilize a delta-6 desaturase and $C_{18/20}$ elongase (also known as delta-6 elongase, the terms can be used interchangeably) (i.e., the "delta-6 desaturase/delta-6 elongase pathway"). More specifically, LA and ALA may be converted to GLA and STA, respectively, by a delta-6 desaturase; then, a $C_{18/20}$ elongase converts GLA to DGLA and/or STA to ETA.

It is contemplated that the particular functionalities required to be introduced into a specific host organism for production of omega-3/omega-6 fatty acids will depend on the host cell (and its native PUFA profile and/or desaturase/elongase profile), the availability of substrate, and the desired end product(s). For example, expression of the delta-9 elongase/delta-8 desaturase pathway may be preferred in some embodiments, as opposed to expression of the delta-6 desaturase/delta-6 elongase pathway, since PUFAs produced via the former pathway are devoid of GLA.

One skilled in the art will be able to identify various candidate genes encoding each of the enzymes desired for omega-3/omega-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: (1) the substrate specificity of the polypeptide; (2) whether the polypeptide or a component thereof is a rate-limiting enzyme; (3) whether the desaturase or elongase is essential for synthesis of a desired PUFA; and/or (4) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired omega-3/omega-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., delta-6 desaturases, $C_{18-20}$ elongases, delta-5 desaturases, delta-17 desaturases, delta-15 desaturases, delta-9 desaturases, delta-12 desaturases, $C_{14/16}$ elongases, $C_{16/18}$ elongases, delta-9 elongases, delta-8 desaturases, delta-4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Delta-8 Desaturases

In the present invention, nucleotide sequences encoding delta-8 desaturases have been isolated from *Euglena anabaena* (designated herein as "EaD8Des1", "EaD8Des2", "EaD8Des3" and "EaD8Des4").

Thus, the present invention concerns an isolated polynucleotide comprising:

(a) a nucleotide sequence encoding a polypeptide having delta-8 desaturase activity, wherein the polypeptide has at least 80% amino acid identity, based on the Clustal V method of alignment, when compared to an amino acid sequence as set forth in SEQ ID NO:21 [EaD8Des1], SEQ ID NO:22 [EaD8Des2], SEQ ID NO:23 [EaD8Des3] or SEQ ID NO:24 [EaD8Des4];

(b) a nucleotide sequence encoding a polypeptide having delta-8 desaturase activity, wherein the nucleotide sequence has at least 80% sequence identity, based on the BLASTN method of alignment, when compared to a nucleotide sequence as set forth in SEQ ID NO:17 [EaD8Des1], SEQ ID NO:18 [EaD8Des2], SEQ ID NO:19 [EaD8Des3] or SEQ ID NO:20 [EaD8Des4]; or, (c) a complement of the nucleotide sequence of (a) or (b), wherein the complement and the nucleotide sequence consist of the same number of nucleotides and are 100% complementary.

In still another aspect, this invention concerns an isolated polynucleotide comprising a nucleotide sequence encoding a polypeptide having delta-8 desaturase activity, wherein the nucleotide sequence has at least 90% sequence identity, based on the BLASTN method of alignment, when compared to a nucleotide sequence as set forth in SEQ ID NO:17, SEQ ID NO:18, SEQ ID NO:19 or SEQ ID NO:20.

In alternate embodiments, the instant EaD8Des1, EaD8Des2, EaD8Des3 or EaD8Des4 desaturase sequences can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one embodiment of the invention herein, EaD8Des1, EaD8Des2, EaD8Des3 and/or EaD8Des4 could be codon-optimized for expression in *Yarrowia lipolytica*, as taught in PCT Publication No. WO 04/101757 and U.S. Pat. No. 7,125, 672. In alternate embodiments, it may be desirable to modify a portion of the codons encoding EaD8Des1, EaD8Des2, EaD8Des3 and/or EaD8Des4 (as set forth in SEQ ID NOs:17, 18, 19 and 20, respectively) to enhance expression of the gene in a host organism including, but not limited to, a plant or plant part.

One skilled in the art would be able to use the teachings herein to create various other codon-optimized delta-8 desaturase proteins suitable for optimal expression in alternate hosts, based on the wildtype EaD8Des1, EaD8Des2, EaD8Des3 and/or EaD8Des4 sequences. Accordingly, the instant invention relates to any codon-optimized delta-8 desaturase protein that is derived from the wildtype EaD8Des1 (i.e., encoded by SEQ ID NO:17), the wildtype EaD8Des2 (i.e., encoded by SEQ ID NO:18), the wildtype EaD8Des3 (i.e., encoded by SEQ ID NO:19) or the wildtype EaD8Des4 (i.e., encoded by SEQ ID NO:20).

Identification and Isolation of Homologs

Any of the instant desaturase sequences (i.e., EaD8Des1, EaD8Des2, EaD8Des3 or EaD8Des4) or portions thereof may be used to search for delta-8 desaturase homologs in the same or other bacterial, algal, fungal, euglenoid or plant species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of delta-8 desaturase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the delta-8 desaturase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: (1) methods of nucleic acid hybridization; (2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor et al., *Proc. Acad. Sci. USA* 82:1074 (1985); or strand displacement amplification (SDA), Walker et al., *Proc. Natl. Acad. Sci. U.S.A.*, 89:392 (1992)]; and (3) methods of library construction and screening by complementation.

For example, genes encoding similar proteins or polypeptides to the delta-8 desaturases described herein could be isolated directly by using all or a portion of the instant nucleic acid fragments as DNA hybridization probes to screen libraries from e.g., any desired yeast or fungus using methodology well known to those skilled in the art (wherein those organisms producing DGLA and/or ETA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA* 86:5673 (1989); Loh et al., *Science* 243:217 (1989)).

In other embodiments, any of the delta-8 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the delta-8 desaturase nucleic acid fragments described herein are exchanged with a functional domain in an alternate desaturase gene to thereby result in a novel protein. As used herein, "domain" or "functional domain" refer to nucleic acid sequence(s) that are capable of eliciting a biological response in plants.

Methods for Production of Various Omega-3 and/or Omeqa-6 Fatty Acids

It is expected that introduction of chimeric genes encoding the delta-8 desaturases described herein (i.e., EaD8Des1, EaD8Des2, EaD8Des3, EaD8Des4 or other mutant enzymes, codon-optimized enzymes or homologs thereof), under the control of the appropriate promoters will result in increased production of DGLA and/or ETA in the transformed host organism, respectively. As such, the present invention encompasses a method for the direct production of PUFAs comprising exposing a fatty acid substrate (i.e., EDA and/or ETrA) to the desaturase enzymes described herein (e.g., EaD8Des1, EaD8Des2, EaD8Des3 or EaD8Des4), such that the substrate is converted to the desired fatty acid product (i.e., DGLA and/or ETA).

More specifically, it is an object of the present invention to provide a method for the production of DGLA in a host cell (e.g., oleaginous yeast, soybean), wherein the host cell comprises:

(a) a recombinant construct encoding a delta-8 desaturase polypeptide selected from the group consisting of SEQ ID NO:21, SEQ ID NO:22, SEQ ID NO:23 and SEQ ID NO:24; and, (b) a source of EDA; wherein the host cell is grown under conditions such that the delta-8 desaturase is expressed and the EDA is converted to DGLA, and wherein the DGLA is optionally recovered.

In alternate embodiments of the present invention, the delta-8 desaturase may be used for the use of the enzyme for the conversion of ETrA to ETA. Accordingly the invention provides a method for the production of ETA, wherein the host cell comprises:

(a) a recombinant construct encoding a delta-8 desaturase polypeptide selected from the group consisting of SEQ ID NO:21, SEQ ID NO:22, SEQ ID NO:23 and SEQ ID NO:24; and, (b) a source of ETrA;

wherein the host cell is grown under conditions such that the delta-8 desaturase is expressed and the ETrA is converted to ETA, and wherein the ETA is optionally recovered.

Alternatively, each delta-8 desaturase gene and its corresponding enzyme product described herein can be used indirectly for the production of various omega-6 and omega-3 PUFAs, including e.g., DGLA, ETA, ARA, EPA, DPA and/or DHA (see FIG. 1; see also PCT Publication No. WO 2004/101757). Indirect production of omega-3/omega-6 PUFAs occurs wherein the fatty acid substrate is converted indirectly into the desired fatty acid product, via means of an intermediate step(s) or pathway intermediate(s). Thus, it is contemplated that the delta-8 desaturases described herein (i.e., EaD8Des1, EaD8Des2, EaD8Des3, EaD8Des4, or other mutant enzymes, codon-optimized enzymes or homologs thereof) may be expressed in conjunction with additional genes encoding enzymes of the PUFA biosynthetic pathway (e.g., delta-6 desaturases, $C_{18/20}$ elongases, delta-17 desaturases, delta-8 desaturases, delta-15 desaturases, delta-9 desaturases, delta-12 desaturases, $C_{14/16}$ elongases, $C_{16/18}$ elongases, delta-9 elongases, delta-5 desaturases, delta-4 desaturases, $C_{20/22}$ elongases) to result in higher levels of production of longer-chain omega-3/omega-6 fatty acids (e.g., ARA, EPA, DPA and DHA).

In preferred embodiments, the delta-8 desaturases of the present invention will minimally be expressed in conjunction with a delta-9 elongase (e.g., a delta-9 elongase or a codon-optimized delta-9 elongase). However, the particular genes included within a particular expression cassette will depend on the host cell (and its PUFA profile and/or desaturase/elongase profile), the availability of substrate and the desired end product(s).

At times, it may be desirable to minimize by-product fatty acids. The relative abundance of by-product fatty acids could be decreased by increasing total delta-8 desaturase activity. One approach to minimize by-product fatty acids would be to express more than one delta-8 desaturase (i.e., the same or different delta-8 desaturase). For instance, the presence of sciadonic acid (SCI) and/or juniperonic acid (JUP) [commonly found in the seed lipids of gymnosperms (Wolff et al., *Lipids* 35(1):1-22 (2000)), such as those in the Pinaceae family (pine)] might be considered by-product fatty acids of a delta-6 desaturase/delta-6 elongase pathway or delta-9-elongase/delta-8 desaturase pathway. Although these fatty acids are considered to have various health-enhancing properties themselves (Nakane et al., *Biol. Pharm. Bull.* 23: 758-761 (2000)), their presence as by-product fatty acids in an engineered PUFA pathway, such as in an oilseed crop, may not be desirable depending on the application.

The term "delta-6 desaturase/delta-6 elongase pathway" also refers to a biosynthetic pathway for production of long-chain PUFAs. This pathway, at a minimum, comprises a delta-6 desaturase and a delta-6 elongase, thereby enabling biosynthesis of DGLA and/or ETA from LA and ALA, respectively. With expression of other desaturases and elongases, ARA, EPA, DPA and DHA may also be synthesized. Occasionally, a delta-6 elongase may elongate fatty acids other than the intended fatty acid. For instance, delta-6 elongases generally convert GLA to DGLA but some delta-6 elongases may also convert unintended substrates such as LA or ALA to EDA or ETrA, respectively. In a delta-6 desaturase/delta-6 elongase pathway, EDA and ETrA would be considered "by-product fatty acids" as defined below. Addition of a delta-8 desaturase to a delta-6 desaturase/delta-6 elongase pathway would provided a means to convert the "by-product fatty acids" EDA and ETrA back into the "intermediate fatty acids" (as defined previously) DGLA and ETA, respectively.

Plant Expression Systems, Cassettes and Vectors, and Transformation

In one embodiment, this invention concerns a recombinant construct comprising any one of the delta-8 desaturase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the delta-8 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J. Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3):246-53 (1989)); and, (6) a maize H3 histone gene promoter (Atanassova et al., *Plant Mol. Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific delta-8 desaturase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of claim 8.

Also of interest is a method for producing a transformed plant comprising transforming a plant cell with the delta-8 desaturase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol.* Sci. 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci. U.S.A.* 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

Thus, in one embodiment this invention concerns an oilseed plant comprising:
 (a) a first recombinant DNA construct comprising an isolated polynucleotide encoding a delta-8 desaturase polypeptide, operably linked to at least one regulatory sequence; and,
 (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase.

Such additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:
 (a) transforming a cell with the recombinant construct of the invention; and,
 (b) selecting those transformed cells that make long-chain PUFAs.

In still another aspect, this invention concerns a method for producing at least one PUFA in a soybean cell comprising:
 (a) transforming a soybean cell with a first recombinant DNA construct comprising:
  (i) an isolated polynucleotide encoding a delta-8 desaturase polypeptide, operably linked to at least one regulatory sequence; and,
  (ii) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-9 elongase, a delta-12 desaturase, a delta-15 desaturase, a delta-17 desaturase, a $C_{14/16}$ elongase, a $C_{16/18}$ elongase, a $C_{18/20}$ elongase and a $C_{20/22}$ elongase;
 (b) regenerating a soybean plant from the transformed cell of step (a); and,
 (c) selecting those seeds obtained from the plants of step (b) having an altered level of PUFAs when compared to the level in seeds obtained from a nontransformed soybean plant.

In other preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e) or the delta-9 elongase isolated or derived from *Euglena gracilis* as set forth in SEQ ID NO:39.

Microbial Expression Systems, Cassettes and Vectors, and Transformation

The delta-8 desaturase genes and gene products described herein (i.e., EaD8Des1, EaD8Des2, EaD8Des3, EaD8Des4, or other mutant enzymes, codon-optimized enzymes or homologs thereof) may also be produced in heterologous microbial host cells, particularly in the cells of oleaginous yeasts (e.g., *Yarrowia lipolytica*).

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant delta-8 desaturase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication Nos. WO 2004/101757 and WO 2006/052870 for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bb of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation and correct folding of the protein in the host organism; (5) the intrinsic stability of the mRNA and protein of the cloned gene within the host cell; and (6) the codon usage within the cloned gene, such that its frequency approaches the frequency of preferred codon usage of the host cell. Each of these types of modifications are encompassed in the present invention, as means to further optimize expression of the delta-8 desaturases described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (Gen Bank Accession No. AF260230), the LysS gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus (PCT Publication No. WO2004/104167), the Lip1 gene locus (GenBank Accession No. Z50020) and/or the Lip2 gene locus (GenBank Accession No. AJ012632)].

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. 4,880,741 and U.S. Pat. No. 5,071,764 and Chen, D. C. et al. (*Appl. Microbiol. Biotechnol.*, 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication Nos. WO2004/101757 and WO 2006/052870. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura– mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura– phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3– strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant delta-8 desaturases (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. Based on the needs of the Applicants' Assignee, the genes described in the instant invention will be expressed in an oleaginous yeast (and in particular *Yarrowia lipolytica*); however, it is contemplated that because transcription, translation and the protein biosynthetic apparatus is highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia*, *Candida*, *Rhodotorula*, *Rhodosporidium*, *Cryptococcus*, *Trichosporon* and *Lipomyces*. More specifically, illustrative oil-synthesizing yeasts include: *Rhodosporidium toruloides*, *Lipomyces starkeyii*, *L. lipoferus*, *Candida revkaufi*, *C. pulcherrima*, *C. tropicalis*, *C. utilis*, *Trichosporon pullans*, *T. cutaneum*, *Rhodotorula glutinus*, *R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (WO 2006/055322), U.S. patent application Ser. No. 11/265,761 (WO 2006/052870) and U.S. patent application Ser. No. 11/264,737 (WO 2006/052871), respectively.

Other preferred microbial hosts include oleaginous bacteria, algae and other fungi; and, within this broad group of microbial hosts, of particular interest are microorganisms that synthesize omega-3/omega-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present delta-8 desaturase genes under the control of inducible or regulated promoters could yield a transformant organism capable of synthesizing increased quantities of DGLA. The method of transformation of *M. alpina* is described by Mackenzie et al. (*Appl. Environ.*

*Microbiol.*, 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either DGLA or ETA, respectively, comprising:
(a) providing an oleaginous yeast comprising:
 (i) a first recombinant DNA construct comprising an isolated polynucleotide encoding a delta-8 desaturase polypeptide, operably linked to at least one regulatory sequence; and,
 (ii) a source of desaturase substrate consisting of either EDA or ETrA, respectively; and,
(b) growing the yeast of step (a) in the presence of a suitable fermentable carbon source wherein the gene encoding the delta-8 desaturase polypeptide is expressed and EDA is converted to DGLA or ETrA is converted to ETA, respectively; and,
(c) optionally recovering the DGLA or ETA, respectively, of step (b).

Substrate feeding may be required.

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the delta-8 desaturases described herein.

Specifically, in one embodiment this invention concerns an oleaginous yeast comprising:
(a) a first recombinant DNA construct comprising an isolated polynucleotide encoding a delta-8 desaturase polypeptide, operably linked to at least one regulatory sequence; and,
(b) at least one additional recombinant DNA construct comprising an isolated polynucleotide, operably linked to at least one regulatory sequence, encoding a polypeptide selected from the group consisting of: a delta-4 desaturase, a delta-5 desaturase, delta-6 desaturase, a delta-9 desaturase, a delta-12 desaturase, a delta-15 desaturase, a delta-17 desaturase, a delta-9 elongase, a $C_{14/16}$ elongase, a $C_{16-18}$ elongase, a $C_{18-20}$ elongase and a $C_{20/22}$ elongase.

In particularly preferred embodiments, the at least one additional recombinant DNA construct encodes a polypeptide having delta-9 elongase activity, e.g., the delta-9 elongase isolated or derived from *Isochrysis galbana* (GenBank Accession No. AF390174; IgD9e or IgD9eS) or the delta-9 elongase isolated or derived from *Euglena gracilis* as set forth in SEQ ID NO:39.

Metabolic Engineering of Omega-3 and/or Omega-6 Fatty Acid Biosynthesis in Microbes Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This manipulation may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this. To maximize production of omega-6 unsaturated fatty acids, it is well known to one skilled in the art that production is favored in a host microorganism that is substantially free of ALA; thus, preferably, the host is selected or obtained by removing or inhibiting delta-15 or omega-3 type desaturase activity that permits conversion of LA to ALA. Alternatively, it may be desirable to maximize production of omega-3 fatty acids (and minimize synthesis of omega-6 fatty acids). In this example, one could utilize a host microorganism wherein the delta-12 desaturase activity that permits conversion of oleic acid to LA is removed or inhibited; subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

In alternate embodiments, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication Nos. WO 2006/055322, WO 2006/052870 and WO 2006/052871, respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the delta-9 elongase/delta-8 desaturase biosynthetic pathway are introduced into oleaginous yeasts for the production of omega-3 and/or omega-6 fatty acids. It will be particularly useful to express the present the delta-8 desaturase genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial Fermentation Processes for PUFA Production

The transformed host cell is grown under conditions that optimize expression of chimeric desaturase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., Ind. Appl. Single Cell Oils, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(5/6): 463-491 (1992)). A brief review of downstream processing is also available by A. Singh and O. Ward (*Adv. Appl. Microbiol.*, 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details. Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

| Generalized Steps for Soybean Oil and Byproduct Production | | |
|---|---|---|
| Process Step | Process | Impurities Removed and/or By-Products Obtained |
| # 1 | soybean seed | |
| # 2 | oil extraction | meal |
| # 3 | degumming | lecithin |
| # 4 | alkali or physical refining | gums, free fatty acids, pigments |
| # 5 | water washing | soap |

TABLE 3-continued

| Generalized Steps for Soybean Oil and Byproduct Production | | |
|---|---|---|
| Process Step | Process | Impurities Removed and/or By-Products Obtained |
| # 6 | bleaching | color, soap, metal |
| # 7 | (hydrogenation) | |
| # 8 | (winterization) | stearine |
| # 9 | deodorization | free fatty acids, tocopherols, sterols, volatiles |
| # 10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating omega-3 and/or omega-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing omega-3 and/or omega-6 fatty acids as described herein will be suitable for use in a variety of food and feed products including, but not limited to: food analogs, meat products, cereal products, baked foods, snack foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aquous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and include functional foods, medical foods, medical nutritionals and dietary supplements. Additionally, the plant/seed oils, altered seeds and microbial oils of the invention may be used in standard pharmaceutical compositions (e.g., the long-chain PUFA containing oils could readily be incorporated into the any of the above mentioned food products, to thereby produce a functional or medical food). More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

General Methods:

Transformation and Cultivation of Yarrowia lipolytica:

Yarrowia lipolytica strains with ATCC Accession Nos. #20362, #76982 and #90812 were purchased from the American Type Culture Collection (Rockville, Md.). Yarrowia lipolytica strains were typically grown at 28° C. on YPD agar (1% yeast extract, 2% bactopeptone, 2% glucose, 2% agar).

Transformation of Yarrowia lipolytica was performed according to the method of Chen, D. C. et al. (Appl. Microbiol. Biotechnol. 48(2):232-235 (1997)), unless otherwise noted. Briefly, Yarrowia was streaked onto a YPD plate and grown at 30° C. for approximately 18 h. Several large loopfuls of cells were scraped from the plate and resuspended in 1 mL of transformation buffer, comprising: 2.25 mL of 50% PEG, average MW 3350; 0.125 mL of 2 M lithium acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of Yarrowia lipolytica:

Unless otherwise stated, for fatty acid analysis cells were collected by centrifugation and lipids were extracted as described in Bligh, E. G. & Dyer, W. J. (Can. J. Biochem. Physiol. 37:911-917 (1959)). Fatty acid methyl esters were prepared by transesterification of the lipid extract with sodium methoxide (Roughan, G. and Nishida I., *Arch Biochem Biophys.* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 pt of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

Identification of Delta-8 Desaturase Enzyme Homologs From *Euglena anabaena* UTEX 373

The present Example describes the identification of a cDNA fragment (SEQ ID NO:1) encoding a partial delta-8 desaturase from *Euglena anabaena* UTEX 373. This work included the generation of RNA, synthesis of cDNA, generation of a cDNA library and then the identification of a cDNA encoding a partial delta-8 desaturase derived from PCR amplification of the cDNA library using degenerate oligonucleotides based on the *Euglena gracilis* delta-8 desaturase sequence (SEQ ID NO:2; described as Eg5 in PCT Publication No. WO 2006/012325).

Figure 6:
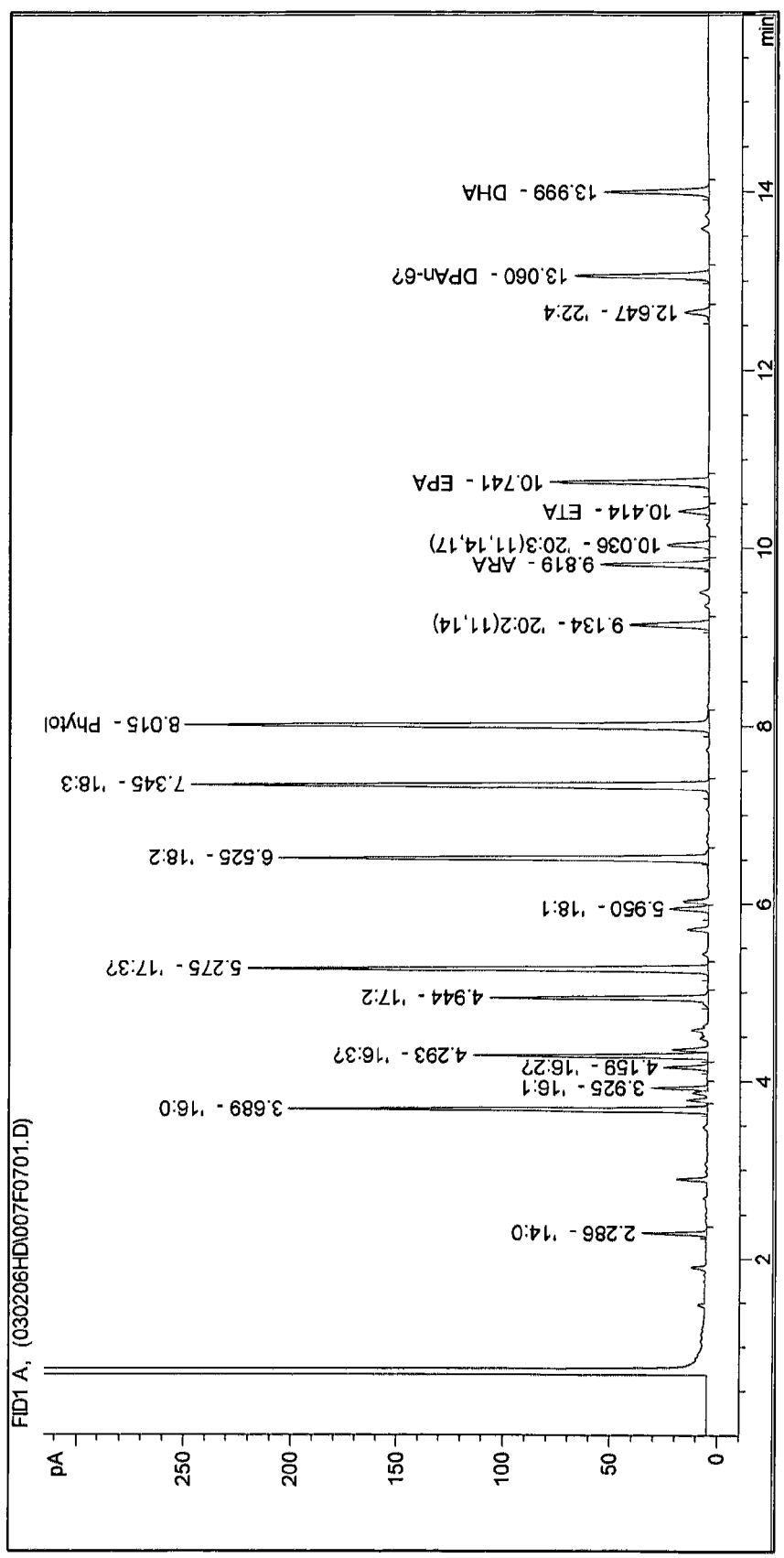
FIG. 6 shows a chromatogram of the lipid profile of an *Euglena anabaena* cell extract as described in the Examples.

Growth of *Euglena anabaena* UTEX 373 and preparation of RNA:

*Euglena anabaena* UTEX 373 was obtained from Dr. Richard Triemer's lab at Michigan State University (East Lansing, Mich.). Approximately 2 mL of culture was removed for lipid analysis and centrifuged at 1,800×g for 5 min. The pellet was washed once with water and re-centrifuged. The resulting pellet was dried for 5 min under vacuum, resuspended in 100 μl_of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 170° C. for 1.0 min, increase to 240° C. at 5° C./min and then hold for an additional 1.0 min. Carrier gas was supplied by a Whatman hydrogen generator. Retention times were compared to those for methyl esters of standards commercially available (Nu-Chek Prep, Inc. Cat. No. U-99-A) and the resulting chromatogram is shown in FIG. 6. The presence of EDA, ERA, EPA and DHA in the fatty acid profile, with the absence of GLA and STA, suggested that *Euglena anabaena* uses the delta-9 elongase/delta-8 desaturase pathway for LC-PUFA biosynthesis and would be a good source for LC-PUFA biosynthetic genes such as, but not limited to, delta-8 desaturases.

The remaining 5 mL of an actively growing culture was transferred into 25 mL of AF-6 Medium (Watanabe & Hiroki, NIES-Collection List of Strains, 5$^{th}$ ed., National Institute for Environmental Studies, Tsukuba, 127 pp (2004)) in a 125 mL glass flask. *Euglena anabaena* cultures were grown at 22° C. with a 16 h light, 8 h dark cycle for 2 weeks with very gentle agitation.

After 2 weeks, the culture (25 mL) was transferred to 100 mL of AF-6 medium in a 500 mL glass bottle and the culture was grown for 1 month as described above. After this time, two 50 mL aliquots were transferred into two separate 500 mL glass bottles containing 250 mL of AF-6 medium and the cultures were grown for two months as described above (giving a total of ~600 mL of culture). After this, the cultures were pelleted by centrifugation at 1,800×g for 10 min, washed once with water and re-centrifuged. Total RNA was extracted from one of the resulting pellets using the RNA STAT-60™ reagent (TEL-TEST, Inc., Friendswood, Tex.) and following the manufacturer's protocol provided (use 5 mL of reagent, dissolved RNA in 0.5 mL of water). In this way, 340 μg of total RNA (680 ug/mL) was obtained from the pellet. The remaining pellet was frozen in liquid nitrogen and stored at -80° C. The mRNA was isolated from all 340 μg of total RNA using the mRNA Purification Kit (Amersham Biosciences, Piscataway, N.J.) following the manufacturer's protocol provided. In this way, 9.0 μg of mRNA was obtained.

Preparation of *Euglena anabaena* cDNA and Generation of cDNA Library eug1c:

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 5.12 μg of mRNA (described above) using the Biotin-attB2-Oligo (dT) primer. After synthesis of the first and second strand, the attB1 adapter was added, ligated and the cDNA was size fractionated using column chromatography. DNA from fractions were concentrated, recombined into pDONR™222 and transformed into *E. coli* ElectroMAX™ DH10B™ T1 Phage-Resistant cells (Invitrogen Corporation). The *Euglena anabaena* library was named eug1c.

The cDNA library eug1c was plated onto LBKan plates (approx. 100,000 colonies), the colonies were scraped off and DNA was isolated using the QIAprep® Spin Miniprep Kit (Qiagen Inc., Valencia, Calif.) following the manufacturer's protocol. In this way, a plasmid DNA sub-library from eug1c was obtained.

Identification of cDNA Fragments Encoding Partial Putative Delta-8 Desaturases:

The plasmid DNA sub-library described above was used as template for degenerate PCR using degenerate primers based on the nucleotide sequence of the *Euglena gracilis* delta-8 fatty acid desaturase (SEQ ID NO:2) and the vector-specific primer pDonor222Eg5-1 (SEQ ID NO:3). The 4 degenerate primers used are shown in Table 4.

TABLE 4

Degenerate Oligonucleotides Used to Amplify a Portion of the Delta-8 Desaturase Genes From *Euglena anabaena* UTEX 373

| Primer | Nucleotide Sequence | SEQ ID NO: |
|---|---|---|
| D8DEG3-1 | RTTRTGNCKATCTTTCCACCA | SEQ ID NO: 4 |
| D8DEG3-2 | RTTRTGNCKGTCTTTCCACCA | SEQ ID NO: 5 |
| D8DEG3-3 | RTTRTGNCKATCCTTCCACCA | SEQ ID NO: 6 |
| D8DEG3-4 | RTTRTGNCKGTCCTTCCACCA | SEQ ID NO: 7 |

A total of 5 reactions were set up for the cDNA sample. The reaction mixture contained 1 μL of cDNA, 1 μL each of the vector-specific and degenerate primer (20 μM) and the PCR was carried out using the Phusion™ High-Fidelity DNA Polymerase (Cat. No. F553S, Finnzymes Oy, Finland) following the manufacturer's protocol. The resulting DNA fragments were cloned into the pCR-Blunt® cloning vector using the Zero Blunt® PCR Cloning Kit (Invitrogen Corporation), following the manufacturer's protocol.

Plasmid DNA from the resulting clones was purified using the QIAprep® Spin Miniprep Kit (Qiagen Inc.) following the manufacturer's protocol and DNA inserts were end-sequenced in 384-well plates, using vector-primed T7 primer (SEQ ID NO:8), M13rev-28 primer (SEQ ID NO:9) with the ABI BigDye version 3 Prism sequencing kit. For the sequencing reaction, 100-200 ng of template and 6.4 µmol of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

A consensus sequence was assembled from the individual sequences obtained and one representative clone, called pHD23-1 (SEQ ID NO:10) having a sequence identical to the consensus was chosen for further study.

Identification of the partial cDNA insert in pHD23-1 (SEQ ID NO:1) as a partial delta-8 desaturase was confirmed using BLAST (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The partial cDNA sequence obtained (SEQ ID NO:1) was translated in all reading frames and compared for similarity to all publicly available protein sequences contained in the "nr" database using the BLASTX algorithm (Gish and States, *Nat. Genet.* 3:266-272 (1993)) provided by the NCBI with the default parameter and the filter turned off. For convenience, the P-value (probability) of observing a match of a cDNA sequence to a sequence contained in the searched databases merely by chance as calculated by BLAST are reported herein as a "pLog" value, which represents the negative of the logarithm of the reported P-value. Accordingly, the greater the pLog value, the greater the likelihood that the cDNA sequence and the BLAST "hit" represent homologous proteins.

The BLASTX search using the nucleotide sequence insert from pHD23-1 revealed similarity of the protein encoded by the partial cDNA (SEQ ID NO:1) to the *Euglena gracilis* delta-8 desaturase amino acid sequence (SEQ ID NO:11) (NCBI Accession No. AAD45877(GI 5639724), locus AAD45877, CDS AF139720; Wallis and Browse, *Arch. Biochem. Biophys.* 365:307-316 (1999)) and yielded a pLog value of 63.4 (E value of 4e-63).

Example 2

Isolation of the Full-Length Delta-8 Desaturases from *Euglena anabaena* UTEX 373

Approximately 17,000 clones of cDNA library euglc were plated onto three large square (24 cm×24 cm) petri plates (Corning, Corning, N.Y.) each containing LB+50 µg/mL kanamycin agar media. Cells were grown overnight at 37° C. and plates were then cooled to room temperature.

Colony Lifts:

Biodyne B 0.45 µm membrane (Cat. No. 60207, Pall Corporation, Pensacola, Fla.) was trimmed to approximately 22 cm×22 cm and the membrane was carefully layered on top of the agar to avoid air bubbles. After incubation for 2 min at room temperature, the membrane was marked for orientation, lifted off with tweezers and placed colony-side up on filter paper soaked with 0.5 M sodium hydroxide and 1.5 M sodium chloride. After denaturation for 4 min, the sodium hydroxide was neutralized by placing the membrane on filter paper soaked with 0.5 M Tris-HCL (pH 7.5) and 1.5 M sodium chloride for 4 min. This step was repeated and the membrane was rinsed briefly in 2×SSC buffer (20×SSC is 3M sodium chloride, 0.3 M sodium citrate; pH 7.0) and air dried on filter paper.

Hybridization:

Membranes were pre-hybridized at 65° C. in 200 mL hybridization solution for 2 h. Hybridization solution contained 6×SSPE (20×SSPE is 3 M sodium chloride, 0.2 M sodium phosphate, 20 mM EDTA; pH 7.4), 5×Denhardt's reagent (100×Denhardt's reagent is 2% (w/v) Ficoll, 2% (w/v) polyvinylpyrrolidone, 2% (w/v) acetylated bovine serum albumin), 0.5% sodium dodecyl sulfate (SDS), 100 µg/mL sheared salmon sperm DNA and 5% dextran sulfate.

A DNA probe was made using an agarose gel purified EcoRI DNA fragment, containing the *Euglena anabaena* delta-8 desaturase partial DNA fragment, from pHD23-1 (described in Example 1) labeled with P32 dCTP using the RadPrime DNA Labeling System (Cat. No. 18428-011, Invitrogen, Carlsbad, Calif.) following the manufacturer's instructions. Unincorporated $P3^2$ dCTP was separated using a NICK column (Cat. No. 17-0855-02, Amersham Biosciences, Piscataway, N.J.) following the manufacturer's instructions. The probe was denatured for 5 min at 100° C., placed on ice for 3 min and half was added to the hybridization solution.

The membrane was hybridized with the probe overnight at 65° C. with gentle shaking and then washed the following day twice with 2×SSC containing 0.5% SDS (5 min each) and twice with 0.2×SSC containing 0.1% SDS (15 min each). After washing, hyperfilm (Cat. No. RPN30K, Amersham Biosciences, Piscataway, N.J.) was exposed to the membrane overnight at −80° C.

Based on alignment of plates with the exposed hyperfilm, positive colonies were picked using the blunt end of a Pasteur pipette into 1 mL of water and vortexed. Several dilutions were made and plated onto small round Petri dishes (82 mm) containing LB media plus 50 µg/mL kanamycin to obtain around 100 well isolated colonies on a single plate. Lifts were done as described above except NytranN membrane circles (Cat, No. 10416116, Schleicher & Schuell, Keene, N.H.) were used and hybridization was carried out in 100 mL using the remaining radiolabeled probe. In this way, positive clones were confirmed.

Individual positive clones were grown at 37° C. in LB+50 µg/mL kanamycin liquid media and plasmid was purified using the QIAprep® Spin Miniprep Kit (Qiagen Inc.) following the manufacturer's protocol. The plasmid insert was sequenced as described in Example 1 with the ABI BigDye version 3 Prism sequencing kit using vector-primed T7 primer (SEQ ID NO:8), vector-primed M13rev-28 primer (SEQ ID NO:9) and the poly(A) tail-primed WobbleT oligonucleotides. Briefly, the WobbleT primer is an equimolar mix of 21 mer poly(T)A, poly(T)C, and poly(T)G, used to sequence the 3' end of cDNA clones. Based on initial sequence data, additional internal fragment sequence was obtained in a similar way using oligonucleotide EaD8seq-1 (SEQ ID NO:12). In this way, the full insert sequences of the euglc delta-8 desaturase clones were obtained.

Sequences were aligned and compared using Sequencher™ (Version 4.2, Gene Codes Corporation, Ann Arbor, Mich.) and in this way, the clones could be categorized into one of four distinct groups based on insert sequence (called EaD8Des1 to EaD8Des4). Representative clones containing the cDNA for each class of sequence were chosen for further study and sequences for each representative plasmid (pLF118-1, pLF118-2, pLF118-3 and pLF118-4) are shown in SEQ ID NO:13, SEQ ID NO:14, SEQ ID NO:15 and SEQ ID NO:16, respectively. The sequence shown by a string of NNNN's represents a region of the polyA tail which was not sequenced. The coding sequences for EaD8Des1, EaD8Des2, EaD8Des3 and EaD8Des4 are shown in SEQ ID NO:17, SEQ ID NO:18, SEQ ID NO:19 and SEQ ID NO:20, respectively. The corresponding amino acid sequences for EaD8Des1, EaD8Des2, EaD8Des3 and EaD8Des4 are shown in SEQ ID NO:21, SEQ ID NO:22, SEQ ID NO:23 and SEQ ID NO:24, respectively.

Example 3

Primary Sequence Analysis of the Delta-8 Desaturase Sequences of *Euglena anabaena* UTEX 373 and Comparison to a Delta-8 Desaturase Sequence of *Euglena gracilis*

The amino acid sequences for EaD8Des1 (SEQ ID NO:21), EaD8Des2 (SEQ ID NO:22), EaD8Des3 (SEQ ID NO:23) and EaD8Des4 (SEQ ID NO:24) were compared using the Clustal W method (using the MegAlign™ v6.1 program of the LASARGENE bioinformatics computing suite (DNASTAR Inc.) with the default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB).

Compared to the EaD8Des1 (SEQ ID NO:21), EaD8Des2 (SEQ ID NO:22) has 3 amino acid substitutions (T110S, M223I & K251T; based on numbering for EaD8Des1), EaD8Des3 (SEQ ID NO:23) has 2 amino acid substitutions (T110S & K251T) and EaD8Des4 (SEQ ID NO:24) has 1 amino acid substitution (T110S).

The amino acid sequences for EaD8Des1 (SEQ ID NO:21), EaD8Des2 (SEQ ID NO:22), EaD8Des3 (SEQ ID NO:23) and EaD8Des4 (SEQ ID NO:24) were evaluated by BLASTP (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases) using default parameters and the filter off. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

All four sequences yielded a pLog value of 177 (P value of e-177) versus the *Euglena gracilis* delta-8 desaturase amino acid sequence (SEQ ID NO:11) (NCBI Accession No. AAD45877(GI 5639724), locus AAD45877, CDS AF139720; Wallis and Browse, *Arch. Biochem. Biophys.* 365: 307-316 (1999)) when compared to the "nr" database. BLAST scores and probabilities indicate that the instant nucleic acid fragments encode entire *Euglena anabaena* delta-8 fatty acid desaturases.

The amino acid sequences for EaD8Des1 (SEQ ID NO:21), EaD8Des2 (SEQ ID NO:22), EaD8Des3 (SEQ ID NO:23) and EaD8Des4 (SEQ ID NO:24) were then compared to the corrected *Euglena gracilis* delta-8 desaturase amino acid sequence (EgD8; SEQ ID NO:25; described as Eg5 in PCT Application No. WO 2006/012325) using BlastP (default parameters, filter off), Clustal V and the Jotun Hein methods of sequence comparison and the % identity using each method is shown in Table 5. The Clustal V alignment of these five amino acid sequences can be seen in FIGS. 7A, 7B and 7C. FIG. 8 is a chart setting forth a comparison of the percent identity (and percent divergence in the lower half triangle), among the five delta-8 desaturase sequences aligned in FIGS. 7A, 7B and 7C.

Sequence percent identity calculations performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) were done using the MegAlign™ v6.1 program of the LASERGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). Sequence percent identity calculations performed by the Jotun Hein method (Hein, J. J., *Meth. Enz.* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2).

TABLE 5

Sequence Comparison of EaD8Des1 (SEQ ID NO: 21), EaD8Des2 (SEQ ID NO: 22), EaD8Des3 (SEQ ID NO: 23) and EaD8Des4 (SEQ ID NO: 24) to EgD8 (SEQ ID NO: 25)

| Desaturase | % Identity to EgD8 (SEQ ID NO: 25) by BLASTP | % Identity to EgD8 (SEQ ID NO: 25) by the Jotun Hein Method | % Identity to EgD8 (SEQ ID NO: 25) by the Clustal V Method |
|---|---|---|---|
| EaD8Des1 (SEQ ID NO: 21) | 73% | 74.4% | 72.1% |
| EaD8Des2 (SEQ ID NO: 22) | 73% | 74.2% | 71.9% |
| EaD8Des3 (SEQ ID NO: 23) | 73% | 74.2% | 71.9% |
| EaD8Des4 (SEQ ID NO: 24) | 73% | 74.2% | 71.9% |

Example 4

Functional Analysis of the *Euglena gracilis* UTEX 373 Delta-8 Desaturases in *Yarrowia lipolytica*

The present Example describes functional analysis of the four EaD8Des in *Yarrowia lipolytica*. This work included the following steps: (1) PCR amplification of the EaD8Des with appropriate restriction sites for cloning from plasmids described in Example 2; (2) cloning of the EaD8Des PCR products into cloning vector pCR-Blunt® (Invitrogen Corporation) to produce pY120-1 to pY120-4; (3) cloning of the EaD8Des genes into *Yarrowia* expression vector pY115 to produce pY175, pY176, pY177 and pY178; and, (4) comparison of lipid profiles within transformant organisms comprising pY175, pY176, pY177 and pY178, after substrate feeding.

PCR Amplification of the EaD8Des Genes:

In order to introduce NotI and NcoI restriction sites at the 5' end of the coding sequences and a NotI site at the 3' end of the coding sequences, each of the EaD8Des genes were PCR amplified. The coding sequences for EaD8Des1 (SEQ ID NO:17), EaD8Des2 (SEQ ID NO:18), EaD8Des3 (SEQ ID NO:19) and EaD8Des4 (SEQ ID NO:20) were amplified from pLF118-1 (SEQ ID NO:13), pLF118-2 (SEQ ID NO:14), pLF118-3 (SEQ ID NO:15) and pLF118-4 (SEQ ID NO:16), respectively, with oligonucleotide primers EaD8-5 (SEQ ID NO:26) and EaD8-3 (SEQ ID NO:27) using the Phusion™ High-Fidelity DNA Polymerase (Cat. No. F553S, Finnzymes Oy, Finland) following the manufacturer's protocol. The resulting DNA fragments were cloned into the pCR-Blunt® cloning vector using the Zero Blunt® PCR Cloning Kit (Invitrogen Corporation), following the manufacturer's protocol, to produce pLF120-1 (SEQ ID NO:28), pLF120-2 (SEQ ID NO:29), pLF120-3 (SEQ ID NO:30) and pLF120-4 (SEQ ID NO:31), respectively.

Construction of *Yarrowia* Expression Vector pY115, pY175, pY176, pY177 and pY178:

Plasmid pY5-30 (which was previously described in PCT Publication No. WO 2005/003310; the contents of which are hereby incorporated by reference), is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (AmpR), for selection in *E. coli*; a *Yarrowia* LEU2 gene, for selection in *Yarrowia*; and a chimeric TEF::GUS::XPR gene. Plasmid pDMW263 (SEQ ID NO:32) was created from pY5-30, by replacing the TEF promoter with the *Yarrowia lipolytica* FBAINm promoter (PCT Publication No. WO 2005/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 6 summarizes the components of pDMW263 (SEQ ID NO:32).

TABLE 6

Components of Plasmid pDMW263

| RE Sites and Nucleotides Within SEQ ID NO: 32 | Description of Fragment and Chimeric Gene Components |
|---|---|
| 4992-4296 | ARS18 sequence (GenBank Accession No. A17608) |
| SalI/SacII (8505-2014) | FBAINm::GUS::XPR, comprising: FBAINm: FBAINm promoter (WO 2005/049805) GUS: *E. coli* gene encoding β-glucuronidase (Jefferson, R. A. *Nature*. 14: 342: 837-838 (1989) XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Figure 2:
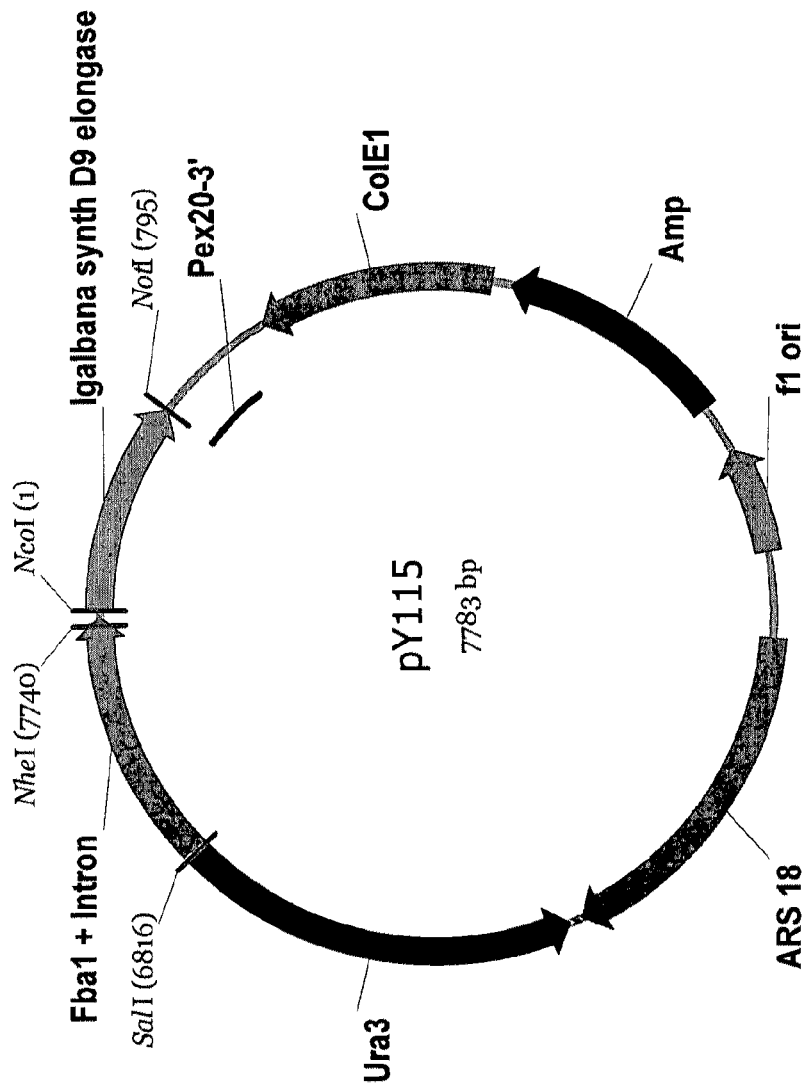
FIG. 2 is a map of plasmid pY115 (SEQ ID NO:34).

The NcoI/SalI DNA fragment from pDMW263 (SEQ ID NO:32), containing the *Yarrowia lipolytica* FBAINm promoter, was cloned into the NcoI/SalI DNA fragment of pDMW237 (SEQ ID NO:33), previously described in PCT Publication No. WO 2006/012325 (the contents of which are hereby incorporated by reference), containing a synthetic delta-9 elongase gene derived from *Isochrysis galbana* and codon-optimized for expression in *Yarrowia lipolytica*, to produce pY115 (SEQ ID NO:34; FIG. 2). In FIG. 2, the modified FBAINm promoter is called FBA1+Intron. It is also FBA1+Intron in other figures, as well as YAR FBA1 PRO+ Intron and these terms are used interchangeably with FBAINm.

Figure 3:
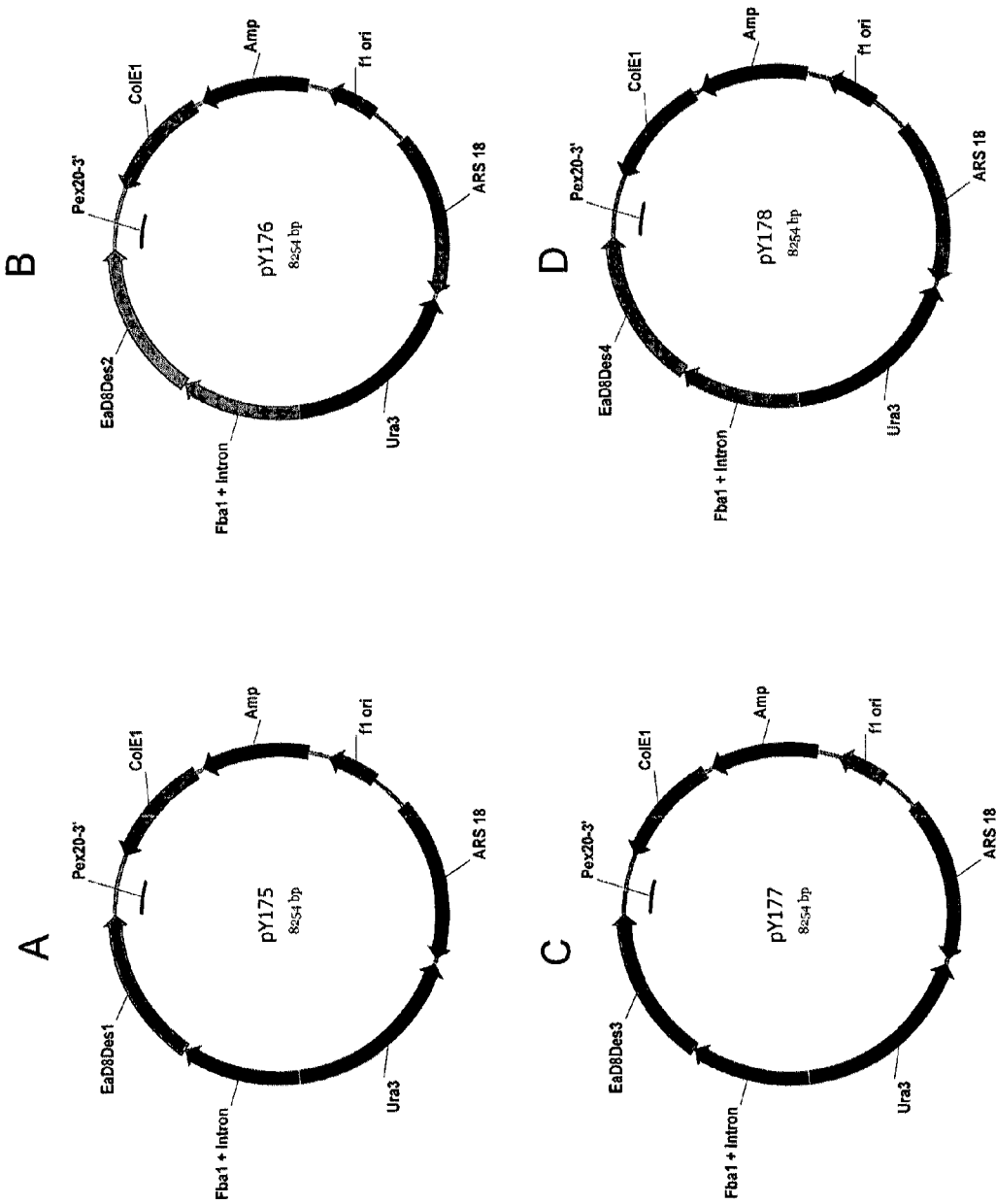
FIG. 3A is a map of plasmid pY175 (SEQ ID NO:35).
FIG. 3B is a map of plasmid pY176 (SEQ ID NO:36).
FIG. 3C is a map of plasmid pY177 (SEQ ID NO:37).
FIG. 3D is a map of plasmid and pY178 (SEQ ID NO:38).

The NcoI/NotI DNA fragments from pLF120-1 (SEQ ID NO:28), pLF120-2 (SEQ ID NO:29), pLF120-3 (SEQ ID NO:30) and pLF120-4 (SEQ ID NO:31), containing each EaD8Des, were cloned into the NcoI/NotI DNA fragment from pY115, containing the *Yarrowia lipolytica* FBAINm promoter, to produce pY175 (SEQ ID NO:35; FIG. 3A), pY176 (SEQ ID NO:36; FIG. 3B), pY177 (SEQ ID NO:37; FIG. 3C) and pY178 (SEQ ID NO:38; FIG. 3D), respectively.

Functional Anlaysis of the Four EaD8Des Genes in *Yarrowia lipolytica*:

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a MM plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto MM plates containing 200 mg/mL 5-FOA and MM plates lacking uracil and uridine to confirm uracil Ura3 auxotrophy.

Strain Y2224 was transformed with pY175 (SEQ ID NO:35; FIG. 3A), pY176 (SEQ ID NO:36; FIG. 3B), pY177 (SEQ ID NO:7; FIG. 3C) and pY178 (SEQ ID NO:38; FIG. 3D) as described in the General Methods.

Single colonies of transformant *Yarrowia lipolytica* containing pY175-pY178 were grown in 3 mL minimal media lacking uracil supplemented with 0.2% tergitol at 30° C. for 1 day. After this, 0.1 mL was transferred to 3 mL of the same medium supplemented with eicosadienoic acid [EDA-20:2 (11,14)] or eicosatrienoic acid [ERA-20:3(11,14,17)] to 0.175 mM. These were incubated for 16 h at 30° C., 250 rpm and then pellets were obtained by centrifugation. Cells were washed once with water, pelleted by centrifugation and air dried. Pellets were transesterified (Roughan, G. and Nishida, I., *Arch. Biochem. Biophys.* 276(1):38-46 (1990)) with 500 µL of 1% sodium methoxide for 30 min. at 50° C. after which 500 µL of 1M sodium chloride and 100 µL of heptane were added. After thorough mixing and centrifugation, fatty acid methyl esters (FAMEs) were analyzed by GC. FAMEs (5 µL injected from hexane layer) were separated and quantified using a Hewlett-Packard 6890 Gas Chromatograph fitted with an Omegawax 320 fused silica capillary column (Cat. No. 24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.).

The fatty acid profiles for *Yarrowia lipolytica* expressing pY175-pY178 are shown in FIG. 4. Percent C20 desaturation (C20% delta-8 desat) was calculated either by dividing the wt. % for DGLA by the sum of the wt. % for EDA and DGLA and multiplying by 100 to express as a % or by dividing the wt. % for ETA by the sum of the wt. % for ERA and DTA and multiplying by 100 to express as a %, depending on which substrate was fed (EDA or ERA). Averages are indicated by Ave. followed by appropriate header. The ratio of desaturation of EDA to ERA is calculated by dividing the Ave. C20% delta-8 desat for EDA by that of ERA.

All of the *Euglena anabaena* delta-8 desaturases function similarly well in *Yarrowia* and convert approximately 50% of the EDA to DGLA. There appears to be a slight preference for the EDA over ERA with a EDA/ERA ratio of 1.1 to 1.2.

Example 5

Construction of Soybean Expression Vector pKR1152 for Co-Expression of the *Euglena anabaena* UTEX 373 Delta-8 Desaturase (EaD8Des3) with a Delta-9 *Elongase* Derived from *Euglena gracilis* (EgD9e)

Figure 5:
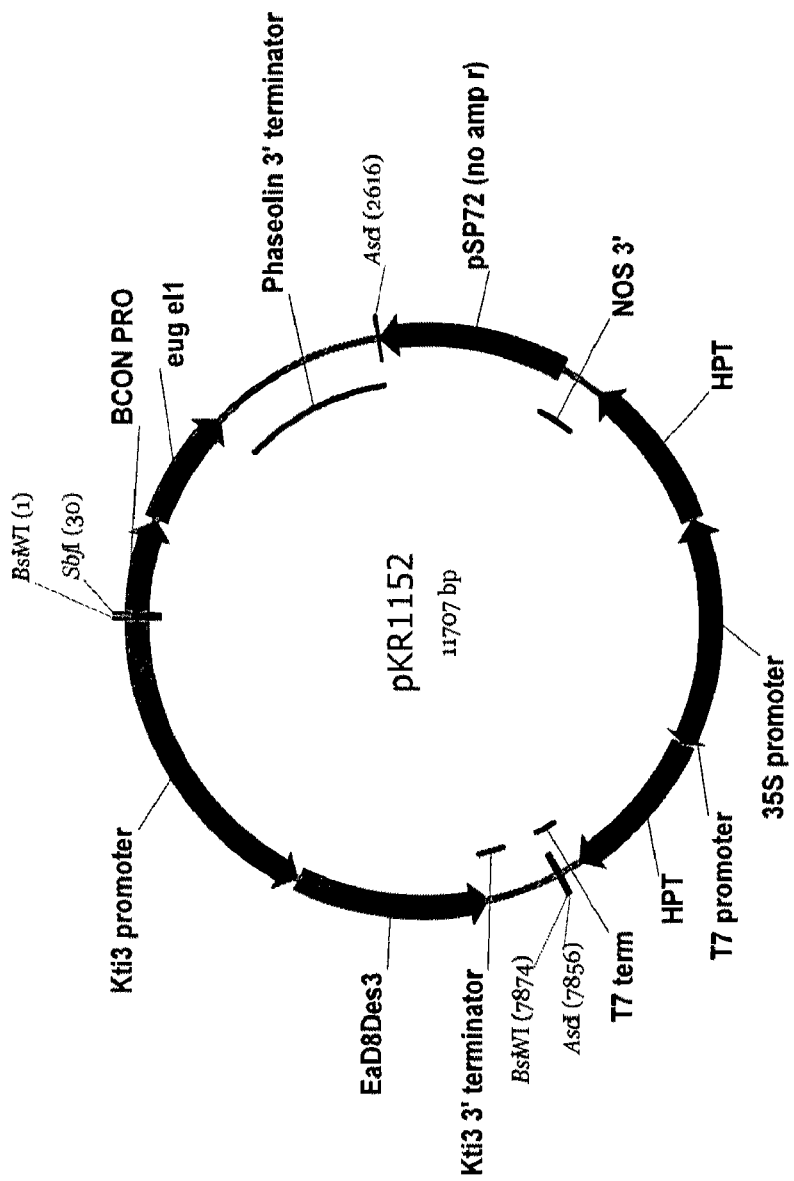
FIG. 5 is a map of pKR1152 (SEQ ID NO:47).

The present Example describes construction of a soybean vector for co-expression of EaD8Des3 with EgD9e.
*Euglena gracilis* Delta-9 Elongase (EgD9e):
A clone from the Euglena cDNA library (eeglc), called eeg1c.pk001.n5f, containing the *Euglena gracilis* delta-9 elongase (EgD9e; SEQ ID NO:39; which is described in U.S. application Ser. No. 11/601,563 (filed Nov., 16, 2006, which published May 24, 2007; the contents of which are hereby incorporated by reference) was used as template to amplifiy EgD9elo with oligonucleotide primers oEugEL1-1 (SEQ ID NO:40) and oEugEL1-2 (SEQ ID NO:41) using the VentR® DNA Polymerase (Cat. No. MO254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906 (SEQ ID NO:42).
A starting plasmid pKR72 (ATCC Accession No. PTA-6019; SEQ ID NO:43, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/HPT/T7term cassette), and a bacterial origin of replication (ori) for selection and replication in bacteria (e.g., *E. coli*). In addition, pKR72 also contains HPT, flanked by the 35S promoter (Odell et al., *Nature* 313:810-812 (1985)) and NOS 3' transcription terminator (Depicker et al., *J. Mol. Appl. Genet.* 1:561-570 (1982)) (35S/HPT/NOS3' cassette) for selection in plants such as soybean. pKR72 also contains a NotI restriction site, flanked by the promoter for the α' subunit of β-conglycinin (Beachy et al., *EMBO J.* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site.
EgD9e was released from pKR906 (SEQ ID NO:42) by digestion with NotI and cloned into the NotI site of pKR72 (SEQ ID NO:43) to produce pKR912 (SEQ ID NO:44). In some instances, pKR912 is referred to as pKR1010 but they are identical.
*Euglena anabaena* UTEX 373 Delta-8 Desaturase (EaD8Des3):
Vector pKR457 (SEQ ID NO:45), which was previously described in PCT Publication No. WO 2005/047479 (the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965, followed by the soy albumin transcription terminator, which was previously described in PCT Publication No. WO 2004/071467 (Kti/NotI/Kti3'Salb3' cassette).
The NotI fragment of pLF120-3 (SEQ ID NO:30), containing the EaD8Des3 gene was cloned into the NotI site of pKR457 (SEQ ID NO:45), to produce pKR1138 (SEQ ID NO:46).
The BsiWI fragment from pKR1138 (SEQ ID NO:46), containing the EaD8Des3 gene, was cloned into the BsiWI site of pKR912 (SEQ ID NO:44) to produce pKR1152 (SEQ ID NO:47; FIG. 5). In FIG. 5, the *Euglena gracilis* delta-9 elongase (EgD9e) is called eug el1.

Example 6

Production and Model System Transformation of Somatic Soybean Embryo

Cultures with Soybean Expression Vectors and Plant Regeneration Culture Conditions:
Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 mL of fresh liquid SB196 (the preferred subculture interval is every 7 days).
Soybean embryogenic suspension cultures are transformed with the soybean expression plasmids by the method of particle gun bombardment (Klein et al., *Nature* 327:70 (1987)) using a DuPont Biolistic PDS1000/HE instrument (helium retrofit) for all transformations.
Soybean Embryogenic Suspension Culture Initiation:
Soybean cultures are initiated twice each month with 5-7 days between each initiation. Pods with immature seeds from available soybean plants are picked 45-55 days after planting. Seeds are removed from the pods and placed into a sterilized magenta box. The soybean seeds are sterilized by shaking them for 15 min in a 5% Clorox solution with 1 drop of Ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. When cultures are being prepared for production transformation, cotyledons are transferred to plates containing SB1 medium (25-30 cotyledons per plate). Plates are wrapped with fiber tape and are maintained at 26° C. with cool white fluorescent lights on 16:8 h day/night photoperiod at light intensity of 60-80 pE/m2/s for eight weeks, with a media change after 4 weeks. When cultures are being prepared for model system experiments, cotyledons are transferred to plates containing SB199 medium (25-30 cotyledons per plate) for 2 weeks, and then transferred to SB1 for 2-4 weeks. Light and temperature conditions are the same as described above. After incubation on SB1 medium, secondary embryos are cut and placed into SB196 liquid media for 7 days.
Preparation of DNA for Bombardment:
Either an intact plasmid or a DNA plasmid fragment containing the genes of interest and the selectable marker gene are used for bombardment. Fragments from soybean expression plasmids are obtained by gel isolation of digested plasmids. In each case, 100 µg of plasmid DNA is used in 0.5 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 1.5 h. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 μL aliquot of sterile distilled water containing 3 mg of gold particles (3 mg gold) is added to 30 μL of a 10 ng/μL DNA solution (either intact plasmid or DNA fragment prepared as described herein), 25 μL 5M $CaCl_2$ and 20 μL of 0.1 M spermidine. The mixture is shaken 3 min on level 3 of a vortex shaker and spun for 10 sec in a bench microfuge. The supernatant is removed, followed by a wash with 400 μL 100% ethanol and another brief centrifugation. The 400 μL ethanol is removed and the pellet is resuspended in 40 μL of 100% ethanol. Five μL of DNA suspension is dispensed to each flying disk of the Biolistic PDS1000/HE instrument disk. Each 5 μL aliquot contains approximately 0.375 mg gold per bombardment (e.g., per disk).

For model system transformations, the protocol is identical except for a few minor changes (i.e., 1 mg of gold particles is added to 5 μL of a 1 μg/μL DNA solution, 50 μL of a 2.5M $CaCl_2$ is used and the pellet is ultimately resuspended in 85 μL of 100% ethanol thus providing 0.058 mg of gold particles per bombardment).

Tissue Preparation and Bombardment with DNA:

Approximately 150-200 mg of seven day old embryogenic suspension cultures is placed in an empty, sterile 60×15 mm petri dish and the dish is covered with plastic mesh. The chamber is evacuated to a vacuum of 27-28 inches of mercury, and tissue is bombarded one or two shots per plate with membrane rupture pressure set at 1100 PSI. Tissue is placed approximately 3.5 inches from the retaining/stopping screen. Model system transformation conditions are identical except 100-150 mg of embryogenic tissue is used, rupture pressure is set at 650 PSI and tissue is place approximately 2.5 inches from the retaining screen.

Selection of Transformed Embryos:

Transformed embryos are selected either using hygromycin (when the hygromycin B phosphotransferase (HPT) gene is used as the selectable marker) or chlorsulfuron (when the acetolactate synthase (ALS) gene is used as the selectable marker).

Following bombardment, the tissue is placed into fresh SB196 media and cultured as described above. Six to eight days post-bombardment, the SB196 is exchanged with fresh SB196 containing either 30 mg/L hygromycin or 100 ng/mL chlorsulfuron, depending on the selectable marker used. The selection media is refreshed weekly. Four to six weeks post-selection, green, transformed tissue is observed growing from untransformed, necrotic embryogenic clusters.

Embryo Maturation:

For production transformations, isolated, green tissue is removed and inoculated into multiwell plates to generate new, clonally propagated, transformed embryogenic suspension cultures. Transformed embryogenic clusters are cultured for four-six weeks in multiwell plates at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 μE/m²s. After this time embryo clusters are removed to a solid agar media, SB166, for one-two weeks and then subcultured to SB103 medium for 3-4 weeks to mature embryos. After maturation on plates in SB103, individual embryos are removed from the clusters, dried and screened for alterations in their fatty acid compositions as described in Example 7.

For model system transformations, embryos are matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters are removed to 35 mL of SB228 (SHaM liquid media) in a 250 mL Erlenmeyer flask. Tissue is maintained in SHaM liquid media on a rotary shaker at 130 rpm and 26° C. with cool white fluorescent lights on a 16:8 hr day/night photoperiod at a light intensity of 60-85 pE/m2/s for 2 weeks as embryos mature. Embryos grown for 2 weeks in SHaM liquid media are equivalent in size and fatty acid content to embryos cultured on SB166/SB103 for 5-8 weeks.

After maturation in SHaM liquid media, individual embryos are removed from the clusters, dried and screened for alterations in their fatty acid compositions as described in Example 7.

Media Recipes:

SB 196—FN Lite Liquid Proliferation Medium (per liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g glucose
2 mL 2,4-D (20 mg/L final concentration)
pH 5.7
8 g TC agar SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite

SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g activated charcoal
pH 5.7
2 g gelrite

SB 103 Solid Medium (per liter)

1 package MS salts (Gibco/BRL—Cat. No. 11117-066)
1 mL B5 vitamins 1000× stock
60 g maltose
750 mg $MgCl_2$ hexahydrate
pH 5.7
2 g gelrite

SB 71-4 Solid Medium (Per Liter)

1 bottle Gamborg's B5 salts w/sucrose (Gibco/BRL—Cat. No. 21153-036)
pH 5.7
5 g TC agar

2,4-D Stock

Obtain premade from Phytotech Cat. No. D 295—concentration 1 mg/mL

B5 Vitamins Stock (Per 100 mL)

Store aliquots at −20° C.
    10 g myo-inositol
    100 mg nicotinic acid
    100 mg pyridoxine HCl
    1 g thiamine
If the solution does not dissolve quickly enough, apply a low level of heat via the hot stir plate.

SB 228—Soybean Histodifferentiation & Maturation (SHaM) (Per Liter)

| | |
|---|---|
| DDI $H_2O$ | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |

Adjust volume to 900 mL
pH 5.8
Autoclave
Add to cooled media (≦30° C.):

| | |
|---|---|
| *Glutamine (final concentration 30 mM) 4% | 110 mL |

*Note:
Final volume will be 1010 mL after glutamine addition.

Since glutamine degrades relatively rapidly, it may be preferable to add immediately prior to using media. Expiration 2 weeks after glutamine is added; base media can be kept longer w/o glutamine.

FN-Lite Macro for SHAM 10×—Stock #1 (Per Liter)

| | |
|---|---|
| $(NH_4)2SO_4$ (ammonium sulfate) | 4.63 g |
| $KNO_3$ (potassium nitrate) | 28.3 g |
| $MgSO_4*7H_2O$ (magnesium sulfate heptahydrate) | 3.7 g |
| $KH_2PO_4$ (potassium phosphate, monobasic) | 1.85 g |
| Bring to volume | |
| Autoclave | |

MS Micro 1000×—Stock #2 (Per 1 Liter)

| | |
|---|---|
| $H_3BO_3$ (boric acid) | 6.2 g |
| $MnSO_4*H_2O$ (manganese sulfate monohydrate) | 16.9 g |
| $ZnSO4*7H20$ (zinc sulfate heptahydrate) | 8.6 g |
| $Na_2MoO_4*2H20$ (sodium molybdate dihydrate) | 0.25 g |
| $CuSO_4*5H_2O$ (copper sulfate pentahydrate) | 0.025 g |
| $CoCl_2*6H_2O$ (cobalt chloride hexahydrate) | 0.025 g |
| KI (potassium iodide) | 0.8300 g |
| Bring to volume | |
| Autoclave | |

FeEDTA 100×—Stock #3 (Per Liter)

| | |
|---|---|
| $Na_2EDTA*$ (sodium EDTA) | 3.73 g |
| $FeSO_4*7H_2O$ (iron sulfate heptahydrate) | 2.78 g |

*EDTA must be completely dissolved before adding iron.

Bring to Volume
Solution is photosensitive. Bottle(s) should be wrapped in foil to omit light.
Autoclave

Ca 100×—Stock #4 (Per Liter)

| | |
|---|---|
| $CaCl_2*2H_2O$ (calcium chloride dihydrate) | 44 g |
| Bring to Volume | |
| Autoclave | |

B5 Vitamin 1000×—Stock #5 (Per Liter)

| | |
|---|---|
| Thiamine*HCl | 10 g |
| Nicotinic Acid | 1 g |
| Pyridoxine*HCl | 1 g |
| Myo-Inositol | 100 g |
| Bring to Volume | |
| Store frozen | |

4% Glutamine—Stock #6 (Per Liter)

| | |
|---|---|
| DDI water heated to 30° C. | 900 mL |
| L-Glutamine | 40 g |
| Gradually add while stirring and applying low heat. | |
| Do not exceed 35° C. | |
| Bring to Volume | |
| Filter Sterilize | |
| Store frozen* | |

*Note:
Warm thawed stock in 31° C. bath to fully dissolve crystals.

Regeneration of Soybean Somatic Embryos into Plants:

In order to obtain whole plants from embryogenic suspension cultures, the tissue must be regenerated. Embyros are matured as described in above. After subculturing on medium SB103 for 3 weeks, individual embryos can be removed from the clusters and screened for alterations in their fatty acid compositions as described in Example 7. It should be noted that any detectable phenotype, resulting from the expression of the genes of interest, could be screened at this stage. This would include, but not be limited to, alterations in fatty acid profile, protein profile and content, carbohydrate content, growth rate, viability, or the ability to develop normally into a soybean plant.

Matured individual embryos are desiccated by placing them into an empty, small petri dish (35×10 mm) for approximately 4 to 7 days. The plates are sealed with fiber tape (creating a small humidity chamber). Desiccated embryos are planted into SB71-4 medium where they are left to germinate under the same culture conditions described above. Germinated plantlets are removed from germination medium and rinsed thoroughly with water and then are planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for fatty acids.

Example 7

Fatty Acid Analysis of Transgenic Somatic Soybean Embryos

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, more specifically Example 3). Most importantly, the model system is also predictive of the fatty acid composition of seeds from plants derived from transgenic embryos.

A subset of soybean embryos for each event generated from either production transformation or model system transformation (as described in Example 6) are harvested in the following way. Embryos (5-10 embryos) from each event are picked into glass GC vials and fatty acid methyl esters are prepared by transesterification. For transesterification, 50 µL of trimethylsulfonium hydroxide (TMSH) and 0.5 mL of hexane is added to the embryos in glass vials and incubated for 30 min at room temperature while shaking. Fatty acid methyl esters (5 µL injected from hexane layer) are separated and quantified using a Hewlett-Packard 6890 Gas Chromatograph fitted with an Omegawax 320 fused silica capillary column (Cat. No. 24152, Supelco Inc.). The oven temperature is programmed to hold at 220° C. for 2.6 min, increase to 240° C. at 20° C./min and then hold for an additional 2.4 min. Carrier gas is supplied by a Whatman hydrogen generator. Retention times are compared to those for methyl esters of standards commercially available (Nu-Chek Prep, Inc.). Events having good phenotype can be re-analyzed by GC using identical conditions except the oven temperature is held at 150° C. for 1 min and then increased to 240° C. at 5° C.

Example 8

Construction of Alternate Soybean Expression Vectors for Expression of *Euglena anabaena* UTEX 373 Delta-8 Desaturases (EaD8Des1-4)

In addition to the genes, promoters, terminators and gene cassettes described herein, one skilled in the art can appreciate that other promoter/gene/terminator cassette combinations can be synthesized in a way similar to, but not limited to, that described herein for expression of EaD8Des3. Similarly, it may be desirable to express other PUFA genes (such as those described below in Table 9), for co-expression with any of the delta-8 desaturases of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 7) and a transcription terminator (such as those listed in, but not limited to, Table 8) is used to clone the desired gene. NotI sites can be added to a gene of interest such as those listed in, but not limited to, Table 9 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 7

Seed-specific Promoters

| Promoter | Organism | Promoter Reference |
|---|---|---|
| β-conglycinin α'-subunit | soybean | Beachy et al., *EMBO J.* 4: 3047-3053 (1985) |
| kunitz trypsin inhibitor | soybean | Jofuku et al., *Plant Cell* 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., *Mol. Gen. Genet.* 225: 148-157 (1991) |
| β-conglycinin β-subunit | soybean | WO 2004/071467 |
| BD30 (also called P34) | soybean | WO 2004/071467 |
| legumin A2 | pea | Rerie et al., *Mol. Gen. Genet.* 225: 148-157 (1991) |

TABLE 8

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 9

PUFA Biosynthetic Pathway Genes

| Gene | Organism | Reference |
|---|---|---|
| delta-6 desaturase | *Saprolegnia diclina* | WO 2002/081668 |
| delta-6 desaturase | *Mortierella alpina* | U.S. Pat. No. 5,968,809 |
| elongase | *Mortierella alpina* | WO 2000/12720 U.S. Pat. No. 6,403,349 |
| delta-5 desaturase | *Mortierella alpina* | U.S. Pat. No. 6,075,183 |
| delta-5 desaturase | *Saprolegnia diclina* | WO 2002/081668 |
| delta-5 desaturase | *Peridinium* sp. | U.S. patent application No. 11/748,637 |
| delta-5 desaturase | *Euglena gracilis* | U.S. patent application No. 11/748,629 |
| delta-15 desaturase | *Fusarium moniliforme* | WO 2005/047479 |
| delta-17 desaturase | *Saprolegnia diclina* | WO 2002/081668 |
| elongase | *Thraustochytrium aureum* | WO 2002/08401 U.S. Pat. No. 6,677,145 |
| elongase | *Pavlova* sp. | Pereira et al., *Biochem. J.* 384: 357-366 (2004) |
| delta-4 desaturase | *Schizochytrium aggregatum* | WO 2002/090493 U.S. Pat. No. 7,045,683 |
| delta-4 desaturase | *Isochrysis galbana* | WO 2002/090493 U.S. Pat. No. 7,045,683 |
| delta-4 desaturase | *Thraustochytrium aureum* | WO 2002/090493 U.S. Pat. No. 7,045,683 |
| delta-4 desaturase | *Euglena gracilis* | U.S. patent application No. 10/552,127 |

TABLE 9-continued

PUFA Biosynthetic Pathway Genes

| Gene | Organism | Reference |
|---|---|---|
| delta-9 elongase | *Isochrysis galbana* | WO 2002/077213 |
| delta-9 elongase | *Euglena gracilis* | U.S. patent application No. 11/601,563 |
| delta-9 elongase | *Eutreptiella* sp. CCMP389 | U.S. patent application No. 11/601,564 |
| delta-8 desaturase | *Euglena gracilis* | WO 2000/34439 U.S. Pat. No. 6,825,017 WO 2004/057001 WO 2006/012325 |
| delta-8 desaturase | *Acanthamoeba castellanii* | Sayanova et al., *FEBS Lett.* 580: 1946-1952 (2006) |
| delta-8 desaturase | *Pavlova salina* | WO 2005/103253 |
| delta-8 desaturase | *Pavlova lutheri* | U.S. patent application No. 11/737,772 |
| delta-8 desaturase | *Tetruetrepia pomquetensis* CCMP1491 | U.S. patent application No. 11/876,115 |
| delta-8 desaturase | *Eutreptiella* sp. CCMP389 | U.S. patent application No. 11/876,115 |
| delta-8 desaturase | *Eutreptiella cf_gymnastica* CCMP1594 | U.S. patent application No. 11/876,115 |

Example 9

Synthesis of a Codon-Optimized Delta-8 Desaturase Gene for *Yarrowia lipolytica* (EaD8S)

The codon usage of the delta-8 desaturase gene (EaD8Des3; SEQ ID NO:19) of *Euglena anabaena* was optimized for expression in *Yarrowia lipolytica*, in a manner similar to that described in PCT Publication No. WO 2004/101753. Specifically, a codon-optimized delta-8 desaturase gene (designated "EaD8S", SEQ ID NO:48) was designed based on the coding sequence of EaD8Des3 (SEQ ID NOs:19 and 23), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, Gene, 265(1-2):11-23 (2001)). In addition to modification of the translation initiation site, 231 bp of the 1260 bp coding region were modified (18.3%) and 208 codons were optimized (49.5%). The GC content was reduced from 56.8% within the wild type gene (i.e., EaD8Des3) to 54.8% within the synthetic gene (i.e., EaD8S). A NcoI site and NotI sites were incorporated around the translation initiation codon and after the stop codon of EaD8S (SEQ ID NO:48), respectively. FIGS. 9A and 9B shows a comparison of the nucleotide sequences of EaD8Des3 (SEQ ID NO:19) and EaD8S (SEQ ID NO:48). The codon optimized EaD8S gene did not change any amino acid sequence of EaD8Des3 (SEQ ID NO:23). The designed EaD8S gene was synthesized by GenScript Corporation (Piscataway, N.J.) and cloned into pUC57 (GenBank Accession No. Y14837) to generate pEaD8S (SEQ ID NO:49; FIG. 10).

Based on the teachings herein concerning vector construction and suitable promoter and terminators for use in *Yarrowia lipolytica*, one of skill in the art will be able to construct additional plasmids suitable for expression of EaD8S (SEQ ID NO:48).

Example 10

Identification of a Delta-9 Elongase from *Euglena anabaena* UTEX 373

The present example describes the identification of delta-9 elongases from a Euglena anabaena UTEX 373 cDNA library. This work is also described in U.S. Provisional Application No. 60/911,925 (filed Apr. 16, 2007;.

Growth of *Euglena anabaena* UTEX 373 and Preparation of RNA

Amplified cDNA library eug1c was plated and colonies lifted as described in Example 1. A DNA probe was made using an agarose gel purified NcoI/NotI DNA fragment containing the *Euglena gracilis* delta-9 elongase gene, from pKR906 (SEQ ID NO:42; Example 5 and WO 2007/061845, which published May 31, 2007; the contents of which are hereby incorporated by reference) labeled with $P^{32}$ dCTP using the RadPrime DNA Labeling System (Cat. No. 18428-011, Invitrogen, Carlsbad, Calif.) following the manufacturer's instructions.

Colony lifts were probed and positives were identified and confirmed as described in Example 2. Plasmid DNA was isolated and sequenced exactly as described in Example 1 and sequences were aligned and compared using Sequencher™ (Version 4.2, Gene Codes Corporation, Ann Arbor, Mich.). In this way, the clones could be categorized into one of two distinct groups based on insert sequence (designated EaD9Elo1 and EaD9Elo2). EaD9Elo1 is also called EaD9e within but they are identical. Representative clones containing the cDNA for each class of sequence were chosen for further study, and the sequences for each representative plasmid (pLF121-1 and pLF121-2) are shown in SEQ ID NO:50 and SEQ ID NO:51, respectively. The sequence shown by a string of NNNN's represents a region of the polyA tail which was not sequenced. The coding sequences for EaD9Elo1 and EaD9Elo2 are shown in SEQ ID NO:52 and SEQ ID NO:53, respectively. The corresponding amino acid sequences for EaD9Elo1 and EaD9Elo2 are shown in SEQ ID NO:54 and SEQ ID NO:55, respectively.

Example 11

Construction of Soybean Expression Vector pKR1150 for Co-Expression of the *Euglena anabaena* UTEX 373 Delta-8 Desaturase (EaD8Des3) with a Delta-9 Elongase Derived from *Euglena anabaena* UTEX 373 (EaD9Elo1)

The present Example describes construction of a soybean vector for co-expression of EaD8Des3 with EaD9Elo1.

In order to introduce NotI and NcoI restriction sites at the 5' end of the coding sequences and a NotI site at the 3' end of the coding sequences, EaD9Elo1 was PCR amplified from pLF121-1 (SEQ ID NO:50; Example 10) with oligonucleotide primers oEAd9el1-1 (SEQ ID NO:56) and oEAd9el1-2 (SEQ ID NO:57) using the Phusion™ High-Fidelity DNA Polymerase (Cat. No. F553S, Finnzymes Oy, Finland) following the manufacturer's protocol. The resulting DNA fragments were cloned into the pCR-Blunt☐ cloning vector using the Zero Blunt☐ PCR Cloning Kit (Invitrogen Corporation), following the manufacturer's protocol, to produce pKR1137 (SEQ ID NO:58).

EaD9Elo1 was released from pKR1137 (SEQ ID NO:58) by digestion with NotI and cloned into the NotI site of pKR72 (SEQ ID NO:43; Example 5) to produce pKR1140 (SEQ ID NO:59).

Vector pKR1138 (SEQ ID NO:46; Example 5) was digested with BsiWI and the fragment containing EaD8Des3 was cloned into the BsiWI site of pKR1140 (SEQ ID NO:59) to give pKR1150 (SEQ ID NO:60). A schematic depiction of pKR1150 is shown in FIG. 11. In FIG. 11, EaD9Elo1 is called EAd9elong.

Example 12

Construction of an *Arabidopsis* Expression Vector pKR1192 for Expression of a *Euglena anabaena* delta-9 Elongase with a *Euglena anabaena* delta-8 Desaturase The AscI fragment of pKR1140 (SEQ ID NO:59; Example 11) was cloned into the AscI fragment of pKR277 (which is described in PCT Publication No. WO 04/071467) to produce pKR1173 (SEQ ID NO:61).

The Gy1/Pavelo/legA2 cassette was released from plasmid pKR336 (described in PCT Publication Nos. WO 04/071467; the contents of which are hereby incorporated by reference) by digestion with PstI/BamHI and cloned into the PstI/BamHI site of pKR268 (described in PCT Publication Nos. WO 04/071467) to produce pKR393 (SEQ ID NO:62). The Pavelo gene was released from pKR393 (SEQ ID NO:62) by digestion with NotI and the vector was re-ligated to from pKR407 (SEQ ID NO:63).

The NotI fragment from pLF120-3 (SEQ ID NO:30; Example 4), containing EaD8Des3 was cloned into the NotI fragment of pKR407 (SEQ ID NO:63) to produce pKR1176 (SEQ ID NO:64).

The PstI fragment from pKR1176 (SEQ ID NO:64), containing EaD8Des3 was cloned into the SbfI fragment of pKR1173 (SEQ ID NO:160 61) to produce pKR1178 (SEQ ID NO:65).

The AscI fragment of pKR1178 (SEQ ID NO:65), containing EaD9elo1 and EaD8Des3, was cloned into the AscI site of pKR92 (which was previously described in WO2007/061845 published on May 31, 2007 to produce pKR1192 (SEQ ID NO:66). A schematic depiction of pKR1192 is shown in FIG. 12. In FIG. 12, EaD9Elo1 is called EA D9elong but they are identical. In this way, EaD9Elo1 was expressed in *Arabidopsis* under control of the soybean beta-conglycinin promoter and the EaD8Des3 was expressed under control of the soybean glycinin Gy1 promoter. The soybean beta-conglycinin promoter and Gy1 promoter function as a strong, seed-specific promoters in *Arabidopsis*.

Example 13

Functional Analyses Of Delta-8 Desaturase In Soy

The present example describes the transformation and expression in soybean somatic embryos of pKR1152 (SEQ ID NO:47; Example 5) and pKR1150 (SEQ ID NO:60; Example 11).

Soybean embryogenic suspension culture (cv. Jack) was transformed with each of the vectors above and embryos were matured in soybean histodifferentiation and maturation liquid medium (SHaM liquid media; Schmidt et al., *Cell Biology and Morphogenesis*, 24:393 (2005)) as described in Example 6 and previously described in PCT Publication No. WO 2007/136877, published Nov. 29, 2007 (the contents of which are hereby incorporated by reference).

After maturation in SHaM liquid media a subset of transformed soybean embryos (i.e., 5-6 embryos per event) were harvested and analyzed as described herein.

In this way, approximately 30 events transformed with either pKR1152 (SEQ ID NO:47; Example 5; called Experiment MSE2136) or pKR1150 (SEQ ID NO:60; Example 11; called MSE2130) were analyzed and the five events having the highest average DGLA content (average of the 5 embryos analyzed) are shown in FIG. 13 or 14, respectively. In FIGS. 13 and 14, fatty acids are identified as 16:0 (palmitate), 18:0 (stearic acid), 18:1 (oleic acid), LA, ALA, EDA, ERA, DGLA and ETA. Fatty acid compositions are expressed as a weight percent (wt. %) of total fatty acids.

In FIGS. 13 and 14, elongation activity is expressed as % delta-9 elongation of C18 fatty acids (C18% delta-9 elong), calculated according to the following formula: ([product]/[substrate+product])*100. More specifically, the combined percent elongation for LA and ALA is determined as: ([DGLA+ETA+EDA+ERA]/[LA+ALA+DGLA+ETA+EDA+ERA])*100.

In FIGS. 13 and 14, the combined percent desaturation for EDA and ERA is shown as "C20% delta-8 desat", determined as: ([DGLA+ETA]/[DGLA+ETA+EDA+ERA])*100. This is also referred to as the overall % desaturation.

Example 14

Functional Analysis of *Arabidopsis* Seed Transformed with pKR1192 for Expression of a *Euglena anabaena* Delta-9 Elongase with a *Euglena anabaena* Delta-8 Desaturase in *Arabidopsis*

A fad3/fae1 double mutant (Smith et al., *Planta* 217:507-516 (2003)) of *Arabidopsis* produces seed where the ALA and 20:1 fatty acid content is less than 2.0%. The fad3/fae1 double mutant *Arabidopsis* plants were transformed with pKR1192 (SEQ ID NO:66), and plants were grown, maintained and seed was harvested as previously described in WO 2007/061845 (the contents of which are hereby incorporated by reference).

Segregating T2 seed was obtained from 21 individual events for each and bulk T2 seed lipid profiles for each event were obtained by transesterification with TMSH as described in herein with the following modifiations. For each event, a small scoopful of seeds (approximately 25-50 seed each scoopful) was crushed in 50 µL of TMSH in a 1.5 mL eppendorf tube. After shaking in TMSH for 15 min., 400 µL of heptane was added and the tubes were vortexed well, shaken for an additional 15 min and centrifuged at 13,000×g for 1 min. After shaking, the heptane layer was removed into glass GC vials and the fatty acid methyl esters were analyzed as described in herein.

The lipid profiles of T2 bulk seed for the 21 transformed events is shown in FIG. 15. Fatty acids are identified as 16:0 (palmitate), 18:0 (stearic acid), 18:1 (oleic acid), LA, ALA, 20:0 (eicosanoic acid), 20:1 (eicosenoic acid), EDA, DGLA, ERA and ETA; and, fatty acid compositions listed in FIG. x5 are expressed as a weight percent (wt. %) of total fatty acids.

In FIGS. 15, the combined percent desaturation for EDA and ERA is shown as "C20% delta-8 desat", determined as: ([DGLA+ETA]/[DGLA+ETA+EDA+ERA])*100. This is also referred to as the overall % desaturation.

What is claimed is:

1. An isolated polypeptide having delta-8 desaturase activity
wherein the isolated polypeptide comprises an amino acid sequence having at least 90% amino acid sequence identity, based on the Clustal V method of alignment, when compared to the amino acid sequence as set forth in SEQ ID NO:21, SEQ ID NO:22, SEQ ID NO:23 or SEQ ID NO:24.

2. The isolated polypeptide of claim 1, wherein the amino acid sequence of the isolated polypeptide has at least 95% amino acid sequence identity, based on the Clustal V method of alignment, when compared to the amino acid sequence as set forth in SEQ ID NO:21, SEQ ID NO:22, SEQ ID NO:23 or SEQ ID NO:24.

3. The isolated polypeptide of claim 2, wherein the amino acid sequence of the isolated polypeptide comprises the amino acid sequence as set forth in SEQ ID NO:21, SEQ ID NO:22, SEQ ID NO:23 or SEQ ID NO:24.

4. The isolated polypeptide of claim 1, wherein the isolated polypeptide is encoded by a nucleotide sequence having at least 90% nucleotide sequence identity, based on the BLASTN method of alignment, when compared to the nucleotide sequence as set forth in SEQ ID NO:17, SEQ ID NO:18, SEQ ID NO:19 or SEQ ID NO:20.

5. The isolated polypeptide of claim 4, wherein the isolated polypeptide is encoded by a nucleotide sequence having at least 95% nucleotide sequence identity, based on the BLASTN method of alignment, when compared to the nucleotide sequence as set forth in SEQ ID NO:17, SEQ ID NO:18, SEQ ID NO:19 or SEQ ID NO:20.

6. The isolated polypeptide of claim 5, wherein the isolated polypeptide is encoded by the nucleotide sequence of SEQ ID NO:17, SEQ ID NO:18, SEQ ID NO:19 or SEQ ID NO:20.

* * * * *

SEQUENCE LISTING

<160> NUMBER OF SEQ ID NOS: 66

<210> SEQ ID NO 1
<211> LENGTH: 604
<212> TYPE: DNA
<213> ORGANISM: Euglena anabaena

<400> SEQUENCE: 1
gccaactttg tacaaaaaag ttggattttt tttcggccca cgatctcaca tggtgaaaag      60
gccagcactt ccgctgaccg ttgatggtgt cacctatgat gtgtctgcct ggttgaacca     120
tcatccaggg ggtgctgaca tcattgagaa ctaccgcggt cgtgatgcca ctgatgtctt     180
tatggttatg cactctgaaa atgctgtgag taaactaaga aggatgccta tcatggaacc     240
atcatctcca ctgacgccta cgccaccgaa acccaactca gacgaaccgc aggaggattt     300
ccgcaagctc cgagatgagc tcatcgcagc aggaatgttc gacgcatcac cgatgtggta     360
cgcatataag acgctcacta cgctgggcct cggggtcctc gcggtgctat tgatgaccca     420
gtggcactgg tacctcgtcg gggcaatcgt gttgggcatt cacttccaac aaatgggttg     480
gttgtcgcac gatatctgcc accatcagct gttcaaggac cgatcgatca acaacgccat     540
cggcttgctt ttcgggaacg tcttgcaagg gttctctgtg acctggtgga aggacagtca     600
caac                                                                  604

<210> SEQ ID NO 2
<211> LENGTH: 1263
<212> TYPE: DNA
<213> ORGANISM: Euglena gracilis

```
<400> SEQUENCE: 2
atgaagtcaa agcgccaagc gcttcccctt acaattgatg gaacaacata tgatgtgtct    60
gcctgggtca atttccaccc tggtggtgcg gaaattatag agaattacca aggaagggat   120
gccactgatg ccttcatggt tatgcactct caagaagcct tcgacaagct caagcgcatg   180
cccaaaatca atcccagttc tgagttgcca ccccaggctg cagtgaatga agctcaagag   240
gatttccgga agctccgaga agagttgatc gcaactggca tgtttgatgc ctcccccctc   300
tggtactcat acaaaatcag caccacactg ggccttggag tgctgggtta tttcctgatg   360
gttcagtatc agatgtattt cattggggca gtgttgcttg ggatgcacta tcaacagatg   420
ggctggcttt tcatgacat ttgccaccac cagactttca agaaccggaa ctggaacaac   480
ctcgtgggac tggtatttgg caatggtctg caaggttttt ccgtgacatg gtggaaggac   540
agacacaatg cacatcattc ggcaaccaat gttcaagggc acgaccctga tattgacaac   600
ctccccctct tagcctggtc tgaggatgac gtcacgggg cgtcaccgat tcccgcaag   660 ctcattcagt tccagcagta ctatttcttg gtcatctgta tcttgttgcg gttcatttgg   720
tgtttccaga gcgtgttgac cgtgcgcagt ttgaaggaca gagataacca attctatcgc   780
tctcagtata agaaggaggc cattggcctc gccctgcact ggaccttgaa gaccctgttc   840
cacttattct ttatgcccag catcctcaca tcgctgttgg tgttttcgt ttcggagctg   900 gttggcggct tcggcattgc gatcgtggtg ttcatgaacc actacccact ggagaagatc   960
ggggactcag tctgggatgg ccatggattc tcggttggcc agatccatga gaccatgaac  1020
attcggcgag ggattatcac agattggttt ttcggaggct tgaattacca gattgagcac  1080
catttgtggc cgaccctccc tcgccacaac ctgacagcgg ttagctacca ggtggaacag  1140
ctgtgccaga agcacaacct gccgtatcgg aacccgctgc cccatgaagg gttggtcatc  1200
ctgctgcgct atctggcggt gttcgcccgg atggcggaga agcaacccgc ggggaaggct  1260
cta                                                                1263

<210> SEQ ID NO 3
<211> LENGTH: 27
<212> TYPE: DNA
<213> ORGANISM: Artificial Sequence
<220> FEATURE:
<223> OTHER INFORMATION: specific primer pDonor222Eg5-1

<400> SEQUENCE: 3
gccaactttg tacaaaaaag ttggatt                                       27

<210> SEQ ID NO 4
<211> LENGTH: 21
<212> TYPE: DNA
<213> ORGANISM: Artificial Sequence
<220> FEATURE:
<223> OTHER INFORMATION: primer D8DEG3-1
<220> FEATURE:
<221> NAME/KEY: misc_feature
<222> LOCATION: (7)..(7)
<223> OTHER INFORMATION: n is a, c, g, or t

<400> SEQUENCE: 4
rttrtgncka tctttccacc a                                             21

<210> SEQ ID NO 5
<211> LENGTH: 21
<212> TYPE: DNA
<213> ORGANISM: Artificial Sequence
<220> FEATURE:
```

<223> OTHER INFORMATION: primer D8DEG3-2
<220> FEATURE:
<221> NAME/KEY: misc_feature
<222> LOCATION: (7)..(7)
<223> OTHER INFORMATION: n is a, c, g, or t

<400> SEQUENCE: 5
rttrtgnckg tctttccacc a                                            21

<210> SEQ ID NO 6
<211> LENGTH: 21
<212> TYPE: DNA
<213> ORGANISM: Artificial Sequence
<220> FEATURE:
<223> OTHER INFORMATION: primer D8DEG3-3
<220> FEATURE:
<221> NAME/KEY: misc_feature
<222> LOCATION: (7)..(7)
<223> OTHER INFORMATION: n is a, c, g, or t

<400> SEQUENCE: 6
rttrtgncka tccttccacc a                                            21

<210> SEQ ID NO 7
<211> LENGTH: 21
<212> TYPE: DNA
<213> ORGANISM: Artificial Sequence
<220> FEATURE:
<223> OTHER INFORMATION: primer D8DEG3-4
<220> FEATURE:
<221> NAME/KEY: misc_feature
<222> LOCATION: (7)..(7)
<223> OTHER INFORMATION: n is a, c, g, or t

<400> SEQUENCE: 7
rttrtgnckg tccttccacc a                                            21

<210> SEQ ID NO 8
<211> LENGTH: 19
<212> TYPE: DNA
<213> ORGANISM: Artificial Sequence
<220> FEATURE:
<223> OTHER INFORMATION: primer 8-T7

<400> SEQUENCE: 8
ggaaacagct atgaccatg                                               19

<210> SEQ ID NO 9
<211> LENGTH: 22
<212> TYPE: DNA
<213> ORGANISM: Artificial Sequence
<220> FEATURE:
<223> OTHER INFORMATION: primer M13-28Rev

<400> SEQUENCE: 9
gtaatacgac tcactatagg gc                                           22

<210> SEQ ID NO 10
<211> LENGTH: 4116
<212> TYPE: DNA
<213> ORGANISM: Artificial Sequence
<220> FEATURE:
<223> OTHER INFORMATION: plasmid pHD23-1

<400> SEQUENCE: 10
cctgaattcc agcacactgg cggccgttac tagtggatcc gagctcggta ccaagcttga      60
tgcatagctt gagtattcta acgcgtcacc taaatagctt ggcgtaatca tggtcatagc     120

```
tgtttcctgt gtgaaattgt tatccgctca caattccaca caacatacga gccggaagca     180
taaagtgtaa agcctggggt gcctaatgag tgagctaact cacattaatt gcgttgcgct     240
cactgcccgc tttccagtcg ggaaacctgt cgtgccagct gcattaatga atcggccaac     300
gcgcggggag aggcggtttg cgtattgggc gctcttccgc ttcctcgctc actgactcgc     360
tgcgctcggt cgttcggctg cggcgagcgg tatcagctca ctcaaaggcg gtaatacggt     420
tatccacaga atcaggggat aacgcaggaa agaacatgtg agcaaaaggc cagcaaaagg     480
ccaggaaccg taaaaaggcc gcgttgctgg cgttttttcca taggctccgc cccctgacg      540 agcatcacaa aaatcgacgc tcaagtcaga ggtggcgaaa cccgacagga ctataaagat     600
accaggcgtt tccccctgga agctccctcg tgcgctctcc tgttccgacc ctgccgctta     660
ccggatacct gtccgccttt ctcccttcgg aagcgtggc gctttctcat agctcacgct      720
gtaggtatct cagttcggtg taggtcgttc gctccaagct gggctgtgtg cacgaacccc     780
ccgttcagcc cgaccgctgc gccttatccg gtaactatcg tcttgagtcc aacccggtaa     840
gacacgactt atcgccactg gcagcagcca ctggtaacag gattagcaga gcgaggtatg     900
taggcggtgc tacagagttc ttgaagtggt ggcctaacta cggctacact agaagaacag     960
tatttggtat ctgcgctctg ctgaagccag ttaccttcgg aaaaagagtt ggtagctctt    1020
gatccggcaa acaaaccacc gctggtagcg gtggtttttt tgtttgcaag cagcagatta    1080
cgcgcagaaa aaaggatctc aagaagatcc tttgatcttt tctacgggg tctgacgctc     1140 agtggaacga aaactcacgt taagggattt tggtcatgag attatcaaaa aggatcttca    1200
cctagatcct tttaaattaa aaatgaagtt ttagcacgtg tcagtcctgc tcctcggcca    1260
cgaagtgcac gcagttgccg gccgggtcgc gcagggcgaa ctcccgcccc cacggctgct    1320
cgccgatctc ggtcatggcc ggcccggagg cgtcccggaa gttcgtggac acgacctccg    1380
accactcggc gtacagctcg tccaggccgc gcacccacac ccaggccagg gtgttgtccg    1440
gcaccacctg gtcctggacc gcgctgatga acagggtcac gtcgtcccgg accacaccgg    1500
cgaagtcgtc ctccacgaag tcccgggaga cccgagccg gtcggtccag aactcgaccg     1560
ctccggcgac gtcgcgcgcg gtgagcaccg gaacggcact ggtcaacttg gccatggtgg    1620
ccctcctcac gtgctattat tgaagcattt atcagggtta ttgtctcatg agcggataca    1680
tatttgaatg tatttagaaa aataaacaaa taggggttcc gcgcacattt ccccgaaaag    1740
tgccacctga tgcggtgtga ataccgcac agatgcgtaa ggagaaaata ccgcatcagg     1800
aaattgtaag cgttaataat tcagaagaac tcgtcaagaa ggcgatagaa ggcgatgcgc    1860
tgcgaatcgg gagcggcgat accgtaaagc acgaggaagc ggtcagccca ttcgccgcca    1920
agctcttcag caatatcacg ggtagccaac gctatgtcct gatagcggtc cgccacaccc    1980
agccggccac agtcgatgaa tccagaaaag cggccatttt ccaccatgat attcggcaag    2040
caggcatcgc catgggtcac gacgagatcc tcgccgtcgg catgctcgc cttgagcctg     2100 gcgaacagtt cggctggcgc gagcccctga tgctcttcgt ccagatcatc ctgatcgaca    2160
agaccggctt ccatccgagt acgtgctcgc tcgatgcgat gtttcgcttg gtggtcgaat    2220
gggcaggtag ccggatcaag cgtatgcagc cgccgcattg catcagccat gatggatact    2280
ttctcggcag gagcaaggtg agatgacagg agatcctgcc ccggcacttc gcccaatagc    2340
agccagtccc ttcccgcttc agtgacaacg tcgagcacag ctgcgcaagg aacgcccgtc    2400
gtggccagcc acgatagccg cgctgcctcg tcttgcagtt cattcagggc accggacagg    2460
tcggtcttga caaaaagaac cgggcgcccc tgcgctgaca gccggaacac ggcggcatca    2520
```

-continued

```
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttcccttgtc cagatagccc agtagctgac attcatccgg   2880
ggtcagcacc gtttctgcgg actggctttc tacgtgaaaa ggatctaggt gaagatcctt   2940
tttgataatc tcatgcctga catttatatt ccccagaaca tcaggttaat ggcgttttg    3000
atgtcatttt cgcggtggct gagatcagcc acttcttccc cgataacgga gaccggcaca   3060
ctggccatat cggtggtcat catgcgccag ctttcatccc cgatatgcac accgggtaa    3120
agttcacggg agactttatc tgacagcaga cgtgcactgg ccaggggat caccatccgt     3180
cgccccggcg tgtcaataat atcactctgt acatccacaa acagacgata acggctctct   3240
cttttatagg tgtaaacctt aaactgccgt acgtataggc tgcgcaactg ttgggaaggg   3300
cgatcggtgc gggcctcttc gctattacgc cagctggcga aagggggatg tgctgcaagg   3360
cgattaagtt gggtaacgcc agggttttcc cagtcacgac gttgtaaaac gacggccagt   3420
gaattgtaat acgactcact ataggggcgaa ttgggccctc tagatgcatg ctcgagcggc   3480
cgccagtgtg atggatatct gcagaattca gggccaactt tgtacaaaaa agttggattt   3540
tttttcggcc cacgatctca catggtgaaa aggccagcac ttccgctgac cgttgatggt   3600
gtcacctatg atgtgtctgc ctggttgaac catcatccag ggggtgctga catcattgag   3660
aactaccgcg gtcgtgatgc cactgatgtc tttatggtta tgcactctga aaatgctgtg   3720
agtaaactaa gaaggatgcc tatcatggaa ccatcatctc cactgacgcc tacgccaccg   3780
aaacccaact cagacgaacc gcaggaggat ttccgcaagc tccgagatga gctcatcgca   3840
gcaggaatgt tcgacgcatc accgatgtgg tacgcatata agacgctcac tacgctgggc   3900
ctcggggtcc tcgcggtgct attgatgacc cagtggcact ggtacctcgt cggggcaatc   3960
gtgttgggca ttcacttcca acaaatgggt tggttgtcgc acgatatctg ccaccatcag   4020
ctgttcaagg accgatcgat caacaacgcc atcggcttgc ttttcgggaa cgtcttgcaa   4080
gggttctctg tgacctggtg gaaggacagt cacaac                              4116
```

<210> SEQ ID NO 11
<211> LENGTH: 419
<212> TYPE: PRT
<213> ORGANISM: Euglena gracilis

<400> SEQUENCE: 11

Met Lys Ser Lys Arg Gln Ala Leu Ser Pro Leu Gln Leu Met Glu Gln
1               5                   10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80

Arg Lys Leu Arg Glu Glu Leu Ile Ala Thr Gly Met Phe Asp Ala Ser
                85                  90                  95

```
Pro Leu Trp Tyr Ser Tyr Lys Ile Ser Thr Thr Leu Gly Leu Gly Val
                100                 105                 110

Leu Gly Tyr Phe Leu Met Val Gln Tyr Gln Met Tyr Phe Ile Gly Ala
            115                 120                 125

Val Leu Leu Gly Met His Tyr Gln Gln Met Gly Trp Leu Ser His Asp
130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His Ser Ala Thr Asn Val Gln Gly His
            180                 185                 190

Asp Pro Asp Ile Asp Asn Leu Pro Pro Leu Ala Trp Ser Glu Asp Asp
            195                 200                 205

Val Thr Arg Ala Ser Pro Ile Ser Arg Lys Leu Ile Gln Phe Gln Gln
210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
            275                 280                 285

Ser Leu Leu Val Phe Phe Val Ser Glu Leu Val Gly Gly Phe Gly Ile
            290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
            355                 360                 365

Leu Thr Ala Val Ser Tyr Gln Val Glu Gln Leu Cys Gln Lys His Asn
370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
                405                 410                 415

Lys Ala Leu

<210> SEQ ID NO 12
<211> LENGTH: 20
<212> TYPE: DNA
<213> ORGANISM: Artificial Sequence
<220> FEATURE:
<223> OTHER INFORMATION: primer EaD8seq-1

<400> SEQUENCE: 12
ccaccatcag ctgttcaagg                                              20

<210> SEQ ID NO 13
<211> LENGTH: 4363
<212> TYPE: DNA
<213> ORGANISM: Artificial Sequence
<220> FEATURE:
```

<223> OTHER INFORMATION: plasmid pLF118-1
<220> FEATURE:
<221> NAME/KEY: misc_feature
<222> LOCATION: (4311)..(4350)
<223> OTHER INFORMATION: n is a, c, g, or t

<400> SEQUENCE: 13

```
gtacaaagtt ggcattataa gaaagcattg cttatcaatt tgttgcaacg aacaggtcac      60
tatcagtcaa aataaaatca ttatttgcca tccagctgat atcccctata gtgagtcgta     120
ttacatggtc atagctgttt cctggcagct ctggcccgtg tctcaaaatc tctgatgtta     180
cattgcacaa gataaaaata tatcatcatg ttagaaaaac tcatcgagca tcaaatgaaa     240
ctgcaattta ttcatatcag gattatcaat accatatttt tgaaaaagcc gtttctgtaa     300
tgaaggagaa aactcaccga ggcagttcca taggatggca agatcctggt atcggtctgc     360
gattccgact cgtccaacat caatacaacc tattaatttc ccctcgtcaa aaataaggtt     420
atcaagtgag aaatcaccat gagtgacgac tgaatccggt gagaatggca aaagcttatg     480
catttctttc cagacttgtt caacaggcca gccattacgc tcgtcatcaa aatcactcgc     540
atcaaccaaa ccgttattca ttcgtgattg cgcctgagcg agacgaaata cgcgatcgct     600
gttaaaagga caattacaaa caggaatcga atgcaaccgg cgcaggaaca ctgccagcgc     660
atcaacaata ttttcacctg aatcaggata ttcttctaat acctggaatg ctgttttccc     720
ggggatcgca gtggtgagta accatgcatc atcaggagta cggataaaat gcttgatggt     780
cggaagaggc ataaattccg tcagccagtt tagtctgacc atctcatctg taacatcatt     840
ggcaacgcta cctttgccat gtttcagaaa caactctggc gcatcgggct tcccatacaa     900
tcgatagatt gtcgcacctg attgcccgac attatcgcga gcccatttat acccatataa     960
atcagcatcc atgttggaat ttaatcgcgg cctcgagcaa gacgtttccc gttgaatatg    1020
gctcatagat ctttttctcca tcactgatag ggagtggtaa aataactcca tcaatgatag    1080
agtgtcaaca acatgaccaa aatcccttaa cgtgagttac gcgtattaat tgcgttgcgc    1140
tcactgcccg ctttccagtc gggaaacctg tcgtgccagc tgcattaatg aatcggccaa    1200
cgcgcgggga gaggcggttt gcgtattggg cgctcttccg cttcctcgct cactgactcg    1260
ctgcgctcgg tcgttcggct gcggcgagcg gtatcagctc actcaaaggc ggtaatacgg    1320
ttatccacag aatcagggga taacgcagga aagaacatgt gagcaaaagg ccagcaaaag    1380
gccaggaacc gtaaaaaggc cgcgttgctg gcgtttttcc ataggctccg cccccctgac    1440
gagcatcaca aaaatcgacg ctcaagtcag aggtggcgaa acccgacagg actataaaga    1500
taccaggcgt ttccccctgg aagctccctc gtgcgctctc ctgttccgac cctgccgctt    1560
accggatacc tgtccgcctt tctcccttcg ggaagcgtgg cgctttctca atgctcacgc    1620
tgtaggtatc tcagttcggt gtaggtcgtt cgctccaagc tgggctgtgt gcacgaaccc    1680
cccgttcagc ccgaccgctg cgccttatcc ggtaactatc gtcttgagtc aacccggta    1740
agacacgact tatcgccact ggcagcagcc actggtaaca ggattagcag agcgaggtat    1800
gtaggcggtg ctacagagtt cttgaagtgg tggcctaact acggttacac tagaagaaca    1860
gtatttggta tctgcgctct gctgaagcca gttaccttcg gaaaaagagt tggtagctct    1920
tgatccggca aacaaaccac cgctggtagc ggtggttttt ttgtttgcaa gcagcagatt    1980
acgcgcagaa aaaaggatc tcaagaagat cctttgatct tttctacggg gtctgacgct    2040
cagggaacga cgcgtaccgc tagccaggaa gagtttgtag aaacgcaaaa aggccatccg    2100
tcaggatggc cttctgctta gtttgatgcc tggcagttta tggcgggcgt cctgcccgcc    2160
```

| | |
|---|---|
| accctccggg ccgttgcttc acaacgttca aatccgctcc cggcggattt gtcctactca | 2220 |
| ggagagcgtt caccgacaaa caacagataa acgaaaggc ccagtcttcc gactgagcct | 2280 |
| ttcgttttat ttgatgcctg gcagttccct actctcgcgt taacgctagc atggatgttt | 2340 |
| tcccagtcac gacgttgtaa aacgacggcc agtcttaagc tcgggcccca ataatgatt | 2400 |
| ttattttgac tgatagtgac ctgttcgttg caacaaattg atgagcaatg cttttttata | 2460 |
| atgccaactt tgtacaaaaa agttggtatt ttttttcggc ccacgatctc acatggtgaa | 2520 |
| aaggccagca cttccgctga ccgttgatgg tgtcacctat gatgtgtctg cctggttgaa | 2580 |
| ccatcatcca gggggtgctg acatcattga gaactaccgc ggtcgtgatg ccactgatgt | 2640 |
| ctttatggtt atgcactctg aaaatgctgt gagtaaacta agaaggatgc ctatcatgga | 2700 |
| accatcatct ccactgacgc ctacgccacc gaaacccaac tcagacgaac cgcaggagga | 2760 |
| tttccgcaag ctccgagatg agctcatcgc agcaggaatg ttcgacgcat caccgatgtg | 2820 |
| gtacgcatat aagacgctca ctacgctggg cctcggggtc ctcgcggtgc tattgatgac | 2880 |
| ccagtggcac tggtacctcg tcggggcaat cgtgttgggc attcacttcc aacaaatggg | 2940 |
| ttggttgtcg cacgatatct gccaccatca gctgttcaag gaccgatcga tcaacaacgc | 3000 |
| catcggcttg cttttcggga acgtcttgca agggttctct gtgacctggt ggaaggacag | 3060 |
| gcacaatgca caccactccg ccaccaacgt gcaaggccac gaccccgaca ttgacaacct | 3120 |
| gccgctgctg gcatggtcca aggaggacgt ggagagggcc ggcccgttct cacggcggat | 3180 |
| gatcaagtac cagcaatact acttcttctt catctgtgcc ctcctgaggt tcatctggtg | 3240 |
| cttccagagc atccacacag ccaagggcct gaaggatcgc agcaaccagt actaccgcag | 3300 |
| gcagtacgag aaagagagcg tgggcctggc cctccactgg ggcctgaagg cgttgttcta | 3360 |
| ctactttat atgccaagct tcttgaccgg actcatggtg tttttcgtgt ccgagttgct | 3420 |
| tggggcttc ggcatcgcca tcgtggtgtt catgaaccac taccccctgg agaagatcca | 3480 |
| ggactcggtg tgggacggcc acggcttttg cgccggccag attcacgaaa cgatgaacgt | 3540 |
| ccagcgggga ctcgtcacgg actggttctt cggtgggctg aattaccaaa tcgagcacca | 3600 |
| cctgtggccg acgctgcccc ggcacaacct gacggcggcc agcatcaaag tggagcagtt | 3660 |
| gtgcaagaag cacaacttgc cgtatcgcag ccccccaatg ctggaggggg tgggcatcct | 3720 |
| gatcagctac ctgggcacct tgcccgcat ggtggcaaag gccgacaagg cgtaagtgac | 3780 |
| atggcaccgc tcaggactct gatagttggg ctgacgcttt ggttgtcatc ccttgccct | 3840 |
| tcatatcacc tctggcccga ctcggattct ctctggagct ctaacctgtt caatgtggac | 3900 |
| tgctacacat atgagttcct cggatctctg gggaacagcc tttggaagac tcggcattcc | 3960 |
| tttatgcttg gaaggcttga gacctcttct gcaggactca aggcaaccct cctcagtgtc | 4020 |
| gggaaagagt atttgccttc ggcctgacct gctatacctc acccaacatg cgtcgtggaa | 4080 |
| ttaatgatca ttgttaaagt ttggtgcgat ttctgattgt gcgcaaattg tgcggaggcg | 4140 |
| cggcacacac gttctcctcc ggccatcaca gtccaaggtc aaatttccaa ctctaatcac | 4200 |
| catgatgggc cacagcttg cacactattt ctggcagagc tgcaagaaac tcgccacagt | 4260 |
| gagttttgag agatgttcag tgctgcgcat ttgatcggca ttgtggcctt nnnnnnnnnn | 4320 |
| nnnnnnnnnn nnnnnnnnnn nnnnnnnnnn acccaactt ctt | 4363 |

<210> SEQ ID NO 14
<211> LENGTH: 4307
<212> TYPE: DNA
<213> ORGANISM: Artificial Sequence
<220> FEATURE:

<223> OTHER INFORMATION: plasmid pLF118-2
<220> FEATURE:
<221> NAME/KEY: misc_feature
<222> LOCATION: (4255)..(4294)
<223> OTHER INFORMATION: n is a, c, g, or t

<400> SEQUENCE: 14

```
gtacaaagtt ggcattataa gaaagcattg cttatcaatt tgttgcaacg aacaggtcac      60
tatcagtcaa aataaaatca ttatttgcca tccagctgat atccoctata gtgagtcgta     120
ttacatggtc atagctgttt cctggcagct ctggcccgtg tctcaaaatc tctgatgtta     180
cattgcacaa gataaaaata tatcatcatg ttagaaaaac tcatcgagca tcaaatgaaa     240
ctgcaattta ttcatatcag gattatcaat accatatttt tgaaaaagcc gtttctgtaa     300
tgaaggagaa aactcaccga ggcagttcca taggatggca agatcctggt atcggtctgc     360
gattccgact cgtccaacat caatacaacc tattaatttc ccctcgtcaa aaataaggtt     420
atcaagtgag aaatcaccat gagtgacgac tgaatccggt gagaatggca aaagcttatg     480
catttctttc cagacttgtt caacaggcca gccattacgc tcgtcatcaa aatcactcgc     540
atcaaccaaa ccgttattca ttcgtgattg cgcctgagcg agacgaaata cgcgatcgct     600
gttaaaagga caattacaaa caggaatcga atgcaaccgg cgcaggaaca ctgccagcgc     660
atcaacaata ttttcacctg aatcaggata ttcttctaat acctggaatg ctgttttccc     720
ggggatcgca gtggtgagta accatgcatc atcaggagta cggataaaat gcttgatggt     780
cggaagaggc ataaattccg tcagccagtt tagtctgacc atctcatctg taacatcatt     840
ggcaacgcta cctttgccat gtttcagaaa caactctggc gcatcgggct tcccatacaa     900
tcgatagatt gtcgcacctg attgcccgac attatcgcga gcccatttat acccatataa     960
atcagcatcc atgttggaat ttaatcgcgg cctcgagcaa gacgtttccc gttgaatatg    1020
gctcatagat ctttttctcca tcactgatag ggagtggtaa aataactcca tcaatgatag    1080
agtgtcaaca acatgaccaa aatcccttaa cgtgagttac gcgtattaat tgcgttgcgc    1140
tcactgcccg ctttccagtc gggaaacctg tcgtgccagc tgcattaatg aatcggccaa    1200
cgcgcgggga gaggcggttt gcgtattggg cgctcttccg cttcctcgct cactgactcg    1260
ctgcgctcgg tcgttcggct gcggcgagcg gtatcagctc actcaaaggc ggtaatacgg    1320
ttatccacag aatcagggga taacgcagga aagaacatgt gagcaaaagg ccagcaaaag    1380
gccaggaacc gtaaaaaggc cgcgttgctg gcgtttttcc ataggctccg ccccccctgac   1440
gagcatcaca aaaatcgacg ctcaagtcag aggtggcgaa acccgacagg actataaaga    1500
taccaggcgt ttccccctgg aagctccctc gtgcgctctc ctgttccgac cctgccgctt    1560
accggatacc tgtccgcctt tctcccttcg ggaagcgtgg cgctttctca atgctcacgc    1620
tgtaggtatc tcagttcggt gtaggtcgtt cgctccaagc tgggctgtgt gcacgaaccc    1680
cccgttcagc ccgaccgctg cgccttatcc ggtaactatc gtcttgagtc caacccggta    1740
agacacgact tatcgccact ggcagcagcc actggtaaca ggattagcag agcgaggtat    1800
gtaggcggtg ctacagagtt cttgaagtgg tggcctaact acggttacac tagaagaaca    1860
gtatttggta tctgcgctct gctgaagcca gttaccttcg gaaaaagagt tggtagctct    1920
tgatccggca aacaaaccac cgctggtagc ggtggttttt tgtttgcaa gcagcagatt     1980
acgcgcagaa aaaaaggatc tcaagaagat cctttgatct tttctacggg gtctgacgct    2040
cagggaacga cgcgtaccgc tagccaggaa gagtttgtag aaacgcaaaa aggccatccg    2100
tcaggatggc cttctgctta gtttgatgcc tggcagttta tggcgggcgt cctgcccgcc    2160
```

```
accctccggg ccgttgcttc acaacgttca aatccgctcc cggcggattt gtcctactca    2220
ggagagcgtt caccgacaaa caacagataa aacgaaaggc ccagtcttcc gactgagcct    2280
ttcgttttat ttgatgcctg gcagttccct actctcgcgt taacgctagc atggatgttt    2340
tcccagtcac gacgttgtaa aacgacggcc agtcttaagc tcgggcccca ataatgatt     2400
ttattttgac tgatagtgac ctgttcgttg caacaaattg atgagcaatg cttttttata    2460
atgccaactt tgtacaaaaa agttggattt tttttcggcc cacgatctca catggtgaaa    2520
aggccagcac ttccgctgac cgttgatggt gtcacctatg atgtgtctgc ctggttgaac    2580
catcatccag ggggtgctga catcattgag aactaccgcg tcgtgatgc cactgatgtc     2640
tttatggtta tgcactctga aaatgctgtg agtaaactaa aaggatgcc tatcatggaa     2700
ccatcatctc cactgacgcc tacgccaccg aaacccaact cagacgaacc gcaggaggat    2760
ttccgcaagc tccgagatga gctcatcgca gcaggaatgt tcgacgcatc accgatgtgg    2820
tacgcatata agacgctcag tacgctgggc ctcggggtcc tcgcggtgct attgatgacc    2880
cagtggcact ggtacctcgt cggggcaatc gtgttgggca ttcacttcca acaaatgggt    2940
tggttgtcgc acgatatctg ccaccatcag ctgttcaagg accgatcgat caacaacgcc    3000
atcggcttgc ttttcgggaa cgtcttgcaa gggttctctg tgacctggtg aaggacagg     3060
cacaatgcac accactccgc caccaacgtg caaggccacg accccgacat tgacaacctg    3120
ccgctgctgg catggtccaa ggaggacgtg gagagggccg gcccgttctc acggcggatt    3180
atcaagtacc agcaatacta cttcttcttc atctgtgccc tcctgaggtt catctggtgc    3240
ttccagagca tccacacagc cacgggcctg aaggatcgca gcaaccagta ctaccgcagg    3300
cagtacgaga aagagagcgt gggcctggcc ctccactggg gcctgaaggc gttgttctac    3360
tactttata tgccaagctt cttgaccgga ctcatggtgt ttttcgtgtc cgagttgctt     3420
gggggcttcg gcatcgccat cgtggtgttc atgaaccact accccctgga gaagatccag    3480
gactcggtgt gggacggcca cggcttttgc gccggccaga ttcacgaaac gatgaacgtc    3540
cagcggggac tcgtcacgga ctggttcttc ggtgggctga attaccaaat cgagcaccac    3600
ctgtggccga cgctgccccg gcacaacctg acggcggcca gcatcaaagt ggagcagttg    3660
tgcaagaagc acaacttgcc gtatcgcagc ccccaatgc tggaggggt gggcatcctg      3720
atcagctacc tgggcacctt tgcccgcatg gtggcaaagg ccgacaaggc gtaagtgaca    3780
tggcaccgct caggactctg atagttgggc tgacgctttg gttgtcatcc cttgcccctt    3840
catatccct ctgccctac tcggattctc tctggagctc taacctgttc aatgtggact       3900
gctacacata tgagttcctc ggatctctgg ggaacagcct ttggaagact cggcattcct    3960
ttatgcttgg aaggcttgag acctcttctg caggactcaa ggcaaccctc ctcagtgtcg    4020
ggaaagagta tttgccttcg gcctgacctg ctatacctca cccaacatgc gtcgtggaat    4080
taatgatcat tgttaagagt ttggtgcgat ttctgattgt gcgcaaattg tgcggaggcg    4140
cggcacacac gttctcctcc ggccatcaca gtccaaggtc aaatttccaa ctctaatcac    4200
catgatgggc cacagctttg cacactattt ctggcagagc tgcaagaaac tcgcnnnnnn    4260
nnnnnnnnnn nnnnnnnnnn nnnnnnnnnn nnnnacccaa ctttctt                  4307
```

<210> SEQ ID NO 15
<211> LENGTH: 4307
<212> TYPE: DNA
<213> ORGANISM: Artificial Sequence
<220> FEATURE:
<223> OTHER INFORMATION: plasmid pLF118-3
<220> FEATURE:

<221> NAME/KEY: misc_feature
<222> LOCATION: (4255)..(4294)
<223> OTHER INFORMATION: n is a, c, g, or t

<400> SEQUENCE: 15

| | | | | | |
|---|---|---|---|---|---|
| gtacaaagtt | ggcattataa | gaaagcattg | cttatcaatt | tgttgcaacg | aacaggtcac | 60 |
| tatcagtcaa | aataaaatca | ttatttgcca | tccagctgat | atccctata | gtgagtcgta | 120 |
| ttacatggtc | atagctgttt | cctggcagct | ctggcccgtg | tctcaaaatc | tctgatgtta | 180 |
| cattgcacaa | gataaaaata | tatcatcatg | ttagaaaaac | tcatcgagca | tcaaatgaaa | 240 |
| ctgcaattta | ttcatatcag | gattatcaat | accatatttt | tgaaaagcc | gtttctgtaa | 300 |
| tgaaggagaa | aactcaccga | ggcagttcca | taggatggca | agatcctggt | atcggtctgc | 360 |
| gattccgact | cgtccaacat | caatacaacc | tattaatttc | ccctcgtcaa | aaataaggtt | 420 |
| atcaagtgag | aaatcaccat | gagtgacgac | tgaatccggt | gagaatggca | aaagcttatg | 480 |
| catttctttc | cagacttgtt | caacaggcca | gccattacgc | tcgtcatcaa | aatcactcgc | 540 |
| atcaaccaaa | ccgttattca | ttcgtgattg | cgcctgagcg | agacgaaata | cgcgatcgct | 600 |
| gttaaaagga | caattacaaa | caggaatcga | atgcaaccgg | cgcaggaaca | ctgccagcgc | 660 |
| atcaacaata | ttttcacctg | aatcaggata | ttcttctaat | acctggaatg | ctgttttccc | 720 |
| ggggatcgca | gtggtgagta | accatgcatc | atcaggagta | cggataaaat | gcttgatggt | 780 |
| cggaagaggc | ataaattccg | tcagccagtt | tagtctgacc | atctcatctg | taacatcatt | 840 |
| ggcaacgcta | cctttgccat | gtttcagaaa | caactctggc | gcatcgggct | tcccatacaa | 900 |
| tcgatagatt | gtcgcacctg | attgcccgac | attatcgcga | gcccatttat | acccatataa | 960 |
| atcagcatcc | atgttggaat | ttaatcgcgg | cctcgagcaa | gacgtttccc | gttgaatatg | 1020 |
| gctcatagat | ctttctcca | tcactgatag | ggagtggtaa | aataactcca | tcaatgatag | 1080 |
| agtgtcaaca | acatgaccaa | aatcccttaa | cgtgagttac | gcgtattaat | tgcgttgcgc | 1140 |
| tcactgcccg | ctttccagtc | gggaaacctg | tcgtgccagc | tgcattaatg | aatcggccaa | 1200 |
| cgcgcgggga | gaggcggttt | gcgtattggg | cgctcttccg | cttcctcgct | cactgactcg | 1260 |
| ctgcgctcgg | tcgttcggct | gcggcgagcg | gtatcagctc | actcaaaggc | ggtaatacgg | 1320 |
| ttatccacag | aatcagggga | taacgcagga | aagaacatgt | gagcaaaagg | ccagcaaaag | 1380 |
| gccaggaacc | gtaaaaaggc | cgcgttgctg | gcgttttttcc | ataggctccg | cccccctgac | 1440 |
| gagcatcaca | aaaatcgacg | ctcaagtcag | aggtggcgaa | acccgacagg | actataaaga | 1500 |
| taccaggcgt | ttccccctgg | aagctccctc | gtgcgctctc | ctgttccgac | cctgccgctt | 1560 |
| accggatacc | tgtccgcctt | tctcccttcg | ggaagcgtgg | cgctttctca | atgctcacgc | 1620 |
| tgtaggtatc | tcagttcggt | gtaggtcgtt | cgctccaagc | tgggctgtgt | gcacgaaccc | 1680 |
| cccgttcagc | ccgaccgctg | cgccttatcc | ggtaactatc | gtcttgagtc | caacccggta | 1740 |
| agacacgact | tatcgccact | ggcagcagcc | actggtaaca | ggattagcag | agcgaggtat | 1800 |
| gtaggcggtg | ctacagagtt | cttgaagtgg | tggcctaact | acggttacac | tagaagaaca | 1860 |
| gtatttggta | tctgcgctct | gctgaagcca | gttaccttcg | gaaaaagagt | tggtagctct | 1920 |
| tgatccggca | aacaaaccac | cgctggtagc | ggtggttttt | ttgtttgcaa | gcagcagatt | 1980 |
| acgcgcagaa | aaaaaggatc | tcaagaagat | cctttgatct | tttctacggg | gtctgacgct | 2040 |
| cagggaacga | cgcgtaccgc | tagccaggaa | gagtttgtag | aaacgcaaaa | aggccatccg | 2100 |
| tcaggatggc | cttctgctta | gtttgatgcc | tggcagttta | tggcgggcgt | cctgcccgcc | 2160 |
| accctccggg | ccgttgcttc | acaacgttca | aatccgctcc | cggcggattt | gtcctactca | 2220 |

```
ggagagcgtt caccgacaaa caacagataa aacgaaaggc ccagtcttcc gactgagcct    2280
ttcgttttat ttgatgcctg gcagttccct actctcgcgt taacgctagc atggatgttt    2340
tcccagtcac gacgttgtaa aacgacggcc agtcttaagc tcgggcccca aataatgatt    2400 ttatttttgac tgatagtgac ctgttcgttg caacaaattg atgagcaatg cttttttata    2460
atgccaactt tgtacaaaaa agttggctat ttttttttcgg cccacgatct cacatggtga    2520
aaaggccagc acttccgctg accgttgatg gtgtcaccta tgatgtgtct gcctggttga    2580
accatcatcc agggggtgct gacatcattg agaactaccg cggtcgtgat gccactgatg    2640
tctttatggt tatgcactct gaaaatgctg tgagtaaact aagaaggatg cctatcatgg    2700
aaccatcatc tccactgacg cctacgccac cgaaacccaa ctcagacgaa ccgcaggagg    2760
atttccgcaa gctccgagat gagctcatcg cagcaggaat gttcgacgca tcaccgatgt    2820
ggtacgcata taagacgctc agtacgctgg gcctcggggt cctcgcggtg ctattgatga    2880
cccagtggca ctggtacctc gtcggggcaa tcgtgttggg cattcacttc aacaaatgg     2940 gttggttgtc gcacgatatc tgccaccatc agctgttcaa ggaccgatcg atcaacaacg    3000
ccatcggctt gcttttcggg aacgtcttgc aagggttctc tgtgacctgg tggaaggaca    3060
ggcacaatgc acaccactcc gccaccaacg tgcaaggcca cgaccccgac attgacaacc    3120
tgccgctgct ggcatggtcc aaggaggacg tggagagggc cggcccgttc tcacggcgga    3180
tgatcaagta ccagcaatac tacttcttct tcatctgtgc cctcctgagg ttcatctggt    3240
gcttccagag catccacaca gccacgggcc tgaaggatcg cagcaaccag tactaccgca    3300
ggcagtacga gaaagagagc gtgggcctgg ccctccactg gggcctgaag gcgttgttct    3360 actacttttta tatgccaagc ttcttgaccg gactcatggt gttttttcgtg tccgagttgc    3420 ttgggggctt cggcatcgcc atcgtggtgt tcatgaacca ctaccccctg gagaagatcc    3480
aggactcggt gtgggacggc cacggcttttt gcgccggcca gattcacgaa acgatgaacg    3540
tccagcgggg actcgtcacg gactggttct tcggtgggct gaattaccaa atcgagcacc    3600
acctgtggcc gacgctgccc cggcacaacc tgacggcggc cagcatcaaa gtggagcagt    3660
tgtgcaagaa gcacaacttg ccgtatcgca gcccccaat gctggagggg gtgggcatcc     3720
tgatcagcta cctgggcacc tttgcccgca tggtggcaaa ggccgacaag gcgtaagtga    3780
catggcaccg tcaggactc tgatagttgg gctgacgctt tggttgtcat cccttgcccc     3840
ttcatatcac ctctggccct actcggattc tctctagctc taacctgttc aatgtggact    3900
gctacacata tgagttcctc ggatctctgg gaacagcct ttggaagact cggcattcct     3960
ttatgcttgg aaggcttgag acctcttctg caggactcaa ggcaaccctc ctcagtgtcg    4020
ggaaagagta tttgccttcg gcctgacctg ctatacctca cccaacatgc gtcgtggaat    4080
taatgatcat tgttaagagt ttggtgcgat ttctgattgt gcgcaaattg tgcggaggcg    4140
cggcacacac gttctcctcc ggccatcaca gtccaaggtc aaatttccaa ctctaatcac    4200
catgatgggc cacagctttg cacactattt ctggcagagc tgcaagaaac tcgcnnnnnn    4260
nnnnnnnnnn nnnnnnnnnn nnnnnnnnnn nnnnacccaa ctttctt                  4307
```

<210> SEQ ID NO 16
<211> LENGTH: 4297
<212> TYPE: DNA
<213> ORGANISM: Artificial Sequence
<220> FEATURE:
<223> OTHER INFORMATION: plasmid pLF118-4
<220> FEATURE:
<221> NAME/KEY: misc_feature
<222> LOCATION: (4245)..(4284)

<223> OTHER INFORMATION: n is a, c, g, or t

<400> SEQUENCE: 16

```
gtacaaagtt ggcattataa gaaagcattg cttatcaatt tgttgcaacg aacaggtcac      60
tatcagtcaa aataaaatca ttatttgcca tccagctgat atccnctata gtgagtcgta     120
ttacatggtc atagctgttt cctggcagct ctggcccgtg tctcaaaatc tctgatgtta     180
cattgcacaa gataaaaata tatcatcatg ttagaaaaac tcatcgagca tcaaatgaaa     240
ctgcaattta ttcatatcag gattatcaat accatatttt tgaaaaagcc gtttctgtaa     300
tgaaggagaa aactcaccga ggcagttcca taggatggca agatcctggt atcggtctgc     360
gattccgact cgtccaacat caatacaacc tattaatttc ccctcgtcaa aaataaggtt     420
atcaagtgag aaatcaccat gagtgacgac tgaatccggt gagaatggca aaagcttatg     480
catttctttc cagacttgtt caacaggcca gccattacgc tcgtcatcaa aatcactcgc     540
atcaaccaaa ccgttattca ttcgtgattg cgcctgagcg agacgaaata cgcgatcgct     600
gttaaaagga caattacaaa caggaatcga atgcaaccgg cgcaggaaca ctgccagcgc     660
atcaacaata ttttcacctg aatcaggata ttcttctaat acctggaatg ctgttttccc     720
ggggatcgca gtggtgagta accatgcatc atcaggagta cggataaaat gcttgatggt     780
cggaagaggc ataaattccg tcagccagtt tagtctgacc atctcatctg taacatcatt     840
ggcaacgcta cctttgccat gtttcagaaa caactctggc gcatcgggct tcccatacaa     900
tcgatagatt gtcgcacctg attgcccgac attatcgcga gcccatttat acccatataa     960
atcagcatcc atgttggaat ttaatcgcgg cctcgagcaa gacgtttccc gttgaatatg    1020
gctcatagat cttttctcca tcactgatag ggagtggtaa aataactcca tcaatgatag    1080
agtgtcaaca acatgaccaa aatcccttaa cgtgagttac gcgtattaat tgcgttgcgc    1140
tcactgcccg ctttccagtc gggaaacctg tcgtgccagc tgcattaatg aatcggccaa    1200
cgcgcgggga gaggcggttt gcgtattggg cgctcttccg cttcctcgct cactgactcg    1260
ctgcgctcgg tcgttcggct gcggcgagcg gtatcagctc actcaaaggc ggtaatacgg    1320
ttatccacag aatcagggga taacgcagga aagaacatgt gagcaaaagg ccagcaaaag    1380
gccaggaacc gtaaaaaggc cgcgttgctg gcgtttttcc ataggctccg ccccccctgac   1440
gagcatcaca aaaatcgacg ctcaagtcag aggtggcgaa acccgacagg actataaaga    1500
taccaggcgt ttccccctgg aagctccctc gtgcgctctc ctgttccgac cctgccgctt    1560
accggatacc tgtccgcctt tctcccttcg ggaagcgtgg cgctttctca atgctcacgc    1620
tgtaggtatc tcagttcggt gtaggtcgtt cgctccaagc tgggctgtgt gcacgaaccc    1680
cccgttcagc ccgaccgctg cgccttatcc ggtaactatc gtcttgagtc caacccggta    1740
agacacgact tatcgccact ggcagcagcc actggtaaca ggattagcag agcgaggtat    1800
gtaggcggtg ctacagagtt cttgaagtgg tggcctaact acggtacac tagaagaaca    1860
gtatttggta tctgcgctct gctgaagcca gttaccttcg gaaaaagagt tggtagctct    1920
tgatccggca aacaaaccac cgctggtagc ggtggttttt ttgtttgcaa gcagcagatt    1980
acgcgcagaa aaaaggatc tcaagaagat cctttgatct tttctacggg gtctgacgct    2040
cagtggaacga cgcgtaccgc tagccaggaa gagtttgtag aaacgcaaaa aggccatccg    2100
tcaggatggc cttctgctta gtttgatgcc tggcagttta tggcgggcgt cctgcccgcc    2160
accctccggg ccgttgcttc gcaacgttca aatccgctcc cggcggattt gtcctactca    2220
ggagagcgtt caccgacaaa caacagataa aacgaaaggc ccagtcttcc gactgagcct    2280
```

```
ttcgttttat tgatgcctg gcagttccct actctcgcgt taacgctagc atggatgttt      2340
tcccagtcac gacgttgtaa aacgacggcc agtcttaagc tcgggcccca ataatgatt      2400
ttattttgac tgatagtgac ctgttcgttg caacaaattg atgagcaatg ctttttata      2460
atgccaactt tgtacaaaaa agttggtttc aggcccacga tctcacatgg tgaaaaggcc     2520
agcacttccg ctgaccgttg atggtgtcac ctatgatgtg tctgcctggt gaaccatca     2580
tccaggggt gctgacatca ttgagaacta ccgcggtcgt gatgccactg atgtctttat      2640
ggttatgcac tctgaaaatg ctgtgagtaa actaagaagg atgcctatca tggaaccatc    2700
atctccactg acgcctacgc caccgaaacc caactcagac gaaccgcagg aggatttccg    2760
caagctccga gatgagctca tcgcagcagg aatgttcgac gcatcaccga tgtggtacgc    2820
atataagacg ctcagtacgc tgggcctcgg ggtcctcgcg gtgctattga tgacccagtg    2880
gcactggtac ctcgtcgggg caatcgtgtt gggcattcac ttccaacaaa tgggttggtt    2940
gtcgcacgat atctgccacc atcagctgtt caaggaccga tcgatcaaca acgccatcgg   3000
cttgcttttc gggaacgtct tgcaagggtt ctctgtgacc tggtggaagg acaggcacaa    3060
tgcacaccac tccgccacca acgtgcaagg ccacgacccc gacattgaca acctgccgct    3120
gctggcatgg tccaaggagg acgtggagag ggccggcccg ttctcacggc ggatgatcaa    3180
gtaccagcaa tactacttct tcttcatctg tgccctcctg aggttcatct ggtgcttcca    3240
gagcatccac acagccaagg gcctgaagga tcgcagcaac cagtactacc gcaggcagta    3300
cgagaaagag agcgtgggcc tggccctcca ctgggggctg aaggcgttgt tctactactt    3360
ttatatgcca agcttcttga ccggactcat ggtgttttc gtgtccgagt tgcttggggg     3420
cttcggcatc gccatcgtgg tgttcatgaa ccactacccc ctggagaaga tccaggactc    3480
ggtgtgggac ggccacggct tttgcgccgg ccagattcac gaaacgatga acgtccagcg    3540
gggactcgtc acggactggt tcttcggtgg gctgaattac caaatcgagc accacctgtg   3600
gccgacgctg ccccggcaca acctgacggc ggccagcatc aaagtggagc agttgtgcaa    3660
gaagcacaac ttgccgtatc gcagccccc aatgctggag ggggtgggca tcctgatcag    3720
ctacctgggc acctttgccc gcatggtggc aaaggccgac aaggcgtaag tgacatggca    3780
ccgctcagga ctctgatagt tgggctgacg ctttggttgt catcccttgc cccttcatat    3840
cacctctggc ccgactcgga ttctctctgg agctctaacc tgttcaatgt ggactgctac    3900
acatatgagt tcctcggatc tcgggggaac agcctttgga agactcggca ttcctttatg    3960
cttggaaggc ttgagacctc ttctgcagga ctcaaggcaa ccctcctcag tgtcgggaaa    4020
gagtatttgc cttcggcctg acctgctata cctcacccaa catgcgtcgt ggaattaatg    4080
atcatcgtta agagtttggt gcgatttctg attgtgcgca aattgtgcgg aggcgcggca    4140
cacacgttct cctccagcca tcacagtcca aggtcaaatt tccaactcta atcaccatga    4200
tgggccacag ctttgcacac tatttctggc agagctgcaa gaaannnnnn nnnnnnnnnn    4260
nnnnnnnnnn nnnnnnnnnn nnnnacccaa ctttctt                             4297
```

<210> SEQ ID NO 17
<211> LENGTH: 1260
<212> TYPE: DNA
<213> ORGANISM: Euglena anabaena

<400> SEQUENCE: 17

```
atggtgaaaa ggccagcact tccgctgacc gttgatggtg tcacctatga tgtgtctgcc       60
tggttgaacc atcatccagg gggtgctgac atcattgaga actaccgcgg tcgtgatgcc      120
```

```
actgatgtct ttatggttat gcactctgaa aatgctgtga gtaaactaag aaggatgcct      180
atcatggaac catcatctcc actgacgcct acgccaccga aacccaactc agacgaaccg      240
caggaggatt tccgcaagct ccgagatgag ctcatcgcag caggaatgtt cgacgcatca      300
ccgatgtggt acgcatataa gacgctcact acgctgggcc tcggggtcct cgcggtgcta      360
ttgatgaccc agtggcactg gtacctcgtc ggggcaatcg tgttgggcat tcacttccaa      420
caaatgggtt ggttgtcgca cgatatctgc caccatcagc tgttcaagga ccgatcgatc      480
aacaacgcca tcggcttgct tttcgggaac gtcttgcaag ggttctctgt gacctggtgg      540
aaggacaggc acaatgcaca ccactccgcc accaacgtgc aaggccacga ccccgacatt      600
gacaacctgc cgctgctggc atggtccaag gaggacgtgg agagggccgg cccgttctca      660
cggcggatga tcaagtacca gcaatactac ttcttcttca tctgtgccct cctgaggttc      720
atctggtgct tccagagcat ccacacagcc aagggcctga aggatcgcag caaccagtac      780
taccgcaggc agtacgagaa agagagcgtg ggcctggccc tccactgggg cctgaaggcg      840
ttgttctact acttttatat gccaagcttc ttgaccggac tcatggtgtt tttcgtgtcc      900
gagttgcttg ggggcttcgg catcgccatc gtggtgttca tgaaccacta ccccctggag      960
aagatccagg actcggtgtg ggacggccac ggcttttgcg ccggcagat tcacgaaacg     1020 atgaacgtcc agcggggact cgtcacggac tggttcttcg gtgggctgaa ttaccaaatc     1080
gagcaccacc tgtggccgac gctgccccgg cacaacctga cggcggccag catcaaagtg     1140
gagcagttgt gcaagaagca aacttgccg tatcgcagcc ccccaatgct ggaggggtg     1200 ggcatcctga tcagctacct gggcaccttt gcccgcatgg tggcaaaggc cgacaaggcg     1260
```

<210> SEQ ID NO 18
<211> LENGTH: 1260
<212> TYPE: DNA
<213> ORGANISM: Euglena anabaena

<400> SEQUENCE: 18

```
atggtgaaaa ggccagcact tccgctgacc gttgatggtg tcacctatga tgtgtctgcc       60
tggttgaacc atcatccagg gggtgctgac atcattgaga actaccgcgg tcgtgatgcc      120
actgatgtct ttatggttat gcactctgaa aatgctgtga gtaaactaag aaggatgcct      180
atcatggaac catcatctcc actgacgcct acgccaccga aacccaactc agacgaaccg      240
caggaggatt tccgcaagct ccgagatgag ctcatcgcag caggaatgtt cgacgcatca      300
ccgatgtggt acgcatataa gacgctcagt acgctgggcc tcggggtcct cgcggtgcta      360
ttgatgaccc agtggcactg gtacctcgtc ggggcaatcg tgttgggcat tcacttccaa      420
caaatgggtt ggttgtcgca cgatatctgc caccatcagc tgttcaagga ccgatcgatc      480
aacaacgcca tcggcttgct tttcgggaac gtcttgcaag ggttctctgt gacctggtgg      540
aaggacaggc acaatgcaca ccactccgcc accaacgtgc aaggccacga ccccgacatt      600
gacaacctgc cgctgctggc atggtccaag gaggacgtgg agagggccgg cccgttctca      660
cggcggatta tcaagtacca gcaatactac ttcttcttca tctgtgccct cctgaggttc      720
atctggtgct tccagagcat ccacacagcc acgggcctga aggatcgcag caaccagtac      780
taccgcaggc agtacgagaa agagagcgtg ggcctggccc tccactgggg cctgaaggcg      840
ttgttctact acttttatat gccaagcttc ttgaccggac tcatggtgtt tttcgtgtcc      900
gagttgcttg ggggcttcgg catcgccatc gtggtgttca tgaaccacta ccccctggag      960
aagatccagg actcggtgtg ggacggccac ggcttttgcg ccggcagat tcacgaaacg     1020
```

```
atgaacgtcc agcggggact cgtcacggac tggttcttcg gtgggctgaa ttaccaaatc    1080
gagcaccacc tgtggccgac gctgccccgg cacaacctga cggcggccag catcaaagtg    1140
gagcagttgt gcaagaagca caacttgccg tatcgcagcc ccccaatgct ggaggggtg     1200 ggcatcctga tcagctacct gggcaccttt gcccgcatgg tggcaaaggc cgacaaggcg    1260

<210> SEQ ID NO 19
<211> LENGTH: 1260
<212> TYPE: DNA
<213> ORGANISM: Euglena anabaena

<400> SEQUENCE: 19
atggtgaaaa ggccagcact tccgctgacc gttgatggtg tcacctatga tgtgtctgcc      60
tggttgaacc atcatccagg gggtgctgac atcattgaga actaccgcgg tcgtgatgcc     120
actgatgtct ttatggttat gcactctgaa aatgctgtga gtaaactaag aaggatgcct     180
atcatggaac catcatctcc actgacgcct acgccaccga acccaactc agacgaaccg      240 caggaggatt ccgcaagct ccgagatgag ctcatcgcag caggaatgtt cgacgcatca      300
ccgatgtggt acgcatataa gacgctcagt acgctgggcc tcggggtcct cgcggtgcta     360
ttgatgaccc agtggcactg gtacctcgtc ggggcaatcg tgttgggcat tcacttccaa     420
caaatgggtt ggttgtcgca cgatatctgc caccatcagc tgttcaagga ccgatcgatc     480
aacaacgcca tcggcttgct tttcgggaac gtcttgcaag ggttctctgt gacctggtgg     540
aaggacaggc acaatgcaca ccactccgcc accaacgtgc aaggccacga ccccgacatt     600
gacaacctgc cgctgctggc atggtccaag gaggacgtgg agagggccgg cccgttctca     660
cggcggatga tcaagtacca gcaatactac ttcttcttca tctgtgccct cctgaggttc     720
atctggtgct tccagagcat ccacacagcc acgggcctga aggatcgcag caaccagtac     780
taccgcaggc agtacgagaa agagagcgtg ggcctggccc tccactgggg cctgaaggcg     840
ttgttctact acttttatat gccaagcttc ttgaccggac tcatggtgtt tttcgtgtcc     900
gagttgcttg ggggcttcgg catcgccatc gtgtgttca tgaaccacta ccccctggag     960
aagatccagg actcggtgtg ggacggccac ggcttttgcg ccggccagat tcacgaaacg    1020
atgaacgtcc agcggggact cgtcacggac tggttcttcg gtgggctgaa ttaccaaatc    1080
gagcaccacc tgtggccgac gctgccccgg cacaacctga cggcggccag catcaaagtg    1140
gagcagttgt gcaagaagca caacttgccg tatcgcagcc ccccaatgct ggaggggtg     1200 ggcatcctga tcagctacct gggcaccttt gcccgcatgg tggcaaaggc cgacaaggcg    1260

<210> SEQ ID NO 20
<211> LENGTH: 1260
<212> TYPE: DNA
<213> ORGANISM: Euglena anabaena

<400> SEQUENCE: 20
atggtgaaaa ggccagcact tccgctgacc gttgatggtg tcacctatga tgtgtctgcc      60
tggttgaacc atcatccagg gggtgctgac atcattgaga actaccgcgg tcgtgatgcc     120
actgatgtct ttatggttat gcactctgaa aatgctgtga gtaaactaag aaggatgcct     180
atcatggaac catcatctcc actgacgcct acgccaccga acccaactc agacgaaccg      240 caggaggatt ccgcaagct ccgagatgag ctcatcgcag caggaatgtt cgacgcatca      300
ccgatgtggt acgcatataa gacgctcagt acgctgggcc tcggggtcct cgcggtgcta     360
ttgatgaccc agtggcactg gtacctcgtc ggggcaatcg tgttgggcat tcacttccaa     420
```

```
caaatgggtt ggttgtcgca cgatatctgc caccatcagc tgttcaagga ccgatcgatc    480
aacaacgcca tcggcttgct tttcgggaac gtcttgcaag ggttctctgt gacctggtgg    540
aaggacaggc acaatgcaca ccactccgcc accaacgtgc aaggccacga ccccgacatt    600
gacaacctgc cgctgctggc atggtccaag gaggacgtgg agagggccgg cccgttctca    660
cggcggatga tcaagtacca gcaatactac ttcttcttca tctgtgccct cctgaggttc    720
atctggtgct tccagagcat ccacacagcc aagggcctga aggatcgcag caaccagtac    780
taccgcaggc agtacgagaa agagagcgtg ggcctggccc tccactgggg cctgaaggcg    840
ttgttctact acttttatat gccaagcttc ttgaccggac tcatggtgtt tttcgtgtcc    900
gagttgcttg ggggcttcgg catcgccatc gtggtgttca tgaaccacta ccccctggag    960
aagatccagg actcggtgtg ggacggccac ggcttttgcg ccggccagat tcacgaaacg   1020
atgaacgtcc agcggggact cgtcacggac tggttcttcg gtgggctgaa ttaccaaatc   1080
gagcaccacc tgtggccgac gctgccccgg cacaacctga cggcggccag catcaaagtg   1140
gagcagttgt gcaagaagca caacttgccg tatcgcagcc ccccaatgct ggaggggtg    1200 ggcatcctga tcagctacct gggcaccttt gcccgcatgg tggcaaaggc cgacaaggcg   1260
```

<210> SEQ ID NO 21
<211> LENGTH: 420
<212> TYPE: PRT
<213> ORGANISM: Euglena anabaena

<400> SEQUENCE: 21

```
Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Thr Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
    210                 215                 220

Lys Tyr Gln Gln Tyr Tyr Phe Phe Phe Ile Cys Ala Leu Leu Arg Phe
225                 230                 235                 240
```

```
Ile Trp Cys Phe Gln Ser Ile His Thr Ala Lys Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420

<210> SEQ ID NO 22
<211> LENGTH: 420
<212> TYPE: PRT
<213> ORGANISM: Euglena anabaena

<400> SEQUENCE: 22

Met Val Lys Arg Pro Ala Leu Pro Leu Thr Val Asp Gly Val Thr Tyr
1               5                   10                  15

Asp Val Ser Ala Trp Leu Asn His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190
```

```
Val Gln Gly His Asp Pro Asp Ile Asp Asn Leu Pro Leu Leu Ala Trp
            195                 200                 205

Ser Lys Glu Asp Val Glu Arg Ala Gly Pro Phe Ser Arg Arg Ile Ile
210                 215                 220

Lys Tyr Gln Gln Tyr Tyr Phe Phe Ile Cys Ala Leu Leu Arg Phe
225                 230                 235                 240

Ile Trp Cys Phe Gln Ser Ile His Thr Ala Thr Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
            275                 280                 285

Ser Phe Leu Thr Gly Leu Met Val Phe Val Ser Glu Leu Leu Gly
            290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
            355                 360                 365

Pro Arg His Asn Leu Thr Ala Ala Ser Ile Lys Val Glu Gln Leu Cys
        370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420

<210> SEQ ID NO 23
<211> LENGTH: 420
<212> TYPE: PRT
<213> ORGANISM: Euglena anabaena

<400> SEQUENCE: 23

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
            35                  40                  45

Ser Glu Asn Ala Val Ser Lys Leu Arg Arg Met Pro Ile Met Glu Pro
50                  55                  60

Ser Ser Pro Leu Thr Pro Thr Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
            100                 105                 110

Gly Leu Gly Val Leu Ala Val Leu Leu Met Thr Gln Trp His Trp Tyr
        115                 120                 125

Leu Val Gly Ala Ile Val Leu Gly Ile His Phe Gln Gln Met Gly Trp
    130                 135                 140
```

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
            165                 170                 175

Val Thr Trp Trp Lys Asp Arg His Asn Ala His His Ser Ala Thr Asn
        180                 185                 190

Val Gln Gly His Asp Pro Asp Ile Asp Asn Leu Pro Leu Leu Ala Trp
    195                 200                 205

Ser Lys Glu Asp Val Glu Arg Ala Gly Pro Phe Ser Arg Arg Met Ile
210                 215                 220

Lys Tyr Gln Gln Tyr Tyr Phe Phe Phe Ile Cys Ala Leu Leu Arg Phe
225                 230                 235                 240

Ile Trp Cys Phe Gln Ser Ile His Thr Ala Thr Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Val Ser Glu Leu Leu Gly
    290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
    370                 375                 380

Lys Lys His Asn Leu Pro Tyr Arg Ser Pro Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420

<210> SEQ ID NO 24
<211> LENGTH: 420
<212> TYPE: PRT
<213> ORGANISM: Euglena anabaena

<400> SEQUENCE: 24

Met Val Lys Arg Pro Ala Leu Pro Leu Thr Val Asp Gly Val Thr Tyr
1               5                   10                  15

Asp Val Ser Ala Trp Leu Asn His His Pro Gly Gly Ala Asp Ile Ile
            20                  25                  30

Glu Asn Tyr Arg Gly Arg Asp Ala Thr Asp Val Phe Met Val Met His
        35                  40                  45

Ser Glu Asn Ala Val Ser Lys Leu Arg Arg Met Pro Ile Met Glu Pro
    50                  55                  60

Ser Ser Pro Leu Thr Pro Thr Pro Lys Pro Asn Ser Asp Glu Pro
65                  70                  75                  80

Gln Glu Asp Phe Arg Lys Leu Arg Asp Glu Leu Ile Ala Ala Gly Met
                85                  90                  95

Phe Asp Ala Ser Pro Met Trp Tyr Ala Tyr Lys Thr Leu Ser Thr Leu
                100                 105                 110

Gly Leu Gly Val Leu Ala Val Leu Leu Met Thr Gln Trp His Trp Tyr
            115                 120                 125

Leu Val Gly Ala Ile Val Leu Gly Ile His Phe Gln Gln Met Gly Trp
        130                 135                 140

Leu Ser His Asp Ile Cys His His Gln Leu Phe Lys Asp Arg Ser Ile
145                 150                 155                 160

Asn Asn Ala Ile Gly Leu Leu Phe Gly Asn Val Leu Gln Gly Phe Ser
                165                 170                 175

Val Thr Trp Trp Lys Asp Arg His Asn Ala His His Ser Ala Thr Asn
            180                 185                 190

Val Gln Gly His Asp Pro Asp Ile Asp Asn Leu Pro Leu Leu Ala Trp
        195                 200                 205

Ser Lys Glu Asp Val Glu Arg Ala Gly Pro Phe Ser Arg Arg Met Ile
210                 215                 220

Lys Tyr Gln Gln Tyr Tyr Phe Phe Ile Cys Ala Leu Leu Arg Phe
225                 230                 235                 240

Ile Trp Cys Phe Gln Ser Ile His Thr Ala Lys Gly Leu Lys Asp Arg
                245                 250                 255

Ser Asn Gln Tyr Tyr Arg Arg Gln Tyr Glu Lys Glu Ser Val Gly Leu
            260                 265                 270

Ala Leu His Trp Gly Leu Lys Ala Leu Phe Tyr Tyr Phe Tyr Met Pro
        275                 280                 285

Ser Phe Leu Thr Gly Leu Met Val Phe Val Ser Glu Leu Leu Gly
290                 295                 300

Gly Phe Gly Ile Ala Ile Val Val Phe Met Asn His Tyr Pro Leu Glu
305                 310                 315                 320

Lys Ile Gln Asp Ser Val Trp Asp Gly His Gly Phe Cys Ala Gly Gln
                325                 330                 335

Ile His Glu Thr Met Asn Val Gln Arg Gly Leu Val Thr Asp Trp Phe
            340                 345                 350

Phe Gly Gly Leu Asn Tyr Gln Ile Glu His His Leu Trp Pro Thr Leu
        355                 360                 365

Pro Arg His Asn Leu Thr Ala Ala Ser Ile Lys Val Glu Gln Leu Cys
370                 375                 380

Lys Lys His Asn Leu Pro Tyr Arg Ser Pro Met Leu Glu Gly Val
385                 390                 395                 400

Gly Ile Leu Ile Ser Tyr Leu Gly Thr Phe Ala Arg Met Val Ala Lys
                405                 410                 415

Ala Asp Lys Ala
            420

<210> SEQ ID NO 25
<211> LENGTH: 421
<212> TYPE: PRT
<213> ORGANISM: Euglena gracilis

<400> SEQUENCE: 25

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
 50                  55                  60

Pro Ser Ser Glu Leu Pro Pro Gln Ala Ala Val Asn Glu Ala Gln Glu
 65                  70                  75                  80

Asp Phe Arg Lys Leu Arg Glu Glu Leu Ile Ala Thr Gly Met Phe Asp
                 85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
            115                 120                 125

Gly Ala Val Leu Leu Gly Met His Tyr Gln Met Gly Trp Leu Ser
130                 135                 140

His Asp Ile Cys His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
            195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
            275                 280                 285

Leu Thr Ser Leu Leu Val Phe Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
            355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 26
<211> LENGTH: 34
<212> TYPE: DNA
<213> ORGANISM: Artificial Sequence
<220> FEATURE:
<223> OTHER INFORMATION: oligonucleotide EaD8-5

<400> SEQUENCE: 26
gcggccgcac catggtgaaa aggccagcac ttcc					34

<210> SEQ ID NO 27
<211> LENGTH: 30
<212> TYPE: DNA
<213> ORGANISM: Artificial Sequence
<220> FEATURE:
<223> OTHER INFORMATION: oligonucleotide EaD8-3

<400> SEQUENCE: 27
gcggccgctt acgccttgtc ggcctttgcc					30

<210> SEQ ID NO 28
<211> LENGTH: 4794
<212> TYPE: DNA
<213> ORGANISM: Artificial Sequence
<220> FEATURE:
<223> OTHER INFORMATION: plasmid pLF120-1

<400> SEQUENCE: 28

| | |
|---|---|
| cctgaattcc agcacactgg cggccgttac tagtggatcc gagctcggta ccaagcttga | 60 |
| tgcatagctt gagtattcta acgcgtcacc taaatagctt ggcgtaatca tggtcatagc | 120 |
| tgtttcctgt gtgaaattgt tatccgctca caattccaca caacatacga gccggaagca | 180 |
| taaagtgtaa agcctggggt gcctaatgag tgagctaact cacattaatt gcgttgcgct | 240 |
| cactgcccgc tttccagtcg ggaaacctgt cgtgccagct gcattaatga atcggccaac | 300 |
| gcgcggggag aggcggtttg cgtattgggc gctcttccgc ttcctcgctc actgactcgc | 360 |
| tgcgctcggt cgttcggctg cggcgagcgg tatcagctca ctcaaaggcg gtaatacggt | 420 |
| tatccacaga atcaggggat aacgcaggaa agaacatgtg agcaaaaggc cagcaaaagg | 480 |
| ccaggaaccg taaaaaggcc gcgttgctgg cgtttttcca taggctccgc cccccctgacg | 540 |
| agcatcacaa aaatcgacgc tcaagtcaga ggtggcgaaa cccgacagga ctataaagat | 600 |
| accaggcgtt tccccctgga agctccctcg tgcgctctcc tgttccgacc ctgccgctta | 660 |
| ccggatacct gtccgccttt ctcccttcgg gaagcgtggc gctttctcat agctcacgct | 720 |
| gtaggtatct cagttcggtg taggtcgttc gctccaagct gggctgtgtg cacgaacccc | 780 |
| ccgttcagcc cgaccgctgc gccttatccg gtaactatcg tcttgagtcc aacccggtaa | 840 |
| gacacgactt atcgccactg gcagcagcca ctggtaacag gattagcaga gcgaggtatg | 900 |
| taggcggtgc tacagagttc ttgaagtggt ggcctaacta cggctacact agaagaacag | 960 |
| tatttggtat ctgcgctctg ctgaagccag ttaccttcgg aaaaagagtt ggtagctctt | 1020 |
| gatccggcaa acaaaccacc gctggtagcg tggtttttt tgtttgcaag cagcagatta | 1080 |
| cgcgcagaaa aaaaggatct caagaagatc ctttgatctt ttctacgggg tctgacgctc | 1140 |
| agtggaacga aaactcacgt taagggattt tggtcatgag attatcaaaa aggatcttca | 1200 |
| cctagatcct tttaaattaa aaatgaagtt ttagcacgtg tcagtcctgc tcctcggcca | 1260 |
| cgaagtgcac gcagttgccg gccgggtcgc gcagggcgaa ctcccgcccc cacggctgct | 1320 |
| cgccgatctc ggtcatggcc ggcccggagg cgtcccggaa gttcgtggac acgacctccg | 1380 |
| accactcggc gtacagctcg tccaggccgc gcacccacac ccaggccagg gtgttgtccg | 1440 |
| gcaccacctg gtcctggacc gcgctgatga cagggtcac gtcgtccgg accacaccgg | 1500 |
| cgaagtcgtc ctccacgaag tcccgggaga acccgagccg tcggtccag aactcgaccg | 1560 |
| ctccggcgac gtcgcgcgcg gtgagcaccg gaacggcact ggtcaacttg gccatggtgg | 1620 |

```
ccctcctcac gtgctattat tgaagcattt atcagggtta ttgtctcatg agcggataca   1680
tatttgaatg tatttagaaa aataaacaaa taggggttcc gcgcacattt ccccgaaaag   1740
tgccacctga tgcggtgtga ataccgcac agatgcgtaa ggagaaaata ccgcatcagg    1800
aaattgtaag cgttaataat tcagaagaac tcgtcaagaa ggcgatagaa ggcgatgcgc   1860
tgcgaatcgg gagcggcgat accgtaaagc acgaggaagc ggtcagccca ttcgccgcca   1920
agctcttcag caatatcacg ggtagccaac gctatgtcct gatagcggtc cgccacaccc   1980
agccggccac agtcgatgaa tccagaaaag cggccatttt ccaccatgat attcggcaag   2040
caggcatcgc catgggtcac gacgagatcc tcgccgtcgg gcatgctcgc cttgagcctg   2100
gcgaacagtt cggctggcgc gagccCctga tgctcttcgt ccagatcatc ctgatcgaca   2160
agaccggctt ccatccgagt acgtgctcgc tcgatgcgat gtttcgcttg gtggtcgaat   2220
gggcaggtag ccggatcaag cgtatgcagc cgccgcattg catcagccat gatggatact   2280
ttctcggcag gagcaaggtg agatgacagg agatcctgcc ccggcacttc gcccaatagc   2340
agccagtccc ttcccgcttc agtgacaacg tcgagcacag ctgcgcaagg aacgcccgtc   2400
gtggccagcc acgatagccg cgctgcctcg tcttgcagtt cattcagggc accggacagg   2460
tcggtcttga caaaaagaac cgggcgcccc tgcgctgaca gccggaacac ggcggcatca   2520
gagcagccga ttgtctgttg tgcccagtca tagccgaata gcctctccac ccaagcggcc   2580
ggagaacctg cgtgcaatcc atcttgttca atcatgcgaa acgatcctca tcctgtctct   2640
tgatcagagc ttgatcccct gcgccatcag atccttggcg gcaagaaagc catccagttt   2700
actttgcagg gcttcccaac cttaccagag ggcgccccag ctggcaattc cggttcgctt   2760
gctgtccata aaaccgccca gtctagctat cgccatgtaa gcccactgca agctacctgc   2820
tttctctttg cgcttgcgtt ttccttgtc cagatagccc agtagctgac attcatccgg   2880
ggtcagcacc gtttctgcgg actggctttc tacgtgaaaa ggatctaggt gaagatcctt   2940
tttgataatc tcatgcctga catttatatt ccccagaaca tcaggttaat ggcgtttttg   3000
atgtcatttt cgcggtggct gagatcagcc acttcttccc cgataacgga gaccggcaca   3060
ctggccatat cggtggtcat catgcgccag cttctcatccc cgatatgcac caccgggtaa   3120
agttcacggg agactttatc tgacagcaga cgtgcactgg ccaggggat caccatccgt    3180 cgccccggcg tgtcaataat atcactctgt acatccacaa acagacgata acggctctct   3240
cttttatagg tgtaaacctt aaactgccgt acgtataggc tgcgcaactg ttgggaaggg   3300
cgatcggtgc gggcctcttc gctattacgc cagctggcga aaggggggatg tgctgcaagg   3360 cgattaagtt gggtaacgcc agggttttcc cagtcacgac gttgtaaaac gacggccagt   3420
gaattgtaat acgactcact ataggggcgaa ttgggccctc tagatgcatg ctcgagcggc   3480
cgccagtgtg atggatatct gcagaattca gggcggccgc accatggtga aaaggccagc   3540
acttccgctg accgttgatg gtgtcaccta tgatgtgtct gcctggttga accatcatcc   3600 aggggggtgct gacatcattg agaactaccg cggtcgtgat gccactgatg tctttatggt   3660
tatgcactct gaaaatgctg tgagtaaact aagaaggatg cctatcatgg aaccatcatc   3720
tccactgacg cctacgccac cgaaacccaa ctcagacgaa ccgcaggagg atttccgcaa   3780
gctccgagat gagctcatcg cagcaggaat gttcgacgca tcaccgatgt ggtacgcata   3840
taagacgctc actacgctgg gcctcggggt cctcgcggtg ctattgatga cccagtggca   3900
ctggtacctc gtcggggcaa tcgtgttggg cattcacttc caacaaatgg ttggttgtc    3960 gcacgatatc tgccaccatc agctgttcaa ggaccgatcg atcaacaacg ccatcggctt   4020
```

```
gcttttcggg aacgtcttgc aagggttctc tgtgacctgg tggaaggaca ggcacaatgc    4080
acaccactcc gccaccaacg tgcaaggcca cgaccccgac attgacaacc tgccgctgct    4140
ggcatggtcc aaggaggacg tggagagggc cggcccgttc tcacggcgga tgatcaagta    4200
ccagcaatac tacttcttct tcatctgtgc cctcctgagg ttcatctggt gcttccagag    4260
catccacaca gccaagggcc tgaaggatcg cagcaaccag tactaccgca ggcagtacga    4320
gaaagagagc gtgggcctgg ccctccactg gggcctgaag gcgttgttct actactttta    4380
tatgccaagc ttcttgaccg gactcatggt gttttttcgtg tccgagttgc ttggggcttt   4440
cggcatcgcc atcgtggtgt tcatgaacca ctacccctg gagaagatcc aggactcggt    4500
gtgggacggc cacggctttt gcgccggcca gattcacgaa acgatgaacg tccagcgggg   4560
actcgtcacg gactggttct cggtgggct gaattaccaa atcgagcacc acctgtggcc    4620
gacgctgccc cggcacaacc tgacggcggc cagcatcaaa gtggagcagt tgtgcaagaa   4680
gcacaacttg ccgtatcgca gccccccaat gctggagggg gtgggcatcc tgatcagcta   4740
cctgggcacc tttgcccgca tggtggcaaa ggccgacaag gcgtaagcgg ccgc          4794
```

<210> SEQ ID NO 29
<211> LENGTH: 4794
<212> TYPE: DNA
<213> ORGANISM: Artificial Sequence
<220> FEATURE:
<223> OTHER INFORMATION: plasmid pLF120-2

<400> SEQUENCE: 29

```
ttgtaatacg actcactata gggcgaattg ggccctctag atgcatgctc gagcggccgc      60
cagtgtgatg gatatctgca gaattcaggc ctgaattcca gcacactggc ggccgttact    120
agtggatccg agctcggtac caagcttgat gcatagcttg agtattctaa cgcgtcacct    180
aaatagcttg gcgtaatcat ggtcatagct gtttcctgtg tgaaattgtt atccgctcac    240
aattccacac aacatacgag ccggaagcat aaagtgtaaa gcctggggtg cctaatgagt    300
gagctaactc acattaattg cgttgcgctc actgcccgct ttccagtcgg gaaacctgtc    360
gtgccagctg cattaatgaa tcggccaacg cgcggggaga ggcggtttgc gtattgggcg    420
ctcttccgct tcctcgctca ctgactcgct gcgctcggtc gttcggctgc ggcgagcggt    480
atcagctcac tcaaaggcgg taatacggtt atccacagaa tcaggggata acgcaggaaa    540
gaacatgtga gcaaaaggcc agcaaaaggc caggaaccgt aaaaaggccg cgttgctggc    600
gtttttccat aggctccgcc cccctgacga gcatcacaaa aatcgacgct caagtcagag    660
gtggcgaaac ccgacaggac tataaagata ccaggcgttt ccccctggaa gctccctcgt    720
gcgctctcct gttccgaccc tgccgcttac cggatacctg tccgcctttc tcccttcggg    780
aagcgtggcg ctttctcata gctcacgctg taggtatctc agttcggtgt aggtcgttcg    840
ctccaagctg ggctgtgtgc acgaaccccc cgttcagccc gaccgctgcg ccttatccgg    900
taactatcgt cttgagtcca acccggtaag acacgactta tcgccactgg cagcagccac    960
tggtaacagg attagcagag cgaggtatgt aggcggtgct acagagttct tgaagtggtg   1020
gcctaactac ggctacacta gaagaacagt atttggtatc tgcgctctgc tgaagccagt   1080
taccttcgga aaaagagttg gtagctcttg atccggcaaa caaaccaccg ctggtagcgg   1140
tggttttttt gtttgcaagc agcagattac gcgcagaaaa aaggatctca agaagatcc    1200 tttgatcttt tctacggggt ctgacgctca gtggaacgaa aactcacgtt aagggatttt   1260
ggtcatgaga ttatcaaaaa ggatcttcac ctagatcctt ttaaattaaa aatgaagttt   1320
```

```
tagcacgtgt cagtcctgct cctcggccac gaagtgcacg cagttgccgg ccgggtcgcg      1380
cagggcgaac tcccgccccc acggctgctc gccgatctcg gtcatggccg gcccggaggc      1440
gtcccggaag ttcgtggaca cgacctccga ccactcggcg tacagctcgt ccaggccgcg      1500
cacccacacc caggccaggg tgttgtccgg caccacctgg tcctggaccg cgctgatgaa      1560
cagggtcacg tcgtcccgga ccacaccggc gaagtcgtcc tccacgaagt cccgggagaa      1620
cccgagccgg tcggtccaga actcgaccgc tccggcgacg tcgcgcgcgg tgagcaccgg      1680
aacggcactg gtcaacttgg ccatggtggc cctcctcacg tgctattatt gaagcattta      1740
tcagggttat tgtctcatga gcggatacat atttgaatgt atttagaaaa ataaacaaat      1800
aggggttccg cgcacatttc cccgaaaagt gccacctgat gcggtgtgaa ataccgcaca      1860
gatgcgtaag gagaaaatac cgcatcagga aattgtaagc gttaataatt cagaagaact      1920
cgtcaagaag gcgatagaag gcgatgcgct gcgaatcggg agcggcgata ccgtaaagca      1980
cgaggaagcg gtcagcccat tcgccgccaa gctcttcagc aatatcacgg gtagccaacg      2040
ctatgtcctg atagcggtcc gccacaccca gccggccaca gtcgatgaat ccagaaaagc      2100
ggccattttc caccatgata ttcggcaagc aggcatcgcc atgggtcacg acgagatcct      2160
cgccgtcggg catgctcgcc ttgagcctgg cgaacagttc ggctggcgcg agcccctgat      2220
gctcttcgtc cagatcatcc tgatcgacaa gaccggcttc catccgagta cgtgctcgct      2280
cgatgcgatg tttcgcttgg tggtcgaatg ggcaggtagc cggatcaagc gtatgcagcc      2340
gccgcattgc atcagccatg atggatactt tctcggcagg agcaaggtga gatgacagga      2400
gatcctgccc cggcacttcg cccaatagca gccagtccct tcccgcttca gtgacaacgt      2460
cgagcacagc tgcgcaagga acgcccgtcg tggccagcca cgatagccgc gctgcctcgt      2520
cttgcagttc attcagggca ccggacaggt cggtcttgac aaaaagaacc gggcgcccct      2580
gcgctgacag ccggaacacg gcggcatcag agcagccgat tgtctgttgt gcccagtcat      2640
agccgaatag cctctccacc caagcggccg gagaacctgc gtgcaatcca tcttgttcaa      2700
tcatgcgaaa cgatcctcat cctgtctctt gatcagagct tgatccctg cgccatcaga       2760 tccttggcgg caagaaagcc atccagttta ctttgcaggg cttcccaacc ttaccagagg      2820 gcgcccagc tggcaattcc ggttcgcttg ctgtccataa aaccgcccag tctagctatc       2880
gccatgtaag cccactgcaa gctacctgct ttctctttgc gcttgcgttt tcccttgtcc      2940
agatagccca gtagctgaca ttcatccggg gtcagcaccg tttctgcgga ctggctttct      3000
acgtgaaaag gatctaggtg aagatccttt ttgataatct catgcctgac atttatattc      3060
cccagaacat caggttaatg gcgttttga tgtcattttc gcggtggctg agatcagcca      3120
cttcttcccc gataacggag accggcacac tggccatatc ggtggtcatc atgcgccagc      3180
tttcatcccc gatatgcacc accgggtaaa gttcacggga gactttatct gacagcagac      3240
gtgcactggc caggggatc accatccgtc gccccggcgt gtcaataata tcactctgta      3300
catccacaaa cagacgataa cggctctctc ttttataggt gtaaacctta aactgccgta      3360
cgtataggct gcgcaactgt tgggaagggc gatcggtgcg ggcctcttcg ctattacgcc      3420
agctggcgaa aggggatgt gctgcaaggc gattaagttg ggtaacgcca gggttttccc       3480
agtcacgacg ttgtaaaacg acggccagtg aagcggccgc accatggtga aaaggccagc      3540
acttccgctg accgttgatg gtgtcaccta tgatgtgtct gcctggttga accatcatcc      3600 aggggggtgct gacatcattg agaactaccg cggtcgtgat gccactgatg tctttatggt      3660
tatgcactct gaaaatgctg tgagtaaact aagaaggatg cctatcatgg aaccatcatc      3720
```

| | |
|---|---|
| tccactgacg cctacgccac cgaaacccaa ctcagacgaa ccgcaggagg atttccgcaa | 3780 |
| gctccgagat gagctcatcg cagcaggaat gttcgacgca tcaccgatgt ggtacgcata | 3840 |
| taagacgctc agtacgctgg gcctcggggt cctcgcggtg ctattgatga cccagtggca | 3900 |
| ctggtacctc gtcgggcaa tcgtgttggg cattcacttc aacaaatgg gttggttgtc | 3960 |
| gcacgatatc tgccaccatc agctgttcaa ggaccgatcg atcaacaacg ccatcggctt | 4020 |
| gcttttcggg aacgtcttgc aagggttctc tgtgacctgg tggaaggaca ggcacaatgc | 4080 |
| acaccactcc gccaccaacg tgcaaggcca cgaccccgac attgacaacc tgccgctgct | 4140 |
| ggcatggtcc aaggaggacg tggagagggc cggcccgttc tcacggcgga ttatcaagta | 4200 |
| ccagcaatac tacttcttct tcatctgtgc cctcctgagg ttcatctggt gcttccagag | 4260 |
| catccacaca gccacgggcc tgaaggatcg cagcaaccag tactaccgca ggcagtacga | 4320 |
| gaaagagagc gtgggcctgg ccctccactg gggcctgaag gcgttgttct actacttta | 4380 |
| tatgccaagc ttcttgaccg gactcatggt gttttcgtg tccgagttgc ttgggggctt | 4440 |
| cggcatcgcc atcgtggtgt tcatgaacca ctacccctg gagaagatcc aggactcggt | 4500 |
| gtgggacggc cacggcttt cgccggcca gattcacgaa cgatgaacg tccagcgggg | 4560 |
| actcgtcacg gactggttct cggtgggct gaattaccaa atcgagcacc acctgtggcc | 4620 |
| gacgctgccc cggcacaacc tgacggcggc cagcatcaaa gtgagcagt tgtgcaagaa | 4680 |
| gcacaacttg ccgtatcgca gcccccccaat gctggagggg gtgggcatcc tgatcagcta | 4740 |
| cctgggcacc tttgcccgca tggtggcaaa ggccgacaag gcgtaagcgg ccgc | 4794 |

<210> SEQ ID NO 30
<211> LENGTH: 4794
<212> TYPE: DNA
<213> ORGANISM: Artificial Sequence
<220> FEATURE:
<223> OTHER INFORMATION: plasmid pLF120-3

<400> SEQUENCE: 30

| | |
|---|---|
| ttgtaatacg actcactata gggcgaattg ggccctctag atgcatgctc gagcggccgc | 60 |
| cagtgtgatg gatatctgca gaattcaggc ctgaattcca gcacactggc ggccgttact | 120 |
| agtggatccg agctcggtac caagcttgat gcatagcttg agtattctaa cgcgtcacct | 180 |
| aaatagcttg gcgtaatcat ggtcatagct gtttcctgtg tgaaattgtt atccgctcac | 240 |
| aattccacac aacatacgag ccggaagcat aaagtgtaaa gcctggggtg cctaatgagt | 300 |
| gagctaactc acattaattg cgttgcgctc actgcccgct ttccagtcgg gaaacctgtc | 360 |
| gtgccagctg cattaatgaa tcggccaacg cgcggggaga ggcggtttgc gtattgggcg | 420 |
| ctcttccgct tcctcgctca ctgactcgct gcgctcggtc gttcggctgc ggcgagcggt | 480 |
| atcagctcac tcaaaggcgg taatacggtt atccacagaa tcaggggata acgcaggaaa | 540 |
| gaacatgtga gcaaaaggcc agcaaaaggc caggaaccgt aaaaaggccg cgttgctggc | 600 |
| gtttttccat aggctccgcc cccctgacga gcatcacaaa aatcgacgct caagtcagag | 660 |
| gtggcgaaac ccgacaggac tataaagata ccaggcgttt cccctggaa gctccctcgt | 720 |
| gcgctctcct gttccgaccc tgccgcttac cggatacctg tccgcctttc tcccttcggg | 780 |
| aagcgtggcg ctttctcata gctcacgctg taggtatctc agttcggtgt aggtcgttcg | 840 |
| ctccaagctg ggctgtgtgc acgaaccccc cgttcagccc gaccgctgcg ccttatccgg | 900 |
| taactatcgt cttgagtcca acccggtaag acacgactta tcgccactgg cagcagccac | 960 |
| tggtaacagg attagcagag cgaggtatgt aggcggtgct acagagttct tgaagtggtg | 1020 |

```
gcctaactac ggctacacta gaagaacagt atttggtatc tgcgctctgc tgaagccagt   1080
taccttcgga aaaagagttg gtagctcttg atccggcaaa caaaccaccg ctggtagcgg   1140
tggttttttt gtttgcaagc agcagattac gcgcagaaaa aaggatctca agaagatcc    1200 tttgatcttt tctacggggt ctgacgctca gtggaacgaa aactcacgtt aagggatttt   1260
ggtcatgaga ttatcaaaaa ggatcttcac ctagatcctt ttaaattaaa aatgaagttt   1320
tagcacgtgt cagtcctgct cctcggccac gaagtgcacg cagttgccgg ccgggtcgcg   1380
cagggcgaac tcccgccccc acggctgctc gccgatctcg gtcatggccg gcccggaggc   1440
gtcccggaag ttcgtggaca cgacctccga ccactcggcg tacagctcgt ccaggccgcg   1500
cacccacacc caggccaggg tgttgtccgg caccacctgg tcctggaccg cgctgatgaa   1560
cagggtcacg tcgtcccgga ccacaccggc gaagtcgtcc tccacgaagt cccgggagaa   1620
cccgagccgg tcggtccaga actcgaccgc tccggcgacg tcgcgcgcgg tgagcaccgg   1680
aacggcactg gtcaacttgg ccatggtggc cctcctcacg tgctattatt gaagcattta   1740
tcagggttat tgtctcatga gcggatacat atttgaatgt atttagaaaa ataaacaaat   1800
aggggttccg cgcacatttc cccgaaaagt gccacctgat gcggtgtgaa ataccgcaca   1860
gatgcgtaag gagaaaatac cgcatcagga aattgtaagc gttaataatt cagaagaact   1920
cgtcaagaag gcgatagaag gcgatgcgct gcgaatcggg agcggcgata ccgtaaagca   1980
cgaggaagcg gtcagcccat tcgccgccaa gctcttcagc aatatcacgg gtagccaacg   2040
ctatgtcctg atagcggtcc gccacaccca gccggccaca gtcgatgaat ccagaaaagc   2100
ggccattttc caccatgata ttcggcaagc aggcatcgcc atgggtcacg acgagatcct   2160
cgccgtcggg catgctcgcc ttgagcctgg cgaacagttc ggctggcgcg agccctgat    2220 gctcttcgtc cagatcatcc tgatcgacaa gaccggcttc catccgagta cgtgctcgct   2280
cgatgcgatg tttcgcttgg tggtcgaatg ggcaggtagc cggatcaagc gtatgcagcc   2340
gccgcattgc atcagccatg atggatactt tctcggcagg agcaaggtga gatgacagga   2400
gatcctgccc cggcacttcg cccaatagca gccagtccct tcccgcttca gtgacaacgt   2460
cgagcacagc tgcgcaagga acgcccgtcg tggccagcca cgatagccgc gctgcctcgt   2520
cttgcagttc attcagggca ccggacaggt cggtcttgac aaaaagaacc gggcgcccct   2580
gcgctgacag ccggaacacg gcggcatcag agcagccgat tgtctgttgt gcccagtcat   2640
agccgaatag cctctccacc caagcggccg gagaacctgc gtgcaatcca tcttgttcaa   2700
tcatgcgaaa cgatcctcat cctgtctctt gatcagagct tgatccctg cgccatcaga   2760 tccttggcgg caagaaagcc atccagttta ctttgcaggg cttcccaacc ttaccagagg   2820
gcgccccagc tggcaattcc ggttcgcttg ctgtccataa aaccgcccag tctagctatc   2880
gccatgtaag cccactgcaa gctacctgct ttctctttgc gcttgcgttt tcccttgtcc   2940
agatagccca gtagctgaca ttcatccggg gtcagcaccg tttctgcgga ctggctttct   3000
acgtgaaaag gatctaggtg aagatccttt ttgataatct catgcctgac atttatattc   3060
cccagaacat caggttaatg gcgtttttga tgtcattttc gcggtggctg agatcagcca   3120
cttcttcccc gataacggag accggcacac tggccatatc ggtggtcatc atgcgccagc   3180
tttcatcccc gatatgcacc accgggtaaa gttcacggga gactttatct gacagcagac   3240
gtgcactggc caggggggatc accatccgtc gccccggcgt gtcaataata tcactctgta   3300
catccacaaa cagacgataa cggctctctc ttttataggt gtaaacctta aactgccgta   3360
cgtataggct gcgcaactgt tgggaagggc gatcggtgcg ggcctcttcg ctattacgcc   3420
```

```
agctggcgaa aggggatgt gctgcaaggc gattaagttg ggtaacgcca gggttttccc    3480
agtcacgacg ttgtaaaacg acggccagtg aagcggccgc accatggtga aaaggccagc    3540
acttccgctg accgttgatg gtgtcaccta tgatgtgtct gcctggttga accatcatcc    3600 aggggtgct gacatcattg agaactaccg cggtcgtgat gccactgatg tctttatggt    3660
tatgcactct gaaaatgctg tgagtaaact aagaaggatg cctatcatgg aaccatcatc    3720
tccactgacg cctacgccac cgaaacccaa ctcagacgaa ccgcaggagg atttccgcaa    3780
gctccgagat gagctcatcg cagcaggaat gttcgacgca tcaccgatgt ggtacgcata    3840
taagacgctc agtacgctgg gcctcggggt cctcgcggtg ctattgatga cccagtggca    3900
ctggtacctc gtcggggcaa tcgtgttggg cattcacttc caacaaatgg gttggttgtc    3960
gcacgatatc tgccaccatc agctgttcaa ggaccgatcg atcaacaacg ccatcggctt    4020
gcttttcggg aacgtcttgc aagggttctc tgtgacctgg tggaaggaca ggcacaatgc    4080
acaccactcc gccaccaacg tgcaaggcca cgaccccgac attgacaacc tgccgctgct    4140
ggcatggtcc aaggaggacg tggagagggc cggcccgttc tcacggcgga tgatcaagta    4200
ccagcaatac tacttcttct tcatctgtgc cctcctgagg ttcatctggt gcttccagag    4260
catccacaca gccacgggcc tgaaggatcg cagcaaccag tactaccgca ggcagtacga    4320
gaaagagagc gtgggcctgg ccctccactg gggcctgaag gcgttgttct actacttta    4380 tatgccaagc ttcttgaccg gactcatggt gttttcgtg tccgagttgc ttggggctt    4440 cggcatcgcc atcgtggtgt tcatgaacca ctacccctg gagaagatcc aggactcggt    4500
gtgggacggc cacggctttt gcgccggcca gattcacgaa acgatgaacg tccagcgggg    4560
actcgtcacg gactggttct tcggtgggct gaattaccaa atcgagcacc acctgtggcc    4620
gacgctgccc cggcacaacc tgacggcggc cagcatcaaa gtggagcagt tgtgcaagaa    4680
gcacaacttg ccgtatcgca gccccccaat gctggagggg gtgggcatcc tgatcagcta    4740
cctgggcacc tttgccgca tggtggcaaa ggccgacaag gcgtaagcgg ccgc            4794
```

<210> SEQ ID NO 31
<211> LENGTH: 4794
<212> TYPE: DNA
<213> ORGANISM: Artificial Sequence
<220> FEATURE:
<223> OTHER INFORMATION: plasmid pLF120-4

<400> SEQUENCE: 31

```
ttgtaatacg actcactata gggcgaattg ggccctctag atgcatgctc gagcggccgc      60
cagtgtgatg gatatctgca gaattcaggc ctgaattcca gcacactggc ggccgttact     120
agtggatccg agctcggtac caagcttgat gcatagcttg agtattctaa cgcgtcacct     180
aaatagcttg gcgtaatcat ggtcatagct gtttcctgtg tgaaattgtt atccgctcac     240
aattccacac aacatacgag ccggaagcat aaagtgtaaa gcctggggtg cctaatgagt     300
gagctaactc acattaattg cgttgcgctc actgcccgct ttccagtcgg gaaacctgtc     360
gtgccagctg cattaatgaa tcggccaacg cgcgggaga gcggtttgc gtattgggcg     420 ctcttccgct tcctcgctca ctgactcgct gcgctcggtc gttcggctgc ggcgagcggt     480
atcagctcac tcaaaggcgg taatacggtt atccacagaa tcaggggata acgcaggaaa     540
gaacatgtga gcaaaaggcc agcaaaaggc caggaaccgt aaaaaggccg cgttgctggc     600 gttttttccat aggctccgcc cccctgacga gcatcacaaa aatcgacgct caagtcagag     660
gtggcgaaac ccgacaggac tataaagata ccaggcgttt ccccctggaa gctccctcgt     720
```

```
gcgctctcct gttccgaccc tgccgcttac cggatacctg tccgcctttc tcccttcggg    780
aagcgtggcg ctttctcata gctcacgctg taggtatctc agttcggtgt aggtcgttcg    840
ctccaagctg ggctgtgtgc acgaaccccc cgttcagccc gaccgctgcg ccttatccgg    900
taactatcgt cttgagtcca acccggtaag acacgactta tcgccactgg cagcagccac    960
tggtaacagg attagcagag cgaggtatgt aggcggtgct acagagttct gaagtggtg    1020
gcctaactac ggctacacta gaagaacagt atttggtatc tgcgctctgc tgaagccagt   1080
taccttcgga aaagagttg gtagctcttg atccggcaaa caaaccaccg ctggtagcgg    1140
tggttttttt gtttgcaagc agcagattac gcgcagaaaa aaaggatctc aagaagatcc   1200
tttgatcttt tctacggggt ctgacgctca gtggaacgaa aactcacgtt aagggatttt    1260
ggtcatgaga ttatcaaaaa ggatcttcac ctagatcctt ttaaattaaa aatgaagttt    1320
tagcacgtgt cagtcctgct cctcggccac gaagtgcacg cagttgccgg ccgggtcgcg   1380
cagggcgaac tcccgccccc acggctgctc gccgatctcg gtcatggccg gcccggaggc   1440
gtcccggaag ttcgtggaca cgacctccga ccactcggcg tacagctcgt ccaggccgcg   1500
cacccacacc caggccaggg tgttgtccgg caccacctgg tcctggaccg cgctgatgaa   1560
cagggtcacg tcgtcccgga ccacaccggc gaagtcgtcc tccacgaagt cccgggagaa   1620
cccgagccgg tcgtccaga actcgaccgc tccggcgacg tcgcgcgcgg tgagcaccgg    1680
aacggcactg gtcaacttgg ccatggtggc cctcctcacg tgctattatt gaagcattta   1740
tcagggttat tgtctcatga gcggatacat atttgaatgt atttagaaaa ataaacaaat   1800
aggggttccg cgcacatttc cccgaaaagt gccacctgat gcggtgtgaa ataccgcaca   1860
gatgcgtaag gagaaaatac cgcatcagga aattgtaagc gttaataatt cagaagaact   1920
cgtcaagaag gcgatagaag gcgatgcgct gcgaatcggg agcggcgata ccgtaaagca   1980
cgaggaagcg gtcagcccat tcgccgccaa gctcttcagc aatatcacgg gtagccaacg   2040
ctatgtcctg atagcggtcc gccacaccca gccggccaca gtcgatgaat ccagaaaagc   2100
ggccattttc caccatgata ttcggcaagc aggcatcgcc atgggtcacg acgagatcct   2160
cgccgtcggg catgctcgcc ttgagcctgg cgaacagttc ggctggcgcg agcccctgat   2220
gctcttcgtc cagatcatcc tgatcgacaa gaccggcttc catccgagta cgtgctcgct   2280
cgatgcgatg tttcgcttgg tggtcgaatg ggcaggtagc cggatcaagc gtatgcagcc   2340
gccgcattgc atcagccatg atggatactt tctcggcagg agcaaggtga gatgacagga   2400
gatcctgccc cggcacttcg cccaatagca gccagtccct tcccgcttca gtgacaacgt   2460
cgagcacagc tgcgcaagga acgcccgtcg tggccagcca cgatagccgc gctgcctcgt   2520
cttgcagttc attcagggca ccggacaggt cggtcttgac aaaaagaacc gggcgcccct   2580
gcgctgacag ccggaacacg gcggcatcag agcagccgat tgtctgttgt gcccagtcat   2640
agccgaatag cctctccacc caagcggccg gagaacctgc gtgcaatcca tcttgttcaa   2700
tcatgcgaaa cgatcctcat cctgtctctt gatcagagct tgatccctg cgccatcaga    2760
tccttggcgg caagaaagcc atccagttta ctttgcaggg cttcccaacc ttaccagagg   2820
gcgccccagc tggcaattcc ggttcgcttg ctgtccataa aaccgcccag tctagctatc   2880
gccatgtaag cccactgcaa gctacctgct ttctctttgc gcttgcgttt tcccttgtcc   2940
agatagccca gtagctgaca ttcatccggg gtcagcaccg tttctgcgga ctggctttct   3000
acgtgaaaag gatctaggtg aagatccttt ttgataatct catgcctgac atttatattc   3060
cccagaacat caggttaatg gcgttttga tgtcattttc gcggtggctg agatcagcca   3120
```

```
cttcttcccc gataacggag accggcacac tggccatatc ggtggtcatc atgcgccagc   3180
tttcatcccc gatatgcacc accgggtaaa gttcacggga gactttatct gacagcagac   3240
gtgcactggc cagggggatc accatccgtc gccccggcgt gtcaataata tcactctgta   3300
catccacaaa cagacgataa cggctctctc ttttataggt gtaaaccttta aactgccgta   3360 cgtataggct gcgcaactgt tgggaagggc gatcggtgcg ggcctcttcg ctattacgcc   3420
agctggcgaa aggggggatgt gctgcaaggc gattaagttg ggtaacgcca gggttttccc   3480
agtcacgacg ttgtaaaacg acggccagtg aagcggccgc accatggtga aaaggccagc   3540
acttccgctg accgttgatg gtgtcaccta tgatgtgtct gcctggttga accatcatcc   3600 aggggggtgct gacatcattg agaactaccg cggtcgtgat gccactgatg tctttatggt   3660
tatgcactct gaaaatgctg tgagtaaact aagaaggatg cctatcatgg aaccatcatc   3720
tccactgacg cctacgccac cgaaacccaa ctcagacgaa ccgcaggagg atttccgcaa   3780
gctccgagat gagctcatcg cagcaggaat gttcgacgca tcaccgatgt ggtacgcata   3840
taagacgctc agtacgctgg gcctcggggt cctcgcggtg ctattgatga cccagtggca   3900
ctggtacctc gtcggggcaa tcgtgttggg cattcacttc caacaaatgg gttggttgtc   3960
gcacgatatc tgccaccatc agctgttcaa ggaccgatcg atcaacaacg ccatcggctt   4020
gcttttcggg aacgtcttgc aagggttctc tgtgacctgg tggaaggaca ggcacaatgc   4080
acaccactcc gccaccaacg tgcaaggcca cgaccccgac attgacaacc tgccgctgct   4140
ggcatggtcc aaggaggacg tggagagggc cggcccgttc tcacggcgga tgatcaagta   4200
ccagcaatac tacttcttct tcatctgtgc cctcctgagg ttcatctggt gcttccagag   4260
catccacaca gccacgggcc tgaaggatcg cagcaaccag tactaccgca ggcagtacga   4320
gaaagagagc gtgggcctgg ccctccactg gggcctgaag gcgttgttct actacttttta   4380 tatgccaagc ttcttgaccg gactcatggt gttttttcgtg tccgagttgc ttgggggctt   4440
cggcatcgcc atcgtggtgt tcatgaacca ctaccccctg gagaagatcc aggactcggt   4500
gtgggacggc cacggctttt gcgccggcca gattcacgaa acgatgaacg tccagcgggg   4560
actcgtcacg gactggttct tcggtgggct gaattaccaa atcgagcacc acctgtggcc   4620
gacgctgccc cggcacaacc tgacggcggc cagcatcaaa gtggagcagt tgtgcaagaa   4680
gcacaacttg ccgtatcgca gccccccaat gctggagggg gtgggcatcc tgatcagcta   4740
cctgggcacc tttgcccgca tggtggcaaa ggccgacaag gcgtaagcgg ccgc         4794

<210> SEQ ID NO 32
<211> LENGTH: 9472
<212> TYPE: DNA
<213> ORGANISM: Artificial Sequence
<220> FEATURE:
<223> OTHER INFORMATION: plsmid pDMW263

<400> SEQUENCE: 32
catggcatgg atggtacgtc ctgtagaaac cccaacccgt gaaatcaaaa aactcgacgg     60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
```

```
actgaactgg cagactatcc cgccgggaat ggtgattacc gacgaaaacg gcaagaaaaa      480
gcagtcttac ttccatgatt tctttaacta tgccgggatc catcgcagcg taatgctcta      540
caccacgccg aacacctggg tggacgatat caccgtggtg acgcatgtcg cgcaagactg      600
taaccacgcg tctgttgact ggcaggtggt ggccaatggt gatgtcagcg ttgaactgcg      660
tgatgcggat caacaggtgg ttgcaactgg acaaggcact agcggacttt tgcaagtggt      720
gaatccgcac ctctggcaac cgggtgaagg ttatctctat gaactgtgcg tcacagccaa      780
aagccagaca gagtgtgata tctacccgct tcgcgtcggc atccggtcag tggcagtgaa      840
gggcgaacag ttcctgatta accacaaacc gttctacttt actggctttg gtcgtcatga      900
agatgcggac ttacgtggca aaggattcga taacgtgctg atggtgcacg accacgcatt      960
aatggactgg attggggcca actcctaccg tacctcgcat tacccttacg ctgaagagat     1020
gctcgactgg gcagatgaac atggcatcgt ggtgattgat gaaactgctg ctgtcggctt     1080
taacctctct ttaggcattg gtttcgaagc gggcaacaag ccgaaagaac tgtacagcga     1140
agaggcagtc aacggggaaa ctcagcaagc gcacttacag gcgattaaag agctgatagc     1200
gcgtgacaaa aaccacccaa gcgtggtgat gtggagtatt gccaacgaac ggatacccg     1260 tccgcaagtg cacgggaata tttcgccact ggcggaagca acgcgtaaac tcgacccgac     1320
gcgtccgatc acctgcgtca atgtaatgtt ctgcgacgct cacaccgata ccatcagcga     1380
tctctttgat gtgctgtgcc tgaaccgtta ttacggatgg tatgtccaaa gcggcgattt     1440
ggaaacggca gagaaggtac tggaaaaaga acttctggcc tggcaggaga aactgcatca     1500
gccgattatc atcaccgaat acggcgtgga tacgttagcc gggctgcact caatgtacac     1560
cgacatgtgg agtgaagagt atcagtgtgc atggctggat atgtatcacc gcgtctttga     1620
tcgcgtcagc gccgtcgtcg gtgaacaggt atggaatttc gccgattttg cgacctcgca     1680
aggcatattg cgcgttggcg gtaacaagaa agggatcttc actcgcgacc gcaaaccgaa     1740
gtcggcggct tttctgctgc aaaaacgctg gactggcatg aacttcggtg aaaaaccgca     1800
gcagggaggc aaacaatgat taattaacta gagcggccgc caccgcggcc cgagattccg     1860
gcctcttcgg ccgccaagcg acccgggtgg acgtctagag gtacctagca attaacagat     1920
agtttgccgg tgataattct cttaacctcc cacactcctt tgacataacg atttatgtaa     1980
cgaaactgaa atttgaccag atattgtgtc cgcggtggag ctccagcttt tgttcccttt     2040
agtgagggtt aatttcgagc ttggcgtaat catggtcata gctgtttcct gtgtgaaatt     2100
gttatccgct cacaattcca cacaacatac gagccggaag cataaagtgt aaagcctggg     2160
gtgcctaatg agtgagctaa ctcacattaa ttgcgttgcg ctcactgccc gctttccagt     2220
cgggaaacct gtcgtgccag ctgcattaat gaatcggcca acgcgcgggg agaggcggtt     2280
tgcgtattgg gcgctcttcc gcttcctcgc tcactgactc gctgcgctcg gtcgttcggc     2340
tgcggcgagc ggtatcagct cactcaaagg cggtaatacg gttatccaca gaatcagggg     2400
ataacgcagg aaagaacatg tgagcaaaag gccagcaaaa ggccaggaac cgtaaaaagg     2460
ccgcgttgct ggcgtttttc cataggctcc gcccccctga cgagcatcac aaaaatcgac     2520
gctcaagtca gaggtggcga aacccgacag gactataaag ataccaggcg tttccccctg     2580
gaagctccct cgtgcgctct cctgttccga ccctgccgct taccggatac ctgtccgcct     2640
ttctcccttc gggaagcgtg gcgctttctc atagctcacg ctgtaggtat ctcagttcgg     2700
tgtaggtcgt tcgctccaag ctgggctgtg tgcacgaacc ccccgttcag cccgaccgct     2760
gcgccttatc cggtaactat cgtcttgagt ccaacccggt aagacacgac ttatcgccac     2820
```

```
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaggat   3060 ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata cggttttt cgccctttga   4500 cgttggagtc cacgttcttt aatagtggac tcttgttcca aactggaaca acactcaacc   4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg gccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
```

```
atatattgta tgaacttatt tttattactt agtattatta gacaacttac ttgctttatg    5280
aaaaacactt cctatttagg aaacaattta taatggcagt tcgttcattt aacaatttat    5340
gtagaataaa tgttataaat gcgtatggga aatcttaaat atggatagca taaatgatat    5400
ctgcattgcc taattcgaaa tcaacagcaa cgaaaaaaat cccttgtaca acataaatag    5460
tcatcgagaa atatcaacta tcaaagaaca gctattcaca cgttactatt gagattatta    5520
ttggacgaga atcacacact caactgtctt tctctcttct agaaatacag gtacaagtat    5580
gtactattct cattgttcat acttctagtc atttcatccc acatattcct tggatttctc    5640
tccaatgaat gacattctat cttgcaaatt caacaattat aataagatat accaaagtag    5700
cggtatagtg gcaatcaaaa agcttctctg gtgtgcttct cgtatttatt tttattctaa    5760
tgatccatta aaggtatata tttatttctt gttatataat ccttttgttt attacatggg    5820
ctggatacat aaaggtattt tgatttaatt ttttgcttaa attcaatccc ccctcgttca    5880
gtgtcaactg taatggtagg aaattaccat acttttgaag aagcaaaaaa aatgaaagaa    5940
aaaaaaaatc gtatttccag gttagacgtt ccgcagaatc tagaatgcgg tatgcggtac    6000
attgttcttc gaacgtaaaa gttgcgctcc ctgagatatt gtacattttt gcttttacaa    6060
gtacaagtac atcgtacaac tatgtactac tgttgatgca tccacaacag tttgtttttgt   6120 ttttttttgt tttttttttt tctaatgatt cattaccgct atgtatacct acttgtactt    6180
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaaagaaat acagttcttt gtatcatttg taacaattac cctgtacaaa    6600
ctaaggtatt gaaatcccac aatattccca aagtccaccc cttccaaat tgtcatgcct     6660 acaactcata taccaagcac taacctacca aacaccacta aaaccccaca aaatatatct    6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg ccctttttat agagtcttat    7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320 tcggggcag atccgtgaca gggctcgtac agaccgaacg cctcgttggt gtcgggcaga    7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatggcggc cgagtcgatc agctggtggt tgagctcgag ctggggaat    7560 tcgtccttga ggactcgagt gacagtcttt cgccaaagtc gagaggaggc cagcacgttg    7620
```

```
gccttgtcaa gagaccacac gggaagaggg gggttgtgct gaaggccag gaaggcggcc      7680 attcgggcaa ttcgctcaac ctcaggaacg gagtaggtct cggtgtcgga agcgacgcca      7740
gatccgtcat cctcctttcg ctctccaaag tagatacctc cgacgagctc tcggacaatg      7800
atgaagtcgg tgccctcaac gtttcggatg ggggagagat cggcgagctt gggcgacagc      7860
agctggcagg gtcgcaggtt ggcgtacagg ttcaggtcct ttcgcagctt gaggagaccc      7920
tgctcgggtc gcacgtcggt tcgtccgtcg ggagtggtcc atacggtgtt ggcagcgcct      7980
ccgacagcac cgagcataat agagtcagcc tttcggcaga tgtcgagagt agcgtcggtg      8040
atgggctcgc cctccttctc aatggcagct cctccaatga gtcggtcctc aaacacaaac      8100
tcggtgccgg aggcctcagc aacagacttg agcaccttga cggcctcggc aatcacctcg      8160
gggccacaga gtcgccgcc gagaagaaca atcttcttgg agtcagtctt ggtcttctta      8220
gtttcgggtt ccattgtgga tgtgtgtggt tgtatgtgtg atgtggtgtg tggagtgaaa      8280
atctgtggct ggcaaacgct cttgtatata tacgcacttt tgcccgtgct atgtggaaga      8340
ctaaacctcc gaagattgtg actcaggtag tgcggtatcg gctagggacc caaaccttgt      8400
cgatgccgat agcgctatcg aacgtacccc agccggccgg gagtatgtcg gagggggacat     8460 acgagatcgt caagggtttg tggccaactg gtaaataaat gatgtcgacg tttaaacagt      8520
gtacgcagat ctactataga ggaacattta aattgccccg gagaagacgg ccaggccgcc      8580
tagatgacaa attcaacaac tcacagctga ctttctgcca ttgccactag ggggggcct      8640 ttttatatgg ccaagccaag ctctccacgt cggttgggct gcacccaaca ataaatgggt      8700 aggttgcac caacaaaggg atgggatggg gggtagaaga tacgaggata acggggctca      8760
atggcacaaa taagaacgaa tactgccatt aagactcgtg atccagcgac tgacaccatt      8820
gcatcatcta agggcctcaa aactacctcg gaactgctgc gctgatctgg acaccacaga      8880
ggttccgagc actttaggtt gcaccaaatg tcccaccagg tgcaggcaga aaacgctgga      8940
acagcgtgta cagtttgtct taacaaaaag tgagggcgct gaggtcgagc agggtggtgt      9000
gacttgttat agcctttaga gctgcgaaag cgcgtatgga tttggctcat caggccagat      9060
tgagggtctg tggacacatg tcatgttagt gtacttcaat cgccccctgg atatagcccc      9120
gacaataggc cgtggcctca tttttttgcc ttccgcacat ttccattgct cgatacccac      9180
accttgcttc tcctgcactt gccaaccttaa atactggttt acattgacca acatcttaca      9240 agcgggggc ttgtctaggg tatatataaa cagtggctct cccaatcggt tgccagtctc      9300
tttttccctt tctttcccca cagattcgaa atctaaacta cacatcacag aattccgagc      9360
cgtgagtatc cacgcaaaga tcagtgtcga gacgacgcgt tttgtgtaat gacacaatcc      9420
gaaagtcgct agcaacacac actctctaca caaactaacc cagctctggt ac            9472
```

<210> SEQ ID NO 33
<211> LENGTH: 7879
<212> TYPE: DNA
<213> ORGANISM: Artificial Sequence
<220> FEATURE:
<223> OTHER INFORMATION: plasmid pDMW237

<400> SEQUENCE: 33

```
ggccgcaagt gtggatgggg aagtgagtgc ccggttctgt gtgcacaatt ggcaatccaa        60
gatggatgga ttcaacacag ggatatagcg agctacgtgg tggtgcgagg atatagcaac      120 ggatattttat gtttgacact tgagaatgta cgatacaagc actgtccaag tacaatacta      180
aacatactgt acatactcat actcgtaccc gggcaacggt ttcacttgag tgcagtggct      240
```

```
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt cgcaacgtt gttgccattg    1740 ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc    2580 ctttagggtt ccgatttagt gctttacggc acctcgaccc caaaaaactt gattagggtg   2640
```

```
atggttcacg tagtgggcca tcgccctgat agacggtttt tcgcccttttg acgttggagt   2700
ccacgttctt taatagtgga ctcttgttcc aaactggaac aacactcaac cctatctcgg   2760
tctattctttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat ttttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg ttttttttttg   4320
ttttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tactttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
```

```
acaaactcgg ggtcggatcg ggcaagctca atggtctgct ggagtactc gccagtggcc   5100 agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
agaattcagg agagaccggg ttggcggcgt atttgtgtcc caaaaaacag ccccaattgc   6120
cccggagaag acggccaggc cgcctagatg acaaattcaa caactcacag ctgactttct   6180
gccattgcca ctagggggg gccttttat atggccaagc caagctctcc acgtcggttg   6240
ggctgcaccc aacaataaat gggtagggtt gcaccaacaa agggatggga tgggggtag   6300 aagatacgag gataacgggg ctcaatggca caaataagaa cgaatactgc cattaagact   6360
cgtgatccag cgactgacac cattgcatca tctaagggcc tcaaaactac ctcggaactg   6420
ctgcgctgat ctggacacca cagaggttcc gagcacttta ggttgcacca aatgtcccac   6480
caggtgcagg cagaaaacgc tggaacagcg tgtacagttt gtcttaacaa aaagtgaggg   6540
cgctgaggtc gagcagggtg gtgtgacttg ttatagcctt tagagctgcg aaagcgcgta   6600
tggatttggc tcatcaggcc agattgaggg tctgtggaca catgtcatgt tagtgtactt   6660
caatcgcccc ctggatatag ccccgacaat aggccgtggc ctcattttt tgccttccgc   6720 acatttccat tgctcggtac ccacaccttg cttctcctgc acttgccaac cttaatactg   6780
gtttacattg accaacatct tacaagcggg gggcttgtct agggtatata taaacagtgg   6840
ctctcccaat cggttgccag tctctttttt cctttctttc cccacagatt cgaaatctaa   6900
actacacatc acacaatgcc tgttactgac gtccttaagc gaaagtccgg tgtcatcgtc   6960
ggcgacgatg tccgagccgt gagtatccac gacaagatca gtgtcgagac gacgcgtttt   7020
gtgtaatgac acaatccgaa agtcgctagc aacacacact ctctacacaa actaacccag   7080
ctctccatgg ctctggccaa cgacgctggc gagcgaatct gggctgccgt caccgatccc   7140
gaaatcctca ttggcacctt ctcctacctg ctcctgaagc ctcctcctgcg aaactctggt   7200 ctcgtggacg agaagaaagg agcctaccga acctccatga tctggtacaa cgtcctcctg   7260
gctctcttct ctgccctgtc cttctacgtg actgccaccg ctctcggctg ggactacggt   7320
actggagcct ggctgcgaag acagaccggt gatactcccc agcctctctt tcagtgtccc   7380
tctcctgtct gggactccaa gctgttcacc tggactgcca aggccttcta ctattctaag   7440
```

| | | |
|---|---|---|
| tacgtggagt acctcgacac cgcttggctg gtcctcaagg gcaagcgagt gtcctttctg | 7500 | |
| caggccttcc atcactttgg agctccctgg gacgtctacc tcggcattcg actgcacaac | 7560 | |
| gagggtgtgt ggatcttcat gttctttaac tcgttcattc acaccatcat gtacacctac | 7620 | |
| tatggactga ctgccgctgg ctacaagttc aaggccaagc ctctgatcac tgccatgcag | 7680 | |
| atttgccagt tcgtcggtgg ctttctcctg gtctgggact acatcaacgt tccctgcttc | 7740 | |
| aactctgaca agggcaagct gttctcctgg gctttcaact acgcctacgt cggatctgtc | 7800 | |
| tttctcctgt tctgtcactt cttttaccag gacaacctgg ccaccaagaa atccgctaag | 7860 | |
| gctggtaagc agctttagc | 7879 | |

<210> SEQ ID NO 34
<211> LENGTH: 7783
<212> TYPE: DNA
<213> ORGANISM: Artificial Sequence
<220> FEATURE:
<223> OTHER INFORMATION: plasmid pY115

<400> SEQUENCE: 34

| | | |
|---|---|---|
| catggctctg gccaacgacg ctggcgagcg aatctgggct gccgtcaccg atcccgaaat | 60 | |
| cctcattggc accttctcct acctgctcct gaagcctctc ctgcgaaact ctggtctcgt | 120 | |
| ggacgagaag aaaggagcct accgaacctc catgatctgg tacaacgtcc tcctggctct | 180 | |
| cttctctgcc ctgtccttct acgtgactgc caccgctctc ggctgggact acggtactgg | 240 | |
| agcctggctg cgaagacaga ccggtgatac tccccagcct ctctttcagt gtccctctcc | 300 | |
| tgtctgggac tccaagctgt tcacctggac tgccaaggcc ttctactatt ctaagtacgt | 360 | |
| ggagtacctc gacaccgctt ggctggtcct caagggcaag cgagtgtcct ttctgcaggc | 420 | |
| cttccatcac tttggagctc cctgggacgt ctacctcggc attcgactgc acaacgaggg | 480 | |
| tgtgtggatc ttcatgttct ttaactcgtt cattcacacc atcatgtaca cctactatgg | 540 | |
| actgactgcc gctggctaca gttcaaggc caagcctctg atcactgcca tgcagatttg | 600 | |
| ccagttcgtc ggtggctttc tcctggtctg gactacatc aacgttccct gcttcaactc | 660 | |
| tgacaagggc aagctgttct cctgggcttt caactacgcc tacgtcggat ctgtctttct | 720 | |
| cctgttctgt cacttctttt accaggacaa cctggccacc aagaaatccg ctaaggctgg | 780 | |
| taagcagctt tagcggccgc aagtgtggat ggggaagtga gtgcccggtt ctgtgtgcac | 840 | |
| aattggcaat ccaagatgga tggattcaac acagggatat agcgagctac gtggtggtgc | 900 | |
| gaggatatag caacggatat ttatgtttga cacttgagaa tgtacgatac aagcactgtc | 960 | |
| caagtacaat actaaacata ctgtacatac tcatactcgt acccgggcaa cggtttcact | 1020 | |
| tgagtgcagt ggctagtgct cttactcgta cagtgtgcaa tactgcgtat catagtcttt | 1080 | |
| gatgtatatc gtattcattc atgttagttg cgtacgagcc ggaagcataa agtgtaaagc | 1140 | |
| ctggggtgcc taatgagtga gctaactcac attaattgcg ttgcgctcac tgcccgcttt | 1200 | |
| ccagtcggga aacctgtcgt gccagctgca ttaatgaatc ggccaacgcg cggggagagg | 1260 | |
| cggtttgcgt attgggcgct cttccgcttc ctcgctcact gactcgctgc gctcggtcgt | 1320 | |
| tcggctgcgg cgagcggtat cagctcactc aaaggcggta atacggttat ccacagaatc | 1380 | |
| aggggataac gcaggaaaga acatgtgagc aaaaggccag caaaaggcca ggaaccgtaa | 1440 | |
| aaaggccgcg ttgctggcgt ttttccatag gctccgcccc cctgacgagc atcacaaaaa | 1500 | |
| tcgacgctca agtcagaggt ggcgaaaccc gacaggacta taaagatacc aggcgtttcc | 1560 | |
| ccctggaagc tccctcgtgc gctctcctgt tccgaccctg ccgcttaccg gatacctgtc | 1620 | |

```
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gttttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta atcaatcta aagtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg ttttttcgccc   3480 tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaatttcg ggccaataat ttaaaaaaat   4020
```

```
cgtgttatat aatattatat gtattatata tatacatcat gatgatactg acagtcatgt    4080
cccattgcta aatagacaga ctccatctgc cgcctccaac tgatgttctc aatatttaag    4140
gggtcatctc gcattgttta ataataaaca gactccatct accgcctcca aatgatgttc    4200
tcaaaatata ttgtatgaac ttatttttat tacttagtat tattagacaa cttacttgct    4260
ttatgaaaaa cacttcctat ttaggaaaca atttataatg gcagttcgtt catttaacaa    4320
tttatgtaga ataaatgtta taaatgcgta tgggaaatct taaatatgga tagcataaat    4380
gatatctgca ttgcctaatt cgaaatcaac agcaacgaaa aaaatcccctt gtacaacata   4440 aatagtcatc gagaaatatc aactatcaaa gaacagctat tcacacgtta ctattgagat    4500
tattattgga cgagaatcac acactcaact gtctttctct cttctagaaa tacaggtaca    4560
agtatgtact attctcattg ttcatacttc tagtcatttc atcccacata ttccttggat    4620
ttctctccaa tgaatgacat tctatcttgc aaattcaaca attataataa gatataccaa    4680
agtagcggta tagtggcaat caaaaagctt ctctggtgtg cttctcgtat ttatttttat    4740
tctaatgatc cattaaaggt atatatttat ttcttgttat ataatccttt tgtttattac    4800
atgggctgga tacataaagg tattttgatt taattttttg cttaaattca atcccccctc    4860
gttcagtgtc aactgtaatg gtaggaaatt accatacttt tgaagaagca aaaaaaatga    4920
aagaaaaaaa aaatcgtatt tccaggttag acgttccgca gaatctagaa tgcggtatgc    4980
ggtacattgt tcttcgaacg taaaagttgc gctccctgag atattgtaca tttttgcttt    5040
tacaagtaca agtacatcgt acaactatgt actactgttg atgcatccac aacagtttgt    5100
tttgtttttt tttgttttt tttttttctaa tgattcatta ccgctatgta tacctacttg    5160
tacttgtagt aagccgggtt attggcgttc aattaatcat agacttatga atctgcacgg    5220
tgtgcgctgc gagttacttt tagcttatgc atgctacttg ggtgtaatat tgggatctgt    5280
tcggaaatca acggatgctc aatcgatttc gacagtaatt aattaagtca tacacaagtc    5340
agctttcttc gagcctcata taagtataag tagttcaacg tattagcact gtacccagca    5400
tctccgtatc gagaaacaca acaacatgcc ccattggaca gatcatgcgg atacacaggt    5460
tgtgcagtat catacatact cgatcagaca ggtcgtctga ccatcataca agctgaacaa    5520
gcgctccata cttgcacgct ctctatatac acagttaaat tacatatcca tagtctaacc    5580
tctaacagtt aatcttctgg taagcctccc agccagcctt ctggtatcgc ttggcctcct    5640
caataggatc tcggttctgg ccgtacagac ctcggccgac aattatgata tccgttccgg    5700
tagacatgac atcctcaaca gttcggtact gctgtccgag agcgtctccc ttgtcgtcaa    5760
gacccacccc gggggtcaga ataagccagt cctcagagtc gcccttaggt cggttctggg    5820
caatgaagcc aaccacaaac tcggggtcgg atcgggcaag ctcaatggtc tgcttggagt    5880
actcgccagt ggccagagag cccttgcaag acagctcggc cagcatgagc agacctctgg    5940
ccagcttctc gttgggagag gggactagga actccttgta ctgggagttc tcgtagtcag    6000
agacgtcctc cttcttctgt tcagagacag tttcctcggc accagctcgc aggccagcaa    6060
tgattccggt tccgggtaca ccgtgggcgt tggtgatatc ggaccactcg gcgattcggt    6120
gacaccggta ctggtgcttg acagtgttgc caatatctgc gaactttctg tcctcgaaca    6180
ggaagaaacc gtgcttaaga gcaagttcct tgaggggag cacagtgccg gcgtaggtga    6240
agtcgtcaat gatgtcgata tgggttttga tcatgcacac ataaggtccg accttatcgg    6300
caagctcaat gagctccttg gtggtggtaa catccagaga agcacacagg ttggttttct    6360
tggctgccac gagcttgagc actcgagcgg caaaggcgga cttgtggacg ttagctcgag    6420
```

```
cttcgtagga gggcattttg gtggtgaaga ggagactgaa ataaatttag tctgcagaac    6480
tttttatcgg aaccttatct ggggcagtga agtatatgtt atggtaatag ttacgagtta    6540
gttgaactta tagatagact ggactatacg gctatcggtc caaattagaa agaacgtcaa    6600
tggctctctg ggcgtcgcct ttgccgacaa aaatgtgatc atgatgaaag ccagcaatga    6660
cgttgcagct gatattgttg tcggccaacc gcgccgaaaa cgcagctgtc agacccacag    6720
cctccaacga agaatgtatc gtcaaagtga tccaagcaca ctcatagttg gagtcgtact    6780
ccaaaggcgg caatgacgag tcagacagat actcgtcgac gtttaaacag tgtacgcaga    6840
tctactatag aggaacattt aaattgcccc ggagaagacg gccaggccgc ctagatgaca    6900
aattcaacaa ctcacagctg actttctgcc attgccacta gggggggggcc ttttttatatg    6960 gccaagccaa gctctccacg tcggttgggc tgcacccaac aataaatggg tagggttgca    7020
ccaacaaagg gatgggatgg gggtagaag atacgaggat aacggggctc aatggcacaa    7080
ataagaacga atactgccat taagactcgt gatccagcga ctgacaccat tgcatcatct    7140
aagggcctca aaactacctc ggaactgctg cgctgatctg acaccacag aggttccgag    7200 cactttaggt tgcaccaaat gtcccaccag gtgcaggcag aaaacgctgg aacagcgtgt    7260
acagtttgtc ttaacaaaaa gtgagggcgc tgaggtcgag cagggtggtg tgacttgtta    7320
tagcctttag agctgcgaaa gcgcgtatgg atttggctca tcaggccaga ttgagggtct    7380
gtggacacat gtcatgttag tgtacttcaa tcgcccctg gatatagccc cgacaatagg    7440
ccgtggcctc atttttttgc cttccgcaca tttccattgc tcgatacca caccttgctt    7500 ctcctgcact tgccaacctt aatactggtt tacattgacc aacatcttac aagcgggggg    7560
cttgtctagg gtatatataa acagtggctc tcccaatcgg ttgccagtct ctttttttcct   7620 ttctttcccc acagattcga aatctaaact acacatcaca gaattccgag ccgtgagtat    7680
ccacgacaag atcagtgtcg agacgacgcg ttttgtgtaa tgacacaatc cgaaagtcgc    7740
tagcaacaca cactctctac acaaactaac ccagctctgg tac                      7783
```

<210> SEQ ID NO 35
<211> LENGTH: 8254
<212> TYPE: DNA
<213> ORGANISM: Artificial Sequence
<220> FEATURE:
<223> OTHER INFORMATION: plasmid pY175

<400> SEQUENCE: 35

```
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc ggcaacggtt tcacttgagt gcagtggcta     240
gtgctcttac tcgtacagtg tgcaatactg cgtatcatag tctttgatgt atatcgtatt     300
cattcatgtt agttgcgtac gagccggaag cataaagtgt aaagcctggg gtgcctaatg     360
agtgagctaa ctcacattaa ttgcgttgcg ctcactgccc gctttccagt cgggaaacct     420
gtcgtgccag ctgcattaat gaatcggcca acgcgcgggg agaggcggtt tgcgtattgg     480
gcgctcttcc gcttcctcgc tcactgactc gctgcgctcg tcgttcggc tgcggcgagc     540 ggtatcagct cactcaaagg cggtaatacg gttatccaca gaatcagggg ataacgcagg     600
aaagaacatg tgagcaaaag gccagcaaaa ggccaggaac cgtaaaaagg ccgcgttgct     660
ggcgtttttc cataggctcc gcccccctga cgagcatcac aaaaatcgac gctcaagtca     720
```

```
gaggtggcga aacccgacag gactataaag ataccaggcg tttccccctg gaagctccct      780
cgtgcgctct cctgttccga ccctgccgct taccggatac ctgtccgcct ttctcccttc      840
gggaagcgtg gcgctttctc atagctcacg ctgtaggtat ctcagttcgg tgtaggtcgt      900
tcgctccaag ctgggctgtg tgcacgaacc ccccgttcag cccgaccgct gcgccttatc      960
cggtaactat cgtcttgagt ccaacccggt aagacacgac ttatcgccac tggcagcagc     1020
cactggtaac aggattagca gagcgaggta tgtaggcggt gctacagagt tcttgaagtg     1080
gtggcctaac tacggctaca ctagaaggac agtatttggt atctgcgctc tgctgaagcc     1140
agttaccttc ggaaaaagag ttggtagctc ttgatccggc aaacaaacca ccgctggtag     1200
cggtggtttt tttgtttgca agcagcagat tacgcgcaga aaaaaaggat ctcaagaaga     1260
tcctttgatc ttttctacgg ggtctgacgc tcagtggaac gaaaactcac gttaagggat     1320
tttggtcatg agattatcaa aaaggatctt cacctagatc cttttaaatt aaaaatgaag     1380
ttttaaatca atctaaagta tatatgagta aacttggtct gacagttacc aatgcttaat     1440
cagtgaggca cctatctcag cgatctgtct atttcgttca tccatagttg cctgactccc     1500
cgtcgtgtag ataactacga tacggagggg cttaccatct ggccccagtg ctgcaatgat     1560
accgcgagac ccacgctcac cggctccaga tttatcagca ataaaccagc cagccggaag     1620
ggccgagcgc agaagtggtc ctgcaacttt atccgcctcc atccagtcta ttaattgttg     1680
ccgggaagct agagtaagta gttcgccagt taatagtttg cgcaacgttg ttgccattgc     1740
tacaggcatc gtggtgtcac gctcgtcgtt tggtatggct tcattcagct ccggttccca     1800
acgatcaagg cgagttacat gatccccat gttgtgcaaa aaagcggtta gctccttcgg     1860
tcctccgatc gttgtcagaa gtaagttggc cgcagtgtta tcactcatgg ttatggcagc     1920
actgcataat tctcttactg tcatgccatc cgtaagatgc ttttctgtga ctggtgagta     1980
ctcaaccaag tcattctgag aatagtgtat gcggcgaccg agttgctctt gcccggcgtc     2040
aatacgggat aataccgcgc cacatagcag aactttaaaa gtgctcatca ttggaaaacg     2100
ttcttcgggg cgaaaactct caaggatctt accgctgttg agatccagtt cgatgtaacc     2160
cactcgtgca cccaactgat cttcagcatc ttttactttc accagcgttt ctgggtgagc     2220
aaaaacagga aggcaaaatg ccgcaaaaaa gggaataagg gcgacacgga aatgttgaat     2280
actcatactc ttcctttttc aatattattg aagcatttat cagggttatt gtctcatgag     2340
cggatacata tttgaatgta tttagaaaaa taaacaaata ggggttccgc gcacatttcc     2400
ccgaaaagtg ccacctgacg cgccctgtag cggcgcatta agcgcggcgg gtgtggtggt     2460
tacgcgcagc gtgaccgcta cacttgccag cgccctagcg cccgctcctt tcgctttctt     2520
cccttccttt ctcgccacgt tcgccggctt tccccgtcaa gctctaaatc ggggctccc     2580
tttagggttc cgatttagtg ctttacggca cctcgacccc aaaaaacttg attagggtga     2640
tggttcacgt agtgggccat cgccctgata gacggttttt cgccctttga cgttggagtc     2700
cacgttcttt aatagtggac tcttgttcca aactggaaca acactcaacc ctatctcggt     2760
ctattctttt gatttataag ggattttgcc gatttcggcc tattggttaa aaaatgagct     2820
gatttaacaa aaatttaacg cgaattttaa caaatatta cgcttacaa tttccattcg     2880
ccattcaggc tgcgcaactg ttgggaaggg cgatcggtgc gggcctcttc gctattacgc     2940
cagctggcga aaggggatg tgctgcaagg cgattaagtt gggtaacgcc agggttttcc     3000
cagtcacgac gttgtaaaac gacggccagt gaattgtaat acgactcact ataggcgaa     3060
ttgggtaccg ggcccccct cgaggtcgat ggtgtcgata agcttgatat cgaattcatg     3120
```

```
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga aatcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt ttttttttgt    4320
ttttttttt  tctaatgatt cattaccgct atgtatacct acttgtactt gtagtaagcc    4380
gggttattgg cgttcaatta atcatagact tatgaatctg cacggtgtgc gctgcgagtt    4440
actttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgcatcct     4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160
gagagggac  taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
```

```
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct     5700 tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa     6060
catttaaatt gccccggaga agacggccag gccgcctaga tgacaaattc aacaactcac    6120
agctgacttt ctgccattgc cactaggggg gggccttttt atatggccaa gccaagctct    6180
ccacgtcggt tgggctgcac ccaacaataa atgggtaggt tgcaccaac aaagggatgg     6240 gatgggggt agaagatacg aggataacgg ggctcaatgg cacaaataag aacgaatact     6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttaac    6480
aaaaagtgag ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttccttctt tccccacaga     6840 ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca tggtgaaaag gccagcactt ccgctgaccg    7020
ttgatggtgt cacctatgat gtgtctgcct ggttgaacca tcatccaggg ggtgctgaca    7080
tcattgagaa ctaccgcggt cgtgatgcca ctgatgtctt tatggttatg cactctgaaa    7140
atgctgtgag taaactaaga aggatgccta tcatggaacc atcatctcca ctgacgccta    7200
cgccaccgaa acccaactca gacgaaccgc aggaggattt ccgcaagctc cgagatgagc    7260
tcatcgcagc aggaatgttc gacgcatcac cgatgtggta cgcatataag acgctcacta    7320
cgctgggcct cggggtcctc gcggtgctat tgatgaccca gtggcactgg tacctcgtcg    7380
gggcaatcgt gttgggcatt cacttccaac aaatggggttg gttgtcgcac gatatctgcc    7440
accatcagct gttcaaggac cgatcgatca acaacgccat cggcttgctt ttcgggaacg    7500
tcttgcaagg gttctctgtg acctggtgga aggacaggca caatgcacac cactccgcca    7560
ccaacgtgca aggccacgac cccgacattg acaacctgcc gctgctggca tggtccaagg    7620
aggacgtgga gagggccggc ccgttctcac ggcggatgat caagtaccag caatactact    7680
tcttcttcat ctgtgccctc ctgaggttca tctggtgctt ccagagcatc cacacagcca    7740
agggcctgaa ggatcgcagc aaccagtact accgcaggca gtacgagaaa gagagcgtgg    7800
gcctggccct ccactggggc ctgaaggcgt tgttctacta cttttatatg ccaagcttct    7860
tgaccggact catggtgttt ttcgtgtccg agttgcttgg gggcttcggc atcgccatcg    7920
```

```
tggtgttcat gaaccactac cccctggaga agatccagga ctcggtgtgg gacggccacg    7980
gcttttgcgc cggccagatt cacgaaacga tgaacgtcca gcggggactc gtcacggact    8040
ggttcttcgg tgggctgaat taccaaatcg agcaccacct gtggccgacg ctgcccggc     8100 acaacctgac ggcggccagc atcaaagtgg agcagttgtg caagaagcac aacttgccgt    8160
atcgcagccc cccaatgctg gaggggtgg gcatcctgat cagctacctg gcacctttg      8220 cccgcatggt ggcaaaggcc gacaaggcgt aagc                                8254

<210> SEQ ID NO 36
<211> LENGTH: 8254
<212> TYPE: DNA
<213> ORGANISM: Artificial Sequence
<220> FEATURE:
<223> OTHER INFORMATION: plasmid pY176

<400> SEQUENCE: 36
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc ggcaacggtt tcacttgagt gcagtggcta    240
gtgctcttac tcgtacagtg tgcaatactg cgtatcatag tctttgatgt atatcgtatt    300
cattcatgtt agttgcgtac gagccggaag cataaagtgt aaagcctggg gtgcctaatg    360
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg tcgttcggc tgcggcgagc     540 ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660 ggcgttttc cataggctcc gccccctga cgagcatcac aaaaatcgac gctcaagtca      720
gaggtggcga aacccgacag gactataaag ataccaggcg tttccccctg gaagctccct    780
cgtgcgctct cctgttccga ccctgccgct taccggatac ctgtccgcct ttctcccttc    840
gggaagcgtg gcgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaaggat ctcaagaaga   1260
tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaccagc cagccggaag    1620 ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
```

```
tacaggcatc gtggtgtcac gctcgtcgtt tggtatggct tcattcagct ccggttccca    1800
acgatcaagg cgagttacat gatcccccat gttgtgcaaa aaagcggtta gctccttcgg    1860
tcctccgatc gttgtcagaa gtaagttggc cgcagtgtta tcactcatgg ttatggcagc    1920
actgcataat tctcttactg tcatgccatc cgtaagatgc ttttctgtga ctggtgagta    1980
ctcaaccaag tcattctgag aatagtgtat gcggcgaccg agttgctctt gcccggcgtc    2040
aatacgggat aataccgcgc cacatagcag aactttaaaa gtgctcatca ttggaaaacg    2100
ttcttcgggg cgaaaactct caaggatctt accgctgttg agatccagtt cgatgtaacc    2160
cactcgtgca cccaactgat cttcagcatc ttttactttc accagcgttt ctgggtgagc    2220
aaaaacagga aggcaaaatg ccgcaaaaaa gggaataagg gcgacacgga aatgttgaat    2280
actcatactc ttcctttttc aatattattg aagcatttat cagggttatt gtctcatgag    2340
cggatacata tttgaatgta tttagaaaaa taaacaaata ggggttccgc gcacatttcc    2400
ccgaaaagtg ccacctgacg cgccctgtag cggcgcatta gcgcggcgg gtgtggtggt    2460 tacgcgcagc gtgaccgcta cacttgccag cgccctagcg cccgctcctt tcgctttctt    2520
cccttccttt ctcgccacgt tcgccggctt tccccgtcaa gctctaaatc ggggggctccc    2580 tttagggttc cgatttagtg ctttacggca cctcgacccc aaaaaacttg attagggtga    2640
tggttcacgt agtgggccat cgccctgata cggtttttt cgcccttttga cgttggagtc    2700 cacgttcttt aatagtggac tcttgttcca aactggaaca acactcaacc ctatctcggt    2760
ctattctttt gatttataag ggattttgcc gatttcggcc tattggttaa aaaatgagct    2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc    2940
cagctggcga aaggggggatg tgctgcaagg cgattaagtt gggtaacgcc agggttttcc    3000
cagtcacgac gttgtaaaac gacggccagt gaattgtaat acgactcact ataggggcgaa    3060 ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga atcttaaat atggatagca taaatgatat ctgcattgcc    3600
taattcgaaa tcaacagcaa cgaaaaaaat cccttgtaca acataaatag tcatcgagaa    3660
atatcaacta tcaaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020 aaaggtatt tgatttaatt ttttgcttaa attcaatccc cctcgttca gtgtcaactg    4080 taatggtagg aaattaccat acttttgaag aagcaaaaaa aatgaaagaa aaaaaaaatc    4140
```

```
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt ttttttttgt    4320
tttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160
gagaggggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct    5700 tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa    6060
catttaaatt gccccggaga agacggccag gccgcctaga tgacaaattc aacaactcac    6120
agctgacttt ctgccattgc cactagggggg gggcctttt atatggccaa gccaagctct    6180
ccacgtcggt tgggctgcac ccaacaataa atgggtaggg ttgcaccaac aaagggatgg    6240 gatgggggt agaagatacg aggataacgg ggctcaatgg cacaaataag aacgaatact    6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttaac    6480
aaaaagtgag ggcgctgagg tcgagcaggg tggtgtgact tgttatagcc tttagagctg    6540
```

| | |
|---|---|
| cgaaagcgcg tatggatttg gctcatcagg ccagattgag ggtctgtgga cacatgtcat | 6600 |
| gttagtgtac ttcaatcgcc ccctggatat agccccgaca ataggccgtg gcctcatttt | 6660 |
| tttgccttcc gcacatttcc attgctcgat acccacacct tgcttctcct gcacttgcca | 6720 |
| accttaatac tggtttacat tgaccaacat cttacaagcg gggggcttgt ctagggtata | 6780 |
| tataaacagt ggctctccca atcggttgcc agtctctttt ttcctttctt tccccacaga | 6840 |
| ttcgaaatct aaactacaca tcacagaatt ccgagccgtg agtatccacg acaagatcag | 6900 |
| tgtcgagacg acgcgttttg tgtaatgaca caatccgaaa gtcgctagca acacacactc | 6960 |
| tctacacaaa ctaacccagc tctggtacca tggtgaaaag gccagcactt ccgctgaccg | 7020 |
| ttgatggtgt cacctatgat gtgtctgcct ggttgaacca tcatccaggg ggtgctgaca | 7080 |
| tcattgagaa ctaccgcggt cgtgatgcca ctgatgtctt tatggttatg cactctgaaa | 7140 |
| atgctgtgag taaactaaga aggatgccta tcatggaacc atcatctcca ctgacgccta | 7200 |
| cgccaccgaa acccaactca gacgaaccgc aggaggattt ccgcaagctc cgagatgagc | 7260 |
| tcatcgcagc aggaatgttc gacgcatcac cgatgtggta cgcatataag acgctcagta | 7320 |
| cgctgggcct cggggtcctc gcggtgctat tgatgaccca gtggcactgg tacctcgtcg | 7380 |
| gggcaatcgt gttgggcatt cacttccaac aaatgggttg gttgtcgcac gatatctgcc | 7440 |
| accatcagct gttcaaggac cgatcgatca acaacgccat cggcttgctt ttcgggaacg | 7500 |
| tcttgcaagg gttctctgtg acctggtgga aggacaggca caatgcacac cactccgcca | 7560 |
| ccaacgtgca aggccacgac cccgacattg acaacctgcc gctgctggca tggtccaagg | 7620 |
| aggacgtgga gagggccggc ccgttctcac ggcggattat caagtaccag caatactact | 7680 |
| tcttcttcat ctgtgccctc ctgaggttca tctggtgctt ccagagcatc cacacagcca | 7740 |
| cgggcctgaa ggatcgcagc aaccagtact accgcaggca gtacgagaaa gagagcgtgg | 7800 |
| gcctggccct ccactgggc ctgaaggcgt tgttctacta cttttatatg ccaagcttct | 7860 |
| tgaccggact catggtgttt ttcgtgtccg agttgcttgg gggcttcggc atcgccatcg | 7920 |
| tggtgttcat gaaccactac cccctggaga agatccagga ctcggtgtgg gacggccacg | 7980 |
| gcttttgcgc cggccagatt cacgaaacga tgaacgtcca gcgggactc gtcacggact | 8040 |
| ggttcttcgg tgggctgaat taccaaatcg agcaccacct gtggccgacg ctgccccggc | 8100 |
| acaacctgac ggcggccagc atcaaagtgg agcagttgtg caagaagcac aacttgccgt | 8160 |
| atcgcagccc cccaatgctg gaggggtgg gcatcctgat cagctacctg gcgcactttg | 8220 |
| cccgcatggt ggcaaaggcc gacaaggcgt aagc | 8254 |

<210> SEQ ID NO 37
<211> LENGTH: 8254
<212> TYPE: DNA
<213> ORGANISM: Artificial Sequence
<220> FEATURE:
<223> OTHER INFORMATION: plasmid pY177

<400> SEQUENCE: 37

| | |
|---|---|
| ggccgcaagt gtggatgggg aagtgagtgc ccggttctgt gtgcacaatt ggcaatccaa | 60 |
| gatggatgga ttcaacacag ggatatagcg agctacgtgg tggtgcgagg atatagcaac | 120 |
| ggatatttat gtttgacact tgagaatgta cgatacaagc actgtccaag tacaatacta | 180 |
| aacatactgt acatactcat actcgtaccc ggcaacggtt tcacttgagt gcagtggcta | 240 |
| gtgctcttac tcgtacagtg tgcaatactg cgtatcatag tctttgatgt atatcgtatt | 300 |
| cattcatgtt agttgcgtac gagccggaag cataaagtgt aaagcctggg gtgcctaatg | 360 |

```
agtgagctaa ctcacattaa ttgcgttgcg ctcactgccc gctttccagt cgggaaacct    420
gtcgtgccag ctgcattaat gaatcggcca acgcgcgggg agaggcggtt tgcgtattgg    480
gcgctcttcc gcttcctcgc tcactgactc gctgcgctcg gtcgttcggc tgcggcgagc    540
ggtatcagct cactcaaagg cggtaatacg gttatccaca gaatcagggg ataacgcagg    600
aaagaacatg tgagcaaaag gccagcaaaa ggccaggaac cgtaaaaagg ccgcgttgct    660
ggcgtttttc cataggctcc gcccccctga cgagcatcac aaaaatcgac gctcaagtca    720
gaggtggcga aacccgacag gactataaag ataccaggcg tttccccctg gaagctccct    780
cgtgcgctct cctgttccga ccctgccgct taccggatac ctgtccgcct ttctcccttc    840
gggaagcgtg cgctttctc atagctcacg ctgtaggtat ctcagttcgg tgtaggtcgt    900
tcgctccaag ctgggctgtg tgcacgaacc ccccgttcag cccgaccgct gcgccttatc    960
cggtaactat cgtcttgagt ccaacccggt aagacacgac ttatcgccac tggcagcagc   1020
cactggtaac aggattagca gagcgaggta tgtaggcggt gctacagagt tcttgaagtg   1080
gtggcctaac tacggctaca ctagaaggac agtatttggt atctgcgctc tgctgaagcc   1140
agttaccttc ggaaaaagag ttggtagctc ttgatccggc aaacaaacca ccgctggtag   1200
cggtggtttt tttgtttgca agcagcagat tacgcgcaga aaaaaggat ctcaagaaga   1260 tcctttgatc ttttctacgg ggtctgacgc tcagtggaac gaaaactcac gttaagggat   1320
tttggtcatg agattatcaa aaaggatctt cacctagatc cttttaaatt aaaaatgaag   1380
ttttaaatca atctaaagta tatatgagta aacttggtct gacagttacc aatgcttaat   1440
cagtgaggca cctatctcag cgatctgtct atttcgttca tccatagttg cctgactccc   1500
cgtcgtgtag ataactacga tacgggaggg cttaccatct ggccccagtg ctgcaatgat   1560
accgcgagac ccacgctcac cggctccaga tttatcagca ataaaccagc cagccggaag   1620
ggccgagcgc agaagtggtc ctgcaacttt atccgcctcc atccagtcta ttaattgttg   1680
ccgggaagct agagtaagta gttcgccagt taatagtttg cgcaacgttg ttgccattgc   1740
tacaggcatc gtggtgtcac gctcgtcgtt tggtatggct tcattcagct ccggttccca   1800
acgatcaagg cgagttacat gatccccat gttgtgcaaa aaagcggtta gctccttcgg   1860
tcctccgatc gttgtcagaa gtaagttggc cgcagtgtta tcactcatgg ttatggcagc   1920
actgcataat tctcttactg tcatgccatc cgtaagatgc ttttctgtga ctggtgagta   1980
ctcaaccaag tcattctgag aatagtgtat gcggcgaccg agttgctctt gcccggcgtc   2040
aatacgggat aataccgcgc cacatagcag aactttaaaa gtgctcatca ttggaaaacg   2100
ttcttcgggg cgaaaactct caaggatctt accgctgttg agatccagtt cgatgtaacc   2160
cactcgtgca cccaactgat cttcagcatc ttttactttc accagcgttt ctgggtgagc   2220
aaaaacagga aggcaaaatg ccgcaaaaaa gggaataagg gcgacacgga aatgttgaat   2280
actcatactc ttcctttttc aatattattg aagcatttat cagggttatt gtctcatgag   2340
cggatacata tttgaatgta tttagaaaaa taaacaaata ggggttccgc gcacatttcc   2400
ccgaaaagtg ccacctgacg cgccctgtag cggcgcatta agcgcggcgg gtgtggtggt   2460
tacgcgcagc gtgaccgcta cacttgccag cgccctagcg cccgctcctt tcgctttctt   2520
cccttccttt ctcgccacgt tcgccggctt tccccgtcaa gctctaaatc ggggctccc   2580 tttagggttc cgatttagtg ctttacggca cctcgacccc aaaaaacttg attagggtga   2640
tggttcacgt agtgggccat cgccctgata gacggttttt cgccctttga cgttggagtc   2700
cacgttcttt aatagtggac tcttgttcca aactggaaca acactcaacc ctatctcggt   2760
```

```
ctattcttttt gatttataag ggattttgcc gatttcggcc tattggttaa aaaatgagct    2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc    2940
cagctggcga aggggggatg tgctgcaagg cgattaagtt gggtaacgcc agggttttcc    3000
cagtcacgac gttgtaaaac gacggccagt gaattgtaat acgactcact ataggcgaa    3060 ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga atcttaaat atggatagca taaatgatat ctgcattgcc    3600
taattcgaaa tcaacagcaa cgaaaaaaat cccttgtaca acataaatag tcatcgagaa    3660
atatcaacta tcaagaaca gctattcaca cgttactatt gagattatta ttggacgaga    3720
atcacacact caactgtctt tctctcttct agaaatacag gtacaagtat gtactattct    3780
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgtttttgt ttttttttgt    4320 tttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgcatcct    4920 caacagttcg gtactgctgt ccgagagcgt ctcccttgtc gtcaagaccc accccggggg    4980
tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctgccagc ttctcgttgg    5160
```

```
gagaggggac taggaactcc ttgtactggg agttctcgta gtcagagacg tcctccttct    5220
tctgttcaga dacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct     5700
tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta acagtgtac gcagatctac tatagaggaa      6060
catttaaatt gccccggaga agacggccag gccgcctaga tgacaaattc aacaactcac    6120
agctgacttt ctgccattgc cactagggg gggcctttt atatggccaa gccaagctct        6180
ccacgtcggt tgggctgcac ccaacaataa atgggtaggg ttgcaccaac aaagggatgg    6240
gatgggggt agaagatacg aggataacgg ggctcaatgg cacaaataag aacgaatact      6300
gccattaaga ctcgtgatcc agcgactgac accattgcat catctaaggg cctcaaaact    6360
acctcggaac tgctgcgctg atctggacac cacagaggtt ccgagcactt taggttgcac    6420
caaatgtccc accaggtgca ggcagaaaac gctggaacag cgtgtacagt ttgtcttaac    6480
aaaaagtgag ggcgctgagg tcgagcaggg tggtgtgact tgttatagcc tttagagctg    6540
cgaaagcgcg tatggatttg gctcatcagg ccagattgag ggtctgtgga cacatgtcat    6600
gttagtgtac ttcaatcgcc ccctggatat agccccgaca ataggccgtg gcctcatttt    6660
tttgccttcc gcacatttcc attgctcgat acccacacct tgcttctcct gcacttgcca    6720
accttaatac tggtttacat tgaccaacat cttacaagcg gggggcttgt ctagggtata    6780
tataaacagt ggctctccca atcggttgcc agtctctttt ttcctttctt tccccacaga    6840
ttcgaaatct aaactacaca tcacagaatt ccgagccgtg agtatccacg acaagatcag    6900
tgtcgagacg acgcgttttg tgtaatgaca caatccgaaa gtcgctagca acacacactc    6960
tctacacaaa ctaacccagc tctggtacca tggtgaaaag gccagcactt ccgctgaccg    7020
ttgatggtgt cacctatgat gtgtctgcct ggttgaacca tcatccaggg ggtgctgaca    7080
tcattgagaa ctaccgcggt cgtgatgcca ctgatgtctt tatggttatg cactctgaaa    7140
atgctgtgag taaactaaga aggatgccta tcatggaacc atcatctcca ctgacgccta    7200
cgccaccgaa acccaactca gacgaaccgc aggaggattt ccgcaagctc cgagatgagc    7260
tcatcgcagc aggaatgttc gacgcatcac cgatgtggta cgcatataag acgctcagta    7320
cgctgggcct cggggtcctc gcggtgctat tgatgaccca gtggcactgg tacctcgtcg    7380
ggcaatcgt gtttgggcatt cacttccaac aaatggggttg gttgtcgcac gatatctgcc      7440
accatcagct gttcaaggac cgatcgatca acaacgccat cggcttgctt ttcgggaacg    7500
tcttgcaagg gttctctgtg acctggtgga aggacaggca caatgcacac cactccgcca    7560
```

```
ccaacgtgca aggccacgac cccgacattg acaacctgcc gctgctgcca tggtccaagg    7620
aggacgtgga gagggccggc ccgttctcac ggcggatgat caagtaccag caatactact    7680
tcttcttcat ctgtgccctc ctgaggttca tctggtgctt ccagagcatc cacacagcca    7740
cgggcctgaa ggatcgcagc aaccagtact accgcaggca gtacgagaaa gagagcgtgg    7800
gcctggccct ccactggggc ctgaaggcgt tgttctacta cttttatatg ccaagcttct    7860
tgaccggact catggtgttt ttcgtgtccg agttgcttgg gggcttcggc atcgccatcg    7920
tggtgttcat gaaccactac cccctggaga agatccagga ctcggtgtgg gacggccacg    7980
gcttttgcgc cggccagatt cacgaaacga tgaacgtcca gcgggactc gtcacggact    8040 ggttcttcgg tgggctgaat taccaaatcg agcaccacct gtggccgacg ctgccccggc    8100
acaacctgac ggcggccagc atcaaagtgg agcagttgtg caagaagcac aacttgccgt    8160
atcgcagccc cccaatgctg gagggggtgg gcatcctgat cagctacctg gcacctttg    8220 cccgcatggt ggcaaaggcc gacaaggcgt aagc                                8254

<210> SEQ ID NO 38
<211> LENGTH: 8254
<212> TYPE: DNA
<213> ORGANISM: Artificial Sequence
<220> FEATURE:
<223> OTHER INFORMATION: plasmid pY178

<400> SEQUENCE: 38
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc ggcaacggtt tcacttgagt gcagtggcta     240
gtgctcttac tcgtacagtg tgcaatactg cgtatcatag tctttgatgt atatcgtatt     300
cattcatgtt agttgcgtac gagccggaag cataaagtgt aaagcctggg gtgcctaatg     360
agtgagctaa ctcacattaa ttgcgttgcg ctcactgccc gctttccagt cgggaaacct     420
gtcgtgccag ctgcattaat gaatcggcca acgcgcgggg agaggcggtt tgcgtattgg     480
gcgctcttcc gcttcctcgc tcactgactc gctgcgctcg tcgttcggc tgcggcgagc     540 ggtatcagct cactcaaagg cggtaatacg gttatccaca gaatcagggg ataacgcagg     600
aaagaacatg tgagcaaaag gccagcaaaa ggccaggaac cgtaaaaagg ccgcgttgct     660
ggcgtttttc cataggctcc gccccctga cgagcatcac aaaaatcgac gctcaagtca     720
gaggtggcga aacccgacag gactataaag ataccaggcg tttccccctg gaagctccct     780
cgtgcgctct cctgttccga ccctgccgct taccggatac ctgtccgcct ttctcccttc     840
gggaagcgtg cgctttctc atagctcacg ctgtaggtat ctcagttcgg tgtaggtcgt     900
tcgctccaag ctgggctgtg tgcacgaacc ccccgttcag cccgaccgct gcgccttatc     960
cggtaactat cgtcttgagt ccaacccggt aagacacgac ttatcgccac tggcagcagc    1020
cactggtaac aggattagca gagcgaggta tgtaggcggt gctacagagt tcttgaagtg    1080
gtggcctaac tacggctaca ctagaaggac agtatttggt atctgcgctc tgctgaagcc    1140
agttaccttc ggaaaaagag ttggtagctc ttgatccggc aaacaaacca ccgctggtag    1200
cggtggtttt tttgtttgca agcagcagat tacgcgcaga aaaaaaggat ctcaagaaga    1260
tcctttgatc ttttctacgg ggtctgacgc tcagtggaac gaaaactcac gttaagggat    1320
tttggtcatg agattatcaa aaaggatctt cacctagatc cttttaaatt aaaaatgaag    1380
```

```
ttttaaatca atctaaagta tatatgagta aacttggtct gacagttacc aatgcttaat    1440
cagtgaggca cctatctcag cgatctgtct atttcgttca tccatagttg cctgactccc    1500
cgtcgtgtag ataactacga tacgggaggg cttaccatct ggccccagtg ctgcaatgat    1560
accgcgagac ccacgctcac cggctccaga tttatcagca ataaaccagc cagccggaag    1620
ggccgagcgc agaagtggtc ctgcaacttt atccgcctcc atccagtcta ttaattgttg    1680
ccgggaagct agagtaagta gttcgccagt taatagtttg cgcaacgttg ttgccattgc    1740
tacaggcatc gtggtgtcac gctcgtcgtt tggtatggct tcattcagct ccggttccca    1800
acgatcaagg cgagttacat gatccccat gttgtgcaaa aaagcggtta gctccttcgg    1860
tcctccgatc gttgtcagaa gtaagttggc cgcagtgtta tcactcatgg ttatggcagc    1920
actgcataat tctcttactg tcatgccatc cgtaagatgc ttttctgtga ctggtgagta    1980
ctcaaccaag tcattctgag aatagtgtat gcggcgaccg agttgctctt gcccggcgtc    2040
aatacgggat aataccgcgc cacatagcag aactttaaaa gtgctcatca ttggaaaacg    2100
ttcttcgggg cgaaaactct caaggatctt accgctgttg agatccagtt cgatgtaacc    2160
cactcgtgca cccaactgat cttcagcatc ttttactttc accagcgttt ctgggtgagc    2220
aaaaacagga aggcaaaatg ccgcaaaaaa gggaataagg gcgacacgga aatgttgaat    2280
actcatactc ttcctttttc aatattattg aagcatttat cagggttatt gtctcatgag    2340
cggatacata tttgaatgta tttagaaaaa taaacaaata ggggttccgc gcacatttcc    2400
ccgaaaagtg ccacctgacg cgccctgtag cggcgcatta agcgcggcgg gtgtggtggt    2460
tacgcgcagc gtgaccgcta cacttgccag cgccctagcg cccgctcctt tcgctttctt    2520
cccttccttt ctcgccacgt tcgccggctt tccccgtcaa gctctaaatc gggggctccc    2580
tttagggttc cgatttagtg ctttacggca cctcgacccc aaaaaacttg attagggtga    2640
tggttcacgt agtgggccat cgccctgata gacggttttt cgccctttga cgttggagtc    2700
cacgttcttt aatagtggac tcttgttcca aactggaaca acactcaacc ctatctcggt    2760
ctattctttt gatttataag ggattttgcc gatttcggcc tattggttaa aaaatgagct    2820
gatttaacaa aaatttaacg cgaattttaa caaaatatta acgcttacaa tttccattcg    2880
ccattcaggc tgcgcaactg ttgggaaggg cgatcggtgc gggcctcttc gctattacgc    2940
cagctggcga aggggggatg tgctgcaagg cgattaagtt gggtaacgcc agggttttcc    3000
cagtcacgac gttgtaaaac gacggccagt gaattgtaat acgactcact atagggcgaa    3060
ttgggtaccg ggccccccct cgaggtcgat ggtgtcgata agcttgatat cgaattcatg    3120
tcacacaaac cgatcttcgc ctcaaggaaa cctaattcta catccgagag actgccgaga    3180
tccagtctac actgattaat tttcgggcca ataatttaaa aaaatcgtgt tatataatat    3240
tatatgtatt atatatatac atcatgatga tactgacagt catgtcccat tgctaaatag    3300
acagactcca tctgccgcct ccaactgatg ttctcaatat ttaaggggtc atctcgcatt    3360
gtttaataat aaacagactc catctaccgc ctccaaatga tgttctcaaa atatattgta    3420
tgaacttatt tttattactt agtattatta gacaacttac ttgctttatg aaaaacactt    3480
cctatttagg aaacaattta taatggcagt tcgttcattt aacaatttat gtagaataaa    3540
tgttataaat gcgtatggga aatcttaaat atggatagca taaatgatat ctgcattgcc    3600
taattcgaaa tcaacagcaa cgaaaaaaat cccttgtaca acataaatag tcatcgagaa    3660
atatcaacta tcaagaaaca gctattcaca cgttactatt gagattatta ttggacgaga    3720
atcacacact caactgtctt tctctcttct agaaatacag gtacaagtat gtactattct    3780
```

```
cattgttcat acttctagtc atttcatccc acatattcct tggatttctc tccaatgaat    3840
gacattctat cttgcaaatt caacaattat aataagatat accaaagtag cggtatagtg    3900
gcaatcaaaa agcttctctg gtgtgcttct cgtatttatt tttattctaa tgatccatta    3960
aaggtatata tttatttctt gttatataat ccttttgttt attacatggg ctggatacat    4020
aaaggtattt tgatttaatt ttttgcttaa attcaatccc ccctcgttca gtgtcaactg    4080
taatggtagg aaattaccat acttttgaag aagcaaaaaa aatgaaagaa aaaaaaaatc    4140
gtatttccag gttagacgtt ccgcagaatc tagaatgcgg tatgcggtac attgttcttc    4200
gaacgtaaaa gttgcgctcc ctgagatatt gtacattttt gcttttacaa gtacaagtac    4260
atcgtacaac tatgtactac tgttgatgca tccacaacag tttgttttgt ttttttttgt    4320
tttttttttt tctaatgatt cattaccgct atgtatacct acttgtactt gtagtaagcc    4380
gggttattgg cgttcaatta atcatagact tatgaatctg cacggtgtgc gctgcgagtt    4440
acttttagct tatgcatgct acttgggtgt aatattggga tctgttcgga aatcaacgga    4500
tgctcaatcg atttcgacag taattaatta agtcatacac aagtcagctt tcttcgagcc    4560
tcatataagt ataagtagtt caacgtatta gcactgtacc cagcatctcc gtatcgagaa    4620
acacaacaac atgccccatt ggacagatca tgcggataca caggttgtgc agtatcatac    4680
atactcgatc agacaggtcg tctgaccatc atacaagctg aacaagcgct ccatacttgc    4740
acgctctcta tatacacagt taaattacat atccatagtc taacctctaa cagttaatct    4800
tctggtaagc ctcccagcca gccttctggt atcgcttggc ctcctcaata ggatctcggt    4860
tctggccgta cagacctcgg ccgacaatta tgatatccgt tccggtagac atgacatcct    4920
caacagttcg gtactgctgt ccgagagcgt ctcccttgtc gtcaagaccc accccgggg    4980 tcagaataag ccagtcctca gagtcgccct taggtcggtt ctgggcaatg aagccaacca    5040
caaactcggg gtcggatcgg gcaagctcaa tggtctgctt ggagtactcg ccagtggcca    5100
gagagccctt gcaagacagc tcggccagca tgagcagacc tctggccagc ttctcgttgg    5160 gagagggac taggaactcc ttgtactggg agttctcgta gtcagagacg tcctccttct    5220
tctgttcaga gacagtttcc tcggcaccag ctcgcaggcc agcaatgatt ccggttccgg    5280
gtacaccgtg ggcgttggtg atatcggacc actcggcgat tcggtgacac cggtactggt    5340
gcttgacagt gttgccaata tctgcgaact ttctgtcctc gaacaggaag aaaccgtgct    5400
taagagcaag ttccttgagg gggagcacag tgccggcgta ggtgaagtcg tcaatgatgt    5460
cgatatgggt tttgatcatg cacacataag gtccgacctt atcggcaagc tcaatgagct    5520
ccttggtggt ggtaacatcc agagaagcac acaggttggt tttcttggct gccacgagct    5580
tgagcactcg agcggcaaag gcggacttgt ggacgttagc tcgagcttcg taggagggca    5640
ttttggtggt gaagaggaga ctgaaataaa tttagtctgc agaactttt atcggaacct    5700 tatctggggc agtgaagtat atgttatggt aatagttacg agttagttga acttatagat    5760
agactggact atacggctat cggtccaaat tagaaagaac gtcaatggct ctctgggcgt    5820
cgcctttgcc gacaaaaatg tgatcatgat gaaagccagc aatgacgttg cagctgatat    5880
tgttgtcggc caaccgcgcc gaaaacgcag ctgtcagacc cacagcctcc aacgaagaat    5940
gtatcgtcaa agtgatccaa gcacactcat agttggagtc gtactccaaa ggcggcaatg    6000
acgagtcaga cagatactcg tcgacgttta aacagtgtac gcagatctac tatagaggaa    6060
catttaaatt gccccggaga agacggccag gccgcctaga tgacaaattc aacaactcac    6120
agctgacttt ctgccattgc cactaggggg gggccttttt atatggccaa gccaagctct    6180
```

```
ccacgtcggt tgggctgcac ccaacaataa atgggtaggg ttgcaccaac aaagggatgg     6240 gatgggggt agaagatacg aggataacgg ggctcaatgg cacaaataag aacgaatact     6300
gccattaaga ctcgtgatcc agcgactgac accattgcat catctaaggg cctcaaaact     6360
acctcggaac tgctgcgctg atctggacac cacagaggtt ccgagcactt taggttgcac     6420
caaatgtccc accaggtgca ggcagaaaac gctggaacag cgtgtacagt ttgtcttaac     6480
aaaaagtgag ggcgctgagg tcgagcaggg tggtgtgact tgttatagcc tttagagctg     6540
cgaaagcgcg tatggatttg gctcatcagg ccagattgag ggtctgtgga cacatgtcat     6600
gttagtgtac ttcaatcgcc ccctggatat agccccgaca ataggccgtg gcctcatttt     6660
tttgccttcc gcacatttcc attgctcgat acccacacct tgcttctcct gcacttgcca     6720
accttaatac tggtttacat tgaccaacat cttacaagcg gggggcttgt ctagggtata     6780
tataaacagt ggctctccca atcggttgcc agtctctttt ttcctttctt tccccacaga     6840
ttcgaaatct aaactacaca tcacagaatt ccgagccgtg agtatccacg acaagatcag     6900
tgtcgagacg acgcgttttg tgtaatgaca caatccgaaa gtcgctagca acacacactc     6960
tctacacaaa ctaacccagc tctggtacca tggtgaaaag gccagcactt ccgctgaccg     7020
ttgatggtgt cacctatgat gtgtctgcct ggttgaacca tcatccaggg ggtgctgaca     7080
tcattgagaa ctaccgcggt cgtgatgcca ctgatgtctt tatggttatg cactctgaaa     7140
atgctgtgag taaactaaga aggatgccta tcatggaacc atcatctcca ctgacgccta     7200
cgccaccgaa acccaactca gacgaaccgc aggaggattt ccgcaagctc cgagatgagc     7260
tcatcgcagc aggaatgttc gacgcatcac cgatgtggta cgcatataag acgctcagta     7320
cgctgggcct cggggtcctc gcggtgctat tgatgaccca gtggcactgg tacctcgtcg     7380
gggcaatcgt gttgggcatt cacttccaac aaatggggttg gttgtcgcac gatatctgcc     7440
accatcagct gttcaaggac cgatcgatca acaacgccat cggcttgctt ttcgggaacg     7500
tcttgcaagg gttctctgtg acctggtgga aggacaggca caatgcacac cactccgcca     7560
ccaacgtgca aggccacgac cccgacattg acaacctgcc gctgctggca tggtccaagg     7620
aggacgtgga gagggccggc ccgttctcac ggcggatgat caagtaccag caatactact     7680
tcttcttcat ctgtgccctc ctgaggttca tctggtgctt ccagagcatc cacacagcca     7740
agggcctgaa ggatcgcagc aaccagtact accgcaggca gtacgagaaa gagagcgtgg     7800
gcctggccct ccactgggc ctgaaggcgt tgttctacta cttttatatg ccaagcttct     7860
tgaccggact catggtgttt ttcgtgtccg agttgcttgg gggcttcggc atcgccatcg     7920
tggtgttcat gaaccactac cccctggaga agatccagga ctcggtgtgg gacggccacg     7980
gcttttgcgc cggccagatt cacgaaacga tgaacgtcca gcggggactc gtcacggact     8040
ggttcttcgg tgggctgaat taccaaatcg agcaccacct gtggccgacg ctgccccggc     8100
acaacctgac ggcggccagc atcaaagtgg agcagttgtg caagaagcac aacttgccgt     8160
atcgcagccc cccaatgctg gaggggtgg gcatcctgat cagctacctg ggcaccttg     8220 cccgcatggt ggcaaaggcc gacaaggcgt aagc                                8254

<210> SEQ ID NO 39
<211> LENGTH: 777
<212> TYPE: DNA
<213> ORGANISM: Euglena gracilis

<400> SEQUENCE: 39
atggaggtgg tgaatgaaat agtctcaatt gggcaggaag ttttacccaa agttgattat         60
```

```
gcccaactct ggagtgatgc cagtcactgt gaggtgcttt acttgtccat cgcatttgtc    120
atcttgaagt tcactcttgg ccccttggt ccaaaaggtc agtctcgtat gaagtttgtt    180
ttcaccaatt acaaccttct catgtccatt tattcgttgg gatcattcct ctcaatggca    240
tatgccatgt acaccatcgg tgttatgtct gacaactgcg agaaggcttt tgacaacaac    300
gtcttcagga tcaccacgca gttgttctat ttgagcaagt tcctggagta tattgactcc    360
ttctatttgc cactgatggg caagcctctg acctggttgc aattcttcca tcatttgggg    420
gcaccgatgg atatgtggct gttctataat taccgaaatg aagctgtttg gattttttgtg   480 ctgttgaatg gtttcatcca ctggatcatg tacggttatt attggaccag attgatcaag    540
ctgaagttcc ccatgccaaa atccctgatt acatcaatgc agatcattca attcaatgtt    600
ggtttctaca ttgtctggaa gtacaggaac attccctgtt atcgccaaga tgggatgagg    660
atgtttggct ggttcttcaa ttactttat gttggcacag tcttgtgttt gttcttgaat    720
ttctatgtgc aaacgtatat cgtcaggaag cacaagggag ccaaaaagat tcagtga      777

<210> SEQ ID NO 40
<211> LENGTH: 30
<212> TYPE: DNA
<213> ORGANISM: Artificial Sequence
<220> FEATURE:
<223> OTHER INFORMATION: primer oEugEL1

<400> SEQUENCE: 40
agcggccgca ccatggaggt ggtgaatgaa                                      30

<210> SEQ ID NO 41
<211> LENGTH: 30
<212> TYPE: DNA
<213> ORGANISM: Artificial Sequence
<220> FEATURE:
<223> OTHER INFORMATION: primer oEugEL1-2

<400> SEQUENCE: 41
tgcggccgct cactgaatct ttttggctcc                                      30

<210> SEQ ID NO 42
<211> LENGTH: 4311
<212> TYPE: DNA
<213> ORGANISM: Artificial Sequence
<220> FEATURE:
<223> OTHER INFORMATION: plasmid pKR906

<400> SEQUENCE: 42
agcggccgca ccatggaggt ggtgaatgaa atagtctcaa ttgggcagga agttttaccc     60
aaagttgatt atgcccaact ctggagtgat gccagtcact gtgaggtgct ttacttgtcc    120
atcgcatttg tcatcttgaa gttcactctt ggccccttg gtccaaaagg tcagtctcgt    180
atgaagtttg ttttccaccaa ttacaacctt ctcatgtcca tttattcgtt gggatcattc    240
ctctcaatgg catatgccat gtacaccatc ggtgttatgt ctgacaactg cgagaaggct    300
tttgacaaca acgtcttcag gatcaccacg cagttgttct atttgagcaa gttcctggag    360
tatattgact ccttctattt gccactgatg ggcaagcctc tgacctggtt gcaattcttc    420
catcatttgg gggcaccgat ggatatgtgg ctgttctata ttaccgaaa tgaagctgtt    480 tggattttttg tgctgttgaa tggtttcatc cactggatca tgtacggtta ttattggacc    540
agattgatca agctgaagtt ccccatgcca aaatccctga ttacatcaat gcagatcatt    600
caattcaatg ttggtttcta cattgtctgg aagtacagga acattccctg ttatcgccaa    660
```

```
gatgggatga ggatgtttgg ctggttcttc aattactttt atgttggcac agtcttgtgt    720
ttgttcttga atttctatgt gcaaacgtat atcgtcagga agcacaaggg agccaaaaag    780
attcagtgag cggccgcacc tgaattccag cacactggcg gccgttacta gtggatccga    840
gctcggtacc aagcttgatg catagcttga gtattctaac gcgtcaccta aatagcttgg    900
cgtaatcatg gtcatagctg tttcctgtgt gaaattgtta tccgctcaca attccacaca    960
acatacgagc cggaagcata aagtgtaaag cctggggtgc ctaatgagtg agctaactca   1020
cattaattgc gttgcgctca ctgcccgctt tccagtcggg aaacctgtcg tgccagctgc   1080
attaatgaat cggccaacgc gcggggagag gcggtttgcg tattgggcgc tcttccgctt   1140
cctcgctcac tgactcgctg cgctcggtcg ttcggctgcg gcgagcggta tcagctcact   1200
caaaggcggt aatacggtta tccacagaat caggggataa cgcaggaaag aacatgtgag   1260
caaaaggcca gcaaaagccc aggaaccgta aaaaggccgc gttgctggcg ttttccata    1320 ggctccgccc ccctgacgag catcacaaaa atcgacgctc aagtcagagg tggcgaaacc   1380
cgacaggact ataaagatac caggcgtttc ccccctggaag ctccctcgtg cgctctcctg   1440
ttccgaccct gccgcttacc ggatacctgt ccgcctttct cccttcggga agcgtggcgc   1500
tttctcatag ctcacgctgt aggtatctca gttcggtgta ggtcgttcgc tccaagctgg   1560
gctgtgtgca cgaaccccc gttcagcccg accgctgcgc cttatccggt aactatcgtc   1620
ttgagtccaa cccggtaaga cacgacttat cgccactggc agcagccact ggtaacagga   1680
ttagcagagc gaggtatgta ggcggtgcta cagagttctt gaagtggtgg cctaactacg   1740
gctacactag aaggacagta tttggtatct gcgctctgct gaagccagtt accttcggaa   1800
aaagagttgg tagctcttga tccggcaaac aaaccaccgc tggtagcggt ggtttttttg   1860
tttgcaagca gcagattacg cgcagaaaaa aaggatctca agaagatcct ttgatctttt   1920
ctacggggtc tgacgctcag tggaacgaaa actcacgtta agggattttg gtcatgagat   1980
tatcaaaaag gatcttcacc tagatccttt taaattaaaa atgaagtttt agcacgtgtc   2040
agtcctgctc ctcggccacg aagtgcacg agttgccggc cgggtcgcgc agggcgaact   2100
cccgccccca cggctgctcg ccgatctcgg tcatggccgg cccggaggcg tcccggaagt   2160
tcgtggacac gacctccgac cactcggcgt acagctcgtc caggccgcgc acccacaccc   2220
aggccagggt gttgtccggc accacctggt cctggaccgc gctgatgaac agggtcacgt   2280
cgtcccggac cacaccggcg aagtcgtcct ccacgaagtc ccgggagaac ccgagccggt   2340
cggtccagaa ctcgaccgct ccggcgacgt cgcgcgcggt gagcaccgga acggcactgg   2400
tcaacttggc catggtggcc ctcctcacgt gctattattg aagcatttat cagggttatt   2460
gtctcatgag cggatacata tttgaatgta tttagaaaaa taaacaaata ggggttccgc   2520
gcacatttcc ccgaaaagtg ccacctgtat gcggtgtgaa ataccgcaca gatgcgtaag   2580
gagaaaatac cgcatcagga aattgtaagc gttaataatt cagaagaact cgtcaagaag   2640
gcgatagaag gcgatgcgct gcgaatcggg agcggcgata ccgtaaagca cgaggaagcg   2700
gtcagcccat tcgccgccaa gctcttcagc aatatcacgg gtagccaacg ctatgtcctg   2760
atagcggtcc gccacaccca gccggccaca gtcgatgaat ccagaaaagc ggccattttc   2820
caccatgata ttcggcaagc aggcatcgcc atgggtcacg acgagatcct cgccgtcggg   2880
catgctcgcc ttgagcctgg cgaacagttc ggctggcgcg agccctgat gctcttcgtc   2940 cagatcatcc tgatcgacaa gaccggcttc catccgagta cgtgctcgct cgatgcgatg   3000
tttcgcttgg tggtcgaatg ggcaggtagc cggatcaagc gtatgcagcc gccgcattgc   3060
```

| | |
|---|---:|
| atcagccatg atggatactt tctcggcagg agcaaggtga gatgacagga gatcctgccc | 3120 |
| cggcacttcg cccaatagca gccagtccct tcccgcttca gtgacaacgt cgagcacagc | 3180 |
| tgcgcaagga acgcccgtcg tggccagcca cgatagccgc gctgcctcgt cttgcagttc | 3240 |
| attcagggca ccggacaggt cggtcttgac aaaaagaacc gggcgcccct gcgctgacag | 3300 |
| ccggaacacg gcggcatcag agcagccgat tgtctgttgt gcccagtcat agccgaatag | 3360 |
| cctctccacc caagcggccg gagaacctgc gtgcaatcca tcttgttcaa tcatgcgaaa | 3420 |
| cgatcctcat cctgtctctt gatcagagct tgatccctg cgccatcaga tccttggcgg | 3480 |
| cgagaaagcc atccagttta ctttgcaggg cttcccaacc ttaccagagg gcgccccagc | 3540 |
| tgcaattcc ggttcgcttg ctgtccataa aaccgcccag tctagctatc gccatgtaag | 3600 |
| cccactgcaa gctacctgct ttctctttgc gcttgcgttt tcccttgtcc agatagccca | 3660 |
| gtagctgaca ttcatccggg gtcagcaccg tttctgcgga ctggctttct acgtgaaaag | 3720 |
| gatctaggtg aagatccttt ttgataatct catgcctgac atttatattc cccagaacat | 3780 |
| caggttaatg gcgtttttga tgtcattttc gcggtggctg agatcagcca cttcttcccc | 3840 |
| gataacggag accggcacac tggccatatc ggtggtcatc atgcgccagc tttcatcccc | 3900 |
| gatatgcacc accgggtaaa gttcacggga gactttatct gacagcagac gtgcactggc | 3960 |
| caggggatc accatccgtc gccccggcgt gtcaataata tcactctgta catccacaaa | 4020 |
| cagacgataa cggctctctc ttttataggt gtaaaccta aactgccgta cgtataggct | 4080 |
| gcgcaactgt tgggaagggc gatcggtgcg ggcctcttcg ctattacgcc agctggcgaa | 4140 |
| agggggatgt gctgcaaggc gattaagttg gtaacgcca gggttttccc agtcacgacg | 4200 |
| ttgtaaaacg acggccagtg aattgtaata cgactcacta tagggcgaat tgggccctct | 4260 |
| agatgcatgc tcgagcggcc gccagtgtga tggatatctg cagaattcag g | 4311 |

<210> SEQ ID NO 43
<211> LENGTH: 7085
<212> TYPE: DNA
<213> ORGANISM: Artificial Sequence
<220> FEATURE:
<223> OTHER INFORMATION: plasmid pKR72

<400> SEQUENCE: 43

| | |
|---|---:|
| gtacggatcc gtcgacggcg cgcccgatca tccggatata gttcctcctt tcagcaaaaa | 60 |
| accccctcaag acccgtttag aggccccaag gggttatgct agttattgct cagcggtggc | 120 |
| agcagccaac tcagcttcct ttcgggcttt gttagcagcc ggatcgatcc aagctgtacc | 180 |
| tcactattcc tttgccctcg gacgagtgct ggggcgtcgg tttccactat cggcgagtac | 240 |
| ttctacacag ccatcggtcc agacggccgc gcttctgcgg gcgatttgtg tacgcccgac | 300 |
| agtcccggct ccggatcgga cgattgcgtc gcatcgaccc tgcgcccaag ctgcatcatc | 360 |
| gaaattgccg tcaaccaagc tctgatagag ttggtcaaga ccaatgcgga gcatatacgc | 420 |
| ccggagccgc ggcgatcctg caagctccgg atgcctccgc tcgaagtagc gcgtctgctg | 480 |
| ctccatacaa gccaaccacg gcctccagaa gaagatgttg gcgacctcgt attgggaatc | 540 |
| cccgaacatc gcctcgctcc agtcaatgac cgctgttatg cggccattgt ccgtcaggac | 600 |
| attgttggag ccgaaatccg cgtgcacgag gtgccggact cggggcagt cctcggccca | 660 |
| aagcatcagc tcatcgagag cctgcgcgac ggacgcactg acggtgtcgt ccatcacagt | 720 |
| ttgccagtga tacacatggg gatcagcaat cgcgcatatg aaatcacgcc atgtagtgta | 780 |
| ttgaccgatt ccttgcggtc cgaatgggcc gaacccgctc gtctggctaa gatcggccgc | 840 |

```
agcgatcgca tccatagcct ccgcgaccgg ctgcagaaca gcgggcagtt cggtttcagg    900
caggtcttgc aacgtgacac cctgtgcacg gcgggagatg caataggtca ggctctcgct    960
gaattcccca atgtcaagca cttccggaat cgggagcgcg gccgatgcaa agtgccgata   1020
aacataacga tctttgtaga aaccatcggc gcagctattt acccgcagga catatccacg   1080
ccctcctaca tcgaagctga agcacgaga ttcttcgccc tccgagagct gcatcaggtc   1140
ggagacgctg tcgaactttt cgatcagaaa cttctcgaca gacgtcgcgg tgagttcagg   1200
cttttccatg ggtatatctc cttcttaaag ttaaacaaaa ttatttctag agggaaaccg   1260
ttgtggtctc cctatagtga gtcgtattaa tttcgcggga tcgagatcga tccaattcca   1320
atcccacaaa aatctgagct taacagcaca gttgctcctc tcagagcaga atcgggtatt   1380
caacaccctc atatcaacta ctacgttgtg tataacggtc cacatgccgg tatatacgat   1440
gactggggtt gtacaaaggc ggcaacaaac ggcgttcccg gagttgcaca caagaaattt   1500
gccactatta cagaggcaag agcagcagct gacgcgtaca caacaagtca gcaaacagac   1560
aggttgaact tcatccccaa aggagaagct caactcaagc ccaagagctt gctaaggcc    1620
ctaacaagcc caccaaagca aaaagcccac tggctcacgc taggaaccaa aaggcccagc   1680
agtgatccag ccccaaaaga gatctccttt gccccggaga ttacaatgga cgatttcctc   1740
tatctttacg atctaggaag gaagttcgaa ggtgaaggtg acgacactat gttcaccact   1800
gataatgaga aggttagcct cttcaatttc agaaagaatg ctgacccaca gatggttaga   1860
gaggcctacg cagcaggtct catcaagacg atctacccga gtaacaatct ccaggagatc   1920
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca agatacagt    2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
```

```
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta agaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt ttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat tctttgctga taaaaaaata aaataaaaga   5340
agctaagcac acggtcaacc attgctctac tgctaaaagg gttatgtgta gtgttttact   5400
gcataaatta tgcagcaaac aagacaactc aaattaaaaa atttcctttg cttgtttttt   5460
tgttgtctct gacttgactt tcttgtggaa gttggttgta taaggattgg gacaccattg   5520
tccttcttaa tttaatttta ttctttgctg ataaaaaaaa aaatttcata tagtgttaaa   5580
taataatttg ttaaataacc aaaaagtcaa atatgtttac tctcgtttaa ataattgaga   5640
```

```
ttcgtccagc aaggctaaac gattgtatag atttatgaca atatttactt ttttatagat    5700
aaatgttata ttataataaa tttatataca tatattatat gttatttatt attattttaa    5760
atccttcaat attttatcaa accaactcat aattttttt ttatctgtaa gaagcaataa    5820
aattaaatag acccacttta aggatgatcc aacctttata cagagtaaga gagttcaaat    5880
agtacccttt catatacata tcaactaaaa tattagaaat atcatggatc aaaccttata    5940
aagacattaa ataagtggat aagtataata tataaatggg tagtatataa tatataaatg    6000
gatacaaact tctctctta taattgttat gtctccttaa catcctaata taatacataa    6060
gtgggtaata tataatatat aaatggagac aaacttcttc cattataatt gttatgtctt    6120
cttaacactt atgtctcgtt cacaatgcta aggttagaat tgtttagaaa gtcttatagt    6180
acacatttgt ttttgtacta tttgaagcat tccataagcc gtcacgattc agatgattta    6240
taataataag aggaaattta tcatagaaca ataaggtgca tagatagagt gttaatatat    6300
cataacatcc tttgtttatt catagaagaa gtgagatgga gctcagttat tatactgtta    6360
catggtcgga tacaatattc catgctctcc atgagctctt acacctacat gcattttagt    6420
tcatacttgc ggccgcagta tatcttaaat tctttaatac ggtgtactag gatattgaac    6480
tggttcttga tgatgaaaac ctgggccgag attgcagcta tttatagtca taggtcttgt    6540
taacatgcat ggacatttgg ccacggggtg gcatgcagtt tgacgggtgt tgaaataaac    6600
aaaaatgagg tggcggaaga gaatacgagt ttgaggttgg gttagaaaca caaatgtga    6660 gggctcatga tggttgagt tggtgaatgt tttgggctgc tcgattgaca cctttgtgag    6720
tacgtgttgt tgtgcatggc ttttggggtc cagtttttt ttcttgacgc ggcgatcctg    6780
atcagctagt ggataagtga tgtccactgt gtgtgattgc gttttgtttt gaattttatg    6840
aacttagaca ttgctatgca aaggatactc tcattgtgtt ttgtcttctt tgttccttg    6900 gcttttctt atgatccaag agactagtca gtgttgtggc attcgagact accaagatta    6960
attatgatgg gggaaggata agtaactgat tagtacggac tgttaccaaa ttaattaata    7020
agcggcaaat gaagggcatg gatcaaaagc ttggatctcc tgcaggatct ggccggccgg    7080
atctc                                                               7085
```

<210> SEQ ID NO 44
<211> LENGTH: 7873
<212> TYPE: DNA
<213> ORGANISM: Artificial Sequence
<220> FEATURE:
<223> OTHER INFORMATION: plasmid pKR912

<400> SEQUENCE: 44

```
ggccgcaagt atgaactaaa atgcatgtag gtgtaagagc tcatggagag catggaatat      60
tgtatccgac catgtaacag tataataact gagctccatc tcacttcttc tatgaataaa     120
caaaggatgt tatgatatat taacactcta tctatgcacc ttattgttct atgataaatt     180
tcctcttatt attataaatc atctgaatcg tgacggctta tggaatgctt caaatagtac     240
aaaaacaaat gtgtactata agactttcta acaattcta accttagcat gtgaacgag      300 acataagtgt taagaagaca taacaattat aatggaagaa gtttgtctcc atttatatat     360
tatatattac ccacttatgt attatattag gatgttaagg agacataaca attataaaga     420
gagaagtttg tatccattta tatattatat actacccatt tatatattat acttatccac     480
ttatttaatg tctttataag gtttgatcca tgatatttct aatatttag ttgatatgta      540 tatgaaaggg tactatttga actctcttac tctgtataaa ggttggatca tccttaaagt     600
```

```
gggtctattt aatttattg cttcttacag ataaaaaaa aattatgagt tggtttgata    660
aaatattgaa ggatttaaaa taataataaa taacatataa tatatgtata taaatttatt   720
ataaataaac atttatctat aaaaaagtaa atattgtcat aaatctatac aatcgtttag   780
ccttgctgga cgaatctcaa ttatttaaac gagagtaaac atatttgact ttttggttat   840
ttaacaaatt attatttaac actatatgaa attttttttt ttatcagcaa agaataaaat   900
taaattaaga aggacaatgg tgtcccaatc cttatacaac caacttccac aagaaagtca   960
agtcagagac aacaaaaaaa caagcaaagg aaatttttta atttgagttg tcttgtttgc  1020
tgcataattt atgcagtaaa acactacaca taacccttt agcagtagag caatggttga  1080
ccgtgtgctt agcttctttt attttatttt tttatcagca aagaataaat aaaataaaat  1140
gagacacttc agggatgttt caacaagctt ggcgcgccgt tctatagtgt cacctaaatc  1200
gtatgtgtat gatacataag gttatgtatt aattgtagcc gcgttctaac gacaatatgt  1260
ccatatggtg cactctcagt acaatctgct ctgatgccgc atagttaagc cagccccgac  1320
acccgccaac acccgctgac gcgccctgac gggcttgtct gctcccggca tccgcttaca  1380
gacaagctgt gaccgtctcc gggagctgca tgtgtcagag gttttcaccg tcatcaccga  1440
aacgcgcgag acgaaagggc ctcgtgatac gcctattttt ataggttaat gtcatgacca  1500
aaatccctta acgtgagttt tcgttccact gagcgtcaga ccccgtagaa aagatcaaag  1560
gatcttcttg agatcctttt tttctgcgcg taatctgctg cttgcaaaca aaaaaaccac  1620
cgctaccagc ggtggtttgt ttgccggatc aagagctacc aactcttttt ccgaaggtaa  1680
ctggcttcag cagagcgcag ataccaaata ctgtccttct agtgtagccg tagttaggcc  1740
accacttcaa gaactctgta gcaccgccta catacctcgc tctgctaatc ctgttaccag  1800
tggctgctgc cagtggcgat aagtcgtgtc ttaccgggtt ggactcaaga cgatagttac  1860
cggataaggc gcagcggtcg ggctgaacgg ggggttcgtg cacacagccc agcttggagc  1920
gaacgaccta caccgaactg agatacctac agcgtgagca ttgagaaagc gccacgcttc  1980
ccgaagggag aaaggcggac aggtatccgg taagcggcag ggtcggaaca ggagagcgca  2040
cgagggagct ccaggggga acgcctggt atctttatag tcctgtcggg tttcgccacc  2100
tctgacttga gcgtcgattt ttgtgatgct cgtcagggg gcggagccta tggaaaaacg  2160
ccagcaacgc ggccttttta cggttcctgg ccttttgctg gccttttgct cacatgttct  2220
ttcctgcgtt atcccctgat tctgtggata accgtattac cgcctttgag tgagctgata  2280
ccgctcgccg cagccgaacg accgagcgca gcgagtcagt gagcgaggaa gcggaagagc  2340
gcccaatacg caaaccgcct ctccccgcgc gttggccgat tcattaatgc aggttgatcg  2400
attcgacatc gatctagtaa catagatgac accgcgcgcg ataattatc ctagtttgcg  2460
cgctatattt tgttttctat cgcgtattaa atgtataatt gcgggactct aatcataaaa  2520
acccatctca taaataacgt catgcattac atgttaatta ttacatgctt aacgtaattc  2580
aacagaaatt atatgataat catcgcaaga ccggcaacag gattcaatct taagaaactt  2640
tattgccaaa tgtttgaacg atctgcttcg acgcactcct tctttaggta cctcactatt  2700
cctttgccct cggacgagtg ctgggcgtc ggtttccact atcggcgagt acttctacac  2760
agccatcggt ccagacggcc gcgcttctgc gggcgatttg tgtacgcccg acagtcccgg  2820
ctccggatcg gacgattgcg tcgcatcgac cctgcgccca agctgcatca tcgaaattgc  2880
cgtcaaccaa gctctgatag agttggtcaa gaccaatgcg gagcatatac gcccggagcc  2940
gcggcgatcc tgcaagctcc ggatgcctcc gctcgaagta gcgcgtctgc tgctccatac  3000
```

```
aagccaacca cggcctccag aagaagatgt tggcgacctc gtattgggaa tccccgaaca    3060
tcgcctcgct ccagtcaatg accgctgtta tgcggccatt gtccgtcagg acattgttgg    3120
agccgaaatc cgcgtgcacg aggtgccgga cttcggggca gtcctcggcc caaagcatca    3180
gctcatcgag agcctgcgcg acggacgcac tgacggtgtc gtccatcaca gtttgccagt    3240
gatacacatg gggatcagca atcgcgcata tgaaatcacg ccatgtagtg tattgaccga    3300
ttccttgcgg tccgaatggg ccgaacccgc tcgtctggct aagatcggcc gcagcgatcg    3360
catccatggc ctccgcgacc ggctgcagaa cagcgggcag ttcggtttca ggcaggtctt    3420
gcaacgtgac accctgtgca cggcgggaga tgcaataggt caggctctcg ctgaattccc    3480
caatgtcaag cacttccgga atcgggagcg cggccgatgc aaagtgccga taaacataac    3540
gatctttgta gaaaccatcg gcgcagctat ttacccgcag gacatatcca cgccctccta    3600
catcgaagct gaaagcacga gattcttcgc cctccgagag ctgcatcagg tcggagacgc    3660
tgtcgaactt ttcgatcaga aacttctcga cagacgtcgc ggtgagttca ggcttttca    3720 tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgt ggttggaacg tcttcttttt ccacgatgct cctcgtgggt ggggtccat    3960 cttcgggacc actgtcggca gaggcatctt gaatgatagc cttccttta tcgcaatgat    4020 ggcatttgta ggagccacct tccttttcta ctgtcctttc gatgaagtga cagatagctg    4080
ggcaatggaa tccgaggagg tttcccgaaa ttatcctttg ttgaaaagtc tcaatagccc    4140
tttggtcttc tgagactgta tctttgacat ttttggagta gaccagagtg tcgtgctcca    4200
ccatgttgac gaagatttc ttcttgtcat tgagtcgtaa aagactctgt atgaactgtt    4260
cgccagtctt cacggcgagt tctgttagat cctcgatttg aatcttagac tccatgcatg    4320
gccttagatt cagtaggaac taccttttta gagactccaa tctctattac ttgccttggt    4380
ttatgaagca agccttgaat cgtccatact ggaatagtac ttctgatctt gagaaatatg    4440
tctttctctg tgttcttgat gcaattagtc ctgaatcttt tgactgcatc tttaaccttc    4500
ttgggaaggt atttgatctc ctggagattg ttactcgggt agatcgtctt gatgagacct    4560
gctgcgtagg cctctctaac catctgtggg tcagcattct ttctgaaatt gaagaggcta    4620
accttctcat tatcagtggt gaacatagtg tcgtcacctt caccttcgaa cttccttcct    4680
agatcgtaaa gatagaggaa atcgtccatt gtaatctccg gggcaaagga gatctctttt    4740
ggggctggat cactgctggg cctttttggtt cctagcgtga gccagtgggc ttttgctttt    4800
ggtgggcttg ttagggcctt agcaaagctc ttgggcttga gttgagcttc tccttttgggg    4860 atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggag caactgtgct gttaagctca    5100 gattttgtg ggattggaat tggatcgatc tcgatcccgc gaaattaata cgactcacta    5160
tagggagacc acaacggttt ccctctagaa ataattttgt ttaactttaa gaaggagata    5220
tacccatgga aaagcctgaa ctcaccgcga cgtctgtcga agtttctg atcgaaaagt    5280 tcgacagcgt ctccgacctg atgcagctct cggagggcga agaatctcgt gctttcagct    5340
tcgatgtagg agggcgtgga tatgtcctgc gggtaaatag ctgcgccgat ggtttctaca    5400
```

```
aagatcgtta tgtttatcgg cactttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacgagcgg gttcggccca ttcggaccgc    5640
aaggaatcgg tcaatacact acatggcgtg atttcatatg cgcgattgct gatccccatg    5700
tgtatcactg gcaaactgtg atggacgaca ccgtcagtgc gtccgtcgcg caggctctcg    5760
atgagctgat gctttgggcc gaggactgcc ccgaagtccg gcacctcgtg cacgcggatt    5820
tcggctccaa caatgtcctg acggacaatg gccgcataac agcggtcatt gactggagcg    5880
aggcgatgtt cggggattcc caatacgagg tcgccaacat cttcttctgg aggccgtggt    5940
tggcttgtat ggagcagcag acgcgctact tcgagcggga gcatccggag cttgcaggat    6000
cgccgcggct ccgggcgtat atgctccgca ttggtcttga ccaactctat cagagcttgg    6060
ttgacggcaa tttcgatgat gcagcttggg cgcagggtcg atgcgacgca atcgtccgat    6120
ccggagccgg gactgtcggg cgtacacaaa tcgcccgcag aagcgcggcc gtctggaccg    6180
atggctgtgt agaagtactc gccgatagtg aaaccgacg ccccagcact cgtccgaggg    6240
caaaggaata gtgaggtaca gcttggatcg atccggctgc taacaaagcc cgaaaggaag    6300
ctgagttggc tgctgccacc gctgagcaat aactagcata ccccttgggg cctctaaac    6360 gggtcttgag gggttttttg ctgaaaggag gaactatatc cggatgatcg ggcgcgccgt    6420
cgacggatcc gtacgagatc cggccggcca gatcctgcag gagatccaag cttttgatcc    6480
atgcccttca tttgccgctt attaattaat ttggtaacag tccgtactaa tcagttactt    6540
atccttcccc catcataatt aatcttggta gtctcgaatg ccacaacact gactagtctc    6600
ttggatcata agaaaaagcc aaggaacaaa agaagacaaa acacaatgag agtatccttt    6660
gcatagcaat gtctaagttc ataaaattca aacaaaaacg caatcacaca cagtggacat    6720
cacttatcca ctagctgatc aggatcgccg cgtcaagaaa aaaaaactgg accccaaaag    6780
ccatgcacaa caacacgtac tcacaaaggt gtcaatcgag cagcccaaaa cattcaccaa    6840
ctcaacccat catgagccct cacatttgtt gtttctaacc caacctcaaa ctcgtattct    6900
cttccgccac ctcattttg tttatttcaa cacccgtcaa actgcatgcc accccgtggc    6960
caaatgtcca tgcatgttaa caagacctat gactataaat agctgcaatc tcggcccagg    7020
ttttcatcat caagaaccag ttcaatatcc tagtacaccg tattaaagaa tttaagatat    7080
actgcggccg caccatggag gtggtgaatg aaatagtctc aattgggcag gaagttttac    7140
ccaaagttga ttatgcccaa ctctggagtg atgccagtca ctgtgaggtg ctttacttgt    7200
ccatcgcatt tgtcatcttg aagttcactc ttggcccct tggtccaaaa ggtcagtctc    7260
gtatgaagtt tgttttcacc aattacaacc ttctcatgtc catttattcg ttgggatcat    7320
tcctctcaat ggcatatgcc atgtacacca tcggtgttat gtctgacaac tgcgagaagg    7380
cttttgacaa caacgtcttc aggatcacca cgcagttgtt ctatttgagc aagttcctgg    7440
agtatattga ctccttctat ttgccactga tgggcaagcc tctgacctgg ttgcaattct    7500
tccatcattt gggggcaccg atggatatgt ggctgttcta taattaccga aatgaagctg    7560 tttgatttt tgtgctgttg aatggtttca tccactggat catgtacggt tattattgga    7620
ccagattgat caagctgaag ttccccatgc aaaatccct gattacatca atgcagatca    7680
ttcaattcaa tgttggtttc tacattgtct ggaagtacag gaacattccc tgttatcgcc    7740
aagatgggat gaggatgttt ggctggttct tcaattactt ttatgttggc acagtcttgt    7800
```

```
gtttgttctt gaatttctat gtgcaaacgt atatcgtcag gaagcacaag ggagccaaaa    7860
agattcagtg agc                                                      7873

<210> SEQ ID NO 45
<211> LENGTH: 5252
<212> TYPE: DNA
<213> ORGANISM: Artificial Sequence
<220> FEATURE:
<223> OTHER INFORMATION: plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 45
gtacgtgggc ggatcccccg ggctgcagga attcactggc cgtcgtttta caacgtcgtg      60
actgggaaaa ccctggcgtt acccaactta atcgccttgc agcacatccc cctttcgcca     120
gctggcgtaa tagcgaagag gcccgcaccg atcgcccttc ccaacagttg cgcagcctga     180
atggcgaatg gcgcctgatg cggtattttc tccttacgca tctgtgcggt atttcacacc     240
gcatatggtg cactctcagt acaatctgct ctgatgccgc atagttaagc cagccccgac     300
acccgccaac acccgctgac gcgccctgac gggcttgtct gctcccggca tccgcttaca     360
gacaagctgt gaccgtctcc gggagctgca tgtgtcagag gttttcaccg tcatcaccga     420
aacgcgcgag acgaaagggc ctcgtgatac gcctattttt ataggttaat gtcatgataa     480
taatggtttc ttagacgtca ggtggcactt ttcggggaaa tgtgcgcgga acccctattt     540
gtttattttt ctaaatacat tcaaatatgt atccgctcat gagacaataa ccctgataaa     600
tgcttcaata atattgaaaa aggaagagta tgagtattca acatttccgt gtcgccctta     660
ttcccttttt tgcggcattt tgccttcctg ttttgctcac ccagaaacg ctggtgaaag      720 taaaagatgc tgaagatcag ttgggtgcac gagtgggtta tcgaactg gatctcaaca      780 gcggtaagat ccttgagagt tttcgccccg aagaacgttt tccaatgatg agcacttttta    840 aagttctgct atgtggcgcg gtattatccc gtattgacgc cgggcaagag caactcggtc     900
gccgcataca ctattctcag aatgacttgg ttgagtactc accagtcaca gaaaagcatc     960
ttacggatgg catgacagta agagaattat gcagtgctgc cataaccatg agtgataaca    1020
ctgcggccaa cttacttctg acaacgatcg gaggaccgaa ggagctaacc gcttttttgc    1080
acaacatggg ggatcatgta actcgccttg atcgttggga accggagctg aatgaagcca    1140
taccaaacga cgagcgtgac accacgatgc ctgtagcaat ggcaacaacg ttgcgcaaac    1200
tattaactgg cgaactactt actctagctt cccggcaaca attaatagac tggatggagg    1260
cggataaagt tgcaggacca cttctgcgct cggcccttcc ggctggctgg tttattgctg    1320
ataaatctgg agccggtgag cgtgggtctc gcggtatcat tgcagcactg gggccagatg    1380
gtaagccctc ccgtatcgta gttatctaca cgacggggag tcaggcaact atggatgaac    1440
gaaatagaca gatcgctgag ataggtgcct cactgattaa gcattggtaa ctgtcagacc    1500
aagtttactc atatatactt tagattgatt taaaacttca tttttaattt aaaaggatct    1560
aggtgaagat cctttttgat aatctcatga ccaaaatccc ttaacgtgag ttttcgttcc    1620
actgagcgtc agaccccgta gaaaagatca aggatcttc ttgagatcct ttttttctgc     1680
gcgtaatctg ctgcttgcaa acaaaaaaac caccgctacc agcggtggtt tgtttgccgg    1740
atcaagagct accaactctt tttccgaagg taactggctt cagcagagcg cagataccaa    1800
atactgtcct tctagtgtag ccgtagttag gccaccactt caagaactct gtagcaccgc    1860
```

```
ctacatacct cgctctgcta atcctgttac cagtggctgc tgccagtggc gataagtcgt    1920
gtcttaccgg gttggactca agacgatagt taccggataa ggcgcagcgg tcgggctgaa    1980
cggggggttc gtgcacacag cccagcttgg agcgaacgac ctacaccgaa ctgagatacc    2040
tacagcgtga gctatgagaa agcgccacgc ttcccgaagg gagaaaggcg gacaggtatc    2100
cggtaagcgg cagggtcgga acaggagagc gcacgaggga gcttccaggg ggaaacgcct    2160
ggtatcttta tagtcctgtc gggtttcgcc acctctgact tgagcgtcga ttttttgtgat   2220 gctcgtcagg ggggcggagc ctatggaaaa acgccagcaa cgcggccttt ttacggttcc    2280
tggccttttg ctggcctttt gctcacatgt tctttcctgc gttatcccct gattctgtgg    2340
ataaccgtat taccgccttt gagtgagctg ataccgctcg ccgcagccga acgaccgagc    2400
gcagcgagtc agtgagcgag gaagcggaag agcgcccaat acgcaaaccg cctctccccg    2460
cgcgttggcc gattcattaa tgcagctggc acgacaggtt tcccgactgg aaagcgggca    2520
gtgagcgcaa cgcaattaat gtgagttagc tcactcatta ggcaccccag gctttacact    2580
ttatgcttcc ggctcgtatg ttgtgtggaa ttgtgagcgg ataacaattt cacacaggaa    2640
acagctatga ccatgattac gccaagcttg catgcctgca ggtcgactcg acgtacgtcc    2700
tcgaagagaa gggttaataa cacattttt aacattttta acacaaattt tagttattta    2760
aaaatttatt aaaaaattta aaataagaag aggaactctt taaataaatc taacttacaa    2820
aatttatgat ttttaataag ttttcaccaa taaaaaatgt cataaaaata tgttaaaaag    2880
tatattatca atattctctt tatgataaat aaaaagaaaa aaaaaataaa agttaagtga    2940
aaatgagatt gaagtgactt taggtgtgta taaatatatc aaccccgcca acaatttatt    3000
taatccaaat atattgaagt atattattcc atagccttta tttatttata tatttattat    3060
ataaaagctt tatttgttct aggttgttca tgaaatattt ttttggtttt atctccgttg    3120
taagaaaatc atgtgctttg tgtcgccact cactattgca gctttttcat gcattggtca    3180
gattgacggt tgattgtatt tttgtttttt atggttttgt gttatgactt aagtcttcat    3240
ctctttatct cttcatcagg tttgatggtt acctaatatg gtccatgggt acatgcatgg    3300
ttaaattagg tggccaactt tgttgtgaac gatagaattt tttttatatt aagtaaacta    3360
tttttatatt atgaaataat aataaaaaaa atatttatc attattaaca aaatcatatt     3420
agttaatttg ttaactctat aataaaagaa atactgtaac attcacatta catggtaaca    3480
tctttccacc ctttcatttg ttttttgttt gatgactttt tttcttgttt aaatttattt    3540
cccttctttt aaatttggaa tacattatca tcatatataa actaaaatac taaaaacagg    3600
attacacaaa tgataaataa taacacaaat atttataaat ctagctgcaa tatatttaaa    3660
ctagctatat cgatattgta aaataaaact agctgcattg atactgataa aaaaatatca    3720
tgtgctttct ggactgatga tgcagtatac ttttgacatt gcctttattt tatttttcag    3780
aaaagctttc ttagttctgg gttcttcatt atttgtttcc catctccatt gtgaattgaa    3840
tcatttgctt cgtgtcacaa atacaattta gntaggtaca tgcattggtc agattcacgg    3900
tttattatgt catgacttaa gttcatggta gtacattacc tgccacgcat gcattatatt    3960
ggttagattt gataggcaaa tttggttgtc aacaatataa atataaataa tgttttata    4020 ttacgaaata acagtgatca aaacaaacag ttttatcttt attaacaaga ttttgttttt    4080
gtttgatgac gttttttaat gtttacgctt tccccttct tttgaattta gaacacttta     4140
tcatcataaa atcaaatact aaaaaaatta catatttcat aaataataac acaaatattt    4200
ttaaaaaatc tgaaataata atgaacaata ttacatatta tcacgaaaat tcattaataa    4260
```

```
aaatattata taaataaaat gtaatagtag ttatatgtag gaaaaaagta ctgcacgcat    4320
aatatataca aaaagattaa aatgaactat tataaataat aacactaaat taatggtgaa    4380
tcatatcaaa ataatgaaaa agtaaataaa atttgtaatt aacttctata tgtattacac    4440
acacaaataa taaataatag taaaaaaaat tatgataaat atttaccatc tcataagata    4500
tttaaaataa tgataaaaat atagattatt ttttatgcaa ctagctagcc aaaaagagaa    4560
cacgggtata tataaaaaga gtacctttaa attctactgt acttccttta ttcctgacgt    4620
ttttatatca agtggacata cgtgaagatt ttaattatca gtctaaatat ttcattagca    4680
cttaatactt ttctgtttta ttcctatcct ataagtagtc ccgattctcc caacattgct    4740
tattcacaca actaactaag aaagtcttcc atagccccccc aagcggccgc gacacaagtg    4800
tgagagtact aaataaatgc tttggttgta cgaaatcatt acactaaata aaataatcaa    4860
agcttatata tgccttccgc taaggccgaa tgcaaagaaa ttggttcttt ctcgttatct    4920
tttgccactt ttactagtac gtattaatta ctacttaatc atctttgttt acggctcatt    4980
atatccggtc tagaggatcc aaggccgcga agttaaaagc aatgttgtca cttgtcgtac    5040
taacacatga tgtgatagtt tatgctagct agctataaca taagctgtct ctgagtgtgt    5100
tgtatattaa taaagatcat cactggtgaa tggtgatcgt gtacgtaccc tacttagtag    5160
gcaatggaag cacttagagt gtgctttgtg catggccttg cctctgtttt gagacttttg    5220
taatgttttc gagtttaaat ctttgccttt gc                                 5252
```

<210> SEQ ID NO 46
<211> LENGTH: 6526
<212> TYPE: DNA
<213> ORGANISM: Artificial Sequence
<220> FEATURE:
<223> OTHER INFORMATION: plasmid pKR1138
<220> FEATURE:
<221> NAME/KEY: misc_feature
<222> LOCATION: (4340)..(4340)
<223> OTHER INFORMATION: n is a, c, g, or t

<400> SEQUENCE: 46

```
ggccgcgaca caagtgtgag agtactaaat aaatgctttg gttgtacgaa atcattacac      60
taaataaaat aatcaaagct tatatatgcc ttccgctaag gccgaatgca aagaaattgg     120
ttctttctcg ttatcttttg ccacttttac tagtacgtat taattactac ttaatcatct     180
ttgtttacgg ctcattatat ccggtctaga ggatccaagg ccgcgaagtt aaaagcaatg     240
ttgtcacttg tcgtactaac acatgatgtg atagtttatg ctagctagct ataacataag     300
ctgtctctga gtgtgttgta tattaataaa gatcatcact ggtgaatggt gatcgtgtac     360
gtaccctact tagtaggcaa tggaagcact tagagtgtgc tttgtgcatg gccttgcctc     420
tgttttgaga cttttgtaat gttttcgagt ttaaatcttt gccttgcgt acgtgggcgg     480 atccccgggg ctgcaggaat tcactggccg tcgttttaca acgtcgtgac tgggaaaacc     540
ctggcgttac ccaacttaat cgccttgcag cacatccccc tttcgccagc tggcgtaata     600
gcgaagaggc ccgcaccgat cgcccttccc aacagttgcg cagcctgaat ggcgaatggc     660
gcctgatgcg gtattttctc cttacgcatc tgtgcggtat tcacaccgc atatggtgca     720 ctctcagtac aatctgctct gatgccgcat agttaagcca gccccgacac cgccaacac     780 ccgctgacgc gccctgacgg gcttgtctgc tcccggcatc cgcttacaga caagctgtga     840
ccgtctccgg gagctgcatg tgtcagaggt tttcaccgtc atcaccgaaa cgcgcgagac     900
gaaagggcct cgtgatacgc ctatttttat aggttaatgt catgataata atggtttctt     960
```

```
agacgtcagg tggcactttt cggggaaatg tgcgcggaac ccctatttgt ttatttttct    1020
aaatacattc aaatatgtat ccgctcatga gacaataacc ctgataaatg cttcaataat    1080
attgaaaaag gaagagtatg agtattcaac atttccgtgt cgcccttatt ccctttttttg   1140 cggcattttg ccttcctgtt tttgctcacc cagaaacgct ggtgaaagta aaagatgctg    1200
aagatcagtt gggtgcacga gtgggttaca tcgaactgga tctcaacagc ggtaagatcc    1260
ttgagagttt tcgccccgaa gaacgttttc caatgatgag cacttttaaa gttctgctat    1320
gtggcgcggt attatcccgt attgacgccg ggcaagagca actcggtcgc cgcatacact    1380
attctcagaa tgacttggtt gagtactcac cagtcacaga aaagcatctt acggatggca    1440
tgacagtaag agaattatgc agtgctgcca taaccatgag tgataacact gcggccaact    1500
tacttctgac aacgatcgga ggaccgaagg agctaaccgc ttttttgcac aacatggggg    1560
atcatgtaac tcgccttgat cgttgggaac cggagctgaa tgaagccata ccaaacgacg    1620
agcgtgacac cacgatgcct gtagcaatgg caacaacgtt gcgcaaacta ttaactggcg    1680
aactacttac tctagcttcc cggcaacaat taatagactg gatggaggcg gataaagttg    1740
caggaccact tctgcgctcg gcccttccgg ctggctggtt tattgctgat aaatctggag    1800
ccggtgagcg tgggtctcgc ggtatcattg cagcactggg gccagatggt aagccctccc    1860
gtatcgtagt tatctacacg acggggagtc aggcaactat ggatgaacga atagacaga    1920 tcgctgagat aggtgcctca ctgattaagc attggtaact gtcagaccaa gtttactcat    1980
atatacttta gattgattta aaacttcatt tttaatttaa aaggatctag gtgaagatcc    2040
tttttgataa tctcatgacc aaaatccctt aacgtgagtt ttcgttccac tgagcgtcag    2100
accccgtaga aaagatcaaa ggatcttctt gagatccttt ttttctgcgc gtaatctgct    2160
gcttgcaaac aaaaaaacca ccgctaccag cggtggtttg tttgccggat caagagctac    2220
caactctttt tccgaaggta actggcttca gcagagcgca gataccaaat actgtccttc    2280
tagtgtagcc gtagttaggc caccacttca agaactctgt agcaccgcct acatacctcg    2340
ctctgctaat cctgttacca gtggctgctg ccagtggcga taagtcgtgt cttaccgggt    2400
tggactcaag acgatagtta ccggataagg cgcagcggtc gggctgaacg gggggttcgt    2460
gcacacagcc cagcttggag cgaacgacct acaccgaact gagatacccta cagcgtgagc    2520 tatgagaaag cgccacgctt cccgaaggga gaaaggcgga caggtatccg gtaagcggca    2580
gggtcggaac aggagagcgc acgagggagc ttccaggggg aaacgcctgg tatctttata    2640
gtcctgtcgg gtttcgccac ctctgacttg agcgtcgatt tttgtgatgc tcgtcagggg    2700
ggcggagcct atggaaaaac gccagcaacg cggccttttt acggttcctg gccttttgct    2760
ggccttttgc tcacatgttc tttcctgcgt tatccctga ttctgtggat aaccgtatta    2820
ccgcctttga gtgagctgat accgctcgcc gcagccgaac gaccgagcgc agcgagtcag    2880
tgagcgagga agcggaagag cgcccaatac gcaaaccgcc tctccccgcg cgttggccga    2940
ttcattaatg cagctggcac gacaggtttc ccgactggaa agcgggcagt gagcgcaacg    3000
caattaatgt gagttagctc actcattagg caccccaggc tttacacttt atgcttccgg    3060
ctcgtatgtt gtgtggaatt gtgagcggat aacaatttca cacaggaaac agctatgacc    3120
atgattacgc caagcttgca tgcctgcagg tcgactcgac gtacgtcctc gaagagaagg    3180
gttaataaca cattttttaa catttttaac acaatttta gttatttaaa aatttattaa    3240
aaaatttaaa ataagaagag gaactctta aataaatcta acttacaaaa tttatgattt    3300
ttaataagtt ttcaccaata aaaaatgtca taaaaatatg ttaaaaagta tattatcaat    3360
```

```
attctctttta tgataaataa aaagaaaaaa aaaataaaag ttaagtgaaa atgagattga   3420
agtgacttta  ggtgtgtata aatatatcaa ccccgccaac aatttattta atccaaatat   3480
attgaagtat  attattccat agcctttatt tatttatata tttattatat aaaagcttta   3540
tttgttctag  gttgttcatg aaatattttt ttggttttat ctccgttgta agaaaatcat   3600
gtgctttgtg  tcgccactca ctattgcagc tttttcatgc attggtcaga ttgacggttg   3660
attgtatttt  tgtttttttat ggttttgtgt tatgacttaa gtcttcatct ctttatctct   3720
tcatcaggtt  tgatggttac ctaatatggt ccatgggtac atgcatggtt aaattaggtg   3780
gccaactttg  ttgtgaacga tagaattttt tttatattaa gtaaactatt tttatattat   3840
gaaataataa  taaaaaaaat attttatcat tattaacaaa atcatattag ttaatttgtt   3900
aactctataa  taaaagaaat actgtaacat tcacattaca tggtaacatc tttccaccct   3960
ttcatttgtt  ttttgtttga tgactttttt tcttgtttaa atttatttcc cttcttttaa   4020
atttggaata  cattatcatc atatataaac taaaatacta aaaacaggat tacacaaatg   4080
ataaataata  acacaaatat ttataaatct agctgcaata tatttaaact agctatatcg   4140
atattgtaaa  ataaaactag ctgcattgat actgataaaa aaatatcatg tgctttctgg   4200
actgatgatg  cagtatactt ttgacattgc ctttatttta ttttttcagaa aagctttctt   4260
agttctgggt  tcttcattat ttgtttccca tctccattgt gaattgaatc atttgcttcg   4320
tgtcacaaat  acaatttagn taggtacatg cattggtcag attcacggtt tattatgtca   4380
tgacttaagt  tcatggtagt acattacctg ccacgcatgc attatattgg ttagatttga   4440
taggcaaatt  tggttgtcaa caatataaat ataaataatg ttttatatt  acgaaataac   4500
agtgatcaaa  acaaacagtt ttatctttat taacaagatt ttgttttttgt ttgatgacgt   4560
ttttaatgt   ttacgctttc ccccttcttt tgaatttaga acactttatc atcataaaat   4620
caaatactaa  aaaaattaca tatttcataa ataataacac aaatattttt aaaaaatctg   4680
aaataataat  gaacaatatt acatattatc acgaaaattc attaataaaa atattatata   4740
aataaaatgt  aatagtagtt atatgtagga aaaaagtact gcacgcataa tatatacaaa   4800
aagattaaaa  tgaactatta taaataataa cactaaatta atggtgaatc atatcaaaat   4860
aatgaaaaag  taaataaaat ttgtaattaa cttctatatg tattacacac acaaataata   4920
aataatagta  aaaaaaatta tgataaatat ttaccatctc ataagatatt taaaataatg   4980
ataaaaatat  agattatttt ttatgcaact agctagccaa aaagagaaca cgggtatata   5040
taaaagagt   acctttaaat tctactgtac ttcctttatt cctgacgttt ttatatcaag   5100
tggacatacg  tgaagatttt aattatcagt ctaaatattt cattagcact taatacttt   5160
ctgttttatt  cctatcctat aagtagtccc gattctccca acattgctta ttcacacaac   5220
taactaagaa  agtcttccat agcccccaa  gcggccgcac catggtgaaa aggccagcac   5280
ttccgctgac  cgttgatggt gtcacctatg atgtgtctgc ctggttgaac catcatccag   5340
ggggtgctga  catcattgag aactaccgcg gtcgtgatgc cactgatgtc tttatggtta   5400
tgcactctga  aaatgctgtg agtaaactaa gaaggatgcc tatcatggaa ccatcatctc   5460
cactgacgcc  tacgccaccg aaacccaact cagacgaacc gcaggaggat ttccgcaagc   5520
tccgagatga  gctcatcgca gcaggaatgt tcgacgcatc accgatgtgg tacgcatata   5580
agacgctcag  tacgctgggc ctcggggtcc tcgcggtgct attgatgacc cagtggcact   5640
ggtacctcgt  cggggcaatc gtgttgggca ttcacttcca acaaatgggt tggttgtcgc   5700
acgatatctg  ccaccatcag ctgttcaagg accgatcgat caacaacgcc atcggcttgc   5760
```

```
tttcgggaa cgtcttgcaa gggttctctg tgacctggtg gaaggacagg cacaatgcac    5820
accactccgc caccaacgtg caaggccacg accccgacat tgacaacctg ccgctgctgg    5880
catggtccaa ggaggacgtg gagagggccg gcccgttctc acggcggatg atcaagtacc    5940
agcaatacta cttcttcttc atctgtgccc tcctgaggtt catctggtgc ttccagagca    6000
tccacacagc cacgggcctg aaggatcgca gcaaccagta ctaccgcagg cagtacgaga    6060
aagagagcgt gggcctggcc ctccactggg gcctgaaggc gttgttctac tacttttata    6120
tgccaagctt cttgaccgga ctcatggtgt ttttcgtgtc cgagttgctt ggggcttcg     6180
gcatcgccat cgtggtgttc atgaaccact accccctgga gaagatccag gactcggtgt    6240
gggacggcca cggcttttgc gccggccaga ttcacgaaac gatgaacgtc cagcggggac    6300
tcgtcacgga ctggttcttc ggtgggctga attaccaaat cgagcaccac ctgtggccga    6360
cgctgccccg gcacaacctg acggcggcca gcatcaaagt ggagcagttg tgcaagaagc    6420
acaacttgcc gtatcgcagc cccccaatgc tggaggggt gggcatcctg atcagctacc     6480
tgggcacctt tgcccgcatg gtggcaaagg ccgacaaggc gtaagc                  6526
```

<210> SEQ ID NO 47
<211> LENGTH: 11707
<212> TYPE: DNA
<213> ORGANISM: Artificial Sequence
<220> FEATURE:
<223> OTHER INFORMATION: plasmid pKR1152
<220> FEATURE:
<221> NAME/KEY: misc_feature
<222> LOCATION: (10532)..(10532)
<223> OTHER INFORMATION: n is a, c, g, or t

<400> SEQUENCE: 47

```
gtacgagatc cggccggcca gatcctgcag gagatccaag cttttgatcc atgcccttca      60
tttgccgctt attaattaat ttggtaacag tccgtactaa tcagttactt atccttcccc     120
catcataatt aatcttggta gtctcgaatg ccacaacact gactagtctc ttggatcata     180
agaaaaagcc aaggaacaaa agaagacaaa acacaatgag agtatccttt gcatagcaat     240
gtctaagttc ataaaattca aacaaaaacg caatcacaca cagtggacat cacttatcca     300
ctagctgatc aggatcgccg cgtcaagaaa aaaaaactgg accccaaaag ccatgcacaa     360
caacacgtac tcacaaaggt gtcaatcgag cagcccaaaa cattcaccaa ctcaacccat     420
catgagccct cacatttgtt gtttctaacc caacctcaaa ctcgtattct cttccgccac     480
ctcattttg tttatttcaa caccgtcaa actgcatgcc accccgtggc caaatgtcca      540
tgcatgttaa caagacctat gactataaat agctgcaatc tcggcccagg ttttcatcat     600
caagaaccag ttcaatatcc tagtacaccg tattaaagaa tttaagatat actgcggccg     660
caccatggag gtggtgaatg aaatagtctc aattgggcag gaagttttac ccaaagttga     720
ttatgcccaa ctctggagtg atgccagtca ctgtgaggtg ctttacttgt ccatcgcatt     780
tgtcatcttg aagttcactc ttggccccct tggtccaaaa ggtcagtctc gtatgaagtt     840
tgttttcacc aattacaacc ttctcatgtc catttattcg ttgggatcat tcctctcaat     900
ggcatatgcc atgtacacca tcggtgttat gtctgacaac tgcgagaagg cttttgacaa     960
caacgtcttc aggatcacca cgcagttgtt ctatttgagc aagttcctgg agtatattga    1020
ctccttctat ttgccactga tgggcaagcc tctgacctgg ttgcaattct tccatcattt    1080
ggggggcaccg atggatatgt ggctgttcta taattaccga aatgaagctg tttgatttt    1140
tgtgctgttg aatggtttca tccactggat catgtacggt tattattgga ccagattgat    1200
```

```
caagctgaag ttccccatgc caaaatccct gattacatca atgcagatca ttcaattcaa    1260
tgttggtttc tacattgtct ggaagtacag gaacattccc tgttatcgcc aagatgggat    1320
gaggatgttt ggctggttct tcaattactt ttatgttggc acagtcttgt gtttgttctt    1380
gaatttctat gtgcaaacgt atatcgtcag gaagcacaag ggagccaaaa agattcagtg    1440
agcggccgca agtatgaact aaaatgcatg taggtgtaag agctcatgga gagcatggaa    1500
tattgtatcc gaccatgtaa cagtataata actgagctcc atctcacttc ttctatgaat    1560
aaacaaagga tgttatgata tattaacact ctatctatgc accttattgt tctatgataa    1620
atttcctctt attattataa atcatctgaa tcgtgacggc ttatggaatg cttcaaatag    1680
tacaaaaaca aatgtgtact ataagacttt ctaaacaatt ctaaccttag cattgtgaac    1740
gagacataag tgttaagaag acataacaat tataatggaa gaagtttgtc tccatttata    1800
tattatatat tacccactta tgtattatat taggatgtta aggagacata acaattataa    1860
agagagaagt ttgtatccat ttatatatta tatactaccc atttatatat tatacttatc    1920
cacttattta atgtctttat aaggtttgat ccatgatatt tctaatattt tagttgatat    1980
gtatatgaaa gggtactatt tgaactctct tactctgtat aaaggttgga tcatccttaa    2040
agtgggtcta tttaatttta ttgcttctta cagataaaaa aaaaattatg agttggtttg    2100
ataaaatatt gaaggattta aaataataat aaataacata taatatatgt atataaattt    2160
attataatat aacatttatc tataaaaaag taaatattgt cataaatcta tacaatcgtt    2220
tagccttgct ggacgaatct caattatttta aacgagagta aacatatttg acttttttggt    2280
tatttaacaa attattattt aacactatat gaaatttttt tttttatcag caaagaataa    2340
aattaaatta agaaggacaa tggtgtccca atccttatac aaccaacttc cacaagaaag    2400
tcaagtcaga gacaacaaaa aaacaagcaa aggaaatttt ttaatttgag ttgtcttgtt    2460
tgctgcataa tttatgcagt aaaacactac acataacct tttagcagta gagcaatggt    2520
tgaccgtgtg cttagcttct tttattttat tttttttatca gcaaagaata aataaaataa    2580
aatgagacac ttcagggatg tttcaacaag cttggcgcgc cgttctatag tgtcacctaa    2640
atcgtatgtg tatgatacat aaggttatgt attaattgta gccgcgttct aacgacaata    2700
tgtccatatg gtgcactctc agtacaatct gctctgatgc cgcatagtta agccagcccc    2760
gacacccgcc aacacccgct gacgcgccct gacgggcttg tctgctcccg gcatccgctt    2820
acagacaagc tgtgaccgtc tccgggagct gcatgtgtca gaggttttca ccgtcatcac    2880
cgaaacgcgc gagacgaaag ggcctcgtga tacgcctatt tttataggtt aatgtcatga    2940
ccaaaatccc ttaacgtgag ttttcgttcc actgagcgtc agaccccgta gaaaagatca    3000
aaggatcttc ttgagatcct ttttttctgc gcgtaatctg ctgcttgcaa acaaaaaaac    3060
caccgctacc agcggtggtt tgtttgccgg atcaagagct accaactctt tttccgaagg    3120
taactggctt cagcagagcg cagataccaa atactgtcct tctagtgtag ccgtagttag    3180
gccaccactt caagaactct gtagcaccgc ctacatacct cgctctgcta atcctgttac    3240
cagtggctgc tgccagtggc gataagtcgt gtcttaccgg gttggactca agacgatagt    3300
taccggataa ggcgcagcgg tcgggctgaa cggggggttc gtgcacacag cccagcttgg    3360
agcgaacgac ctacaccgaa ctgagatacc tacagcgtga gcattgagaa agcgccacgc    3420
ttcccgaagg gagaaaggcg gacaggtatc cggtaagcgg cagggtcgga acaggagagc    3480
gcacgaggga gcttccaggg ggaaacgcct ggtatcttta gtcctgtc gggtttcgcc    3540
acctctgact tgagcgtcga ttttgtgat gctcgtcagg gggcggagc ctatggaaaa    3600
```

```
acgccagcaa cgcggccttt ttacggttcc tggccttttg ctggccttt gctcacatgt   3660
tctttcctgc gttatcccct gattctgtgg ataaccgtat taccgccttt gagtgagctg   3720
ataccgctcg ccgcagccga acgaccgagc gcagcgagtc agtgagcgag gaagcggaag   3780
agcgcccaat acgcaaaccg cctctccccg cgcgttggcc gattcattaa tgcaggttga   3840
tcgattcgac atcgatctag taacatagat gacaccgcgc gcgataattt atcctagttt   3900
gcgcgctata ttttgttttc tatcgcgtat taaatgtata attgcgggac tctaatcata   3960
aaaacccatc tcataaataa cgtcatgcat tacatgttaa ttattacatg cttaacgtaa   4020
ttcaacagaa attatatgat aatcatcgca agaccggcaa caggattcaa tcttaagaaa   4080
ctttattgcc aaatgtttga acgatctgct tcgacgcact ccttctttag gtacctcact   4140
attcctttgc cctcggacga gtgctggggc gtcggtttcc actatcggcg agtacttcta   4200
cacagccatc ggtccagacg gccgcgcttc tgcgggcgat ttgtgtacgc ccgacagtcc   4260
cggctccgga tcggacgatt gcgtcgcatc gaccctgcgc ccaagctgca tcatcgaaat   4320
tgccgtcaac caagctctga tagagttggt caagaccaat gcggagcata tacgcccgga   4380
gccgcggcga tcctgcaagc tccggatgcc tccgctcgaa gtagcgcgtc tgctgctcca   4440
tacaagccaa ccacggcctc cagaagaaga tgttggcgac ctcgtattgg gaatccccga   4500
acatcgcctc gctccagtca atgaccgctg ttatgcggcc attgtccgtc aggacattgt   4560
tggagccgaa atccgcgtgc acgaggtgcc ggacttcggg gcagtcctcg gcccaaagca   4620
tcagctcatc gagagcctgc gcgacggacg cactgacggt gtcgtccatc acagtttgcc   4680
agtgatacac atggggatca gcaatcgcgc atatgaaatc acgccatgta gtgtattgac   4740
cgattccttg cggtccgaat gggccgaacc cgctcgtctg gctaagatcg gccgcagcga   4800
tcgcatccat ggcctccgcg accggctgca gaacagcggg cagttcggtt tcaggcaggt   4860
cttgcaacgt gacaccctgt gcacggcggg agatgcaata ggtcaggctc tcgctgaatt   4920
ccccaatgtc aagcacttcc ggaatcggga gcgcggccga tgcaaagtgc cgataaacat   4980
aacgatcttt gtagaaacca tcggcgcagc tatttacccg caggacatat ccacgccctc   5040
ctacatcgaa gctgaaagca cgagattctt cgccctccga gagctgcatc aggtcggaga   5100
cgctgtcgaa cttttcgatc agaaacttct cgacagacgt cgcggtgagt tcaggctttt   5160
tcatggttta ataagaagag aaaagagttc ttttgttatg gctgaagtaa tagagaaatg   5220
agctcgagcg tgtcctctcc aaatgaaatg aacttcctta tatagaggaa gggtcttgcg   5280
aaggatagtg ggattgtgcg tcatcccttc cgtcagtgga gatgtcacat caatccactt   5340
gctttgaaga cgtggttgga acgtcttctt ttttccacgat gctcctcgtg ggtgggggtc   5400
catctttggg accactgtcg gcagaggcat cttgaatgat agcctttcct ttatcgcaat   5460
gatggcattt gtaggagcca ccttcctttt ctactgtcct ttcgatgaag tgacagatag   5520
ctgggcaatg gaatccgagg aggtttcccg aaattatcct tgttgaaaa gtctcaatag   5580
ccctttggtc ttctgagact gtatctttga cattttgga gtagaccaga gtgtcgtgct   5640
ccaccatgtt gacgaagatt ttcttcttgt cattgagtcg taaaagactc tgtatgaact   5700
gttcgccagt cttcacggcg agttctgtta gatcctcgat ttgaatctta gactccatgc   5760
atggccttag attcagtagg aactaccttt ttagagactc caatctctat tacttgcctt   5820
ggtttatgaa gcaagccttg aatcgtccat actggaatag tacttctgat cttgagaaat   5880
atgtcttcct ctgtgttctt gatgcaatta gtcctgaatc ttttgactgc atctttaacc   5940
ttcttgggaa ggtatttgat ctcctggaga ttgttactcg ggtagatcgt cttgatgaga   6000
```

```
cctgctgcgt aggcctctct aaccatctgt gggtcagcat tctttctgaa attgaagagg    6060
ctaaccttct cattatcagt ggtgaacata gtgtcgtcac cttcaccttc gaacttcctt    6120
cctagatcgt aaagatagag gaaatcgtcc attgtaatct ccggggcaaa ggagatctct    6180 tttgggctg gatcactgct gggccttttg gttcctagcg tgagccagtg ggcttttttgc    6240 tttggtgggc ttgttagggc cttagcaaag ctcttgggct tgagttgagc ttctcctttg    6300
gggatgaagt tcaacctgtc tgtttgctga cttgttgtgt acgcgtcagc tgctgctctt    6360
gcctctgtaa tagtggcaaa tttcttgtgt gcaactccgg gaacgccgtt tgttgccgcc    6420
tttgtacaac cccagtcatc gtatataccg gcatgtggac cgttatacac aacgtagtag    6480
ttgatatgag ggtgttgaat acccgattct gctctgagag gagcaactgt gctgttaagc    6540
tcagattttt gtgggattgg aattggatcg atctcgatcc cgcgaaatta atacgactca    6600 ctataggag accacaacgg tttccctcta gaaataattt tgtttaactt taagaaggag    6660
atatacccat ggaaaagcct gaactcaccg cgacgtctgt cgagaagttt ctgatcgaaa    6720
agttcgacag cgtctccgac ctgatgcagc tctcggaggg cgaagaatct cgtgctttca    6780
gcttcgatgt aggagggcgt ggatatgtcc tgcgggtaaa tagctgcgcc gatggtttct    6840
acaaagatcg ttatgtttat cggcactttg catcggccgc gctcccgatt ccggaagtgc    6900
ttgacattgg ggaattcagc gagagcctga cctattgcat ctcccgccgt gcacagggtg    6960
tcacgttgca agacctgcct gaaaccgaac tgcccgctgt tctgcagccg gtcgcggagg    7020
ctatggatgc gatcgctgcg gccgatctta gccagacgag cgggttcggc ccattcggac    7080
cgcaaggaat cggtcaatac actacatggc gtgatttcat atgcgcgatt gctgatcccc    7140
atgtgtatca ctggcaaact gtgatggacg acaccgtcag tgcgtccgtc gcgcaggctc    7200
tcgatgagct gatgctttgg gccgaggact gccccgaagt ccggcacctc gtgcacgcgg    7260
atttcggctc caacaatgtc ctgacggaca atggccgcat aacagcggtc attgactgga    7320
gcgaggcgat gttcggggat tcccaatacg aggtcgccaa catcttcttc tggaggccgt    7380
ggttggcttg tatggagcag cagacgcgct acttcgagcg gaggcatccg gagcttgcag    7440
gatcgccgcg gctccgggcg tatatgctcc gcattggtct tgaccaactc tatcagagct    7500
tggttgacgg caatttcgat gatgcagctt gggcgcaggg tcgatgcgac gcaatcgtcc    7560
gatccggagc cgggactgtc gggcgtacac aaatcgcccg cagaagcgcg gccgtctgga    7620
ccgatggctg tgtagaagta ctcgccgata gtggaaaccg acgccccagc actcgtccga    7680
gggcaaagga atagtgaggt acagcttgga tcgatccggc tgctaacaaa gcccgaaagg    7740
aagctgagtt ggctgctgcc accgctgagc aataactagc ataaccccctt ggggcctcta    7800 aacgggtctt gaggggtttt tgctgaaag gaggaactat atccggatga tcgggcgcgc    7860
cgtcgacgga tccgtacgca aaggcaaaga tttaaactcg aaaacattac aaaagtctca    7920
aaacagaggc aaggccatgc acaaagcaca ctctaagtgc ttccattgcc tactaagtag    7980
ggtacgtaca cgatcaccat tcaccagtga tgatctttat taatatacaa cacactcaga    8040
gacagcttat gttatagcta gctagcataa actatcacat catgtgttag tacgacaagt    8100
gacaacattg cttttaactt cgcggccttg gatcctctag accggatata atgagccgta    8160
aacaaagatg attaagtagt aattaatacg tactagtaaa agtggcaaaa gataacgaga    8220
aagaaccaat ttctttgcat tcggccttag cggaaggcat atataagctt tgattattt    8280 atttagtgta atgatttcgt acaaccaaag catttattta gtactctcac acttgtgtcg    8340
cggccgctta cgccttgtcg gcctttgcca ccatgcgggc aaaggtgccc aggtagctga    8400
```

```
tcaggatgcc caccccctcc agcattgggg ggctgcgata cggcaagttg tgcttcttgc   8460
acaactgctc cactttgatg ctggccgccg tcaggttgtg ccggggcagc gtcggccaca   8520
ggtggtgctc gatttggtaa ttcagcccac cgaagaacca gtccgtgacg agtccccgct   8580
ggacgttcat cgtttcgtga atctggccgg cgcaaaagcc gtggccgtcc cacaccgagt   8640
cctggatctt ctccaggggg tagtggttca tgaacaccac gatggcgatg ccgaagcccc   8700
caagcaactc ggacacgaaa acaccatga gtccggtcaa gaagcttggc atataaaagt   8760
agtagaacaa cgccttcagg ccccagtgga gggccaggcc cacgctctct ttctcgtact   8820
gcctgcggta gtactggttg ctgcgatcct tcaggcccgt ggctgtgtgg atgctctgga   8880
agcaccagat gaacctcagg agggcacaga tgaagaagaa gtagtattgc tggtacttga   8940
tcatccgccg tgagaacggg ccggccctct ccacgtcctc cttggaccat gccagcagcg   9000
gcaggttgtc aatgtcgggg tcgtggcctt gcacgttggt ggcggagtgg tgtgcattgt   9060
gcctgtcctt ccaccaggtc acagagaacc cttgcaagac gttcccgaaa agcaagccga   9120
tggcgttgtt gatcgatcgg tccttgaaca gctgatggtg gcagatatcg tgcgacaacc   9180
aacccatttg ttggaagtga atgcccaaca cgattgcccc gacgaggtac cagtgccact   9240
gggtcatcaa tagcaccgcg aggaccccga ggcccagcgt actgagcgtc ttatatgcgt   9300
accacatcgg tgatgcgtcg aacattcctg ctgcgatgag ctcatctcgg agcttgcgga   9360
aatcctcctg cggttcgtct gagttgggtt tcggtggcgt aggcgtcagt ggagatgatg   9420
gttccatgat aggcatcctt cttagtttac tcacagcatt ttcagagtgc ataaccataa   9480
agacatcagt ggcatcacga ccgcggtagt tctcaatgat gtcagcaccc cctggatgat   9540
ggttcaacca ggcagacaca tcataggtga caccatcaac ggtcagcgga agtgctggcc   9600
ttttcaccat ggtgcggccg cttgggggc tatggaagac tttcttagtt agttgtgtga   9660
ataagcaatg ttgggagaat cgggactact tataggatag gaataaaaca gaaaagtatt   9720
aagtgctaat gaaatatttta gactgataat taaaatcttc acgtatgtcc acttgatata   9780
aaaacgtcag gaataaagga agtacagtag aatttaaagg tactcttttt atatataccc   9840
gtgttctctt tttggctagc tagttgcata aaaaataatc tatattttta tcattatttt   9900 aaaatatctta tgagatggta aatatttatc ataatttttt ttactattat ttattatttg   9960
tgtgtgtaat acatatagaa gttaattaca aattttattt acttttcat tattttgata  10020 tgattcacca ttaatttagt gttattattt ataatagttc attttaatct ttttgtatat  10080
attatgcgtg cagtactttt ttcctacata taactactat tacattttat ttatataata  10140
tttttattaa tgaattttcg tgataatatg taatattgtt cattattatt tcagatttt  10200 taaaaatatt tgtgttatta tttatgaaat atgtaatttt tttagtattt gattttatga  10260
tgataaagtg ttctaaattc aaaagaaggg ggaaagcgta acattaaaa aacgtcatca  10320 aacaaaaaca aaatcttgtt aataaagata aaactgtttg ttttgatcac tgttatttcg  10380
taatataaaa acattattta tatttatatt gttgacaacc aaatttgcct atcaaatcta  10440
accaatataa tgcatgcgtg gcaggtaatg tactaccatg aacttaagtc atgacataat  10500
aaaccgtgaa tctgaccaat gcatgtacct anctaaattg tatttgtgac acgaagcaaa  10560
tgattcaatt cacaatggag atgggaaaca aataatgaag aacccagaac taagaaagct  10620
tttctgaaaa ataaaataaa ggcaatgtca aaagtatact gcatcatcag tccagaaagc  10680
acatgatatt ttttttatcag tatcaatgca gctagtttta tttacaata tcgatatagc  10740 tagtttaaat atattgcagc tagatttata aatatttgtg ttattattta tcatttgtgt  10800
```

```
aatcctgttt ttagtatttt agtttatata tgatgataat gtattccaaa tttaaaagaa    10860
gggaaataaa tttaaacaag aaaaaaagtc atcaaacaaa aacaaatga aagggtggaa     10920 agatgttacc atgtaatgtg aatgttacag tatttctttt attatagagt taacaaatta    10980
actaatatga ttttgttaat aatgataaaa tatttttttt attattattt cataatataa    11040
aaatagttta cttaatataa aaaaaattct atcgttcaca acaaagttgg ccacctaatt    11100
taaccatgca tgtacccatg gaccatatta ggtaaccatc aaacctgatg aagagataaa    11160
gagatgaaga cttaagtcat aacacaaaac cataaaaaac aaaatacaa tcaaccgtca     11220 atctgaccaa tgcatgaaaa agctgcaata gtgagtggcg acacaaagca catgattttc    11280
ttacaacgga gataaaacca aaaaaatatt tcatgaacaa cctagaacaa ataaagcttt    11340
tatataataa atatataaat aaataaaggc tatggaataa tatacttcaa tatatttgga    11400
ttaaataaat tgttggcggg gttgatatat ttatacacac ctaaagtcac ttcaatctca    11460
ttttcactta acttttattt ttttttttctt tttatttatc ataaagagaa tattgataat   11520
atacttttta acatattttt atgacatttt ttattggtga aaacttatta aaaatcataa    11580 atttttgtaag ttagatttat ttaaagagtt cctcttctta tttaaattt tttaataaat    11640 ttttaaataa ctaaaatttg tgttaaaaat gttaaaaaat gtgttattaa cccttctctt    11700
cgaggac                                                              11707
```

<210> SEQ ID NO 48
<211> LENGTH: 1260
<212> TYPE: DNA
<213> ORGANISM: Artificial Sequence
<220> FEATURE:
<223> OTHER INFORMATION: codon-optimized delta-8 desaturase gene
      (designated "EaD8S")

<400> SEQUENCE: 48

```
atggtcaagc gacccgctct gcctctcacc gtggacggtg tcacctacga cgtttctgcc     60
tggctcaacc accatcccgg aggtgccgac attatcgaga actaccgagg tcgggatgct    120
accgacgtct tcatggttat gcactccgag aacgccgtgt ccaaactcag acgaatgccc    180
atcatggaac cttcctctcc cctgactcca cacctcccca agccaaactc cgacgaacct    240
caggaggatt tccgaaagct cgcgagacgag ctcattgctg caggcatgtt cgatgcctct    300
cccatgtggt acgcttacaa gaccctgtcg actctcggac tgggtgtcct tgccgtgctg    360
ttgatgaccc agtggcactg gtacctggtt ggtgctatcg tcctcggcat tcactttcaa    420
cagatgggat ggctctcgca cgacatttgc catcaccagc tgttcaagga ccgatccatc    480
aacaatgcca ttggcctgct cttcggaaac gtgcttcagg gcttttctgt cacttggtgg    540
aaggaccgac acaacgctca tcactccgcc accaacgtgc agggtcacga tcccgacatc    600
gacaacctgc ctctcctggc gtggtccaag gaggacgtcg agcgagctgg cccgttttct    660
cgacggatga tcaagtacca acagtattac ttcttttttca tctgtgccct tctgcgattc    720
atctggtgct ttcagtccat tcatactgcc acgggtctca aggatcgaag caatcagtac    780
tatcgaagac agtacgagaa ggagtccgtc ggtctggcac tccactgggg tctcaaggcc    840
ttgttctact atttctacat gccctcgttt ctcaccggac tcatggtgtt cttgtctcc    900 gagctgcttg gtggcttcgg aattgccatc gttgtcttca tgaaccacta ccctctggag    960
aagattcagg actccgtgtg ggatggtcat ggcttctgtg ctggacagat tcacgagacc    1020
atgaacgttc agcgaggcct cgtcacagac tggttttccg gtggcctcaa ctaccagatc   1080
```

| | |
|---|---|
| gaacatcacc tgtggcctac tcttcccaga cacaacctca ccgctgcctc catcaaagtg | 1140 |
| gagcagctgt gcaagaagca caacctgccc taccgatctc ctcccatgct cgaaggtgtc | 1200 |
| ggcattctta tctcctacct gggcaccttc gctcgaatgg ttgccaaggc agacaaggcc | 1260 |

<210> SEQ ID NO 49
<211> LENGTH: 3983
<212> TYPE: DNA
<213> ORGANISM: Artificial Sequence
<220> FEATURE:
<223> OTHER INFORMATION: DNA sequence of the plasmid pEaD8S

<400> SEQUENCE: 49

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tccatggtca agcgaccgc tctgcctctc accgtggacg gtgtcaccta | 480 |
| cgacgtttct gcctggctca accaccatcc cggaggtgcc gacattatcg agaactaccg | 540 |
| aggtcgggat gctaccgacg tcttcatggt tatgcactcc gagaacgccg tgtccaaact | 600 |
| cagacgaatg cccatcatgg aaccttcctc tcccctgact ccaacacctc ccaagccaaa | 660 |
| ctccgacgaa cctcaggagg atttccgaaa gctgcgagac gagctcattg ctgcaggcat | 720 |
| gttcgatgcc tctcccatgt ggtacgctta caagaccctg tcgactctcg gactgggtgt | 780 |
| ccttgccgtg ctgttgatga cccagtggca ctggtacctg gttggtgcta tcgtcctcgg | 840 |
| cattcacttt caacagatgg gatggctctc gcacgacatt tgccatcacc agctgttcaa | 900 |
| ggaccgatcc atcaacaatg ccattggcct gctcttcgga aacgtgcttc agggcttttc | 960 |
| tgtcacttgg tggaaggacc gacacaacgc tcatcactcc gccaccaacg tgcagggtca | 1020 |
| cgatcccgac atcgacaacc tgcctctcct ggcgtggtcc aaggaggacg tcgagcgagc | 1080 |
| tggcccgttt tctcgacgga tgatcaagta ccaacagtat tacttctttt tcatctgtgc | 1140 |
| ccttctgcga ttcatctggt gctttcagtc cattcatact gccacgggtc tcaaggatcg | 1200 |
| aagcaatcag tactatcgaa gacagtacga gaaggagtcc gtcggtctgg cactccactg | 1260 |
| gggtctcaag gccttgttct actatttcta catgcccctcg tttctcaccg gactcatggt | 1320 |
| gttctttgtc tccgagctgc ttggtggctt cggaattgcc atcgttgtct tcatgaacca | 1380 |
| ctaccctctg gagaagattc aggactccgt gtgggatggt catggcttct gtgctggaca | 1440 |
| gattcacgag accatgaacg ttcagcgagg cctcgtcaca gactggtttt tcggtggcct | 1500 |
| caactaccag atcgaacatc acctgtggcc tactcttccc agacacaacc tcaccgctgc | 1560 |
| ctccatcaaa gtggagcagc tgtgcaagaa gcacaacctg ccctaccgat ctcctcccat | 1620 |
| gctcgaaggt gtcggcattc ttatctccta cctgggcacc ttcgctcgaa tggttgccaa | 1680 |
| ggcagacaag gcctaagcgg ccgcatcgga tcccgggccc gtcgactgca gaggcctgca | 1740 |
| tgcaagcttg gcgtaatcat ggtcatagct gtttcctgtg tgaaattgtt atccgctcac | 1800 |
| aattccacac aacatacgag ccggaagcat aaagtgtaaa gcctggggtg cctaatgagt | 1860 |
| gagctaactc acattaattg cgttgcgctc actgcccgct ttccagtcgg gaaacctgtc | 1920 |

```
gtgccagctg cattaatgaa tcggccaacg cgcggggaga ggcggtttgc gtattgggcg    1980
ctcttccgct tcctcgctca ctgactcgct gcgctcggtc gttcggctgc ggcgagcggt    2040
atcagctcac tcaaaggcgg taatacggtt atccacagaa tcaggggata acgcaggaaa    2100
gaacatgtga gcaaaaggcc agcaaaaggc caggaaccgt aaaaaggccg cgttgctggc    2160 gttttttccat aggctccgcc cccctgacga gcatcacaaa aatcgacgct caagtcagag    2220
gtggcgaaac ccgacaggac tataaagata ccaggcgttt ccccctggaa gctccctcgt    2280
gcgctctcct gttccgaccc tgccgcttac cggatacctg tccgcctttc tcccttcggg    2340
aagcgtggcg ctttctcata gctcacgctg taggtatctc agttcggtgt aggtcgttcg    2400
ctccaagctg ggctgtgtgc acgaaccccc cgttcagccc gaccgctgcg ccttatccgg    2460
taactatcgt cttgagtcca acccggtaag acacgactta tcgccactgg cagcagccac    2520
tggtaacagg attagcagag cgaggtatgt aggcggtgct acagagttct tgaagtggtg    2580
gcctaactac ggctacacta agaacagt atttggtatc tgcgctctgc tgaagccagt    2640
taccttcgga aaaagagttg gtagctcttg atccggcaaa caaaccaccg ctggtagcgg    2700
tggttttttt gtttgcaagc agcagattac gcgcagaaaa aaggatctc aagaagatcc    2760 tttgatcttt tctacggggt ctgacgctca gtggaacgaa aactcacgtt aagggatttt    2820
ggtcatgaga ttatcaaaaa ggatcttcac ctagatcctt ttaaattaaa aatgaagttt    2880
taaatcaatc taaagtatat atgagtaaac ttggtctgac agttaccaat gcttaatcag    2940
tgaggcacct atctcagcga tctgtctatt tcgttcatcc atagttgcct gactccccgt    3000
cgtgtagata actacgatac gggagggctt accatctggc cccagtgctg caatgatacc    3060
gcgagaccca cgctcaccgg ctccagattt atcagcaata aaccagccag ccggaagggc    3120
cgagcgcaga agtggtcctg caactttatc cgcctccatc cagtctatta attgttgccg    3180
ggaagctaga gtaagtagtt cgccagttaa tagtttgcgc aacgttgttg ccattgctac    3240
aggcatcgtg gtgtcacgct cgtcgtttgg tatggcttca ttcagctccg gttcccaacg    3300
atcaaggcga gttacatgat cccccatgtt gtgcaaaaaa gcggttagct ccttcggtcc    3360
tccgatcgtt gtcagaagta agttggccgc agtgttatca ctcatggtta tggcagcact    3420
gcataattct cttactgtca tgccatccgt aagatgcttt tctgtgactg gtgagtactc    3480
aaccaagtca ttctgagaat agtgtatgcg gcgaccgagt tgctcttgcc cggcgtcaat    3540
acgggataat accgcgccac atagcagaac tttaaaagtg ctcatcattg gaaaacgttc    3600
ttcggggcga aaactctcaa ggatcttacc gctgttgaga tccagttcga tgtaacccac    3660
tcgtgcaccc aactgatctt cagcatcttt tactttcacc agcgtttctg ggtgagcaaa    3720
aacaggaagg caaaatgccg caaaaaaggg aataagggcg acacggaaat gttgaatact    3780
catactcttc cttttcaat attattgaag catttatcag ggttattgtc tcatgagcgg    3840
atacatattt gaatgtattt agaaaaataa acaaataggg gttccgcgca catttccccg    3900
aaaagtgcca cctgacgtct aagaaaccat tattatcatg acattaacct ataaaaatag    3960
gcgtatcacg aggccctttc gtc                                           3983
```

<210> SEQ ID NO 50
<211> LENGTH: 3668
<212> TYPE: DNA
<213> ORGANISM: Artificial Sequence
<220> FEATURE:
<223> OTHER INFORMATION: pLF121-1
<220> FEATURE:
<221> NAME/KEY: misc_feature
<222> LOCATION: (3616)..(3655)

<223> OTHER INFORMATION: n is a, c, g, or t

<400> SEQUENCE: 50

```
gtacaaagtt ggcattataa gaaagcattg cttatcaatt tgttgcaacg aacaggtcac    60
tatcagtcaa aataaaatca ttatttgcca tccagctgat atccctata gtgagtcgta   120
ttacatggtc atagctgttt cctggcagct ctggcccgtg tctcaaaatc tctgatgtta   180
cattgcacaa gataaaaata tatcatcatg ttagaaaaac tcatcgagca tcaaatgaaa   240
ctgcaattta ttcatatcag gattatcaat accatatttt tgaaaaagcc gtttctgtaa   300
tgaaggagaa aactcaccga ggcagttcca taggatggca agatcctggt atcggtctgc   360
gattccgact cgtccaacat caatacaacc tattaatttc ccctcgtcaa aaataaggtt   420
atcaagtgag aaatcaccat gagtgacgac tgaatccggt gagaatggca aaagcttatg   480
catttctttc cagacttgtt caacaggcca gccattacgc tcgtcatcaa aatcactcgc   540
atcaaccaaa ccgttattca ttcgtgattg cgcctgagcg agacgaaata cgcgatcgct   600
gttaaaagga caattacaaa caggaatcga atgcaaccgg cgcaggaaca ctgccagcgc   660
atcaacaata ttttcacctg aatcaggata ttcttctaat acctggaatg ctgttttccc   720
ggggatcgca gtggtgagta accatgcatc atcaggagta cggataaaat gcttgatggt   780
cggaagaggc ataaattccg tcagccagtt tagtctgacc atctcatctg taacatcatt   840
ggcaacgcta cctttgccat gtttcagaaa caactctggc gcatcgggct tcccatacaa   900
tcgatagatt gtcgcacctg attgcccgac attatcgcga gcccatttat acccatataa   960
atcagcatcc atgttggaat ttaatcgcgg cctcgagcaa gacgtttccc gttgaatatg  1020
gctcatagat ctttttctcca tcactgtatag ggagtggtaa aataactcca tcaatgatag  1080
agtgtcaaca acatgaccaa aatcccttaa cgtgagttac gcgtattaat tgcgttgcgc  1140
tcactgcccg ctttccagtc gggaaacctg tcgtgccagc tgcattaatg aatcggccaa  1200
cgcgcgggga gaggcggttt gcgtattggg cgctcttccg cttcctcgct cactgactcg  1260
ctgcgctcgg tcgttcggct gcggcgagcg gtatcagctc actcaaaggc ggtaatacgg  1320
ttatccacag aatcagggga taacgcagga aagaacatgt gagcaaaagg ccagcaaaag  1380
gccaggaacc gtaaaaaggc cgcgttgctg gcgtttttcc ataggctccg ccccctgac   1440
gagcatcaca aaaatcgacg ctcaagtcag aggtggcgaa acccgacagg actataaaga  1500
taccaggcgt ttccccctgg aagctccctc gtgcgctctc ctgttccgac cctgccgctt  1560
accggatacc tgtccgcctt tctcccttcg ggaagcgtgg cgctttctca atgctcacgc  1620
tgtaggtatc tcagttcggt gtaggtcgtt cgctccaagc tgggctgtgt gcacgaaccc  1680
cccgttcagc ccgaccgctg cgccttatcc ggtaactatc gtcttgagtc aacccggta   1740
agacacgact tatcgccact ggcagcagcc actggtaaca ggattagcag agcgaggtat  1800
gtaggcggtg ctacagagtt cttgaagtgg tggcctaact acggttacac tagaagaaca  1860
gtatttggta tctgcgctct gctgaagcca gttaccttcg aaaaagagt tggtagctct    1920
tgatccggca aacaaccacc gctggtagc ggtggttttt ttgtttgcaa gcagcagatt   1980
acgcgcagaa aaaaggatc tcaagaagat cctttgatct tttctacggg gtctgacgct  2040
cagggaacga cgcgtaccgc tagccaggaa gagtttgtag aaacgcaaaa aggccatccg  2100
tcaggatggc cttctgctta gtttgatgcc tggcagttta tggcgggcgt cctgcccgcc  2160
accctccggg ccgttgcttc acaacgttca aatccgctcc cggcggattt gtcctactca  2220
ggagagcgtt caccgacaaa caacagataa aacgaaaggc ccagtcttcc gactgagcct  2280
```

```
ttcgttttat ttgatgcctg gcagttccct actctcgcgt taacgctagc atggatgttt    2340
tcccagtcac gacgttgtaa aacgacggcc agtcttaagc tcgggcccca ataatgatt     2400 ttattttgac tgatagtgac ctgttcgttg caacaaattg atgagcaatg ctttttata     2460 atgccaactt tgtacaaaaa agttggtttt tttcggtcta aaatggaagc agccaaagaa    2520
ttggtttcca tcgtccaaga ggagctcccc aaggtggact atgcccagct ttggcaggat    2580
gccagcagct gtgaggtcct ttacctctcg gtggcattcg tggcgatcaa gttcatgctg    2640
cgcccactgg acctgaagcg ccaggccacc ttgaagaagc tgttcacagc atacaacttc    2700
ctcatgtcga tctattcctt tggctccttc ctggccatgg cctatgccct atcagtaact    2760
ggcatcctct ccggcgactg tgagacggcg ttcaacaacg atgtgttcag gatcacaact    2820
cagctgttct acctcagcaa gttcgtagag tacatcgact ccttctacct tcccctttatg   2880 gacaagccac tgtcgttcct tcagttcttc catcatttgg gggcccccat tgacatgtgg    2940
ctattctaca aataccgcaa cgaaggagtc tggatctttg tcctgttgaa tgggttcatt    3000
cactggatca tgtacggtta ctattggacg cggctcatca agctgaactt ccccatgccc    3060
aagaacctga tcacctccat gcagatcatc cagttcaatg tcgggttcta catcgtctgg    3120
aagtaccgca atgtgccatg ctaccgccag gatgggatgc gcatgtttgc ctggatcttc    3180
aactactggt atgtcgggac ggtcttgctg ctgttcctca ctttttacgt gcagacgtac    3240
atccggaagc cgaggaagaa ccgagggaag aaggagtagg ccacatggcg cctgcgctgg    3300
aggaaacggt acgctcggat ggtgcactgc acttgcactc cgccgtttct agcctccct    3360 cgctctaacc actgcggcat gcctgcttga ggcgtgacgt tgcctcgtat gatacagttt    3420
acacccttcc cacagcccac ggagctggtg actgtttcca gcgtctgcag atcattgatc    3480
tggtgcaatg tgcacagacc aagcccctct aacgtcttgc ggtgtaccgc tcgacactca    3540
ctgcaagaga cagatggctg agcatgttat agcccttac attctaccct tcgtcccaac    3600
ctgaccgtca cattcnnnnn nnnnnnnnnn nnnnnnnnnn nnnnnnnnnn nnnnnaccca    3660
actttctt                                                             3668
```

<210> SEQ ID NO 51
<211> LENGTH: 3684
<212> TYPE: DNA
<213> ORGANISM: Artificial Sequence
<220> FEATURE:
<223> OTHER INFORMATION: pLF121-2
<220> FEATURE:
<221> NAME/KEY: misc_feature
<222> LOCATION: (3632)..(3671)
<223> OTHER INFORMATION: n is a, c, g, or t

<400> SEQUENCE: 51

```
gtacaaagtt ggcattataa gaaagcattg cttatcaatt tgttgcaacg aacaggtcac    60
tatcagtcaa aataaaatca ttatttgcca tccagctgat atccctata gtgagtcgta     120 ttacatggtc atagctgttt cctggcagct ctggcccgtg tctcaaaatc tctgatgtta    180
cattgcacaa gataaaaata tatcatcatg ttagaaaaac tcatcgagca tcaaatgaaa    240
ctgcaattta ttcatatcag gattatcaat accatatttt tgaaaaagcc gtttctgtaa    300
tgaaggagaa aactcaccga ggcagttcca taggatggca agatcctggt atcggtctgc    360
gattccgact cgtccaacat caatacaacc tattaatttc ccctcgtcaa aaataaggtt    420
atcaagtgag aaatcaccat gagtgacgac tgaatccggt gagaatggca aaagcttatg    480
catttctttc cagacttgtt caacaggcca gccattacgc tcgtcatcaa aatcactcgc    540
```

```
atcaaccaaa ccgttattca ttcgtgattg cgcctgagcg agacgaaata cgcgatcgct    600
gttaaaagga caattacaaa caggaatcga atgcaaccgg cgcaggaaca ctgccagcgc    660
atcaacaata ttttcacctg aatcaggata ttcttctaat acctggaatg ctgttttccc    720
ggggatcgca gtggtgagta accatgcatc atcaggagta cggataaaat gcttgatggt    780
cggaagaggc ataaattccg tcagccagtt tagtctgacc atctcatctg taacatcatt    840
ggcaacgcta cctttgccat gtttcagaaa caactctggc gcatcgggct tcccatacaa    900
tcgatagatt gtcgcacctg attgcccgac attatcgcga gcccatttat acccatataa    960
atcagcatcc atgttggaat ttaatcgcgg cctcgagcaa gacgtttccc gttgaatatg   1020
gctcatagat cttttctcca tcactgatag ggagtggtaa ataactccca tcaatgatag   1080
agtgtcaaca acatgaccaa aatcccttaa cgtgagttac gcgtattaat tgcgttgcgc   1140
tcactgcccg ctttccagtc gggaaacctg tcgtgccagc tgcattaatg aatcggccaa   1200
cgcgcgggga gaggcggttt gcgtattggg cgctcttccg cttcctcgct cactgactcg   1260
ctgcgctcgg tcgttcggct gcggcgagcg gtatcagctc actcaaaggc ggtaatacgg   1320
ttatccacag aatcagggga taacgcagga aagaacatgt gagcaaaagg ccagcaaaag   1380
gccaggaacc gtaaaaaggc cgcgttgctg gcgtttttcc ataggctccg cccccctgac   1440
gagcatcaca aaaatcgacg ctcaagtcag aggtggcgaa acccgacagg actataaaga   1500
taccaggcgt ttccccctgg aagctccctc gtgcgctctc ctgttccgac cctgccgctt   1560
accggatacc tgtccgcctt tctcccttcg ggaagcgtgg cgctttctca atgctcacgc   1620
tgtaggtatc tcagttcggt gtaggtcgtt cgctccaagc tgggctgtgt gcacgaaccc   1680
cccgttcagc ccgaccgctg cgccttatcc ggtaactatc gtcttgagtc aacccggta   1740
agacacgact tatcgccact ggcagcagcc actggtaaca ggattagcag agcgaggtat   1800
gtaggcggtg ctacagagtt cttgaagtgg tggcctaact acggttacac tagaagaaca   1860
gtatttggta tctgcgctct gctgaagcca gttaccttcg gaaaaagagt tggtagctct   1920
tgatccggca aacaaaccac cgctggtagc ggtggttttt tgtttgcaa gcagcagatt    1980
acgcgcagaa aaaaaggatc tcaagaagat cctttgatct tttctacggg gtctgacgct   2040
cagggaacga cgcgtaccgc tagccaggaa gagtttgtag aaacgcaaaa aggccatccg   2100
tcaggatggc cttctgctta gtttgatgcc tggcagttta tggcgggcgt cctgcccgcc   2160
accctccggg ccgttgcttc acaacgttca aatccgctcc cggcggattt gtcctactca   2220
ggagagcgtt caccgacaaa caacagataa aacgaaaggc ccagtcttcc gactgagcct   2280
ttcgttttat ttgatgcctg gcagttccct actctcgcgt taacgctagc atggatgttt   2340
tcccagtcac gacgttgtaa aacgacggcc agtcttaagc tcgggcccca ataatgatt    2400
ttattttgac tgatagtgac ctgttcgttg caacaaattg atgagcaatg cttttttata   2460
atgccaactt tgtacaaaaa agttggattt ttttcggtc taaaatggaa gcagccaaag    2520
aattggtttc catcgtccaa gaggagctcc ccaaggtgga ctatgcccag ctttggcagg   2580
acgccagcag ctgtgaggtc ctttacctct cggtggcatt cgtggcgatc aagttcatgc   2640
tgcgcccact ggacctgaag cgccaggcca ccttgaagaa gctgttcaca gcatacaact   2700
tcctcatgtc gatctattcc tttggctcct tcctggccat ggcctatgcc ctatcagtaa   2760
ctggcatcct ctccggcgac tgtgagacag cgttcaacaa cgatgtgttc aggatcacaa   2820
ctcagctgtt ctacctcagc aagttcgtag agtacatcga ctccttctac cttcccctta   2880
tggacaagcc actgtcgttc cttcagttct tccatcattt gggggctccc attgacatgt   2940
```

```
ggctattcta caaataccgc aacgaaggag tctggatctt tgtcctgttg aatgggttca    3000
ttcactggat catgtacggt tactactgga cgcggctcat caagctgaac ttccccatgc    3060
ccaagaacct gatcacctcc atgcagatca tccagttcaa tgtcgggttc tacatcgtct    3120
ggaagtaccg caatgtgcca tgctaccgcc aggatgggat gcgcatgttt gcctggatct    3180
tcaactactg gtacgtcggg acggtcttgc tgctgttcct caacttttac gtgcagacgt    3240
acatccggaa gccgaggaag aaccaaggga agaaggagta ggccacatgg cgcctgcgct    3300
ggaggaaacg gtacgctcgg atggtgcact gcacttgcac tccgccgctt ctagcctccc    3360
ctcgctctaa cctctgcgac atgcctgctt gaggcgtgac gttgcctcgt gcgatacagt    3420
ttacacccct cccatggccc acggagcagg tgactgtctc cagcgtctgc aattctgatc    3480
attggtctgg tgcaatgtgc gcagaccaag cccctctaac gtcttgcggt gtaccgctcg    3540
acactcactg cacgagacag atggctgagc atgttatagc ccctgacatt ctacccttcg    3600
tccttacctg accgtcacat tcatgcttac cnnnnnnnnn nnnnnnnnnn nnnnnnnnnn    3660
nnnnnnnnnn nacccaactt tctt                                          3684

<210> SEQ ID NO 52
<211> LENGTH: 774
<212> TYPE: DNA
<213> ORGANISM: Euglena anabaena
<220> FEATURE:
<221> NAME/KEY: misc_feature
<223> OTHER INFORMATION: EaD9Elo1 CDS

<400> SEQUENCE: 52
atggaagcag ccaagaaatt ggtttccatc gtccaagagg agctccccaa ggtggactat      60
gcccagcttt ggcaggatgc cagcagctgt gaggtccttt acctctcggt ggcattcgtg     120
gcgatcaagt tcatgctgcg cccactggac ctgaagcgcc aggccacctt gaagaagctg     180
ttcacagcat acaacttcct catgtcgatc tattcctttg ctccttcct ggccatggcc      240 tatgccctat cagtaactgg catcctctcc ggcgactgtg agacggcgtt caacaacgat     300
gtgttcagga tcacaactca gctgttctac ctcagcaagt tcgtagagta catcgactcc     360
ttctaccttc cccttatgga caagccactg tcgttccttc agttcttcca tcatttgggg    420
gcccccattg acatgtggct attctacaaa taccgcaacg aaggagtctg gatctttgtc    480
ctgttgaatg ggttcattca ctggatcatg tacggttact attggacgcg gctcatcaag    540
ctgaacttcc ccatgcccaa gaacctgatc acctccatgc agatcatcca gttcaatgtc    600
gggttctaca tcgtctggaa gtaccgcaat gtgccatgct accgccagga tgggatgcgc    660
atgtttgcct ggatcttcaa ctactggtat gtcgggacgg tcttgctgct gttcctcaac    720
ttttacgtgc agacgtacat ccggaagccg aggaagaacc agggaagaa ggag           774

<210> SEQ ID NO 53
<211> LENGTH: 774
<212> TYPE: DNA
<213> ORGANISM: Euglena anabaena
<220> FEATURE:
<221> NAME/KEY: misc_feature
<223> OTHER INFORMATION: EaD9Elo2 CDS

<400> SEQUENCE: 53
atggaagcag ccaagaaatt ggtttccatc gtccaagagg agctccccaa ggtggactat      60
gcccagcttt ggcaggacgc cagcagctgt gaggtccttt acctctcggt ggcattcgtg     120
gcgatcaagt tcatgctgcg cccactggac ctgaagcgcc aggccacctt gaagaagctg     180
```

-continued

```
ttcacagcat acaacttcct catgtcgatc tattcctttg gctccttcct ggccatggcc    240
tatgccctat cagtaactgg catcctctcc ggcgactgtg agacagcgtt caacaacgat    300
gtgttcagga tcacaactca gctgttctac ctcagcaagt tcgtagagta catcgactcc    360
ttctaccttc cccttatgga caagccactg tcgttccttc agttcttcca tcatttgggg    420
gctcccattg acatgtggct attctacaaa taccgcaacg aaggagtctg gatctttgtc    480
ctgttgaatg ggttcattca ctggatcatg tacggttact actggacgcg gctcatcaag    540
ctgaacttcc ccatgcccaa gaacctgatc acctccatgc agatcatcca gttcaatgtc    600
gggttctaca tcgtctggaa gtaccgcaat gtgccatgct accgccagga tgggatgcgc    660
atgtttgcct ggatcttcaa ctactggtac gtcgggacgg tcttgctgct gttcctcaac    720
ttttacgtgc agacgtacat ccggaagccg aggaagaacc aagggaagaa ggag           774
```

<210> SEQ ID NO 54
<211> LENGTH: 258
<212> TYPE: PRT
<213> ORGANISM: Euglena anabaena
<220> FEATURE:
<221> NAME/KEY: MISC_FEATURE
<223> OTHER INFORMATION: EaD9Elo1 aa sequence

<400> SEQUENCE: 54

```
Met Glu Ala Ala Lys Glu Leu Val Ser Ile Val Gln Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
    130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
    210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Arg Gly Lys
                245                 250                 255

Lys Glu
```

<210> SEQ ID NO 55
<211> LENGTH: 258
<212> TYPE: PRT
<213> ORGANISM: Euglena anabaena
<220> FEATURE:
<221> NAME/KEY: MISC_FEATURE
<223> OTHER INFORMATION: EaD9Elo2 aa sequence

<400> SEQUENCE: 55

```
Met Glu Ala Ala Lys Glu Leu Val Ser Ile Val Gln Glu Glu Leu Pro
1               5                   10                  15

Lys Val Asp Tyr Ala Gln Leu Trp Gln Asp Ala Ser Ser Cys Glu Val
            20                  25                  30

Leu Tyr Leu Ser Val Ala Phe Val Ala Ile Lys Phe Met Leu Arg Pro
        35                  40                  45

Leu Asp Leu Lys Arg Gln Ala Thr Leu Lys Lys Leu Phe Thr Ala Tyr
    50                  55                  60

Asn Phe Leu Met Ser Ile Tyr Ser Phe Gly Ser Phe Leu Ala Met Ala
65                  70                  75                  80

Tyr Ala Leu Ser Val Thr Gly Ile Leu Ser Gly Asp Cys Glu Thr Ala
                85                  90                  95

Phe Asn Asn Asp Val Phe Arg Ile Thr Thr Gln Leu Phe Tyr Leu Ser
            100                 105                 110

Lys Phe Val Glu Tyr Ile Asp Ser Phe Tyr Leu Pro Leu Met Asp Lys
        115                 120                 125

Pro Leu Ser Phe Leu Gln Phe Phe His His Leu Gly Ala Pro Ile Asp
    130                 135                 140

Met Trp Leu Phe Tyr Lys Tyr Arg Asn Glu Gly Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Asn Phe Pro Met Pro Lys Asn Leu Ile Thr Ser
            180                 185                 190

Met Gln Ile Ile Gln Phe Asn Val Gly Phe Tyr Ile Val Trp Lys Tyr
        195                 200                 205

Arg Asn Val Pro Cys Tyr Arg Gln Asp Gly Met Arg Met Phe Ala Trp
    210                 215                 220

Ile Phe Asn Tyr Trp Tyr Val Gly Thr Val Leu Leu Leu Phe Leu Asn
225                 230                 235                 240

Phe Tyr Val Gln Thr Tyr Ile Arg Lys Pro Arg Lys Asn Gln Gly Lys
                245                 250                 255

Lys Glu
```

<210> SEQ ID NO 56
<211> LENGTH: 33
<212> TYPE: DNA
<213> ORGANISM: Artificial Sequence
<220> FEATURE:
<223> OTHER INFORMATION: oligonucleotide oEAd9el1-1

<400> SEQUENCE: 56
agcggccgca ccatggaagc agccaaagaa ttg                                33

<210> SEQ ID NO 57
<211> LENGTH: 26
<212> TYPE: DNA
<213> ORGANISM: Artificial Sequence
<220> FEATURE:

<223> OTHER INFORMATION: oligonucleotide oEAd9el1-2

<400> SEQUENCE: 57
tgcggccgct actccttctt ccctcg 26

<210> SEQ ID NO 58
<211> LENGTH: 4310
<212> TYPE: DNA
<213> ORGANISM: Artificial Sequence
<220> FEATURE:
<223> OTHER INFORMATION: pKR1137

<400> SEQUENCE: 58

```
aattccagca cactggcggc cgttactagt ggatccgagc tcggtaccaa gcttgatgca    60
tagcttgagt attctaacgc gtcacctaaa tagcttggcg taatcatggt catagctgtt   120
tcctgtgtga attgttatc cgctcacaat tccacacaac atacgagccg aagcataaa    180
gtgtaaagcc tggggtgcct aatgagtgag ctaactcaca ttaattgcgt tgcgctcact   240
gcccgctttc cagtcgggaa acctgtcgtg ccagctgcat taatgaatcg gccaacgcgc   300
ggggagaggc ggtttgcgta ttgggcgctc ttccgcttcc tcgctcactg actcgctgcg   360
ctcggtcgtt cggctgcggc gagcggtatc agctcactca aaggcggtaa tacggttatc   420
cacagaatca ggggataacg caggaaagaa catgtgagca aaaggccagc aaaagcccag   480
gaaccgtaaa aaggccgcgt tgctggcgtt ttccatagg ctccgccccc ctgacgagca   540
tcacaaaaat cgacgctcaa gtcagaggtg gcgaaacccg acaggactat aaagatacca   600
ggcgtttccc cctggaagct ccctcgtgcg ctctcctgtt ccgaccctgc cgcttaccgg   660
atacctgtcc gcctttctcc cttcgggaag cgtggcgctt tctcatagct cacgctgtag   720
gtatctcagt tcggtgtagg tcgttcgctc caagctgggc tgtgtgcacg aaccccccgt   780
tcagcccgac cgctgcgcct tatccggtaa ctatcgtctt gagtccaacc cggtaagaca   840
cgacttatcg ccactggcag cagccactgg taacaggatt agcagagcga ggtatgtagg   900
cggtgctaca gagttcttga agtggtggcc taactacggc tacactagaa ggacagtatt   960
tggtatctgc gctctgctga agccagttac cttcggaaaa agagttggta gctcttgatc  1020
cggcaaacaa accaccgctg gtagcggtgg tttttttgtt tgcaagcagc agattacgcg  1080
cagaaaaaaa ggatctcaag aagatccttt gatcttttct acggggtctg acgctcagtg  1140
gaacgaaaac tcacgttaag ggattttggt catgagatta tcaaaaagga tcttcaccta  1200
gatccttta aattaaaaat gaagttttag cacgtgtcag tcctgctcct cggccacgaa  1260
gtgcacgcag ttgccggccg gtcgcgcag ggcgaactcc cgcccccacg gctgctcgcc  1320
gatctcggtc atggccggcc cggaggcgtc cggaagttc gtggacacga cctccgacca  1380
ctcggcgtac agctcgtcca ggccgcgcac ccacacccag gccagggtgt tgtccggcac  1440
cacctggtcc tggaccgcgc tgatgaacag ggtcacgtcg tcccgggacca caccggcgaa  1500
gtcgtcctcc acgaagtccc gggagaaccc gagccggtcg gtccagaact cgaccgctcc  1560
ggcgacgtcg cgcgcggtga gcaccggaac ggcactggtc aacttggcca tggtggccct  1620
cctcacgtgc tattattgaa gcatttatca gggttattgt ctcatgagcg gatacatatt  1680
tgaatgtatt tagaaaaata aacaaatagg ggttccgcgc acatttcccc gaaaagtgcc  1740
acctgtatgc ggtgtgaaat accgcacaga tgcgtaagga gaaataccg catcaggaaa  1800
ttgtaagcgt taataattca gaagaactcg tcaagaaggc gatagaaggc gatgcgctgc  1860
gaatcgggag cggcgatacc gtaaagcacg aggaagcggt cagcccattc gccgccaagc  1920
```

```
tcttcagcaa tatcacgggt agccaacgct atgtcctgat agcggtccgc cacacccagc    1980
cggccacagt cgatgaatcc agaaaagcgg ccatttccca ccatgatatt cggcaagcag    2040
gcatcgccat gggtcacgac gagatcctcg ccgtcgggca tgctcgcctt gagcctggcg    2100
aacagttcgg ctggcgcgag cccctgatgc tcttcgtcca gatcatcctg atcgacaaga    2160
ccggcttcca tccgagtacg tgctcgctcg atgcgatgtt tcgcttggtg gtcgaatggg    2220
caggtagccg gatcaagcgt atgcagccgc cgcattgcat cagccatgat ggatactttc    2280
tcggcaggag caaggtgaga tgacaggaga tcctgccccg gcacttcgcc aatagcagc    2340 cagtcccttc ccgcttcagt gacaacgtcg agcacagctg cgcaaggaac gcccgtcgtg    2400
gccagccacg atagccgcgc tgcctcgtct tgcagttcat tcagggcacc ggacaggtcg    2460
gtcttgacaa aaagaaccgg gcgcccctgc gctgacagcc ggaacacggc ggcatcagag    2520
cagccgattg tctgttgtgc ccagtcatag ccgaatagcc tctccaccca gcggccgga    2580 gaacctgcgt gcaatccatc ttgttcaatc atgcgaaacg atcctcatcc tgtctcttga    2640
tcagagcttg atccctgcg ccatcagatc cttggcggcg agaaagccat ccagtttact    2700
ttgcagggct tcccaacctt accagagggc gccccagctg gcaattccgg ttcgcttgct    2760
gtccataaaa ccgcccagtc tagctatcgc catgtaagcc cactgcaagc tacctgcttt    2820
ctctttgcgc ttgcgttttc ccttgtccag atagcccagt agctgacatt catccggggt    2880
cagcaccgtt tctgcggact ggcttttcta cgtgaaaagga tctaggtgaa atccttttt    2940 gataatctca tgcctgacat ttatattccc cagaacatca ggttaatggc gttttttgatg    3000 tcattttcgc ggtggctgag atcagccact tcttccccga taacggagac cggcacactg    3060
gccatatcgg tggtcatcat gcgccagctt tcatccccga tatgcaccac cgggtaaagt    3120
tcacgggaga ctttatctga cagcagacgt gcactggcca gggggatcac catccgtcgc    3180
cccggcgtgt caataatatc actctgtaca tccacaaaca gacgataacg gctctctctt    3240
ttataggtgt aaaccttaaa ctgccgtacg tataggctgc gcaactgttg ggaagggcga    3300
tcggtgcggg cctcttcgct attacgccag ctggcgaaag gggatgtgc tgcaaggcga    3360 ttaagttggg taacgccagg gttttcccag tcacgacgtt gtaaaacgac ggccagtgaa    3420
ttgtaatacg actcactata gggcgaattg ggccctctag atgcatgctc gagcggccgc    3480
cagtgtgatg gatatctgca gaattcagga gcggccgcac catggaagca gccaaagaat    3540
tggtttccat cgtccaagag gagctcccca aggtggacta tgcccagctt tggcaggatg    3600
ccagcagctg tgaggtcctt tacctctcgg tggcattcgt ggcgatcaag ttcatgctgc    3660
gcccactgga cctgaagcgc caggccacct tgaagaagct gttcacagca tacaacttcc    3720
tcatgtcgat ctattccttt ggctccttcc tggccatggc ctatgcccta tcagtaactg    3780
gcatcctctc cggcgactgt gagacggcgt tcaacaacga tgtgttcagg atcacaactc    3840
agctgttcta cctcagcaag ttcgtagagt acatcgactc cttctacctt cccccttatgg    3900 acaagccact gtcgttcctt cagttcttcc atcatttggg ggcccccatt gacatgtggc    3960
tattctacaa ataccgcaac gaaggagtct ggatctttgt cctgttgaat gggttcattc    4020
actggatcat gtacggttac tattggacgc ggctcatcaa gctgaacttc cccatgccca    4080
agaacctgat cacctccatg cagatcatcc agttcaatgt cgggttctac atcgtctgga    4140
agtaccgcaa tgtgccatgc taccgccagg atgggatgcg catgtttgcc tggatcttca    4200
actactggta tgtcgggacg gtcttgctgc tgttcctcaa cttttacgtg cagacgtaca    4260
tccggaagcc gaggaagaac cgagggaaga aggagtagcg gccgcacctg    4310
```

<210> SEQ ID NO 59
<211> LENGTH: 7872
<212> TYPE: DNA
<213> ORGANISM: Artificial Sequence
<220> FEATURE:
<223> OTHER INFORMATION: pKR1140

<400> SEQUENCE: 59

| | | | | | |
|---|---|---|---|---|---|
| ggccgcaagt | atgaactaaa | atgcatgtag | gtgtaagagc | tcatggagag | catggaatat | 60 |
| tgtatccgac | catgtaacag | tataataact | gagctccatc | tcacttcttc | tatgaataaa | 120 |
| caaaggatgt | tatgatatat | taacactcta | tctatgcacc | ttattgttct | atgataaatt | 180 |
| tcctcttatt | attataaatc | atctgaatcg | tgacggctta | tggaatgctt | caaatagtac | 240 |
| aaaaacaaat | gtgtactata | agactttcta | aacaattcta | accttagcat | tgtgaacgag | 300 |
| acataagtgt | taagaagaca | taacaattat | aatggaagaa | gtttgtctcc | atttatatat | 360 |
| tatatattac | ccacttatgt | attatattag | gatgttaagg | agacataaca | attataaaga | 420 |
| gagaagtttg | tatccattta | tatattatat | actacccatt | tatatattat | acttatccac | 480 |
| ttatttaatg | tctttataag | gtttgatcca | tgatatttct | aatattttag | ttgatatgta | 540 |
| tatgaaaggg | tactatttga | actctcttac | tctgtataaa | ggttggatca | tccttaaagt | 600 |
| gggtctattt | aattttattg | cttcttacag | ataaaaaaaa | aattatgagt | tggtttgata | 660 |
| aaatattgaa | ggatttaaaa | taataataaa | taacatataa | tatatgtata | taaatttatt | 720 |
| ataatataac | atttatctat | aaaaaagtaa | atattgtcat | aaatctatac | aatcgtttag | 780 |
| ccttgctgga | cgaatctcaa | ttatttaaac | gagagtaaac | atatttgact | ttttggttat | 840 |
| ttaacaaatt | attatttaac | actatatgaa | attttttttt | ttatcagcaa | agaataaaat | 900 |
| taaattaaga | aggacaatgg | tgtcccaatc | cttatacaac | caacttccac | aagaaagtca | 960 |
| agtcagagac | aacaaaaaaa | caagcaaagg | aaattttta | atttgagttg | tcttgtttgc | 1020 |
| tgcataattt | atgcagtaaa | acactacaca | taacccttt | agcagtagag | caatggttga | 1080 |
| ccgtgtgctt | agcttctttt | atttattttt | tttatcagca | aagaataaat | aaaataaaat | 1140 |
| gagacacttc | agggatgttt | caacaagctt | ggcgcgccgt | tctatagtgt | cacctaaatc | 1200 |
| gtatgtgtat | gatacataag | gttatgtatt | aattgtagcc | gcgttctaac | gacaatatgt | 1260 |
| ccatatggtg | cactctcagt | acaatctgct | ctgatgccgc | atagttaagc | cagccccgac | 1320 |
| acccgccaac | acccgctgac | gcgccctgac | gggcttgtct | gctcccggca | tccgcttaca | 1380 |
| gacaagctgt | gaccgtctcc | gggagctgca | tgtgtcagag | gttttcaccg | tcatcaccga | 1440 |
| aacgcgcgag | acgaaagggc | ctcgtgatac | gcctattttt | ataggttaat | gtcatgacca | 1500 |
| aaatccctta | acgtgagttt | tcgttccact | gagcgtcaga | ccccgtagaa | aagatcaaag | 1560 |
| gatcttcttg | agatcctttt | tttctgcgcg | taatctgctg | cttgcaaaca | aaaaaaccac | 1620 |
| cgctaccagc | ggtggtttgt | ttgccggatc | aagagctacc | aactcttttt | ccgaaggtaa | 1680 |
| ctggcttcag | cagagcgcag | ataccaaata | ctgtccttct | agtgtagccg | tagttaggcc | 1740 |
| accacttcaa | gaactctgta | gcaccgccta | catacctcgc | tctgctaatc | ctgttaccag | 1800 |
| tggctgctgc | cagtggcgat | aagtcgtgtc | ttaccgggtt | ggactcaaga | cgatagttac | 1860 |
| cggataaggc | gcagcggtcg | ggctgaacgg | ggggttcgtg | cacacagccc | agcttggagc | 1920 |
| gaacgaccta | caccgaactg | agatacctac | agcgtgagca | ttgagaaagc | gccacgcttc | 1980 |
| ccgaagggag | aaaggcggac | aggtatccgg | taagcggcag | ggtcggaaca | ggagagcgca | 2040 |
| cgagggagct | tccaggggga | aacgcctggt | atctttatag | tcctgtcggg | tttcgccacc | 2100 |

```
tctgacttga gcgtcgattt ttgtgatgct cgtcagggg gcggagccta tggaaaaacg    2160
ccagcaacgc ggccttttta cggttcctgg ccttttgctg gccttttgct cacatgttct    2220
ttcctgcgtt atccctgat tctgtggata accgtattac cgcctttgag tgagctgata     2280
ccgctcgccg cagccgaacg accgagcgca gcgagtcagt gagcgaggaa gcggaagagc    2340
gcccaatacg caaaccgcct ctccccgcgc gttggccgat tcattaatgc aggttgatcg    2400
attcgacatc gatctagtaa catagatgac accgcgcgcg ataatttatc ctagtttgcg    2460
cgctatattt tgttttctat cgcgtattaa atgtataatt gcgggactct aatcataaaa    2520
acccatctca taaataacgt catgcattac atgttaatta ttacatgctt aacgtaattc    2580
aacagaaatt atatgataat catcgcaaga ccggcaacag gattcaatct taagaaactt    2640
tattgccaaa tgtttgaacg atctgcttcg acgcactcct tctttaggta cctcactatt    2700
cctttgccct cggacgagtg ctggggcgtc ggtttccact atcggcgagt acttctacac    2760
agccatcggt ccagacggcc gcgcttctgc gggcgatttg tgtacgcccg acagtcccgg    2820
ctccggatcg gacgattgcg tcgcatcgac cctgcgccca agctgcatca tcgaaattgc    2880
cgtcaaccaa gctctgatag agttggtcaa gaccaatgcg gagcatatac gcccggagcc    2940
gcggcgatcc tgcaagctcc ggatgcctcc gctcgaagta gcgcgtctgc tgctccatac    3000
aagccaacca cggcctccag aagaagatgt tggcgacctc gtattgggaa tccccgaaca    3060
tcgcctcgct ccagtcaatg accgctgtta tgcggccatt gtccgtcagg acattgttgg    3120
agccgaaatc cgcgtgcacg aggtgccgga cttcggggca gtcctcggcc caaagcatca    3180
gctcatcgag agcctgcgcg acggacgcac tgacggtgtc gtccatcaca gtttgccagt    3240
gatacacatg gggatcagca atcgcgcata tgaaatcacg ccatgtagtg tattgaccga    3300
ttccttgcgg tccgaatggg ccgaacccgc tcgtctggct aagatcggcc gcagcgatcg    3360
catccatggc ctccgcgacc ggctgcagaa cagcgggcag ttcggtttca ggcaggtctt    3420
gcaacgtgac accctgtgca cggcgggaga tgcaataggt caggctctcg ctgaattccc    3480
caatgtcaag cacttccgga atcgggagcg cggccgatgc aaagtgccga taaacataac    3540
gatctttgta gaaaccatcg gcgcagctat ttacccgcag gacatatcca cgccctccta    3600
catcgaagct gaaagcacga gattcttcgc cctccgagag ctgcatcagg tcggagacgc    3660
tgtcgaactt ttcgatcaga aacttctcga cagacgtcgc ggtgagttca ggcttttttca   3720
tggtttaata agaagagaaa agagttcttt tgttatggct gaagtaatag agaaatgagc    3780
tcgagcgtgt cctctccaaa tgaaatgaac ttccttatat agaggaaggg tcttgcgaag    3840
gatagtggga ttgtgcgtca tcccttacgt cagtggagat gtcacatcaa tccacttgct    3900
ttgaagacgt ggttggaacg tcttcttttt ccacgatgct cctcgtgggt ggggtccat    3960
ctttgggacc actgtcggca gaggcatctt gaatgatagc cttttcttta tcgcaatgat    4020
ggcatttgta ggagccacct tccttttcta ctgtcctttc gatgaagtga cagatagctg    4080
ggcaatggaa tccgaggagg tttcccgaaa ttatcctttg ttgaaaagtc tcaatagccc    4140
tttggtcttc tgagactgta tctttgacat ttttggagta gaccagagtg tcgtgctcca    4200
ccatgttgac gaagattttc ttcttgtcat tgagtcgtaa aagactctgt atgaactgtt    4260
cgccagtctt cacggcgagt tctgttagat cctcgatttg aatcttagac tccatgcatg    4320
gccttagatt cagtaggaac tacctttta gagactccaa tctctattac ttgccttggt    4380
ttatgaagca agccttgaat cgtccatact ggaatagtac ttctgatctt gagaaatatg    4440
tctttctctg tgttcttgat gcaattagtc ctgaatcttt tgactgcatc tttaaccttc    4500
```

```
ttgggaaggt atttgatctc ctggagattg ttactcgggt agatcgtctt gatgagacct    4560
gctgcgtagg cctctctaac catctgtggg tcagcattct ttctgaaatt gaagaggcta    4620
accttctcat tatcagtggt gaacatagtg tcgtcacctt caccttcgaa cttccttcct    4680
agatcgtaaa gatagaggaa atcgtccatt gtaatctccg gggcaaagga gatctctttt    4740
ggggctggat cactgctggg cctttttggtt cctagcgtga gccagtgggc tttttgcttt    4800
ggtgggcttg ttagggcctt agcaaagctc ttgggcttga gttgagcttc tcctttgggg    4860
atgaagttca acctgtctgt ttgctgactt gttgtgtacg cgtcagctgc tgctcttgcc    4920
tctgtaatag tggcaaattt cttgtgtgca actccgggaa cgccgtttgt tgccgccttt    4980
gtacaacccc agtcatcgta tataccggca tgtggaccgt tatacacaac gtagtagttg    5040
atatgagggt gttgaatacc cgattctgct ctgagaggag caactgtgct gttaagctca    5100 gattttttgtg ggattggaat tggatcgatc tcgatcccgc gaaattaata cgactcacta    5160
tagggagacc acaacggttt ccctctagaa ataattttgt ttaactttaa gaaggagata    5220
tacccatgga aaagcctgaa ctcaccgcga cgtctgtcga agtttctg atcgaaaagt     5280 tcgacagcgt ctccgacctg atgcagctct cggagggcga agaatctcgt gctttcagct    5340
tcgatgtagg agggcgtgga tatgtcctgc gggtaaatag ctgcgccgat ggtttctaca    5400
aagatcgtta tgtttatcgg cactttgcat cggccgcgct cccgattccg gaagtgcttg    5460
acattgggga attcagcgag agcctgacct attgcatctc ccgccgtgca cagggtgtca    5520
cgttgcaaga cctgcctgaa accgaactgc ccgctgttct gcagccggtc gcggaggcta    5580
tggatgcgat cgctgcggcc gatcttagcc agacgagcgg gttcggccca ttcggaccgc    5640
aaggaatcgg tcaatacact acatggcgtg atttcatatg cgcgattgct gatccccatg    5700
tgtatcactg gcaaactgtg atggacgaca ccgtcagtgc gtccgtcgcg caggctctcg    5760
atgagctgat gctttgggcc gaggactgcc ccgaagtccg gcaccgtgtg cacgcggatt    5820
tcggctccaa caatgtcctg acggacaatg gccgcataac agcggtcatt gactggagcg    5880
aggcgatgtt cggggattcc caatacgagg tcgccaacat cttcttctgg aggccgtggt    5940
tggcttgtat ggagcagcag acgcgctact cgagcggag gcatccggag cttgcaggat    6000
cgccgcggct ccgggcgtat atgctccgca ttggtcttga ccaactctat cagagcttgg    6060
ttgacggcaa tttcgatgat gcagcttggg cgcaggtcg atgcgacgca atcgtccgat    6120
ccggagccgg gactgtcggg cgtacacaaa tcgcccgcag aagcgcggcc gtctggaccg    6180
atggctgtgt agaagtactc gccgatagtg gaaaccgacg ccccagcact cgtccgaggg    6240
caaaggaata gtgaggtaca gcttggatcg atccggctgc taacaaagcc cgaaaggaag    6300
ctgagttggc tgctgccacc gctgagcaat aactagcata accccttggg gcctctaaac    6360
gggtcttgag gggttttttg ctgaaaggag gaactatatc cggatgatcg ggcgcgccgt    6420
cgacggatcc gtacgagatc cggcggcca gatcctgcag gagatccaag cttttgatcc    6480
atgcccttca tttgccgctt attaattaat ttggtaacag tccgtactaa tcagttactt    6540
atccttcccc catcataatt aatcttggta gtctcgaatg ccacaacact gactagtctc    6600
ttggatcata agaaaaagcc aaggaacaaa agaagacaaa acacaatgag agtatccttt    6660
gcatagcaat gtctaagttc ataaaattca acaaaaacg caatcacaca cagtggacat    6720
cacttatcca ctagctgatc aggatcgccg cgtcaagaaa aaaaaactgg accccaaaag    6780
ccatgcacaa caacacgtac tcacaaaggt gtcaatcgag cagcccaaaa cattcaccaa    6840
ctcaacccat catgagccct cacatttgtt gtttctaacc caacctcaaa ctcgtattct    6900
```

```
cttccgccac ctcattttg tttatttcaa cacccgtcaa actgcatgcc accccgtggc      6960
caaatgtcca tgcatgttaa caagacctat gactataaat agctgcaatc tcggcccagg      7020
ttttcatcat caagaaccag ttcaatatcc tagtacaccg tattaaagaa tttaagatat      7080
actgcggccg caccatggaa gcagccaaag aattggtttc catcgtccaa gaggagctcc      7140
ccaaggtgga ctatgcccag ctttggcagg atgccagcag ctgtgaggtc ctttacctct      7200
cggtggcatt cgtggcgatc aagttcatgc tgcgcccact ggacctgaag cgccaggcca      7260
ccttgaagaa gctgttcaca gcatacaact tcctcatgtc gatctattcc tttggctcct      7320
tcctggccat ggcctatgcc ctatcagtaa ctggcatcct ctccggcgac tgtgagacgg      7380
cgttcaacaa cgatgtgttc aggatcacaa ctcagctgtt ctacctcagc aagttcgtag      7440
agtacatcga ctccttctac cttccccta tggacaagcc actgtcgttc cttcagttct      7500
tccatcattt gggggccccc attgacatgt ggctattcta caaataccgc aacgaaggag      7560
tctggatctt tgtcctgttg aatgggttca ttcactggat catgtacggt tactattgga      7620
cgcggctcat caagctgaac ttccccatgc caagaacct gatcacctcc atgcagatca      7680
tccagttcaa tgtcgggttc tacatcgtct ggaagtaccg caatgtgcca tgctaccgcc      7740
aggatgggat gcgcatgttt gcctggatct tcaactactg gtatgtcggg acggtcttgc      7800
tgctgttcct caacttttac gtgcagacgt acatccggaa gccgaggaag aaccgaggga      7860
agaaggagta gc                                                         7872
```

<210> SEQ ID NO 60  
<211> LENGTH: 11706  
<212> TYPE: DNA  
<213> ORGANISM: Artificial Sequence  
<220> FEATURE:  
<223> OTHER INFORMATION: pKR1150  
<220> FEATURE:  
<221> NAME/KEY: misc_feature  
<222> LOCATION: (10531)..(10531)  
<223> OTHER INFORMATION: n is a, c, g, or t

<400> SEQUENCE: 60

```
gtacgagatc cggccggcca gatcctgcag gagatccaag cttttgatcc atgcccttca        60
tttgccgctt attaattaat ttggtaacag tccgtactaa tcagttactt atccttcccc       120
catcataatt aatcttggta gtctcgaatg ccacaacact gactagtctc ttggatcata       180
agaaaagcc aaggaacaaa agaagacaaa acacaatgag agtatccttt gcatagcaat        240
gtctaagttc ataaaattca aacaaaaacg caatcacaca cagtggacat cacttatcca       300
ctagctgatc aggatcgccg cgtcaagaaa aaaaactgg accccaaaag ccatgcacaa        360
caacacgtac tcacaaaggt gtcaatcgag cagcccaaaa cattcaccaa ctcaacccat       420
catgagccct cacatttgtt gtttctaacc caacctcaaa ctcgtattct cttccgccac       480
ctcatttttg tttatttcaa cacccgtcaa actgcatgcc accccgtggc caaatgtcca       540
tgcatgttaa caagacctat gactataaat agctgcaatc tcggcccagg ttttcatcat       600
caagaaccag ttcaatatcc tagtacaccg tattaaagaa tttaagatat actgcggccg       660
caccatggaa gcagccaaag aattggtttc catcgtccaa gaggagctcc ccaaggtgga       720
ctatgcccag ctttggcagg atgccagcag ctgtgaggtc ctttacctct cggtggcatt       780
cgtggcgatc aagttcatgc tgcgcccact ggacctgaag cgccaggcca ccttgaagaa       840
gctgttcaca gcatacaact tcctcatgtc gatctattcc tttggctcct tcctggccat       900
ggcctatgcc ctatcagtaa ctggcatcct ctccggcgac tgtgagacgg cgttcaacaa       960
```

```
cgatgtgttc aggatcacaa ctcagctgtt ctacctcagc aagttcgtag agtacatcga    1020
ctccttctac cttccccta tggacaagcc actgtcgttc cttcagttct tccatcattt     1080
gggggccccc attgacatgt ggctattcta caaataccgc aacgaaggag tctggatctt    1140
tgtcctgttg aatgggttca ttcactggat catgtacggt tactattgga cgcggctcat    1200
caagctgaac ttccccatgc ccaagaacct gatcacctcc atgcagatca tccagttcaa    1260
tgtcgggttc tacatcgtct ggaagtaccg caatgtgcca tgctaccgcc aggatgggat    1320
gcgcatgttt gcctggatct tcaactactg gtatgtcggg acggtcttgc tgctgttcct    1380
caacttttac gtgcagacgt acatccggaa gccgaggaag aaccgaggga agaaggagta    1440
gcggccgcaa gtatgaacta aaatgcatgt aggtgtaaga gctcatggag agcatggaat    1500
attgtatccg accatgtaac agtataataa ctgagctcca tctcacttct tctatgaata    1560
aacaaaggat gttatgatat attaacactc tatctatgca ccttattgtt ctatgataaa    1620
tttcctctta ttattataaa tcatctgaat cgtgacggct tatggaatgc ttcaaatagt    1680 acaaaacaa atgtgtacta aagactttc taaacaattc taaccttagc attgtgaacg      1740
agacataagt gttaagaaga cataacaatt ataatggaag aagtttgtct ccatttatat    1800
attatatatt acccacttat gtattatatt aggatgttaa ggagacataa caattataaa    1860
gagagaagtt tgtatccatt tatatattat atactaccca tttatatatt atacttatcc    1920
acttatttaa tgtctttata aggtttgatc catgatattt ctaatatttt agttgatatg    1980
tatatgaaag ggtactattt gaactctctt actctgtata aaggttggat catccttaaa    2040
gtgggtctat ttaattttat tgcttcttac agataaaaaa aaaattatga gttggtttga    2100
taaaatattg aaggatttaa aataataata aataacatat aatatatgta tataaattta    2160
ttataatata acatttatct ataaaaaagt aaatattgtc ataaatctat acaatcgttt    2220
agccttgctg gacgaatctc aattatttaa acgagagtaa acatatttga cttttttggtt   2280 atttaacaaa ttattattta acactatatg aaatttttt ttttatcagc aaagaataaa     2340
attaaattaa gaaggacaat ggtgtcccaa tccttataca accaacttcc acaagaaagt    2400
caagtcagag acaacaaaaa aacaagcaaa ggaaattttt taatttgagt tgtcttgttt    2460
gctgcataat ttatgcagta aaacactaca cataaccctt ttagcagtag agcaatggtt    2520
gaccgtgtgc ttagcttctt ttatttattt tttttatcag caaagaataa ataaaataaa    2580
atgagacact tcagggatgt ttcaacaagc ttggcgcgcc gttctatagt gtcacctaaa    2640
tcgtatgtgt atgatacata aggttatgta ttaattgtag ccgcgttcta acgacaatat    2700
gtccatatgg tgcactctca gtacaatctg ctctgatgcc gcatagttaa gccagccccg    2760
acacccgcca cacccgctg acgcgccctg acgggcttgt ctgctcccgg catccgctta     2820
cagacaagct gtgaccgtct ccgggagctg catgtgtcag aggttttcac cgtcatcacc    2880
gaaacgcgcg agacgaaagg gcctcgtgat acgcctattt ttataggtta atgtcatgac    2940
caaaatccct taacgtgagt tttcgttcca ctgagcgtca gaccccgtag aaaagatcaa    3000
aggatcttct tgagatcctt ttttctgcg cgtaatctgc tgcttgcaaa caaaaaaacc     3060
accgctacca gcggtggttt gtttgccgga tcaagagcta ccaactcttt ttccgaaggt    3120
aactggcttc agcagagcgc agataccaaa tactgtcctt ctagtgtagc cgtagttagg    3180
ccaccacttc aagaactctg tagcaccgcc tacatacctc gctctgctaa tcctgttacc    3240
agtggctgct gccagtggcg ataagtcgtg tcttaccggg ttggactcaa gacgatagtt    3300
accggataag gcgcagcggt cgggctgaac ggggggttcg tgcacacagc ccagcttgga    3360
```

```
gcgaacgacc tacaccgaac tgagatacct acagcgtgag cattgagaaa gcgccacgct    3420
tcccgaaggg agaaaggcgg acaggtatcc ggtaagcggc agggtcggaa caggagagcg    3480
cacgagggag cttccagggg gaaacgcctg gtatctttat agtcctgtcg ggtttcgcca    3540
cctctgactt gagcgtcgat ttttgtgatg ctcgtcaggg gggcggagcc tatggaaaaa    3600
cgccagcaac gcggccttt tacggttcct ggccttttgc tggccttttg ctcacatgtt    3660
ctttcctgcg ttatccctg attctgtgga taaccgtatt accgcctttg agtgagctga    3720
taccgctcgc cgcagccgaa cgaccgagcg cagcgagtca gtgagcgagg aagcggaaga    3780
gcgcccaata cgcaaaccgc ctctccccgc gcgttggccg attcattaat gcaggttgat    3840
cgattcgaca tcgatctagt aacatagatg acaccgcgcg cgataattta tcctagtttg    3900
cgcgctatat tttgttttct atcgcgtatt aaatgtataa ttgcgggact ctaatcataa    3960
aaacccatct cataaataac gtcatgcatt acatgttaat tattacatgc ttaacgtaat    4020
tcaacagaaa ttatatgata atcatcgcaa gaccggcaac aggattcaat cttaagaaac    4080
tttattgcca aatgtttgaa cgatctgctt cgacgcactc cttctttagg tacctcacta    4140
ttcctttgcc ctcggacgag tgctgggcg tcggtttcca ctatcggcga gtacttctac    4200
acagccatcg gtccagacgg ccgcgcttct gcgggcgatt tgtgtacgcc cgacagtccc    4260
ggctccggat cggacgattg cgtcgcatcg accctgcgcc caagctgcat catcgaaatt    4320
gccgtcaacc aagctctgat agagttggtc aagaccaatg cggagcatat acgcccggag    4380
ccgcggcgat cctgcaagct ccggatgcct ccgctcgaag tagcgcgtct gctgctccat    4440
acaagccaac cacggcctcc agaagaagat gttggcgacc tcgtattggg aatccccgaa    4500
catcgcctcg ctccagtcaa tgaccgctgt tatgcggcca ttgtccgtca ggacattgtt    4560
ggagccgaaa tccgcgtgca cgaggtgccg gacttcgggg cagtcctcgg cccaaagcat    4620
cagctcatcg agagcctgcg cgacggacgc actgacggtg tcgtccatca cagtttgcca    4680
gtgatacaca tggggatcag caatcgcgca tatgaaatca cgccatgtag tgtattgacc    4740
gattccttgc ggtccgaatg ggccgaaccc gctcgtctgg ctaagatcgg ccgcagcgat    4800
cgcatccatg gcctccgcga ccggctgcag aacagcgggc agttcggttt caggcaggtc    4860
ttgcaacgtg acaccctgtg cacggcggga gatgcaatag gtcaggctct cgctgaattc    4920
cccaatgtca agcacttccg gaatcgggag cgcggccgat gcaaagtgcc gataaacata    4980
acgatctttg tagaaaccat cggcgcagct atttacccgc aggacatatc cacgccctcc    5040
tacatcgaag ctgaaagcac gagattcttc gccctccgag agctgcatca ggtcggagac    5100
gctgtcgaac ttttcgatca gaaacttctc gacagacgtc gcggtgagtt caggcttttt    5160
catggtttaa taagaagaga aaagagttct tttgttatgg ctgaagtaat agagaaatga    5220
gctcgagcgt gtcctctcca aatgaaatga acttccttat atagaggaag ggtcttgcga    5280
aggatagtgg gattgtgcgt catcccttac gtcagtggaa atgtcacatc aatccacttg    5340
ctttgaagac gtggttggaa cgtcttcttt ttccacgatg ctcctcgtgg gtggggtcc    5400 atctttggga ccactgtcgg cagaggcatc ttgaatgata gccttccctt tatcgcaatg    5460
atggcatttg taggagccac cttccttttc tactgtcctt tcgatgaagt gacagatagc    5520
tgggcaatgg aatccgagga ggtttcccga aattatcctt tgttgaaaag tctcaatagc    5580
cctttggtct tctgagactg tatctttgac attttttggag tagaccagag tgtcgtgctc    5640
caccatgttg acgaagattt tcttcttgtc attgagtcgt aaaagactct gtatgaactg    5700
ttcgccagtc ttcacggcga gttctgttag atcctcgatt tgaatcttag actccatgca    5760
```

```
tggccttaga ttcagtagga actacctttt tagagactcc aatctctatt acttgccttg    5820
gtttatgaag caagccttga atcgtccata ctggaatagt acttctgatc ttgagaaata    5880
tgtctttctc tgtgttcttg atgcaattag tcctgaatct tttgactgca tctttaacct    5940
tcttgggaag gtatttgatc tcctggagat tgttactcgg gtagatcgtc ttgatgagac    6000
ctgctgcgta ggcctctcta accatctgtg ggtcagcatt ctttctgaaa ttgaagaggc    6060
taaccttctc attatcagtg gtgaacatag tgtcgtcacc ttcaccttcg aacttccttc    6120
ctagatcgta aagatagagg aaatcgtcca ttgtaatctc cggggcaaag gagatctctt    6180
ttggggctgg atcactgctg ggccttttgg ttcctagcgt gagccagtgg cttttttgct    6240
ttggtgggct tgttagggcc ttagcaaagc tcttgggctt gagttgagct tctcctttgg    6300
ggatgaagtt caacctgtct gtttgctgac ttgttgtgta cgcgtcagct gctgctcttg    6360
cctctgtaat agtggcaaat tcttgtgtg caactccggg aacgccgttt gttgccgcct     6420
ttgtacaacc ccagtcatcg tatataccgg catgtggacc gttatacaca acgtagtagt    6480
tgatatgagg gtgttgaata cccgattctg ctctgagagg agcaactgtg ctgttaagct    6540 cagattttg tgggattgga attggatcga tctcgatccc gcgaaattaa tacgactcac     6600
tatagggaga ccacaacggt ttccctctag aaataatttt gtttaacttt aagaaggaga    6660
tatacccatg gaaaagcctg aactcaccgc gacgtctgtc gagaagtttc tgatcgaaaa    6720
gttcgacagc gtctccgacc tgatgcagct ctcggagggc gaagaatctc gtgctttcag    6780
cttcgatgta ggagggcgtg gatatgtcct gcgggtaaat agctgcgccg atggtttcta    6840
caaagatcgt tatgtttatc ggcactttgc atcggccgcg ctcccgattc cggaagtgct    6900
tgacattggg gaattcagcg agagcctgac ctattgcatc tcccgccgtg cacagggtgt    6960
cacgttgcaa gacctgcctg aaaccgaact gcccgctgtt ctgcagccgg tcgcggaggc    7020 tatgatgcg atcgctgcgg ccgatcttag ccagacgagc gggttcggcc cattcggacc     7080
gcaaggaatc ggtcaataca ctacatggcg tgatttcata tgcgcgattg ctgatcccca    7140
tgtgtatcac tggcaaactg tgatggacga caccgtcagt gcgtccgtcg cgcaggctct    7200
cgatgagctg atgctttggg ccgaggactg ccccgaagtc cggcacctcg tgcacgcgga    7260
tttcggctcc aacaatgtcc tgacggacaa tggccgcata acagcggtca ttgactggag    7320
cgaggcgatg ttcgggggatt cccaatacga ggtcgccaac atcttcttct ggaggccgtg    7380
gttggcttgt atggagcagc agacgcgcta cttcgagcgg aggcatccgg agcttgcagg    7440
atcgccgcgg ctccgggcgt atatgctccg cattggtctt gaccaactct atcagagctt    7500
ggttgacggc aatttcgatg atgcagcttg ggcgcagggt cgatgcgacg caatcgtccg    7560
atccggagcc gggactgtcg ggcgtacaca atcgcccgc agaagcgcgg ccgtctggac      7620
cgatggctgt gtagaagtac tcgccgatag tggaaaccga cgccccagca ctcgtccgag    7680
ggcaaaggaa tagtgaggta cagcttggat cgatccggct gctaacaaag cccgaaagga    7740
agctgagttg gctgctgcca ccgctgagca ataactagca taaccccttg gggcctctaa    7800
acgggtcttg aggggttttt tgctgaaagg aggaactata tccggatgat cgggcgcgcc    7860
gtcgacggat ccgtacgcaa aggcaaagat ttaaactcga aaacattaca aaagtctcaa    7920
aacagaggca aggccatgca caaagcacac tctaagtgct tccattgcct actaagtagg    7980
gtacgtacac gatcaccatt caccagtgat gatctttatt aatatacaac acactcagag    8040
acagcttatg ttatagctag ctagcataaa ctatcacatc atgtgttagt acgacaagtg    8100
acaacattgc ttttaacttc gcggccttgg atcctctaga ccggatataa tgagccgtaa    8160
```

```
acaaagatga ttaagtagta attaatacgt actagtaaaa gtggcaaaag ataacgagaa    8220
agaaccaatt tctttgcatt cggccttagc ggaaggcata tataagcttt gattatttta    8280
tttagtgtaa tgatttcgta caaccaaagc atttatttag tactctcaca cttgtgtcgc    8340
ggccgcttac gccttgtcgg cctttgccac catgcgggca aaggtgccca ggtagctgat    8400
caggatgccc accccctcca gcattggggg gctgcgatac ggcaagttgt gcttcttgca    8460
caactgctcc actttgatgc tggccgccgt caggttgtgc cggggcagcg tcggccacag    8520
gtggtgctcg atttggtaat tcagcccacc gaagaaccag tccgtgacga gtccccgctg    8580
gacgttcatc gtttcgtgaa tctggccggc gcaaaagccg tggccgtccc acaccgagtc    8640
ctggatcttc tccagggggt agtggttcat gaacaccacg atggcgatgc cgaagccccc    8700
aagcaactcg gacacgaaaa acaccatgag tccggtcaag aagcttggca tataaaagta    8760
gtagaacaac gccttcaggc cccagtggag ggccaggccc acgctctctt tctcgtactg    8820
cctgcggtag tactggttgc tgcgatcctt caggcccgtg gctgtgtgga tgctctggaa    8880
gcaccagatg aacctcagga gggcacagat gaagaagaag tagtattgct ggtacttgat    8940
catccgccgt gagaacgggc cggccctctc cacgtcctcc ttggaccatg ccagcagcgg    9000
caggttgtca atgtcggggt cgtggccttg cacgttggtg gcggagtggt gtgcattgtg    9060
cctgtccttc caccaggtca cagagaaccc ttgcaagacg ttcccgaaaa gcaagccgat    9120
ggcgttgttg atcgatcggt ccttgaacag ctgatggtgg cagatatcgt gcgacaacca    9180
acccatttgt tggaagtgaa tgcccaacac gattgccccg acgaggtacc agtgccactg    9240
ggtcatcaat agcaccgcga ggaccccgag gcccagcgta ctgagcgtct tatatgcgta    9300
ccacatcggt gatgcgtcga acattcctgc tgcgatgagc tcatctcgga gcttgcggaa    9360
atcctcctgc ggttcgtctg agtttggttt cggtggcgta ggcgtcagtg gagatgatgg    9420
ttccatgata ggcatccttc ttagtttact cacagcattt tcagagtgca taaccataaa    9480
gacatcagtg gcatcacgac cgcggtagtt ctcaatgatg tcagcacccc ctggatgatg    9540
gttcaaccag gcagacacat cataggtgac accatcaacg gtcagcggaa gtgctggcct    9600
tttcaccatg gtgcggccgc ttgggggggct atggaagact ttcttagtta gttgtgtgaa    9660
taagcaatgt tgggagaatc gggactactt ataggatagg aataaaacag aaaagtatta    9720
agtgctaatg aaatatttag actgataatt aaaatcttca cgtatgtcca cttgatataa    9780
aaacgtcagg aataaaggaa gtacagtaga atttaaaggt actctttta tatatacccg    9840
tgttctcttt ttggctagct agttgcataa aaaataatct atatttttat cattatttta    9900
aatatcttat gagatggtaa atatttatca taattttttt tactattatt tattatttgt    9960
gtgtgtaata catatagaag ttaattacaa atttttattta cttttcatt atttgatat    10020
gattcaccat taatttagtg ttattattta taatagttca ttttaatctt tttgtatata    10080
ttatgcgtgc agtacttttt tcctacatat aactactatt acattttatt tatataatat    10140
ttttattaat gaattttcgt gataatatgt aatattgttc attattattt cagatttttt    10200
aaaaatattt gtgttattat ttatgaaata tgtaattttt ttagtatttg attttatgat    10260
gataaagtgt tctaaattca aaagaagggg gaaagcgtaa acattaaaaa acgtcatcaa    10320
acaaaaacaa atcttgttta ataaagataa aactgtttgt tttgatcact gttatttcgt    10380
aatataaaaa cattatttat atttatattg ttgacaacca aatttgccta tcaaatctaa    10440
ccaatatataa gcatgcgtgg caggtaatgt actaccatga acttaagtca tgacataata    10500
aaccgtgaat ctgaccaatg catgtaccta nctaaattgt atttgtgaca cgaagcaaat    10560
```

```
gattcaattc acaatggaga tgggaaacaa ataatgaaga acccagaact aagaaagctt    10620
ttctgaaaaa taaataaag gcaatgtcaa aagtatactg catcatcagt ccagaaagca     10680
catgatattt ttttatcagt atcaatgcag ctagttttat tttacaatat cgatatagct    10740
agtttaaata tattgcagct agatttataa atatttgtgt tattatttat catttgtgta    10800
atcctgtttt tagtatttta gtttatatat gatgataatg tattccaaat ttaaagaag     10860 ggaaataaat ttaaacaaga aaaaagtca tcaaacaaaa aacaaatgaa agggtggaaa     10920
gatgttacca tgtaatgtga atgttacagt atttctttta ttatagagtt aacaaattaa    10980
ctaatatgat tttgttaata atgataaaat atttttttta ttattatttc ataatataaa    11040
aatagtttac ttaatataaa aaaaattcta tcgttcacaa caaagttggc cacctaattt    11100
aaccatgcat gtacccatgg accatattag gtaaccatca aacctgatga agagataaag    11160
agatgaagac ttaagtcata acacaaaacc ataaaaaaca aaaatacaat caaccgtcaa    11220
tctgaccaat gcatgaaaaa gctgcaatag tgagtggcga cacaaagcac atgattttct    11280
tacaacggag ataaaaccaa aaaaatattt catgaacaac ctagaacaaa taagcttttt    11340
atataataaa tatataaata aataaaggct atggaataat atacttcaat atatttggat    11400
taaataaatt gttggcgggg ttgatatatt tatacacacc taaagtcact tcaatctcat    11460
tttcacttaa cttttatttt ttttttcttt ttatttatca taaagagaat attgataata    11520
tactttttaa catattttta tgacatttt tattggtgaa aacttattaa aaatcataaa     11580
ttttgtaagt tagattatt taaagagttc ctcttcttat tttaaatttt ttaataaatt     11640
tttaaataac taaaatttgt gttaaaaatg ttaaaaaatg tgttattaac ccttctcttc    11700
gaggac                                                              11706

<210> SEQ ID NO 61
<211> LENGTH: 5146
<212> TYPE: DNA
<213> ORGANISM: Artificial Sequence
<220> FEATURE:
<223> OTHER INFORMATION: pKR1173

<400> SEQUENCE: 61
cgcgcccgat catccggata tagttcctcc tttcagcaaa aaaccctca agacccgttt       60 agaggcccca agggggttatg ctagttattg ctcagcggtg gcagcagcca actcagcttc     120
ctttcgggct tgttagcag ccggatcgat ccaagctgta cctcactatt cctttgccct       180
cggacgagtg ctggggcgtc ggtttccact atcggcgagt acttctacac agccatcggt     240
ccagacggcc gcgcttctgc gggcgatttg tgtacgcccg acagtcccgg ctccggatcg     300
gacgattgcg tcgcatcgac cctgcgccca agctgcatca tcgaaattgc cgtcaaccaa    360
gctctgatag agttggtcaa gaccaatgcg gagcatatac gcccggagcc gcggcgatcc    420
tgcaagctcc ggatgcctcc gctcgaagta gcgcgtctgc tgctccatac aagccaacca    480
cggcctccag aagaagatgt tggcgacctc gtattgggaa tccccgaaca tcgcctcgct    540
ccagtcaatg accgctgtta tgcggccatt gtccgtcagg acattgttgg agccgaaatc    600
cgcgtgcacg aggtgccgga cttcggggca gtcctcggcc caaagcatca gctcatcgag    660
agcctgcgcg acgacgcac tgacggtgtc gtccatcaca gtttgccagt gatacacatg     720
gggatcagca atcgcgcata tgaaatcacg ccatgtagtg tattgaccga ttccttgcgg    780
tccgaatggg ccgaacccgc tcgtctggct aagatcggcc gcagcgatcg catccatagc    840
ctccgcgacc ggctgcagaa cagcgggcag ttcggtttca ggcaggtctt gcaacgtgac    900
```

```
accctgtgca cggcgggaga tgcaataggt caggctctcg ctgaattccc caatgtcaag    960
cacttccgga atcgggagcg cggccgatgc aaagtgccga taaacataac gatctttgta   1020
gaaaccatcg gcgcagctat ttacccgcag gacatatcca cgccctccta catcgaagct   1080
gaaagcacga gattcttcgc cctccgagag ctgcatcagg tcggagacgc tgtcgaactt   1140
ttcgatcaga aacttctcga cagacgtcgc ggtgagttca ggcttttcca tgggtatatc   1200
tccttcttaa agttaaacaa aattatttct agagggaaac cgttgtggtc tccctatagt   1260
gagtcgtatt aatttcgcgg gatcgagatc tgatcaacct gcattaatga atcggccaac   1320
gcgcggggag aggcggtttg cgtattgggc gctcttccgc ttcctcgctc actgactcgc   1380
tgcgctcggt cgttcggctg cggcgagcgg tatcagctca ctcaaaggcg gtaatacggt   1440
tatccacaga atcaggggat aacgcaggaa agaacatgtg agcaaaaggc cagcaaaagg   1500
ccaggaaccg taaaaaggcc gcgttgctgg cgtttttcca taggctccgc cccctgacg    1560
agcatcacaa aaatcgacgc tcaagtcaga ggtggcgaaa cccgacagga ctataaagat   1620
accaggcgtt ccccctggaa gctccctcg tgcgctctcc tgttccgacc ctgccgctta    1680
ccggatacct gtccgccttt ctcccttcgg aagcgtggc gctttctcaa tgctcacgct    1740
gtaggtatct cagttcggtg taggtcgttc gctccaagct gggctgtgtg cacgaacccc   1800
ccgttcagcc cgaccgctgc gccttatccg gtaactatcg tcttgagtcc aacccggtaa   1860
gacacgactt atcgccactg gcagcagcca ctggtaacag gattagcaga gcgaggtatg   1920
taggcggtgc tacagagttc ttgaagtggt ggcctaacta cggctacact agaaggacag   1980
tatttggtat ctgcgctctg ctgaagccag ttaccttcgg aaaaagagtt ggtagctctt   2040
gatccggcaa acaaaccacc gctggtagcg gtggtttttt tgtttgcaag cagcagatta   2100
cgcgcagaaa aaaggatct caagaagatc ctttgatctt ttctacgggg tctgacgctc     2160
agtggaacga aaactcacgt taagggattt tggtcatgac attaacctat aaaaataggc   2220
gtatcacgag gccctttcgt ctcgcgcgtt tcggtgatga cggtgaaaac ctctgacaca   2280
tgcagctccc ggagacggtc acagcttgtc tgtaagcgga tgccgggagc agacaagccc   2340
gtcagggcgc gtcagcgggt gttggcgggt gtcggggctg gcttaactat gcggcatcag   2400
agcagattgt actgagagtg caccatatgg acatattgtc gttagaacgc ggctacaatt   2460
aatacataac cttatgtatc atacacatac gatttaggtg acactataga acggcgcgcc   2520
gtcgacggat ccgtacgaga tccggccggc cagatcctgc aggagatcca gcttttgat    2580
ccatgccctt catttgccgc ttattaatta atttggtaac agtccgtact aatcagttac   2640
ttatccttcc cccatcataa ttaatcttgg tagtctcgaa tgccacaaca ctgactagtc   2700
tcttggatca taagaaaaag ccaaggaaca aagaagaca aaacacaatg agagtatcct    2760
ttgcatagca atgtctaagt tcataaaatt caaacaaaaa cgcaatcaca cacagtggac   2820
atcacttatc cactagctga tcaggatcgc gcgtcaaga aaaaaaact ggaccccaaa      2880
agccatgcac aacaacacgt actcacaaag gtgtcaatcg agcagcccaa acattcacc    2940
aactcaaccc atcatgagcc ctcacatttg ttgtttctaa cccaacctca aactcgtatt   3000
ctcttccgcc acctcatttt tgtttatttc aacacccgtc aaactgcatg ccaccccgtg   3060
gccaaatgtc catgcatgtt aacaagacct atgactataa atagctgcaa tctcggccca   3120
ggttttcatc atcaagaacc agttcaatat cctagtacac cgtattaaag aatttaagat   3180
atactgcggc cgcaccatgg aagcagccaa agaattggtt ccatcgtcc aagaggagct     3240
ccccaaggtg gactatgccc agctttggca ggatgccagc agctgtgagg tcctttacct   3300
```

```
ctcggtggca ttcgtggcga tcaagttcat gctgcgccca ctggacctga agcgccaggc   3360
cacccttgaag aagctgttca cagcatacaa cttcctcatg tcgatctatt cctttggctc   3420
cttcctggcc atggcctatg ccctatcagt aactggcatc ctctccggcg actgtgagac   3480
ggcgttcaac aacgatgtgt tcaggatcac aactcagctg ttctacctca gcaagttcgt   3540
agagtacatc gactccttct accttcccct tatggacaag ccactgtcgt tccttcagtt   3600
cttccatcat ttgggggccc ccattgacat gtggctattc tacaaatacc gcaacgaagg   3660
agtctggatc tttgtcctgt tgaatgggtt cattcactgg atcatgtacg gttactattg   3720
gacgcggctc atcaagctga acttccccat gcccaagaac ctgatcacct ccatgcagat   3780
catccagttc aatgtcgggt tctacatcgt ctggaagtac cgcaatgtgc catgctaccg   3840
ccaggatggg atgcgcatgt ttgcctggat cttcaactac tggtatgtcg ggacggtctt   3900
gctgctgttc ctcaactttt acgtgcagac gtacatccgg aagccgagga agaaccgagg   3960
gaagaaggag tagcggccgc aagtatgaac taaaatgcat gtaggtgtaa gagctcatgg   4020
agagcatgga atattgtatc cgaccatgta acagtataat aactgagctc catctcactt   4080
cttctatgaa taaacaaagg atgttatgat atattaacac tctatctatg caccttattg   4140
ttctatgata aatttcctct tattattata aatcatctga atcgtgacgg cttatggaat   4200
gcttcaaata gtacaaaaac aaatgtgtac tataagactt tctaaacaat tctaaccttta  4260
gcattgtgaa cgagacataa gtgttaagaa gacataacaa ttataatgga agaagtttgt   4320
ctccatttat atattatata ttacccactt atgtattata ttaggatgtt aaggagacat   4380
aacaattata aagagagaag tttgtatcca tttatatatt atatactacc catttatata   4440
ttatacttat ccacttattt aatgtctttta taaggtttga tccatgatat ttctaatatt   4500
ttagttgata tgtatatgaa agggtactat ttgaactctc ttactctgta taaaggttgg   4560
atcatcctta aagtgggtct atttaatttt attgcttctt acagataaaa aaaaaattat   4620
gagttggttt gataaaatat tgaaggattt aaaataataa taataacat ataatatatg    4680
tatataaatt tattataata taacattat ctataaaaaa gtaaatattg tcataaatct     4740
atacaatcgt ttagccttgc tggacgaatc tcaattattt aaacgagagt aaacatattt   4800
gactttttgg ttatttaaca aattattatt taacactata tgaaatttt tttttttatca   4860
gcaaagaata aaattaaatt aagaaggaca atggtgtccc aatccttata caaccaactt   4920
ccacaagaaa gtcaagtcag agacaacaaa aaaacaagca aggaaattt tttaatttga    4980
gttgtcttgt ttgctgcata atttatgcag taaaacacta cacataaccc ttttagcagt   5040
agagcaatgg ttgaccgtgt gcttagcttc ttttatttta tttttttatc agcaaagaat   5100
aaataaaata aaatgagaca cttcagggat gtttcaacaa gcttgg               5146
```

<210> SEQ ID NO 62
<211> LENGTH: 5250
<212> TYPE: DNA
<213> ORGANISM: Artificial Sequence
<220> FEATURE:
<223> OTHER INFORMATION: pKR393

<400> SEQUENCE: 62

```
gatccccgg gctgcaggaa ttcactggcc gtcgttttac aacgtcgtga ctgggaaaac     60
cctggcgtta cccaacttaa tcgccttgca gcacatcccc ctttcgccag ctggcgtaat   120
agcgaagagg cccgcaccga tcgcccttcc caacagttgc gcagcctgaa tggcgaatgg   180
cgcctgatgc ggtattttct ccttacgcat ctgtgcggta tttcacaccg catatggtgc   240
```

```
actctcagta caatctgctc tgatgccgca tagttaagcc agccccgaca cccgccaaca    300
cccgctgacg cgccctgacg ggcttgtctg ctcccggcat ccgcttacag acaagctgtg    360
accgtctccg ggagctgcat gtgtcagagg ttttcaccgt catcaccgaa acgcgcgaga    420
cgaaagggcc tcgtgatacg cctatttta taggttaatg tcatgataat aatggtttct    480
tagacgtcag gtggcacttt tcggggaaat gtgcgcggaa ccctatttg tttattttc    540 taaatacatt caaatatgta tccgctcatg agacaataac cctgataaat gcttcaataa    600
tattgaaaaa ggaagagtat gagtattcaa catttccgtg tcgcccttat tcccttttt    660 gcggcatttt gccttcctgt ttttgctcac ccagaaacgc tggtgaaagt aaaagatgct    720
gaagatcagt tgggtgcacg agtgggttac atcgaactgg atctcaacag cggtaagatc    780
cttgagagtt ttcgccccga agaacgtttt ccaatgatga gcacttttaa agttctgcta    840
tgtggcgcgg tattatcccg tattgacgcc gggcaagagc aactcggtcg ccgcatacac    900
tattctcaga atgacttggt tgagtactca ccagtcacag aaaagcatct tacggatggc    960
atgacagtaa gagaattatg cagtgctgcc ataaccatga gtgataacac tgcggccaac   1020
ttacttctga caacgatcgg aggaccgaag gagctaaccg cttttttgca acatggggg   1080 gatcatgtaa ctcgccttga tcgttgggaa ccggagctga atgaagccat accaaacgac   1140
gagcgtgaca ccacgatgcc tgtagcaatg gcaacaacgt tgcgcaaact attaactggc   1200
gaactactta ctctagcttc ccggcaacaa ttaatagact ggatggaggc ggataaagtt   1260
gcaggaccac ttctgcgctc ggcccttccg gctggctggt ttattgctga taaatctgga   1320
gccggtgagc gtgggtctcg cggtatcatt gcagcactgg ggccagatgg taagccctcc   1380
cgtatcgtag ttatctacac gacggggagt caggcaacta tggatgaacg aaatagacag   1440
atcgctgaga taggtgcctc actgattaag cattggtaac tgtcagacca gtttactca   1500 tatatacttt agattgattt aaaacttcat ttttaattta aaaggatcta ggtgaagatc   1560 cttttgata atctcatgac caaaatccct taacgtgagt tttcgttcca ctgagcgtca   1620
gaccccgtag aaaagatcaa aggatcttct tgagatcctt ttttctgcg cgtaatctgc   1680 tgcttgcaaa caaaaaaacc accgctacca gcggtggttt gtttgccgga tcaagagcta   1740
ccaactcttt ttccgaaggt aactggcttc agcagagcgc agataccaaa tactgtcctt   1800
ctagtgtagc cgtagttagg ccaccacttc aagaactctg tagcaccgcc tacatacctc   1860
gctctgctaa tcctgttacc agtggctgct gccagtggcg ataagtcgtg tcttaccggg   1920
ttggactcaa gacgatagtt accggataag gcgcagcggt cgggctgaac ggggggttcg   1980
tgcacacagc ccagcttgga gcgaacgacc tacaccgaac tgagatacct acagcgtgag   2040
ctatgagaaa gcgccacgct tcccgaaggg agaaaggcgg acaggtatcc ggtaagcggc   2100
agggtcggaa caggagagcg cacgagggag cttccagggg gaaacgcctg gtatctttat   2160
agtcctgtcg ggtttcgcca cctctgactt gagcgtcgat ttttgtgatg ctcgtcaggg   2220
gggcggagcc tatggaaaaa cgccagcaac gcggcctttt tacggttcct ggccttttgc   2280
tggccttttg ctcacatgtt ctttcctgcg ttatcccctg attctgtgga taaccgtatt   2340
accgcctttg agtgagctga taccgctcgc cgcagccgaa cgaccgagcg cagcgagtca   2400
gtgagcgagg aagcggaaga gcgcccaata cgcaaaccgc ctctccccgc gcgttggccg   2460
attcattaat gcagctggca cgacaggttt cccgactgga aagcgggcag tgagcgcaac   2520
gcaattaatg tgagttagct cactcattag gcacccagg cttacactt tatgcttccg   2580 gctcgtatgt tgtgtggaat tgtgagcgga taacaatttc acacaggaaa cagctatgac   2640
```

```
catgattacg ccaagcttgc atgcctgcag gctagcctaa gtacgtactc aaaatgccaa    2700
caaataaaaa aaaagttgct ttaataatgc caaaacaaat taataaaaca cttacaacac    2760
cggatttttt ttaattaaaa tgtgccattt aggataaata gttaatattt ttaataatta    2820
tttaaaaagc cgtatctact aaaatgattt ttatttggtt gaaaatatta atatgtttaa    2880
atcaacacaa tctatcaaaa ttaaactaaa aaaaaaataa gtgtacgtgg ttaacattag    2940
tacagtaata taagaggaaa atgagaaatt aagaaattga aagcgagtct aattttttaaa   3000 ttatgaacct gcatatataa aaggaaagaa agaatccagg aagaaaagaa atgaaaccat    3060
gcatggtccc ctcgtcatca cgagtttctg ccatttgcaa tagaaacact gaaacacctt    3120
tctctttgtc acttaattga gatgccgaag ccacctcaca ccatgaactt catgaggtgt    3180
agcacccaag gcttccatag ccatgcatac tgaagaatgt ctcaagctca gcaccctact    3240
tctgtgacgt gtccctcatt caccttcctc tcttccctat aaataaccac gcctcaggtt    3300
ctccgcttca caactcaaac attctctcca ttggtcctta aacactcatc agtcatcacc    3360
gcggccgcca attcaggtgc ccatgatgtt ggccgcaggc tatcttctag tgctctcggc    3420
cgctcgccag agcttccagc aggacattga caaccccaac ggggcctact cgacctcgtg    3480
gactggcctg cccattgtga tgtctgtggt ctatctcagc ggtgtgtttg ggctcacaaa    3540
gtacttcgag aaccggaagc ccatgacggg gctgaaggac tacatgttca cttacaatct    3600
ctaccaggtg atcatcaacg tgtggtgcgt ggtggccttt ctcctggagg tgcggcgtgc    3660
gggcatgtca ctcatcggca ataaggtgga ccttgggccc aactccttca ggctcggctt    3720
cgtcacgtgg gtgcactaca acaacaagta cgtggagctc ctcgacaccc tatggatggt    3780
gctgcgcaag aagacgcagc aggtctcctt cctccacgtc tatcatcacg tgcttctgat    3840
gtgggcctgg ttcgttgtcg tcaagctcgg caatggtggt gacgcatatt ttggcggtct    3900
catgaactcg atcatccacg tgatgatgta ttcctactac accatggcgc tcctgggctg    3960
gtcatgcccc tggaagcgct acctcacgca ggcacagctc gtgcagtttt gcatctgcct    4020
cgcccactcc acatgggcgg cagtaacggg tgcctacccg tggcgaattt gcttggtgga    4080
ggtgtgggtg atggtgtcca tgctggtgct cttcacacgc ttctaccgcc aggcctatgc    4140
caaggaggcg aaggccaagg aggcgaaaaa gctcgcacag gaggcatcac aggccaaggc    4200
ggtcaaggcg gagtaagtca ctggaggtgg accgcacatg caccacgggc ccggcgagca    4260
gcatggttcg gcgagtcagg cccggtcatg cgtcatggtt ggagtttgca gggcggcagg    4320
tgatcgcctc cgccatgcac ggccacaggc acagccggtc ctctggacgt cccaactttc    4380
aaccgtggtg caaagcacgc tggcgaccgc gagcagcagt cagcgcagcg tgttatcaca    4440
gtgtcgctgg ctgcacgtgc tctctccatc gcggccgcat ttcgcaccaa atcaatgaaa    4500
gtaataatga aaagtctgaa taagaatact taggcttaga tgcctttgtt acttgtgtaa    4560
aataacttga gtcatgtacc tttggcggaa acagaataaa taaaggtgaa attccaatg    4620 ctctatgtat aagttagtaa tacttaatgt gttctacggt tgtttcaata tcatcaaact    4680
ctaattgaaa ctttagaacc acaaatctca atcttttctt aatgaaatga aaatcttaa    4740 ttgtaccatg tttatgttaa acaccttaca attggttgga gaggaggacc aaccgatggg    4800
acaacattgg gagaaagaga ttcaatggag atttggatag gagaacaaca ttctttttca    4860
cttcaataca agatgagtgc aacactaagg atatgtatga actttcaga agctacgaca    4920 acatagatga gtgaggtggt gattcctagc aagaaagaca ttagaggaag ccaaaatcga    4980
acaaggaaga catcaagggc aagagacagg accatccatc tcaggaaaag gagctttggg    5040
```

| atagtccgag aagttgtaca agaaattttt tggagggtga gtgatgcatt gctggtgact | 5100 |
| ttaactcaat caaaattgag aaagaaagaa aagggagggg gctcacatgt gaatagaagg | 5160 |
| gaaacgggag aattttacag ttttgatcta atgggcatcc cagctagtgg taacatattc | 5220 |
| accatgttta accttcacgt acgtctagag | 5250 |

<210> SEQ ID NO 63
<211> LENGTH: 4140
<212> TYPE: DNA
<213> ORGANISM: Artificial Sequence
<220> FEATURE:
<223> OTHER INFORMATION: pKR407

<400> SEQUENCE: 63

| ggccgcattt cgcaccaaat caatgaaagt aataatgaaa agtctgaata agaatactta | 60 |
| ggcttagatg cctttgttac ttgtgtaaaa taacttgagt catgtacctt tggcggaaac | 120 |
| agaataaata aaaggtgaaa ttccaatgct ctatgtataa gttagtaata cttaatgtgt | 180 |
| tctacggttg tttcaatatc atcaaactct aattgaaact ttagaaccac aaatctcaat | 240 |
| cttttcttaa tgaaatgaaa atcttaatt gtaccatgtt tatgttaaac accttacaat | 300 |
| tggttggaga ggaggaccaa ccgatgggac aacattggga gaaagagatt caatggagat | 360 |
| ttggatagga gaacaacatt ctttttcact tcaatacaag atgagtgcaa cactaaggat | 420 |
| atgtatgaga ctttcagaag ctacgacaac atagatgagt gaggtggtga ttcctagcaa | 480 |
| gaaagacatt agaggaagcc aaaatcgaac aaggaagaca tcaagggcaa gagacaggac | 540 |
| catccatctc aggaaaagga gctttgggat agtccgagaa gttgtacaag aaatttttg | 600 |
| gagggtgagt gatgcattgc tggtgacttt aactcaatca aaattgagaa agaaagaaaa | 660 |
| gggagggggc tcacatgtga atagaaggga aacgggagaa ttttacagtt ttgatctaat | 720 |
| gggcatccca gctagtggta acatattcac catgtttaac cttcacgtac gtctagagga | 780 |
| tcccccgggc tgcaggaatt cactggccgt cgttttacaa cgtcgtgact gggaaaaccc | 840 |
| tggcgttacc caacttaatc gccttgcagc acatccccct ttcgccagct ggcgtaatag | 900 |
| cgaagaggcc cgcaccgatc gcccttccca acagttgcgc agcctgaatg gcgaatggcg | 960 |
| cctgatgcgg tattttctcc ttacgcatct gtgcggtatt tcacaccgca tatggtgcac | 1020 |
| tctcagtaca atctgctctg atgccgcata gttaagccag ccccgacacc cgccaacacc | 1080 |
| cgctgacgcg ccctgacggg cttgtctgct cccggcatcc gcttacagac aagctgtgac | 1140 |
| cgtctccggg agctgcatgt gtcagaggtt ttcaccgtca tcaccgaaac gcgcgagacg | 1200 |
| aaagggcctc gtgatacgcc tatttttata ggttaatgtc atgataataa tggtttctta | 1260 |
| gacgtcaggt ggcactttc ggggaaatgt gcgcggaacc cctatttgtt tatttttcta | 1320 |
| aatacattca aatatgtatc cgctcatgag acaataaccc tgataaatgc ttcaataata | 1380 |
| ttgaaaaagg aagagtatga gtattcaaca tttccgtgtc gcccttattc ccttttttgc | 1440 |
| ggcattttgc cttcctgttt tgctcaccc agaaacgctg gtgaaagtaa aagatgctga | 1500 |
| agatcagttg ggtgcacgag tgggttacat cgaactggat ctcaacagcg gtaagatcct | 1560 |
| tgagagtttt cgccccgaag aacgttttcc aatgatgagc acttttaaag ttctgctatg | 1620 |
| tggcgcggta ttatcccgta ttgacgccgg gcaagagcaa ctcggtcgcc gcatacacta | 1680 |
| ttctcagaat gacttggttg agtactcacc agtcacagaa aagcatctta cggatggcat | 1740 |
| gacagtaaga gaattatgca gtgctgccat aaccatgagt gataacactg cggccaactt | 1800 |
| acttctgaca acgatcggag gaccgaagga gctaaccgct ttttgcaca acatggggga | 1860 |

```
tcatgtaact cgccttgatc gttgggaacc ggagctgaat gaagccatac caaacgacga    1920
gcgtgacacc acgatgcctg tagcaatggc aacaacgttg cgcaaactat taactggcga    1980
actacttact ctagcttccc ggcaacaatt aatagactgg atggaggcgg ataaagttgc    2040
aggaccactt ctgcgctcgg cccttccggc tggctggttt attgctgata aatctggagc    2100
cggtgagcgt gggtctcgcg gtatcattgc agcactgggg ccagatggta agccctcccg    2160
tatcgtagtt atctcacacga cggggagtca ggcaactatg gatgaacgaa atagacagat    2220
cgctgagata ggtgcctcac tgattaagca ttggtaactg tcagaccaag tttactcata    2280
tatactttag attgatttaa aacttcattt ttaatttaaa aggatctagg tgaagatcct    2340
ttttgataat ctcatgacca aaatccctta acgtgagttt tcgttccact gagcgtcaga    2400
ccccgtagaa aagatcaaag gatcttcttg agatcctttt tttctgcgcg taatctgctg    2460
cttgcaaaca aaaaaaccac cgctaccagc ggtggtttgt ttgccggatc aagagctacc    2520 aactctttt ccgaaggtaa ctggcttcag cagagcgcag ataccaaata ctgtccttct    2580
agtgtagccg tagttaggcc accacttcaa gaactctgta gcaccgccta catacctcgc    2640
tctgctaatc ctgttaccag tggctgctgc cagtggcgat aagtcgtgtc ttaccgggtt    2700
ggactcaaga cgatagttac cggataaggc gcagcggtcg ggctgaacgg ggggttcgtg    2760
cacacagccc agcttggagc gaacgaccta caccgaactg agatacctac agcgtgagct    2820
atgagaaagc gccacgcttc ccgaagggag aaaggcggac aggtatccgg taagcggcag    2880
ggtcggaaca ggagagcgca cgagggagct tccaggggga aacgcctggt atctttatag    2940
tcctgtcggg tttcgccacc tctgacttga gcgtcgattt tgtgatgct cgtcaggggg    3000 gcggagccta tggaaaaacg ccagcaacgc ggccttttta cggttcctgg ccttttgctg    3060
gccttttgct cacatgttct ttcctgcgtt atcccctgat tctgtggata accgtattac    3120
cgcctttgag tgagctgata ccgctcgccg cagccgaacg accgagcgca gcgagtcagt    3180
gagcgaggaa gcggaagagc gcccaatacg caaaccgcct ctccccgcgc gttggccgat    3240
tcattaatgc agctggcacg acaggttttcc cgactggaaa gcgggcagtg agcgcaacgc    3300
aattaatgtg agttagctca ctcattaggc accccaggct ttacacttta tgcttccggc    3360
tcgtatgttg tgtggaattg tgagcggata acaatttcac acaggaaaca gctatgacca    3420
tgattacgcc aagcttgcat gcctgcaggc tagcctaagt acgtactcaa aatgccaaca    3480
aataaaaaaa aagttgcttt aataatgcca aaacaaatta ataaaacact tacaacaccg    3540
gatttttttt aattaaaatg tgccatttag gataaatagt taatattttt aataattat    3600 taaaaagccg tatctactaa aatgattttt atttggttga aaatattaat atgtttaaat    3660
caacacaatc tatcaaaatt aaactaaaaa aaaaataagt gtacgtggtt aacattagta    3720
cagtaatata agaggaaaat gagaaattaa gaaattgaaa gcgagtctaa ttttttaaatt    3780 atgaacctgc atatataaaa ggaaagaaag aatccaggaa gaaaagaaat gaaaccatgc    3840
atggtcccct cgtcatcacg agtttctgcc atttgcaata gaaacactga acacctttc    3900 tctttgtcac ttaattgaga tgccgaagcc acctcacacc atgaacttca tgaggtgtag    3960
cacccaaggc ttccatagcc atgcatactg aagaatgtct caagctcagc accctacttc    4020
tgtgacgtgt ccctcattca ccttcctctc ttccctataa ataaccacgc ctcaggttct    4080
ccgcttcaca actcaaacat tctctccatt ggtccttaaa cactcatcag tcatcaccgc    4140
```

<210> SEQ ID NO 64
<211> LENGTH: 5414
<212> TYPE: DNA

<213> ORGANISM: Artificial Sequence
<220> FEATURE:
<223> OTHER INFORMATION: pKR1176

<400> SEQUENCE: 64

```
ggccgcattt cgcaccaaat caatgaaagt aataatgaaa agtctgaata agaatactta      60
ggcttagatg cctttgttac ttgtgtaaaa taacttgagt catgtacctt tggcggaaac     120
agaataaata aaaggtgaaa ttccaatgct ctatgtataa gttagtaata cttaatgtgt     180
tctacggttg tttcaatatc atcaaactct aattgaaact ttagaaccac aaatctcaat     240
cttttcttaa tgaaatgaaa aatcttaatt gtaccatgtt tatgttaaac accttacaat     300
tggttggaga ggaggaccaa ccgatgggac aacattggga gaaagagatt caatggagat     360
ttggatagga gaacaacatt ctttttcact tcaatacaag atgagtgcaa cactaaggat     420
atgtatgaga ctttcagaag ctacgacaac atagatgagt gaggtggtga ttcctagcaa     480
gaaagacatt agaggaagcc aaaatcgaac aaggaagaca tcaagggcaa gagacaggac     540
catccatctc aggaaaagga gctttgggat agtccgagaa gttgtacaag aaatttttg      600
gagggtgagt gatgcattgc tggtgactt aactcaatca aaattgagaa agaaagaaaa      660
gggagggggc tcacatgtga atagaaggga aacgggagaa ttttacagtt ttgatctaat     720
gggcatccca gctagtggta acatattcac catgtttaac cttcacgtac gtctagagga     780
tcccccgggc tgcaggaatt cactggccgt cgttttacaa cgtcgtgact gggaaaaccc     840
tggcgttacc caacttaatc gccttgcagc acatcccct ttcgccagct ggcgtaatag      900
cgaagaggcc cgcaccgatc gcccttccca acagttgcgc agcctgaatg gcgaatggcg     960
cctgatgcgg tattttctcc ttacgcatct gtgcggtatt tcacaccgca tatggtgcac    1020
tctcagtaca atctgctctg atgccgcata gttaagccag ccccgacacc cgccaacacc    1080
cgctgacgcg ccctgacggg cttgtctgct cccggcatcc gcttacagac aagctgtgac    1140
cgtctccggg agctgcatgt gtcagaggtt ttcaccgtca tcaccgaaac gcgcgagacg    1200
aaagggcctc gtgatacgcc tatttttata ggttaatgtc atgataataa tggtttctta    1260
gacgtcaggt ggcacttttc ggggaaatgt gcgcggaacc cctatttgtt tatttttcta    1320
aatacattca aatatgtatc cgctcatgag acaataaccc tgataaatgc ttcaataata    1380
ttgaaaaagg aagagtatga gtattcaaca tttccgtgtc gcccttattc ccttttttgc    1440
ggcattttgc cttcctgttt ttgctcaccc agaaacgctg gtgaaagtaa aagatgctga    1500
agatcagttg ggtgcacgag tgggttacat cgaactggat ctcaacagcg gtaagatcct    1560
tgagagtttt cgccccgaag aacgttttcc aatgatgagc acttttaaag ttctgctatg    1620
tggcgcggta ttatcccgta ttgacgccgg gcaagagcaa ctcggtcgcc gcatacacta    1680
ttctcagaat gacttggttg agtactcacc agtcacagaa aagcatctta cggatggcat    1740
gacagtaaga gaattatgca gtgctgccat aaccatgagt gataacactg cggccaactt    1800
acttctgaca acgatcggag gaccgaagga gctaaccgct tttttgcaca acatggggga    1860
tcatgtaact cgccttgatc gttgggaacc ggagctgaat gaagccatac caaacgacga    1920
gcgtgacacc acgatgcctg tagcaatggc aacaacgttg cgcaaactat taactggcga    1980
actacttact ctagcttccc ggcaacaatt aatagactgg atggaggcgg ataaagttgc    2040
aggaccactt ctgcgctcgg cccttccggc tggctggttt attgctgata aatctggagc    2100
cggtgagcgt gggtctcgcg gtatcattgc agcactgggg ccagatggta agccctcccg    2160
tatcgtagtt atctacacga cggggagtca ggcaactatg gatgaacgaa atagacagat    2220
```

```
cgctgagata ggtgcctcac tgattaagca ttggtaactg tcagaccaag tttactcata   2280
tatactttag attgatttaa aacttcattt ttaatttaaa aggatctagg tgaagatcct   2340
ttttgataat ctcatgacca aaatccctta acgtgagttt tcgttccact gagcgtcaga   2400
ccccgtagaa aagatcaaag gatcttcttg agatcctttt tttctgcgcg taatctgctg   2460
cttgcaaaca aaaaaaccac cgctaccagc ggtggtttgt ttgccggatc aagagctacc   2520 aactctttt ccgaaggtaa ctggcttcag cagagcgcag ataccaaata ctgtccttct   2580
agtgtagccg tagttaggcc accacttcaa gaactctgta gcaccgccta catacctcgc   2640
tctgctaatc ctgttaccag tggctgctgc cagtggcgat aagtcgtgtc ttaccgggtt   2700
ggactcaaga cgatagttac cggataaggc gcagcggtcg ggctgaacgg ggggttcgtg   2760
cacacagccc agcttggagc gaacgaccta caccgaactg agatacctac agcgtgagct   2820
atgagaaagc gccacgcttc ccgaagggag aaaggcggac aggtatccgg taagcggcag   2880
ggtcggaaca ggagagcgca cgagggagct tccaggggga aacgcctggt atctttatag   2940
tcctgtcggg tttcgccacc tctgacttga gcgtcgattt tgtgatgct cgtcaggggg   3000 gcggagccta tggaaaaacg ccagcaacgc ggcctttta cggttcctgg ccttttgctg   3060
gccttttgct cacatgttct ttcctgcgtt atcccctgat tctgtggata accgtattac   3120
cgcctttgag tgagctgata ccgctcgccg cagccgaacg accgagcgca gcgagtcagt   3180
gagcgaggaa gcggaagagc gcccaatacg caaaccgcct ctccccgcgc gttggccgat   3240
tcattaatgc agctggcacg acaggtttcc cgactggaaa gcgggcagtg agcgcaacgc   3300
aattaatgtg agttagctca ctcattaggc accccaggct ttacacttta tgcttccggc   3360
tcgtatgttg tgtggaattg tgagcggata acaatttcac acaggaaaca gctatgacca   3420
tgattacgcc aagcttgcat gcctgcaggc tagcctaagt acgtactcaa aatgccaaca   3480
aataaaaaaa aagttgcttt aataatgcca aaacaaatta ataaaacact acaacaccg   3540 gatttttttt aattaaaatg tgccatttag gataaatagt taatatttttt aataattatt   3600 taaaagccg tatctactaa aatgattttt atttggttga aaatattaat atgtttaaat   3660
caacacaatc tatcaaaatt aaactaaaaa aaaataagt gtacgtggtt aacattagta   3720
cagtaatata agaggaaaat gagaaattaa gaaattgaaa gcgagtctaa ttttttaaatt   3780 atgaacctgc atatataaaa ggaaagaaag aatccaggaa gaaaagaaat gaaaccatgc   3840
atggtcccct cgtcatcacg agtttctgcc atttgcaata gaaacactga acacctttc   3900 tctttgtcac ttaattgaga tgccgaagcc acctcacacc atgaacttca tgaggtgtag   3960
cacccaaggc ttccatagcc atgcatactg aagaatgtct caagctcagc accctacttc   4020
tgtgacgtgt ccctcattca ccttcctctc ttccctataa ataaccacgc tcaggttct   4080 ccgcttcaca actcaaacat tctctccatt ggtccttaaa cactcatcag tcatcaccgc   4140
ggccgcacca tggtgaaaag gccagcactt ccgctgaccg ttgatggtgt cacctatgat   4200
gtgtctgcct ggttgaacca tcatccaggg ggtgctgaca tcattgagaa ctaccgcggt   4260
cgtgatgcca ctgatgtctt tatggttatg cactctgaaa atgctgtgag taaactaaga   4320
aggatgccta tcatggaacc atcatctcca ctgacgccta cgccaccgaa acccaactca   4380
gacgaaccgc aggaggattt ccgcaagctc cgagatgagc tcatcgcagc aggaatgttc   4440
gacgcatcac cgatgtggta cgcatataag acgctcagta cgctgggcct cggggtcctc   4500
gcggtgctat tgatgaccca gtggcactgg tacctcgtcg gggcaatcgt gttgggcatt   4560
cacttccaac aaatgggttg gttgtcgcac gatatctgcc accatcagct gttcaaggac   4620
```

| | |
|---|---|
| cgatcgatca acaacgccat cggcttgctt ttcgggaacg tcttgcaagg gttctctgtg | 4680 |
| acctggtgga aggacaggca caatgcacac cactccgcca ccaacgtgca aggccacgac | 4740 |
| cccgacattg acaacctgcc gctgctggca tggtccaagg aggacgtgga gagggccggc | 4800 |
| ccgttctcac ggcggatgat caagtaccag caatactact tcttcttcat ctgtgccctc | 4860 |
| ctgaggttca tctggtgctt ccagagcatc cacacagcca cgggcctgaa ggatcgcagc | 4920 |
| aaccagtact accgcaggca gtacgagaaa gagagcgtgg gcctggccct ccactggggc | 4980 |
| ctgaaggcgt tgttctacta cttttatatg ccaagcttct tgaccggact catggtgttt | 5040 |
| ttcgtgtccg agttgcttgg gggcttcggc atcgccatcg tggtgttcat gaaccactac | 5100 |
| cccctggaga agatccagga ctcggtgtgg gacggccacg cttttgcgc cggccagatt | 5160 |
| cacgaaacga tgaacgtcca gcggggactc gtcacggact ggttcttcgg tgggctgaat | 5220 |
| taccaaatcg agcaccacct gtggccgacg ctgccccggc acaacctgac ggcggccagc | 5280 |
| atcaaagtgg agcagttgtg caagaagcac aacttgccgt atcgcagccc cccaatgctg | 5340 |
| gaggggtgg gcatcctgat cagctacctg ggcacctttg cccgcatggt ggcaaaggcc | 5400 |
| gacaaggcgt aagc | 5414 |

<210> SEQ ID NO 65
<211> LENGTH: 7907
<212> TYPE: DNA
<213> ORGANISM: Artificial Sequence
<220> FEATURE:
<223> OTHER INFORMATION: pKR1178

<400> SEQUENCE: 65

| | |
|---|---|
| ggagatccaa gcttttgatc catgcccttc atttgccgct tattaattaa tttggtaaca | 60 |
| gtccgtacta atcagttact tatccttccc ccatcataat taatcttggt agtctcgaat | 120 |
| gccacaacac tgactagtct cttggatcat aagaaaaagc caaggaacaa aagaagacaa | 180 |
| aacacaatga gagtatcctt tgcatagcaa tgtctaagtt cataaaattc aaacaaaaac | 240 |
| gcaatcacac acagtggaca tcacttatcc actagctgat caggatcgcc gcgtcaagaa | 300 |
| aaaaaaactg gaccccaaaa gccatgcaca acaacacgta ctcacaaagg tgtcaatcga | 360 |
| gcagcccaaa acattcacca actcaaccca tcatgagccc tcacatttgt tgtttctaac | 420 |
| ccaacctcaa actcgtattc tcttccgcca cctcattttt gtttatttca acacccgtca | 480 |
| aactgcatgc caccccgtgg ccaaatgtcc atgcatgtta acaagaccta tgactataaa | 540 |
| tagctgcaat ctcggcccag ttttcatca tcaagaacca gttcaatatc ctagtacacc | 600 |
| gtattaaaga atttaagata tactgcggcc gcaccatgga agcagccaaa gaattggttt | 660 |
| ccatcgtcca agaggagctc cccaaggtgg actatgccca gctttggcag gatgccagca | 720 |
| gctgtgaggt cctttacctc tcggtggcat tcgtggcgat caagttcatg ctgcgcccac | 780 |
| tggacctgaa cgccaggcc accttgaaga agctgttcac agcatacaac ttcctcatgt | 840 |
| cgatctattc ctttggctcc ttcctggcca tggcctatgc cctatcagta actggcatcc | 900 |
| tctccggcga ctgtgagacg gcgttcaaca acgatgtgtt caggatcaca actcagctgt | 960 |
| tctacctcag caagttcgta gagtacatcg actccttcta ccttccccctt atggacaagc | 1020 |
| cactgtcgtt cctcagttc ttccatcatt gggggcccc cattgacatg tggctattct | 1080 |
| acaaataccg caacgaagga gtctggatct tgtcctgtt gaatgggttc attcactgga | 1140 |
| tcatgtacgg ttactattgg acgcggctca tcaagctgaa cttccccatg cccaagaacc | 1200 |
| tgatcaccctc catgcagatc atccagttca atgtcggggtt ctacatcgtc tggaagtacc | 1260 |

```
gcaatgtgcc atgctaccgc caggatggga tgcgcatgtt tgcctggatc ttcaactact    1320
ggtatgtcgg gacggtcttg ctgctgttcc tcaactttta cgtgcagacg tacatccgga    1380
agccgaggaa gaaccgaggg aagaaggagt agcggccgca agtatgaact aaaatgcatg    1440
taggtgtaag agctcatgga gagcatgaaa tattgtatcc gaccatgtaa cagtataata    1500
actgagctcc atctcacttc ttctatgaat aaacaaagga tgttatgata tattaacact    1560
ctatctatgc accttattgt tctatgataa atttcctctt attattataa atcatctgaa    1620
tcgtgacggc ttatggaatg cttcaaatag tacaaaaaca aatgtgtact ataagacttt    1680
ctaaacaatt ctaaccttag cattgtgaac gagacataag tgttaagaag acataacaat    1740
tataatggaa gaagtttgtc tccatttata tattatatat tacccactta tgtattatat    1800
taggatgtta aggagacata acaattataa agagagaagt tgtatccat ttatatatta    1860 tatactaccc atttatatat tacttatc cacttattta atgtctttat aaggtttgat    1920
ccatgatatt tctaatattt tagttgatat gtatatgaaa gggtactatt tgaactctct    1980
tactctgtat aaaggttgga tcatccttaa agtgggtcta tttaattta ttgcttctta    2040 cagataaaaa aaaattatg agttggtttg ataaaatatt gaaggattta aaataataat    2100
aaataacata taatatatgt atataaattt attataatat aacatttatc tataaaaaag    2160
taaatattgt cataaatcta tacaatcgtt tagccttgct ggacgaatct caattattta    2220
aacgagagta aacatatttg acttttggt tatttaacaa attattattt aacactatat    2280
gaaatttttt ttttatcag caaagaataa aattaaatta agaaggacaa tggtgtccca    2340
atccttatac aaccaacttc cacaagaaag tcaagtcaga gacaacaaaa aaacaagcaa    2400 aggaaattt ttaatttgag ttgtcttgtt tgctgcataa tttatgcagt aaaacactac    2460
acataaccct tttagcagta gagcaatggt tgaccgtgtg cttagcttct tttatttat    2520 tttttatca gcaaagaata aataaataa aatgagacac ttcagggatg tttcaacaag    2580
cttggcgcgc ccgatcatcc ggatatagtt cctcctttca gcaaaaaacc cctcaagacc    2640
cgtttagagg ccccaagggg ttatgctagt tattgctcag cggtggcagc agccaactca    2700
gcttcctttc gggctttgtt agcagccgga tcgatccaag ctgtacctca ctattccttt    2760
gccctcggac gagtgctggg gcgtcggttt ccactatcgg cgagtacttc tacacagcca    2820
tcggtccaga cggccgcgct tctgcgggcg atttgtgtac gcccgacagt cccggctccg    2880
gatcggacga ttgcgtcgca tcgaccctgc gcccaagctg catcatcgaa attgccgtca    2940
accaagctct gatagagttg gtcaagacca atgcggagca tatacgcccg gagccgcggc    3000
gatcctgcaa gctccggatg cctccgctcg aagtagcgcg tctgctgctc catacaagcc    3060
aaccacggcc tccagaagaa gatgttggcg acctcgtatt gggaatcccc gaacatcgcc    3120
tcgctccagt caatgaccgc tgttatgcgg ccattgtccg tcaggacatt gttggagccg    3180
aaatccgcgt gcacgaggtg ccggacttcg ggcagtcct cggcccaaag catcagctca    3240
tcgagagcct gcgcgacgga cgcactgacg gtgtcgtcca tcacagtttg ccagtgatac    3300
acatggggat cagcaatcgc gcatatgaaa tcacgccatg tagtgtattg accgattcct    3360
tgcggtccga atgggccgaa cccgctcgtc tggctaagat cggccgcagc gatcgcatcc    3420
atagcctccg cgaccggctg cagaacagcg ggcagttcgg tttcaggcag tcttgcaac    3480 gtgacaccct gtgcacggcg ggagatgcaa taggtcaggc tctcgctgaa ttccccaatg    3540
tcaagcactt ccggaatcgg gagcgcggcc gatgcaaagt gccgataaac ataacgatct    3600
ttgtagaaac catcggcgca gctatttacc cgcaggacat atccacgccc tcctacatcg    3660
```

```
aagctgaaag cacgagattc ttcgccctcc gagagctgca tcaggtcgga gacgctgtcg    3720
aacttttcga tcagaaactt ctcgacagac gtcgcggtga gttcaggctt ttccatgggt    3780
atatctcctt cttaaagtta aacaaaatta tttctagagg gaaaccgttg tggtctccct    3840
atagtgagtc gtattaattt cgcgggatcg agatctgatc aacctgcatt aatgaatcgg    3900
ccaacgcgcg gggagaggcg gtttgcgtat tgggcgctct tccgcttcct cgctcactga    3960
ctcgctgcgc tcggtcgttc ggctgcggcg agcggtatca gctcactcaa aggcggtaat    4020
acggttatcc acagaatcag gggataacgc aggaaagaac atgtgagcaa aaggccagca    4080
aaaggccagg aaccgtaaaa aggccgcgtt gctggcgttt ttccataggc tccgcccccc    4140
tgacgagcat cacaaaaatc gacgctcaag tcagaggtgg cgaaacccga caggactata    4200
aagataccag gcgtttcccc ctggaagctc cctcgtgcgc tctcctgttc cgaccctgcc    4260
gcttaccgga tacctgtccg cctttctccc ttcgggaagc gtggcgcttt ctcaatgctc    4320
acgctgtagg tatctcagtt cggtgtaggt cgttcgctcc aagctgggct gtgtgcacga    4380
accccccgtt cagcccgacc gctgcgcctt atccggtaac tatcgtcttg agtccaaccc    4440
ggtaagacac gacttatcgc cactggcagc agccactggt aacaggatta gcagagcgag    4500
gtatgtaggc ggtgctacag agttcttgaa gtggtggcct aactacggct acactagaag    4560
gacagtattt ggtatctgcg ctctgctgaa gccagttacc ttcggaaaaa gagttggtag    4620
ctcttgatcc ggcaaacaaa ccaccgctgg tagcggtggt ttttttgttt gcaagcagca    4680
gattacgcgc agaaaaaaag gatctcaaga agatcctttg atcttttcta cggggtctga    4740
cgctcagtgg aacgaaaact cacgttaagg gattttggtc atgacattaa cctataaaaa    4800
taggcgtatc acgaggccct ttcgtctcgc gcgtttcggt gatgacggtg aaaacctctg    4860
acacatgcag ctcccggaga cggtcacagc ttgtctgtaa gcggatgccg ggagcagaca    4920
agcccgtcag ggcgcgtcag cgggtgttgg cgggtgtcgg gctggctta actatgcggc    4980 atcagagcag attgtactga gagtgcacca tatggacata ttgtcgttag aacgcggcta    5040
caattaatac ataaccttat gtatcataca catacgattt aggtgacact atagaacggc    5100
gcgccgtcga cggatccgta cgagatccgg ccggccagat cctgcagccc ggggggatcct    5160 ctagacgtac gtgaaggtta aacatggtga atatgttacc actagctggg atgcccatta    5220
gatcaaaact gtaaaattct cccgtttccc ttctattcac atgtgagccc cctcccttt    5280 cttctttct caattttgat tgagttaaag tcaccagcaa tgcatcactc accctccaaa    5340
aaatttcttg tacaacttct cggactatcc caaagctcct tttcctgaga tggatggtcc    5400
tgtctcttgc ccttgatgtc ttccttgttc gatttggct tcctctaatg tctttcttgc    5460
taggaatcac cacctcactc atctatgttg tcgtagcttc tgaaagtctc atacatatcc    5520
ttagtgttgc actcatcttg tattgaagtg aaaaagaatg ttgttctcct atccaaatct    5580
ccattgaatc tctttctccc aatgttgtcc catcggttgg tcctcctctc caaccaattg    5640
taaggtgttt aacataaaca tggtacaatt aagattttc atttcattaa gaaaagattg    5700
agatttgtgt tctaaagtt tcaattagag tttgatgata ttgaaacaac cgtagaacac    5760
attaagtatt actaacttat acatagagca ttggaatttc acctttttatt tattctgttt    5820 ccgccaaagg tacatgactc aagttatttt acacaagtaa caaaggcatc taagcctaag    5880
tattcttatt cagactttc attattactt tcattgattt ggtgcgaaat gcggccgctt    5940
acgccttgtc ggccttttgcc accatgcggg caaaggtgcc caggtagctg atcaggatgc    6000
ccaccccctc cagcattggg gggctgcgat acggcaagtt gtgcttcttg cacaactgct    6060
```

```
ccactttgat gctggccgcc gtcaggttgt gccggggcag cgtcggccac aggtggtgct      6120
cgatttggta attcagccca ccgaagaacc agtccgtgac gagtcccgc tggacgttca      6180 tcgtttcgtg aatctggccg gcgcaaaagc cgtggccgtc ccacaccgag tcctggatct      6240
tctccagggg gtagtggttc atgaacacca cgatggcgat gccgaagccc caagcaact      6300 cggacacgaa aaacaccatg agtccggtca agaagcttgg catataaaag tagtagaaca      6360
acgccttcag gccccagtgg agggccaggc ccacgctctc tttctcgtac tgcctgcgt      6420 agtactggtt gctgcgatcc ttcaggcccg tggctgtgtg gatgctctgg aagcaccaga      6480
tgaacctcag gagggcacag atgaagaaga agtagtattg ctggtacttg atcatccgcc      6540
gtgagaacgg gccggccctc tccacgtcct ccttggacca tgccagcagc ggcaggttgt      6600
caatgtcggg gtcgtggcct tgcacgttgg tggcggagtg tgtgcattg tgcctgtcct      6660 tccaccaggt cacagagaac ccttgcaaga cgttcccgaa aagcaagccg atggcgttgt      6720
tgatcgatcg gtccttgaac agctgatggt ggcagatatc gtgcgacaac caacccattt      6780
gttggaagtg aatgcccaac acgattgccc cgacgaggta ccagtgccac tgggtcatca      6840
atagcaccgc gaggaccccg aggcccagcg tactgagcgt cttatatgcg taccacatcg      6900
gtgatgcgtc gaacattcct gctgcgatga gctcatctcg gagcttgcgg aaatcctcct      6960
gcggttcgtc tgagttgggt ttcggtggcg taggcgtcag tggagatgat ggttccatga      7020
taggcatcct tcttagttta ctcacagcat tttcagagtg cataaccata aagacatcag      7080
tggcatcacg accgcggtag ttctcaatga tgtcagcacc ccctggatga tggttcaacc      7140
aggcagacac atcataggtg acaccatcaa cggtcagcgg aagtgctggc cttttcacca      7200
tggtgcggcc gcggtgatga ctgatgagtg tttaaggacc aatggagaga atgttttgagt     7260 tgtgaagcgg agaacctgag gcgtggttat ttatagggaa gagaggaagg tgaatgaggg      7320
acacgtcaca gaagtagggt gctgagcttg agacattctt cagtatgcat ggctatggaa      7380
gccttgggtg ctacacctca tgaagttcat ggtgtgaggt ggcttcggca tctcaattaa      7440
gtgacaaaga gaaaggtgtt tcagtgtttc tattgcaaat ggcagaaact cgtgatgacg      7500 agggaccat gcatggtttc atttcttttc ttcctggatt ctttctttcc ttttatatat      7560 gcaggtcat aatttaaaaa ttagactcgc tttcaatttc ttaatttctc attttcctct      7620
tatattactg tactaatgtt aaccacgtac acttatttt tttttagttt aattttgata      7680
gattgtgttg atttaaacat attaatattt tcaaccaaat aaaaatcatt ttagtagata      7740
cggcttttta ataattatt aaaaatatta actatttatc ctaaatggca cattttaatt      7800
aaaaaaaatc cggtgttgta agtgttttat taatttgttt tggcattatt aaagcaactt      7860 ttttttatt tgttggcatt ttgagtacgt acttaggcta gcctgca                     7907
```

<210> SEQ ID NO 66
<211> LENGTH: 18661
<212> TYPE: DNA
<213> ORGANISM: Artificial Sequence
<220> FEATURE:
<223> OTHER INFORMATION: pKR1192

<400> SEQUENCE: 66

```
cgcgccagat cctctagagt cgacctgcag gcatgcaagc ttggcgtaat catggtcata       60
gctgtttcct gtgtgaaatt gttatccgct cacaattcca cacaacatac gagccggaag      120
cataaagtgt aaagcctggg gtgcctaatg agtgagctaa ctcacattaa ttgcgttgcg      180
ctcactgccc gctttccagt cgggaaacct gtcgtgccag ctgcattaat gaatcggcca      240
```

```
acgcgcgggg agaggcggtt tgcgtattgg atcgatccct gaaagcgacg ttggatgtta      300
acatctacaa attgccttt  cttatcgacc atgtacgtaa gcgcttacgt ttttggtgga      360
cccttgagga aactggtagc tgttgtgggc ctgtggtctc aagatggatc attaatttcc      420
accttcacct acgatggggg gcatcgcacc ggtgagtaat attgtacggc taagagcgaa      480
tttggcctgt agacctcaat tgcgagcttt ctaatttcaa actattcggg cctaactttt      540
ggtgtgatga tgctgactgg caggatatat accgttgtaa tttgagctcg tgtgaataag      600
tcgctgtgta tgtttgtttg attgtttctg ttggagtgca gcccatttca ccggacaagt      660
cggctagatt gatttagccc tgatgaactg ccgaggggaa gccatcttga gcgcggaatg      720
ggaatggatt tcgttgtaca acgagacgac agaacaccca cgggaccgag cttcgcgagc      780
ttttgtatcc gtggcatcct tggtccggc  gatttgttca cgtccatgag gcgctctcca      840
aaggaacgca tattttccgg tgcaaccttt ccggttcttc ctctactcga cctcttgaag      900
tcccagcatg aatgttcgac cgctccgcaa gcggatcttt ggcgcaacca gccggtttcg      960
cacgtcgatt ctcgcgagcc tgcatacttt ggcaagattg ctgaatgacg ctgatgcttc     1020
atcgcaatct gcgataatgg ggtaagtatc cggtgaaggc cgcaggtcag gccgcctgag     1080
cactcagtgt cttggatgtc cagttccacg gcagctgttg ctcaagcctg ctgatcggag     1140
cgtccgcaag gtcggcgcgg acgtcggcaa gccaggcctg cggatcgatg ttattgagct     1200
tggcgctcat gatcagtgtc gccatgaacg ccgcacgttc agcacaacga tccgatccgg     1260
caaacagcca tgacttcctg ccgagtacat agcctctgag cgttcgttcg gcagcattgt     1320
tcgtcaggca aatcgggccg tcatcgagga atgacgtaat gccatcccat cgcttgagca     1380
tgtaatttat cgcctcggcg acgggagaac tgcgcgacaa tttcccccgc tcggtttcga     1440
gccaatcatg cagctcttcg gcgagtgacc ttgatcaggc caccgccacg accgcggaag     1500
acgaacagat gcctgcgcat cggatcgcgc ttcagcgtct cttgcaccat cagcgacaaa     1560
ccgggaaagc ctttgcgcat gtccgtactt atgtcgccac ttgggagggc ttcgtctacg     1620
tggccttcgt gatcgacgtc ttcgcccgtc gcattgtcgg atggcgggcg agccggacag     1680
cacatgcagg ctttgtcctc gatgccctcg aggaggctca tcatgatcgg cgtcccgctc     1740
atggcggcct agtgcatcac tcggatcgcg gtgttcaata cgtgtccttt cgctattccg     1800
agcggttggc agaagcaggt atcgagccat ctatcggaag cgtcggcgac agcacgacaa     1860
cgccctcgca gaagcgatca acggtcttta caaggccgag gtcattcatc ggcgtggacc     1920
atggaggagc ttcgaagcgg tcgagttcgc taccttggaa tggatagact ggttcaacca     1980
cggcggcttt tgaagcccat cggcaatata ccgccagccg aagacgagga tcagtattac     2040
gccatgctgg acgaagcagc catgctgcg  cattttaacg aaatggcctc cggcaaaccc     2100
ggtgcggttc acttgttgcg tgggaaagtt cacgggactc cgcgcacgag ccttcttcgt     2160
aatagccata tcgaccgaat tgacctgcag gggggggggg gaaagccacg ttgtgtctca     2220
aaatctctga tgttacattg cacaagataa aaatatatca tcatgaacaa taaaactgtc     2280
tgcttacata aacagtaata caaggggtgt tatgagccat attcaacggg aaacgtcttg     2340
ctcgaggccg cgattaaatt ccaacatgga tgctgattta tatgggtata aatgggctcg     2400
cgataatgtc gggcaatcag gtgcgacaat ctatcgattg tatgggaagc ccgatgcgcc     2460
agagttgttt ctgaaacatg gcaaaggtag cgttgccaat gatgttacag atgagatggt     2520
cagactaaac tggctgacgg aatttatgcc tcttccgacc atcaagcatt ttatccgtac     2580
tcctgatgat gcatggttac tcaccactgc gatccccggg aaaacagcat tccaggtatt     2640
```

```
agaagaatat cctgattcag gtgaaaatat tgttgatgcg ctggcagtgt tcctgcgccg    2700
gttgcattcg attcctgttt gtaattgtcc ttttaacagc gatcgcgtat ttcgtctcgc    2760
tcaggcgcaa tcacgaatga ataacggttt ggttgatgcg agtgattttg atgacgagcg    2820
taatggctgg cctgttgaac aagtctggaa agaaatgcat aagcttttgc cattctcacc    2880
ggattcagtc gtcactcatg gtgatttctc acttgataac cttattttg acgaggggaa     2940
attaataggt tgtattgatg ttggacgagt cggaatcgca gaccgatacc aggatcttgc    3000
catcctatgg aactgcctcg gtgagttttc tccttcatta cagaaacggc ttttcaaaa     3060
atatggtatt gataatcctg atatgaataa attgcagttt catttgatgc tcgatgagtt    3120
tttctaatca gaattggtta attggttgta acactggcag agcattacgc tgacttgacg    3180
ggacggcggc tttgttgaat aaatcgaact tttgctgagt tgaaggatca gatcacgcat    3240
cttcccgaca acgcagaccg ttccgtggca aagcaaaagt tcaaaatcac caactggtcc    3300
acctacaaca aagctctcat caaccgtggc tccctcactt tctggctgga tgatggggcg    3360
attcaggcct ggtatgagtc agcaacacct tcttcacgag gcagacctca gcgccccccc    3420
cccctgcag gtcttttcca atgatgagca cttttaaagt tctgctatgt ggcgcggtat     3480
tatcccgtgt tgacgccggg caagagcaac tcggtcgccg catacactat tctcagaatg    3540
acttggttga gtactcacca gtcacagaaa agcatcttac ggatggcatg acagtaagag    3600
aattatgcag tgctgccata accatgagtg ataacactgc ggccaactta cttctgacaa    3660
cgatcggagg accgaaggag ctaaccgctt ttttgcacaa catggggat catgtaactc      3720
gccttgatcg ttgggaaccg gagctgaatg aagccatacc aaacgacgag cgtgacacca    3780
cgatgcctgt agcaatggca acaacgttgc gcaaactatt aactggcgaa ctacttactc    3840
tagcttcccg gcaacaatta atagactgga tgaggcgga taaagttgca ggaccacttc      3900
tgcgctcggc ccttccggct ggctggttta ttgctgataa atctggagcc ggtgagcgtg    3960
ggtctcgcgg tatcattgca gcactggggc cagatggtaa gccctcccgt atcgtagtta    4020
tctacacgac ggggagtcag gcaactatgg atgaacgaaa tagacagatc gctgagatag    4080
gtgcctcact gattaagcat tggtaactgt cagaccaagt ttactcatat atactttaga    4140
ttgatttaaa acttcatttt taatttaaaa ggatctaggt gaagatcctt tttgataatc    4200
tcatgaccaa aatcccttaa cgtgagtttt cgttccactg agcgtcagac cccgtagaaa    4260
agatcaaagg atcttcttga gatccttttt ttctgcgcgt aatctgctgc ttgcaaacaa    4320
aaaaaccacc gctaccagcg gtggtttgtt tgccggatca agagctacca actctttttc    4380
cgaaggtaac tggcttcagc agagcgcaga taccaaatac tgtccttcta gtgtagccgt    4440
agttaggcca ccacttcaag aactctgtag caccgcctac atacctcgct ctgctaatcc    4500
tgttaccagt ggctgctgcc agtggcgata agtcgtgtct taccgggttg gactcaagac    4560
gatagttacc ggataaggcg cagcggtcgg gctgaacggg gggttcgtgc acacagccca    4620
gcttggagcg aacgacctac accgaactga gatacctaca gcgtgagcta tgagaaagcg    4680
ccacgcttcc cgaagggaga aaggcggaca ggtatccggt aagcggcagg gtcggaacag    4740
gagagcgcac gagggagctt ccagggggaa acgcctggta tctttatagt cctgtcgggt    4800
ttcgccacct ctgacttgag cgtcgatttt tgtgatgctc gtcagggggg cggagcctat    4860
ggaaaaacgc cagcaacgcg gcctttttac ggttcctggc cttttgctgg ccttttgctc    4920
acatgttctt tcctgcgtta tcccctgatt ctgtggataa ccgtattacc gcctttgagt    4980
gagctgatac cgctcgccgc agccgaacga ccgagcgcag cgagtcagtg agcgaggaag    5040
```

```
cggaagagcg cctgatgcgg tattttctcc ttacgcatct gtgcggtatt tcacaccgca   5100
tatggtgcac tctcagtaca atctgctctg atgccgcata gttaagccag tatacactcc   5160
gctatcgcta cgtgactggg tcatggctgc gccccgacac ccgccaacac ccgctgacgc   5220
gccctgacgg gcttgtctgc tcccggcatc cgcttacaga caagctgtga ccgtctccgg   5280
gagctgcatg tgtcagaggt tttcaccgtc atcaccgaaa cgcgcgaggc agggtgcctt   5340
gatgtgggcg ccggcggtcg agtggcgacg gcgcggcttg tccgcgccct ggtagattgc   5400
ctggccgtag gccagccatt tttgagcggc cagcggccgc gataggccga cgcgaagcgg   5460
cggggcgtag ggagcgcagc gaccgaaggg taggcgcttt tgcagctct tcggctgtgc   5520 gctggccaga cagttatgca caggccaggc gggttttaag agttttaata agttttaaag   5580
agttttaggc ggaaaaatcg ccttttttct cttttatatc agtcacttac atgtgtgacc   5640
ggttcccaat gtacggcttt gggttcccaa tgtacgggtt ccggttccca atgtacggct   5700
ttgggttccc aatgtacgtg ctatccacag gaaagagacc ttttcgacct ttttcccctg   5760
ctagggcaat ttgccctagc atctgctccg tacattagga accggcggat gcttcgccct   5820
cgatcaggtt gcggtagcgc atgactagga tcgggccagc ctgccccgcc tcctccttca   5880
aatcgtactc cggcaggtca tttgacccga tcagcttgcg cacggtgaaa cagaacttct   5940
tgaactctcc ggcgctgcca ctgcgttcgt agatcgtctt gaacaaccat ctggcttctg   6000
ccttgcctgc ggcgcggcgt gccaggcggt agagaaaacg gccgatgccg ggatcgatca   6060
aaaagtaatc ggggtgaacc gtcagcacgt ccgggttctt gccttctgtg atctcgcggt   6120
acatccaatc agctagctcg atctcgatgt actccggccg cccggtttcg ctctttacga   6180
tcttgtagcg gctaatcaag gcttcaccct cggataccgt caccaggcgg ccgttcttgg   6240
ccttcttcgt acgctgcatg gcaacgtgcg tggtgtttaa ccgaatgcag gtttctacca   6300
ggtcgtcttt ctgctttccg ccatcggctc gccggcagaa cttgagtacg tccgcaacgt   6360
gtggacggaa cacgcggccg ggcttgtctc ccttcccttc ccggtatcgg ttcatggatt   6420
cggttagatg ggaaaccgcc atcagtacca ggtcgtaatc ccacacactg gccatgccgg   6480
ccggccctgc ggaaacctct acgtgccgt ctggaagctc gtagcggatc acctcgccag   6540
ctcgtcggtc acgcttcgac agacggaaaa cggccacgtc catgatgctg cgactatcgc   6600
gggtgcccac gtcatagagc atcggaacga aaaaatctgg ttgctcgtcg cccttgggcg   6660
gcttcctaat cgacggcgca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg gcttggggg ttccagtgcc   6900 attgcagggc cggcagacaa cccagccgct tacgcctggc caaccgcccg ttcctccaca   6960 catgggcat tccacggcgt cggtgcctgg ttgttcttga ttttccatgc cgcctccttt   7020
agccgctaaa attcatctac tcatttattc atttgctcat ttactctggt agctgcgcga   7080
tgtattcaga tagcagctcg gtaatggtct tgccttggcg taccgcgtac atcttcagct   7140
tggtgtgatc ctccgccggc aactgaaagt tgaccgcctt catggctggc gtgtctgcca   7200
ggctggccaa cgttgcagcc ttgctgctgc gtgcgctcgg acggccggca cttagcgtgt   7260
ttgtgctttt gctcattttc tctttacctc attaactcaa atgagttttg atttaatttc   7320
agcggccagc gcctggacct cgcgggcagc gtcgccctcg ggttctgatt caagaacggt   7380
tgtgccggcg gcggcagtgc ctgggtagct cacgcgctgc gtgatacggg actcaagaat   7440
```

```
gggcagctcg tacccggcca gcgcctcggc aacctcaccg ccgatgcgcg tgcctttgat   7500
cgcccgcgac acgacaaagg ccgcttgtag ccttccatcc gtgacctcaa tgcgctgctt   7560
aaccagctcc accaggtcgg cggtggccca tatgtcgtaa gggcttggct gcaccggaat   7620
cagcacgaag tcggctgcct tgatcgcgga cacagccaag tccgccgcct ggggcgctcc   7680
gtcgatcact acgaagtcgc gccggccgat ggccttcacg tcgcggtcaa tcgtcgggcg   7740
gtcgatgccg acaacggtta gcggttgatc ttcccgcacg gccgcccaat cgcgggcact   7800
gccctgggga tcggaatcga ctaacagaac atcggcccg gcgagttgca gggcgcgggc    7860
tagatgggtt gcgatggtcg tcttgcctga cccgcctttc tggttaagta cagcgataac   7920
ttcatgcgtt cccttgcgta tttgtttatt tactcatcgc atcatatacg cagcgaccgc   7980
atgacgcaag ctgttttact caaatacaca tcaccttttt agacggcggc gctcggtttc   8040
ttcagcggcc aagctggccg gccaggccgc cagcttggca tcagacaaac cggccaggat   8100
ttcatgcagc cgcacggttg agacgtgcgc gggcggctcg aacacgtacc cggccgcgat   8160
catctccgcc tcgatctctt cggtaatgaa aaacggttcg tcctggccgt cctggtgcgg   8220
tttcatgctt gttcctcttg gcgttcattc tcggcggccg ccaggcgtc ggcctcggtc     8280
aatgcgtcct cacggaaggc accgcgccgc ctggcctcgg tgggcgtcac ttcctcgctg   8340
cgctcaagtg cgcggtacag ggtcgagcga tgcacgccaa gcagtgcagc cgcctctttc   8400
acggtgcggc cttcctggtc gatcagctcg cgggcgtgcg cgatctgtgc cggggtgagg   8460
gtagggcggg ggccaaactt cacgcctcgg gccttggcgg cctcgcgccc gctccgggtg   8520
cggtcgatga ttagggaacg ctcgaactcg gcaatgccgg cgaacacggt caacaccatg   8580
cggccggccg gcgtggtggt gtcggcccac ggctctgcca ggctacgcag gcccgcgccg   8640
gcctcctgga tgcgctcggc aatgtccagt aggtcgcggg tgctgcgggc caggcggtct   8700
agcctggtca ctgtcacaac gtcgccaggg cgtaggtggt caagcatcct ggccagctcc   8760
gggcggtcgc gcctggtgcc ggtgatcttc tcggaaaaca gcttggtgca gccggccgcg   8820
tgcagttcgg cccgttggtt ggtcaagtcc tggtcgtcgg tgctgacgcg gcatagcccc   8880
agcaggccag cggcggcgct cttgttcatg gcgtaatgtc tccggttcta gtcgcaagta   8940
ttctactta tgcgactaaa acacgcgaca agaaacgcc aggaaaaggg cagggcggca     9000
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
gcgctagcag cacgccatag tgactggcga tgctgtcgga atggacgata tcccgcaaga   9300
ggcccggcag taccggcata accaagccta tgcctacagc atccagggtg acggtgccga   9360
ggatgacgat gagcgcattg ttagatttca tacacggtgc ctgactgcgt tagcaattta   9420
actgtgataa actaccgcat taaagctagc ttgcttggtc gttccgcgtg aacgtcggct   9480
cgattgtacc tgcgttcaaa tactttgcga tcgtgttgcg cgcctgcccg gtgcgtcggc   9540
tgatctcacg gatcgactgc ttctctcgca acgccatccg acggatgatg tttaaaagtc   9600
ccatgtggat cactccgttg ccccgtcgct caccgtgttg ggggaaggt gcacatggct     9660
cagttctcaa tggaaattat ctgcctaacc ggctcagttc tgcgtagaaa ccaacatgca   9720
agctccaccg ggtgcaaagc ggcagcgcg gcaggatata ttcaattgta aatggcttca     9780
tgtccgggaa atctacatgg atcagcaatg agtatgatgg tcaatatgga gaaaagaaa    9840
```

```
gagtaattac caattttttt tcaattcaaa aatgtagatg tccgcagcgt tattataaaa    9900
tgaaagtaca ttttgataaa acgacaaatt acgatccgtc gtatttatag gcgaaagcaa    9960
taaacaaatt attctaattc ggaaatcttt atttcgacgt gtctacattc acgtccaaat   10020
gggggcttag atgagaaact tcacgatcga tgccttgatt tcgccattcc cagataccca   10080
tttcatcttc agattggtct gagattatgc gaaaatatac actcatatac ataaatactg   10140
acagtttgag ctaccaattc agtgtagccc attacctcac ataattcact caaatgctag   10200
gcagtctgtc aactcggcgt caatttgtcg gccactatac gatagttgcg caaattttca   10260
aagtcctggc ctaacatcac acctctgtcg gcggcgggtc ccatttgtga taaatccacc   10320
atatcgaatt aattcagact cctttgcccc agagatcaca atggacgact tcctctatct   10380
ctacgatcta gtcaggaagt tcgacggaga aggtgacgat accatgttca ccactgataa   10440
tgagaagatt agccttttca atttcagaaa gaatgctaac ccacagatgg ttagagaggc   10500
ttacgcagca ggtctcatca agacgatcta cccgagcaat aatctccagg agatcaaata   10560
ccttcccaag aaggttaaag atgcagtcaa aagattcagg actaactgca tcaagaacac   10620
agagaaagat atatttctca agatcagaag tactattcca gtatggacga ttcaaggctt   10680
gcttcacaaa ccaaggcaag taatagagat tggagtctct aaaaaggtag ttcccactga   10740
atcaaaggcc atggagtcaa agattcaaat agaggaccta acagaactcg ccgtaaagac   10800
tggcgaacag ttcatacaga gtctcttacg actcaatgac aagaagaaaa tcttcgtcaa   10860
catggtggag cacgcacacgc ttgtctactc caaaaatatc aaagatacag tctcagaaga   10920
ccaaagggca attgagactt tcaacaaag ggtaatatcc ggaaacctcc tcggattcca   10980
ttgcccagct atctgtcact ttattgtgaa gatagtggaa aaggaaggtg gctcctacaa   11040
atgccatcat tgcgataaag gaaaggccat cgttgaagat gcctctgccg acagtggtcc   11100
caaagatgga cccccaccca cgaggagcat cgtggaaaaa gaagacgttc caaccacgtc   11160
ttcaaagcaa gtggattgat gtgatatctc cactgacgta agggatgacg cacaatccca   11220
ctatccttcg caagaccctt cctctatata aggaagttca tttcatttgg agaggacacg   11280
ctgaaatcac cagtctccaa gcttgcgggg atcgtttcgc atgattgaac aagatggatt   11340
gcacgcaggt tctccggccg cttgggtgga gaggctattc ggctatgact gggcacaaca   11400
gacaatcggc tgctctgatg ccgccgtgtt ccggctgtca gcgcaggggc gcccggttct   11460
ttttgtcaag accgacctgt ccggtgccct gaatgaactg caggacgagg cagcgcggct   11520
atcgtggctg gccacgacgg gcgttccttg cgcagctgtg ctcgacgttg tcactgaagc   11580
gggaagggac tggctgctat tgggcgaagt gccggggcag gatctcctgt catctcacct   11640
tgctcctgcc gagaaagtat ccatcatggc tgatgcaatg cggcggctgc atacgcttga   11700
tccggctacc tgcccattcg accaccaagc gaaacatcgc atcgagcgag cacgtactcg   11760
gatggaagcc ggtcttgtcg atcaggatga tctggacgaa gagcatcagg gctcgcgcc   11820 agccgaactg ttcgccaggc tcaaggcgcg catgcccgac ggcgaggatc tcgtcgtgac   11880
ccatggcgat gcctgcttgc cgaatatcat ggtggaaaat ggccgctttt ctggattcat   11940
cgactgtggc cggctgggtg tggcggaccg ctatcaggac atagcgttgg ctacccgtga   12000
tattgctgaa gagcttggcg gcgaatgggc tgaccgcttc ctcgtgcttt acggtatcgc   12060
cgctcccgat tcgcagcgca tcgccttcta tcgccttctt gacgagttct tctgagcggg   12120
actctggggt tcgaaatgac cgaccaagcg acgcccaacc tgccatcacg agatttcgat   12180
tccaccgccg ccttctatga aaggttgggc ttcggaatcg ttttccggga cgccggctgg   12240
```

```
atgatcctcc agcgcgggga tctcatgctg gagttcttcg cccaccccgg atcgatccaa    12300
cacttacgtt tgcaacgtcc aagagcaaat agaccacgaa cgccggaagg ttgccgcagc    12360
gtgtggattg cgtctcaatt ctctcttgca ggaatgcaat gatgaatatg atactgacta    12420
tgaaactttg agggaatact gcctagcacc gtcacctcat aacgtgcatc atgcatgccc    12480
tgacaacatg aacatcgct attttctga agaattatgc tcgttggagg atgtcgcggc      12540
aattgcagct attgccaaca tcgaactacc cctcacgcat gcattcatca atattattca    12600
tgcggggaaa ggcaagatta atccaactgg caaatcatcc agcgtgattg gtaacttcag    12660
ttccagcgac ttgattcgtt ttggtgctac ccacgttttc aataaggacg agatggtgga    12720
gtaaagaagg agtgcgtcga agcagatcgt tcaaacattt ggcaataaag tttcttaaga    12780
ttgaatcctg ttgccggtct tgcgatgatt atcatataat ttctgttgaa ttacgttaag    12840
catgtaataa ttaacatgta atgcatgacg ttatttatga gatgggtttt tatgattaga    12900
gtcccgcaat tatacattta atacgcgata gaaaacaaaa tatagcgcgc aaactaggat    12960
aaattatcgc gcgcggtgtc atctatgtta ctagatcgat caaacttcgg tactgtgtaa    13020
tgacgatgag caatcgagag gctgactaac aaaaggtaca tcgcgatgga tcgatccatt    13080
cgccattcag gctgcgcaac tgttgggaag ggcgatcggt gcgggcctct tcgctattac    13140
gccagctggc gaaaggggga tgtgctgcaa ggcgattaag ttgggtaacg ccagggtttt    13200
cccagtcacg acgttgtaaa acgacggcca gtgaattcct gcagcccggg ggatccgccc    13260
actcgaggcg cgccgtcgac ggatccgtac gagatccggc cggccagatc ctgcagcccg    13320
ggggatcctc tagacgtacg tgaaggttaa acatggtgaa tatgttacca ctagctggga    13380
tgcccattag atcaaaactg taaaattctc ccgtttccct tctattcaca tgtgagcccc    13440 ctccctttc tttctttctc aattttgatt gagttaaagt caccagcaat gcatcactca     13500
ccctccaaaa aatttcttgt acaacttctc ggactatccc aaagctcctt ttcctgagat    13560
ggatggtcct gtctcttgcc cttgatgtct tccttgttcg attttggctt cctctaatgt    13620 cttctgct aggaatcacc acctcactca tctatgttgt cgtagcttct gaaagtctca       13680
tacatatcct tagtgttgca ctcatcttgt attgaagtga aaaagaatgt tgttctccta    13740
tccaaatctc cattgaatct cttctcccca atgttgtccc atcggttggt cctcctctcc    13800
aaccaattgt aaggtgttta acataaacat ggtacaatta agattttca tttcattaag      13860 aaaagattga gatttgtggt tctaaagttt caattagagt ttgatgatat tgaaacaacc    13920
gtagaacaca ttaagtatta ctaacttata catagagcat tggaatttca ccttttattt    13980
attctgtttc cgccaaaggt acatgactca agttatttta cacaagtaac aaaggcatct    14040
aagcctaagt attcttattc agactttca ttattacttt cattgatttg gtgcgaaatg      14100
cggccgctta cgccttgtcg gcctttgcca ccatgcgggc aaaggtgccc aggtagctga    14160
tcaggatgcc caccccctcc agcattgggg ggctgcgata cggcaagttg tgcttcttgc    14220
acaactgctc cactttgatg ctggccgccg tcaggttgtg ccggggcagc gtcggccaca    14280
ggtggtgctc gatttggtaa ttcagcccac cgaagaacca gtccgtgacg agtccccgct    14340
ggacgttcat cgtttcgtga atctggccgg cgcaaaagcc gtggccgtcc cacaccgagt    14400
cctggatctt ctccaggggg tagtggttca tgaacaccac gatggcgatg ccgaagcccc    14460
caagcaactc ggacacgaaa aacaccatga gtccggtcaa gaagcttggc atataaaagt    14520
agtagaacaa cgccttcagg ccccagtgga gggccaggcc cacgctctct ttctcgtact    14580
gcctgcggta gtactggttg ctgcgatcct tcaggcccgt ggctgtgtgg atgctctgga    14640
```

```
agcaccagat gaacctcagg agggcacaga tgaagaagaa gtagtattgc tggtacttga   14700
tcatccgccg tgagaacggg ccggccctct ccacgtcctc cttggaccat gccagcagcg   14760
gcaggttgtc aatgtcgggg tcgtggcctt gcacgttggt ggcggagtgg tgtgcattgt   14820
gcctgtcctt ccaccaggtc acagagaacc cttgcaagac gttcccgaaa agcaagccga   14880
tggcgttgtt gatcgatcgg tccttgaaca gctgatggtg gcagatatcg tgcgacaacc   14940
aacccatttg ttggaagtga atgcccaaca cgattgcccc gacgaggtac cagtgccact   15000
gggtcatcaa tagcaccgcg aggaccccga ggcccagcgt actgagcgtc ttatatgcgt   15060
accacatcgg tgatgcgtcg aacattcctg ctgcgatgag ctcatctcgg agcttgcgga   15120
aatcctcctg cggttcgtct gagttgggtt tcggtggcgt aggcgtcagt ggagatgatg   15180
gttccatgat aggcatcctt cttagtttac tcacagcatt ttcagagtgc ataaccataa   15240
agacatcagt ggcatcacga ccgcggtagt tctcaatgat gtcagcaccc cctggatgat   15300
ggttcaacca gcagacaca tcataggtga caccatcaac ggtcagcgga agtgctggcc   15360
ttttcaccat ggtgcggccg cggtgatgac tgatgagtgt ttaaggacca atggagagaa   15420
tgtttgagtt gtgaagcgga gaacctgagg cgtggttatt tatagggaag agaggaaggt   15480
gaatgaggga cacgtcacag aagtagggtg ctgagcttga gacattcttc agtatgcatg   15540
gctatgaaag ccttgggtgc tacacctcat gaagttcatg gtgtgaggtg gcttcggcat   15600
ctcaattaag tgacaaagag aaaggtgttt cagtgtttct attgcaaatg gcagaaactc   15660
gtgatgacga ggggaccatg catggtttca tttcttttct tcctggattc tttctttcct   15720
tttatatatg caggttcata atttaaaaat tagactcgct ttcaatttct taatttctca   15780
ttttcctctt atattactgt actaatgtta accacgtaca cttatttttt ttttagttta   15840
attttgatag attgtgttga tttaaacata ttaatatttt caaccaaata aaaatcattt   15900
tagtagatac ggcttttaa ataattatta aaaatattaa ctatttatcc taaatggcac   15960
atttaatta aaaaaaatcc ggtgttgtaa gtgttttatt aattgtttt ggcattatta   16020
aagcaacttt tttttttattt gttggcattt tgagtacgta cttaggctag cctgcaggag   16080
atccaagctt ttgatccatg cccttcattt gccgcttatt aattaatttg gtaacagtcc   16140
gtactaatca gttacttatc cttccccat cataattaat cttggtagtc tcgaatgcca   16200
caacactgac tagtctcttg gatcataaga aaaagccaag gaacaaaaga agacaaaaca   16260
caatgagagt atcctttgca tagcaatgtc taagttcata aaattcaaac aaaaacgcaa   16320
tcacacacag tggacatcac ttatccacta gctgatcagg atcgccgcgt caagaaaaaa   16380
aaactggacc ccaaaagcca tgcacaacaa cacgtactca caaggtgtc aatcgagcag   16440
cccaaaacat tcaccaactc aacccatcat gagccctcac atttgttgtt tctaacccaa   16500
cctcaaactc gtattctctt ccgccacctc attttttgttt atttcaacac ccgtcaaact   16560
gcatgccacc ccgtggccaa atgtccatgc atgttaacaa gacctatgac tataaatagc   16620
tgcaatctcg gcccaggttt tcatcatcaa gaaccagttc aatatcctag tacaccgtat   16680
taaagaattt aagatatact gcggccgcac catggaagca gccaaagaat tggtttccat   16740
cgtccaagag gagctcccca agtggactat gcccagctt tggcaggatg ccagcagctg   16800
tgaggtcctt tacctctcgg tggcattcgt ggcgatcaag ttcatgctgc gcccactgga   16860
cctgaagcgc caggccacct tgaagaagct gttcacagca tacaacttcc tcatgtcgat   16920
ctattccttt ggctccttcc tggccatggc ctatgcccta tcagtaactg gcatcctctc   16980
cggcgactgt gagacggcgt tcaacaacga tgtgttcagg atcacaactc agctgttcta   17040
```

-continued

```
cctcagcaag ttcgtagagt acatcgactc cttctacctt ccccttatgg acaagccact   17100
gtcgttcctt cagttcttcc atcatttggg ggccccatt gacatgtggc tattctacaa    17160
ataccgcaac gaaggagtct ggatctttgt cctgttgaat gggttcattc actggatcat   17220
gtacggttac tattggacgc ggctcatcaa gctgaacttc cccatgccca agaacctgat   17280
cacctccatg cagatcatcc agttcaatgt cgggttctac atcgtctgga agtaccgcaa   17340
tgtgccatgc taccgccagg atgggatgcg catgtttgcc tggatcttca actactggta   17400
tgtcgggacg gtcttgctgc tgttcctcaa cttttacgtg cagacgtaca tccggaagcc   17460
gaggaagaac cgagggaaga aggagtagcg gccgcaagta tgaactaaaa tgcatgtagg   17520
tgtaagagct catggagagc atggaatatt gtatccgacc atgtaacagt ataataactg   17580
agctccatct cacttcttct atgaataaac aaaggatgtt atgatatatt aacactctat   17640
ctatgcacct tattgttcta tgataaattt cctcttatta ttataaatca tctgaatcgt   17700
gacggcttat ggaatgcttc aaatagtaca aaaacaaatg tgtactataa gactttctaa   17760
acaattctaa ccttagcatt gtgaacgaga cataagtgtt aagaagacat aacaattata   17820
atggaagaag tttgtctcca tttatatatt atatattacc cacttatgta ttatattagg   17880
atgttaagga gacataacaa ttataaagag agaagtttgt atccatttat atattatata   17940
ctacccattt atatattata cttatccact tatttaatgt ctttataagg tttgatccat   18000
gatatttcta atattttagt tgatatgtat atgaaagggt actatttgaa ctctcttact   18060
ctgtataaag gttggatcat ccttaaagtg ggtctattta attttattgc ttcttacaga   18120
taaaaaaaaa attatgagtt ggtttgataa aatattgaag gatttaaaat aataataaat   18180
aacatataat atatgtatat aaatttatta taatataaca tttatctata aaaaagtaaa   18240
tattgtcata aatctataca atcgtttagc cttgctggac gaatctcaat tatttaaacg   18300
agagtaaaca tatttgactt tttggttatt taacaaatta ttatttaaca ctatatgaaa   18360 ttttttttt tatcagcaaa gaataaaatt aaattaagaa ggacaatggt gtcccaatcc   18420
ttatacaacc aacttccaca agaaagtcaa gtcagagaca acaaaaaaac aagcaaagga   18480
aattttttaa tttgagttgt cttgtttgct gcataattta tgcagtaaaa cactacacat   18540 aacccttta gcagtagagc aatggttgac cgtgtgctta gcttctttta ttttattttt    18600
ttatcagcaa agaataaata aaataaaatg agacacttca gggatgtttc aacaagcttg   18660
g                                                                  18661
```